United States Patent
Eichenlaub et al.

(10) Patent No.: US 11,802,860 B1
(45) Date of Patent: Oct. 31, 2023

(54) EMISSIONS DETECTION SYSTEM AND METHODS

(71) Applicant: Project Canary, PBC, Denver, CO (US)

(72) Inventors: Nathan C. Eichenlaub, Denver, CO (US); Kieran J. Lynn, Denver, CO (US); William J. Foiles, Denver, CO (US); Jason D. Clark, Fort Lupton, CO (US)

(73) Assignee: PROJECT CANARY, PBC, Denver, CO (US)

( * ) Notice: Subject to any disclaimer, the term of this patent is extended or adjusted under 35 U.S.C. 154(b) by 0 days.

(21) Appl. No.: 17/813,585

(22) Filed: Jul. 19, 2022

Related U.S. Application Data

(60) Provisional application No. 63/323,703, filed on Mar. 25, 2022.

(51) Int. Cl.
*G01N 33/00* (2006.01)
*G01D 21/02* (2006.01)

(52) U.S. Cl.
CPC ......... *G01N 33/0062* (2013.01); *G01D 21/02* (2013.01); *G01N 33/0031* (2013.01); *G01N 2033/0068* (2013.01)

(58) Field of Classification Search
CPC .......... G01N 33/0062; G01N 33/0031; G01N 2033/0068; G01D 21/02
See application file for complete search history.

(56) References Cited

U.S. PATENT DOCUMENTS

| | | | |
|---|---|---|---|
| 3,206,982 A | 9/1965 | Blondfield | |
| 3,662,171 A | 5/1972 | Brengman et al. | |
| 3,780,566 A | 12/1973 | Smith et al. | |
| 3,817,108 A | 6/1974 | Principe et al. | |

(Continued)

FOREIGN PATENT DOCUMENTS

| CH | 703014 A2 | 10/2011 |
|---|---|---|
| CN | 107782374 A | 3/2018 |

(Continued)

OTHER PUBLICATIONS

Aber (Aber, James S., Irene Marzolff, and Johannes Ries. Small-format aerial photography: Principles, techniques and geoscience applications. Elsevier, 2010, "Aber") (Year: 2010).*

(Continued)

*Primary Examiner* — Kristina M Deherrera
*Assistant Examiner* — Fatemeh Esfandiari Nia
(74) *Attorney, Agent, or Firm* — Stephen B. Katsaros; Patent Engineering, LLC

(57) ABSTRACT

In one illustrative configuration, a method of locating an emission source of a target substance at a site is disclosed. The method may include obtaining predicted substance concentrations of the target substance from a prediction model to generate a mapping of a weighted mean of the plurality of the predicted substance concentrations grouped in a predetermined number of feature groups. A simulated plume model is generated for each emission source present at the site to calculate representative circular normal distributions for each air quality monitor. By performing an analysis of the plurality of representative circular normal distributions in relation to the mapping, a target emission source is identified.

11 Claims, 57 Drawing Sheets

(56) References Cited

U.S. PATENT DOCUMENTS

| | | |
|---|---|---|
| 4,135,092 A | 1/1979 | Milly |
| 4,551,719 A | 11/1985 | Carlin et al. |
| 5,132,968 A | 7/1992 | Cephus |
| 5,281,816 A | 1/1994 | Jacobson et al. |
| 5,406,265 A | 4/1995 | Trozzo et al. |
| 5,479,359 A | 12/1995 | Rogero et al. |
| 5,568,121 A | 10/1996 | Lamensdorf |
| 5,604,298 A | 2/1997 | Dosoretz et al. |
| 6,061,141 A | 5/2000 | Goldenberg et al. |
| 6,114,964 A | 9/2000 | Fasano |
| 6,167,766 B1 | 1/2001 | Dunn et al. |
| 6,169,488 B1 | 1/2001 | Ketler |
| 6,252,510 B1 | 6/2001 | Dungan |
| 6,259,956 B1 | 7/2001 | Myers et al. |
| 6,317,029 B1 | 11/2001 | Fleeter |
| 6,415,646 B1 | 7/2002 | Kessel et al. |
| 6,490,530 B1 | 12/2002 | Wyatt |
| 6,794,991 B2 | 9/2004 | Dungan |
| 6,865,926 B2 | 3/2005 | O'Brien et al. |
| 7,075,653 B1 | 7/2006 | Rutherford |
| 7,080,544 B2 | 7/2006 | Stepanik et al. |
| 8,485,019 B2 | 7/2013 | Groves |
| 8,510,059 B2 | 8/2013 | Prince |
| 8,712,335 B2 | 4/2014 | Mathur et al. |
| 8,714,035 B2 | 5/2014 | Mihaylav et al. |
| 8,949,037 B2 | 2/2015 | Prince et al. |
| 9,018,963 B2 | 4/2015 | Sim et al. |
| 9,075,016 B2 | 7/2015 | Groves |
| 9,188,503 B2 | 11/2015 | Kloepper et al. |
| 9,210,541 B2 | 12/2015 | Root et al. |
| 9,754,472 B2 | 9/2017 | Johnson et al. |
| 9,878,656 B2 | 1/2018 | Gergets et al. |
| 9,978,251 B2 | 5/2018 | Gonia et al. |
| 10,021,466 B2 | 7/2018 | Guglielmo et al. |
| 10,031,040 B1 | 7/2018 | Smith et al. |
| 10,089,849 B2 | 10/2018 | Liu et al. |
| 10,119,890 B2 | 11/2018 | Massengale et al. |
| 10,190,976 B2 | 1/2019 | Waxman et al. |
| 10,210,738 B2 | 2/2019 | Johnson, Jr. et al. |
| D842,134 S | 3/2019 | Doi et al. |
| 10,371,682 B2 | 8/2019 | Berndt et al. |
| 10,634,558 B1 | 4/2020 | Scott et al. |
| 10,671,772 B2 | 6/2020 | Luquist et al. |
| 10,697,947 B1 | 6/2020 | Armitage |
| 10,814,028 B2 | 10/2020 | Becker et al. |
| 10,876,890 B2 | 12/2020 | Scott et al. |
| 11,193,822 B2 | 12/2021 | Scott et al. |
| 11,215,593 B2 | 1/2022 | Armitage |
| 11,366,057 B2 | 6/2022 | Scott et al. |
| 11,408,870 B2 | 8/2022 | Armitage |
| 2001/0040509 A1 | 11/2001 | Dungan |
| 2002/0070321 A1 | 6/2002 | Womack |
| 2004/0056771 A1 | 3/2004 | Dungan |
| 2006/0155486 A1 | 7/2006 | Walsh et al. |
| 2008/0048853 A1 | 2/2008 | Leach et al. |
| 2008/0231857 A1 | 9/2008 | Depeursinge et al. |
| 2008/0281528 A1 | 11/2008 | Relle, Jr. |
| 2009/0319058 A1 | 12/2009 | Rovaglio et al. |
| 2010/0094565 A1* | 4/2010 | Prince .................... G08B 21/12 702/22 |
| 2010/0268480 A1 | 10/2010 | Prince |
| 2010/0295673 A1 | 11/2010 | Ahmad |
| 2011/0219891 A1 | 9/2011 | Mihaylov et al. |
| 2012/0012066 A1 | 1/2012 | Beery et al. |
| 2012/0109583 A1 | 5/2012 | Bartlett et al. |
| 2012/0212347 A1 | 8/2012 | Boone |
| 2012/0227983 A1 | 9/2012 | Lymberopoulos et al. |
| 2012/0270205 A1 | 10/2012 | Patel et al. |
| 2014/0196788 A1 | 7/2014 | Taft |
| 2014/0368354 A1 | 12/2014 | Skourlis |
| 2015/0048232 A1 | 2/2015 | Hallauer et al. |
| 2015/0185194 A1 | 7/2015 | Prince et al. |
| 2017/0130480 A1 | 5/2017 | Perkins |
| 2017/0277829 A1 | 9/2017 | Weggler et al. |
| 2017/0336281 A1 | 11/2017 | Waxman et al. |
| 2018/0266933 A1 | 9/2018 | Tamraz et al. |
| 2018/0284735 A1 | 10/2018 | Cella et al. |
| 2019/0110444 A1 | 4/2019 | Boehm |
| 2019/0166413 A1 | 5/2019 | Klinger et al. |
| 2019/0206068 A1 | 7/2019 | Stark et al. |
| 2019/0360311 A1 | 11/2019 | Cardenas et al. |
| 2020/0333307 A1 | 10/2020 | Armitage |
| 2020/0355580 A1 | 11/2020 | Asher |
| 2021/0072080 A1 | 3/2021 | Scott et al. |
| 2021/0123768 A1* | 4/2021 | Rezvani ............. G01C 21/3848 |
| 2021/0397312 A1* | 12/2021 | Haupt .................... G01D 21/02 |
| 2022/0034762 A1 | 2/2022 | Cyrus et al. |
| 2022/0091026 A1 | 3/2022 | Scott et al. |
| 2022/0107189 A1* | 4/2022 | Leen ........................ F17D 5/005 |
| 2022/0164877 A1* | 5/2022 | Kamkar ................. G06N 20/20 |
| 2023/0176023 A1* | 6/2023 | Wang .................. G01N 33/0063 340/632 |

FOREIGN PATENT DOCUMENTS

| | | | |
|---|---|---|---|
| CN | 207351764 U | 5/2018 | |
| CN | 109521162 A | 3/2019 | |
| CN | 110726431 A * | 1/2020 | |
| CN | 209979311 U | 1/2020 | |
| CN | 111859800 A * | 10/2020 | ......... G01N 15/0205 |
| CN | 112084231 A * | 12/2020 | |
| CN | 214667980 U | 11/2021 | |
| CN | 214749208 U | 11/2021 | |
| CN | 113919448 A * | 1/2022 | |
| DE | 10226305 C1 | 10/2003 | |
| DE | 102006034731 A1 | 1/2008 | |
| EP | 1882917 A1 | 1/2008 | |
| EP | 2687844 A2 | 1/2014 | |
| EP | 3001115 A2 | 3/2016 | |
| JP | 2001042052 A * | 2/2001 | |
| JP | 2001042052 A * | 2/2001 | |
| WO | WO-2022023226 A1 * | 2/2022 | |
| WO | 2022056152 A1 | 3/2022 | |

OTHER PUBLICATIONS

U.S. Appl. No. 63/076,829, filed Sep. 10, 2020, Anna Ailene Scott.
U.S. Appl. No. 63/233,694, filed Aug. 16, 2021, Anna Ailene Scott.
"Operational risk management in the energy industry," 2014, Management Solutions, 10 pages (Year: 2014).
Center for Chemical Process Safety, "Guidelines for Chemical Process Quantitative Risk Analysis, Second Edition," "Chapter 1, Chemical Process Quantitative Risk Analysis," 2010, American Institute of Chemical Engineers, pp. 1-55 (Year: 2010).
Center for Chemical Process Safety, "Guidelines for Chemical Process Quantitative Risk Analysis, Second Edition," "Chapter 3, Event Probability and Failure Frequency Analysis," 2010, American Institute of Chemical Engineers, pp. 297-393 (Year: 2010).
Collier-Oxandale, et al., "Understanding the ability of low-cost MOx sensors to quantify ambient VOCs", Atmospheric Measurement Techniques, Mar. 5, 2019, pp. 1441-1460, vol. 12, Copernicus Publications on behalf of the European Geosciences Union, 20 pages.
Control Effectiveness, May 2014, Broadleaf Capital International Pty Ltd, 7 pages (Year: 2014).
Ebermann et al., "Design, Operation and Performance of a Fabry-Perot-Based MWIR Microspectrometer," access date: Nov. 9, 2018, pp. 1-6.
F. I. Khan et al., "Safety weighted hazard index (swehi) a new, user-friendly tool for swift yet comprehensive hazard identification and safety evaluation in chemical process industries," 2001, Transactions of the Institution of Chemical Engineers, vol. 79 Part B, 16 pages (Year: 2001).
Faisal I. Khan et al., "Multivariate hazard identification and ranking system," 1998, Process Safety Progress, vol. 17, No. 3, 14 pages (Year: 1998).
FAQ, Meet Clair Site, access date: Nov. 9, 2018, pp. 1-8.
International Search Report and Written Opinion from the US International Search Authority for International Application No. PCT/US2020/012247 dated Mar. 10, 2020, 13 pages.

(56) References Cited

OTHER PUBLICATIONS

ISA/US, International Search Report and Written Opinion for PCT/US21/49702, received Feb. 7, 2022, 36 pages.

Jim Joy et al., "National minerals industry safety and health risk assessment guideline" 2007, http://www.nost.edu.au/icms_docs/286339_National_M inerals_Industry _ Safety _and_Health_Risk_ Assessment_ Guideline _- J im_Joy.pdf, 164 pages (Year: 2007).

JJS Technical Services, "BW Technologies Rig Rat III Gas Detector (Non-Wireless Version)", , retrieved from the Internet Jul. 19, 2019, 3 pages.

Maureen Hassall, "What is a control?," Aug. 31, 2015, 2015 NSW Mining-Health, Safety, Environment and Community Conference, 33 pages (Year: 2015).

Mohammad Javad Jafari et al., "The credit of fire and explosion index for risk assessment of iso-max unit in an oil refinery," 2012, International Journal of Occupational Hygiene, vol. 4, No. 1, pp. 10-16 (Year: 2012).

Restek Pure Chromatography "TO-Can Canister With Rave Valve cat.# 27416, 27417, 27418, 27419, 27420, 27421, 27422, 27423" Catalog #500-10-002 Date Oct. 2020.

S.M. Miri Lavasani et al., "Fuzzy risk assessment of oil and gas offshore wells," 2011, Process Safety and Environmental Protection , vol. 89, pp. 277-294 (Year: 2011).

Sam Mannan, "Lee's loss prevention in the process industries," 2012, Butterworth-Heinemann, 8 pages (Year: 2012).

Scott et al., "An Air Quality Sensor Network for Greater Baltimore," access date: Nov. 9, 2018, pp. 1-8.

Scott, Meet Clair Site, What causes trouble breathing indoors? blog, access date: Nov. 9, 2018, pp. 1-8.

U.S. Environmental Protection Agency, "Determination of Volatile Organic Compounds (VOCs) in Air Collected in Specially Prepared Canisters and Analyzed by Gas Chromatography-Mass Spectrometry (GC-MS)" Sep. 2019.

United States Environmental Protection Agency, "SPod Fenceline Sensors Under Development", , retrieved from the Internet Jul. 19, 2019, 1 page.

United States Environmental Protection Agency, "Tracking Emissions Using New Fenceline Monitoring Technology", published Jun. 18, 2018, , retrieved from the Internet Jul. 19, 2019, 3 pages.

Wisconsin Department of Natural Resources, "Evaluation of Passive Sampling Techniques for Monitoring Roadway and Neighborhood Exposures to Benzene and Other Mobile Source VOCs" WDNR Publication AM-384 2007.

Zimmerman et al., Atmospheric Measurement Techniques, "A machine learning calibration model using random forests to improve sensor performance for lower-cost air quality monitoring," Jul. 25, 2017, pp. 291-313.

\* cited by examiner (Fig. 40)

Generate a mapping of a weighted mean of the plurality of first predicted substance concentrations grouped in each feature group of a predetermined number of feature groups 4016

Compare a plurality of first measured substance concentrations with the plurality of first predicted substance concentrations of the target substance to create at least an at least one adjustment factor 4016A Obtain from the prediction model, a wind-direction contribution value representative of a contribution of the wind-direction in each of the plurality of first predicted substance concentrations as predicted by the prediction model 4016B Adjust a plurality of wind-direction contribution values corresponding to the plurality of first predicted substance concentrations, using the at least one adjustment factor to obtain a plurality of adjusted wind-direction contribution values 4016C Group the plurality of adjusted wind-direction contribution values into the predetermined number of wind-direction buckets 4016D For each of the predetermined number of wind-direction buckets, determine a weighted mean of the plurality of first predicted substance concentrations grouped in each wind-direction bucket of the predetermined number of wind-direction buckets 4016E Generate the mapping of the weighted mean of the plurality of first predicted substance concentrations grouped in each wind-direction bucket of the predetermined number of wind-direction buckets, for wind directions in a full circle 4016F (Fig. 42)

┌─────────────────────────────────────────────────────────────────┐
│ Obtain a location map of a plurality of emission sources at the site, the │
│ location map comprising a location and an identity associated with each │
│ of the plurality of emission sources 4018 │
└─────────────────────────────────────────────────────────────────┘
                         │
                         ▼
┌─────────────────────────────────────────────────────────────────┐
│ For each emission source of the plurality of emission sources, │
│ generate a simulated plume model, based on a wind-direction 4020 │
│ ┌─────────────────────────────────────────────────────────────┐ │
│ │ Compare a plurality of first measured substance concentrations with │ │
│ │ the plurality of first predicted substance concentrations of the target │ │
│ │ substance to create at least an at least one adjustment factor 4020A │ │
│ └─────────────────────────────────────────────────────────────┘ │
│                              │                                   │
│                              ▼                                   │
│ ┌─────────────────────────────────────────────────────────────┐ │
│ │ Obtain from the prediction model, a wind-direction contribution │ │
│ │ value representative of a contribution of the wind-direction in each │ │
│ │ of the plurality of first predicted substance concentrations as │ │
│ │ predicted by the prediction model 4020B │ │
│ └─────────────────────────────────────────────────────────────┘ │
│                              │                                   │
│                              ▼                                   │
│ ┌─────────────────────────────────────────────────────────────┐ │
│ │ Adjust a plurality of wind-direction contribution values corresponding │ │
│ │ to the plurality of first predicted substance concentrations, using the │ │
│ │ at least one adjustment factor to obtain a plurality of adjusted │ │
│ │ wind-direction contribution values 4020C │ │
│ └─────────────────────────────────────────────────────────────┘ │
└─────────────────────────────────────────────────────────────────┘
                         │
                         ▼
┌─────────────────────────────────────────────────────────────────┐
│ For each emission source of the plurality of emission sources, calculate │
│ a plurality of representative circular normal distributions for each air │
│ quality monitor, using the simulated plume model, by setting a plurality │
│ of presumed flux values to the simulated plume model 4022 │
└─────────────────────────────────────────────────────────────────┘
                         │
                         ▼
┌─────────────────────────────────────────────────────────────────┐
│ Perform an analysis of the plurality of representative circular normal │
│ distributions in relation with the mapping to identify a relevant │
│ representative circular normal distribution from the plurality of │
│ representative circular normal distributions 4024 │
└─────────────────────────────────────────────────────────────────┘
                         │
                         ▼
┌─────────────────────────────────────────────────────────────────┐
│ Quanity a total emission of the target substance at the site by │
│ aggregating the plurality of emission sources 4026 │
└─────────────────────────────────────────────────────────────────┘

FIG. 42

EMISSIONS DETECTION SYSTEM AND METHODS

This application is related to issued U.S. patent application Ser. No. 16/188,793, filed on Nov. 13, 2018 and issued on Apr. 28, 2020 as U.S. Pat. No. 10,634,558, entitled "AIR QUALITY MONITORING SYSTEM AND ENHANCED SPECTROPHOTOMETRIC CHEMICAL SENSOR," which is hereby expressly incorporated by reference in its entirety for all purposes.

This application is related to issued U.S. patent application Ser. No. 16/823,205, filed on Mar. 18, 2020 and issued on Dec. 29, 2020 as U.S. Pat. No. 10,876,890, entitled "AIR QUALITY MONITORING SYSTEM AND ENHANCED SPECTROPHOTOMETRIC CHEMICAL SENSOR," which is hereby expressly incorporated by reference in its entirety for all purposes.

The present application is related to issued U.S. patent application Ser. No. 16/953,908, filed on Nov. 20, 2020 and issued on Nov. 17, 2022 as U.S. Pat. No. 11,193,822, entitled "AIR QUALITY MONITORING SYSTEM AND ENHANCED SPECTROPHOTOMETRIC CHEMICAL SENSOR," which is hereby expressly incorporated by reference in its entirety for all purposes.

The present application is related to expired U.S. Provisional Patent Application Ser. No. 63/076,829, filed on Sep. 10, 2020, entitled "AIR QUALITY MONITORING SYSTEM, ENHANCED SPECTROPHOTOMETRIC CHEMICAL SENSOR, AND RELATED TECHNOLOGIES," which is hereby expressly incorporated by reference in its entirety for all purposes.

The present application is related to co-pending U.S. Provisional Patent Application Ser. No. 63/233,694, filed on Aug. 23, 2021, entitled "AIR QUALITY MONITORING SYSTEM AND Method", which is hereby expressly incorporated by reference in its entirety for all purposes.

The present application is related to co-pending Patent Cooperation Treaty (PCT) Application No. PCT/US2021/049702, filed on Sep. 9, 2021, entitled "AIR QUALITY MONITORING SYSTEM AND METHOD", which is hereby expressly incorporated by reference in its entirety for all purposes.

The present application is related to issued U.S. patent application Ser. No. 17/541,693, filed on Dec. 3, 2021 and issued on Jun. 21, 2022 as U.S. Pat. No. 11,366,057, entitled "AIR QUALITY MONITORING SYSTEM AND METHOD", which is hereby expressly incorporated by reference in its entirety for all purposes.

The present application claims priority to co-pending U.S. Patent Application Ser. No. 63/323,703, filed on Mar. 25, 2022, entitled "EMISSIONS DETECTION SYSTEM AND METHODS", which is hereby expressly incorporated by reference in its entirety for all purposes.

A portion of the disclosure of this patent document contains material which is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

TECHNICAL FIELD

This disclosure pertains generally, but not by way of limitation, to systems and methods for reducing fugitive emissions. In particular, the system(s) and method(s) described herein provide remote monitoring of facilities and/or equipment that often emit gasses.

BACKGROUND OF THE INVENTION

Air quality is important for the health of a population. Countries worldwide spend significant resources on monitoring air quality and controlling air pollution. One of the major problems is that instruments that can accurately monitor air quality are expensive and typically require expertise to operate properly. Currently, air quality monitoring is mainly performed by government agencies and dedicated organizations using specialized instrumentation. As a result, general air quality data often does not provide the fidelity necessary to pinpoint issues at a scale smaller than a regional level. Real-time air quality monitoring at a finer scale may be cost-prohibitive because air quality monitoring instruments can be expensive.

Three types of sensing systems are generally used for measuring compounds in the air: point sensors, line (including long open path) sensors, and imaging sensors. These systems can be statically field-deployed, integrated into handheld devices, or mounted on various vehicles, such as automobiles, drones, and other unmanned aircraft (such as balloons), planes, helicopters, and other manned aircrafts, and on satellites. Static line or imaging sensors can also be mounted on motorized systems to point toward different fields of view of a site. Another aspect of air quality monitoring includes identifying source of emissions, especially in locations like oil drilling rigs to take corrective actions towards the emissions. Similarly, it may be important to quantity the emissions in case of emissions/leakages.

SUMMARY INVENTION

One or more methods of locating and quantifying emissions at a site are disclosed. The above methods are based on obtaining certain parameters using one or more air quality monitors provided at the site. These one or more air quality monitors may include various sensors (as discussed in detail in the subsequent sections of the disclosure) that are able to obtain various atmospheric parameters like wind speed, wind direction, temperature, pressure, and humidity at the site. These one or more air quality monitors further obtain concentrations of a target substance, for example, methane gas, from one or more potential emission sources that may leak the target substance. The methods may further take into account certain parameters which may affect the distribution and concentration of the target substance in the immediate atmosphere surrounding the site. For example, one such parameter is the height of a pressure boundary layer (hPBL).

The above methods further use a prediction model, which may be a Machine Learning-based model. The prediction model is trained over a period of time, for example using the above-mentioned parameters measured over a period of time. The trained prediction model is then used to carry out predictions of the concentration of the target substance that may be measured at each of the one or more air quality monitors provided at the site. A prediction model may be trained specific to each of the one or more air quality monitors. Thereafter, a mapping of a weighted mean of the plurality of first predicted substance concentrations grouped in a predetermined number of feature groups is generated. The predetermined number of feature groups together are representative of feature values over a predetermined range. For example, the mapping may be generated for a predetermined number of wind-direction buckets (e.g., 72 buckets, each corresponding to 5 degrees).

A location map is obtained of the plurality of possible emission sources at the site. Further, for each emission source, a simulated plume model is generated, based on a wind-direction. For example, the simulated plume model may be Gaussian plume model. A plurality of representative circular normal distributions for each air quality monitor are calculated, using the simulated plume model, by setting a plurality of presumed flux values to the simulated plume model. The plurality of representative circular normal distributions is analyzed in relation with the mapping to identify a relevant representative circular normal distribution. This relevant representative circular normal distribution is indicative of a target emission source. As such, the target emission source is determined, based on the above analysis.

The above methods therefore provide for an accurate and computationally easier method of locating the emission source and quantifying the emissions of the target substance at the site. By applying the Machine Learning-based prediction model, the computational requirements (for example, as required for Simulation-based methods) are substantially reduced. Moreover, the prediction model keeps on learning over time, thereby becoming more and more accurate with time.

The above methods, by taking into account various parameters like the hPBL, further enhance the accuracy of predictions as therefore of locating the emission source and quantifying the emissions of the target substance at the site. Further, the above methods obtain a contribution of each of the factors in the prediction performed by the prediction model. For example, isolating wind-direction effect (contribution) on the predicted pollutant concentration leverages statistical methods used in the training of the regression model to isolate the contribution of (only) wind-direction on the observed pollutant concentration. This further allows removal of the effects of: 1) ambient atmospheric concentrations of the targeted pollutant, and 2) removal of the effects of height pressure boundary layer (hPBL), wind-speed, temperature, humidity, etc. without understanding and modeling the factors behind the phenomena of atmospheric concentration and/or effects of hPBL, wind-speed, temperature, humidity, etc. The methods rely on statistical analysis of large amounts of data to train the prediction model (e.g., a trained regression model) that can accurately predict the measured pollutant concentration based on the values of other known parameters, and then examine that model to determine what portion of the predicted concentration can be attributed to only the wind-direction.

In one configuration, a location method for locating an emission source of a target substance at a site is disclosed. The location method may include providing a first air quality monitor comprising: a first sensor responsive to the target substance and a first location at which the first air quality monitor is located on the site. The location method may further include measuring a first set of onsite parameters with the first air quality monitor over a period of time to obtain a plurality of individual measurements of each parameter of the first set of onsite parameters. The plurality of individual measurements of the first set of onsite atmospheric parameters may include a first measured substance concentration of the target substance measured with the first air quality monitor and a first set of individual atmospheric readings. The first set of individual atmospheric readings may include at least one of atmospheric reading selected from: a barometric pressure, an air temperature, and a humidity level. The location method may further include transmitting the first measured substance concentration to a first server, transmitting the first set of individual atmospheric readings to the first server, and procuring a regional atmospheric parameter for the site from a second server. The location method may further include training a prediction model associated with the first air quality monitor, obtaining a plurality of first predicted substance concentrations of the target substance corresponding to the first air quality monitor from the prediction model, with at least: the first set of individual atmospheric readings and the regional atmospheric parameter for the site. The plurality of first predicted substance concentrations may be obtained over a predefined period at a predefined frequency.

The location method may further include generating a mapping of a weighted mean of the plurality of first predicted substance concentrations grouped in each feature group of a predetermined number of feature groups. The predetermined number of feature groups together are representative of feature values over a predetermined range. For example, each feature group is associated with a wind-direction bucket; and a predetermined number of wind-direction buckets together are representative of wind-directions over a full circle. As such, generating the mapping may include comparing a plurality of first measured substance concentrations with the plurality of first predicted substance concentrations of the target substance to create at least an at least one adjustment factor, and obtaining from the prediction model, a wind-direction contribution value representative of a contribution of the wind-direction in each of the plurality of first predicted substance concentrations as predicted by the prediction model. Generating the mapping may further include adjusting a plurality of wind-direction contribution values corresponding to the plurality of first predicted substance concentrations, using the at least one adjustment factor to obtain a plurality of adjusted wind-direction contribution values, and grouping the plurality of adjusted wind-direction contribution values into the predetermined number of wind-direction buckets. Generating the mapping may further include, for each of the predetermined number of wind-direction buckets, determining a weighted mean of the plurality of first predicted substance concentrations grouped in each wind-direction bucket of the predetermined number of wind-direction buckets, and generating the mapping of the weighted mean of the plurality of first predicted substance concentrations grouped in each wind-direction bucket of the predetermined number of wind-direction buckets, for wind directions in a full circle.

The location method may further include obtaining a location map of a plurality of emission sources at the site that may include a location and an identity associated with each of the plurality of emission sources. The location method may further include, for each emission source of the plurality of emission sources: generating a simulated plume model, based on a wind-direction and calculating a plurality of representative circular normal distributions for each air quality monitor, using the simulated plume model, by setting a plurality of presumed flux values to the simulated plume model. The location method may further include performing an analysis of the plurality of representative circular normal distributions in relation with the mapping to identify a relevant representative circular normal distribution from the plurality of representative circular normal distributions. The relevant representative circular normal distribution is indicative of a target emission source. The location method may further include determining the target emission source, based on the analysis and the location map.

In another configuration, a total emissions quantification method for quantifying emissions of a target substance at a site is disclosed. The total emissions quantification method may include providing a first air quality monitor comprising: a first sensor responsive to the target substance and a first location at which the first air quality monitor is located on the site. The total emissions quantification method may further include measuring a first set of onsite parameters with the first air quality monitor over a period of time to obtain a plurality of individual measurements of each parameter of the first set of onsite parameters. The plurality of individual measurements of the first set of onsite parameters may include a first measured substance concentration of the target substance measured with the first air quality monitor and a first set of individual atmospheric readings. The first set of individual atmospheric readings comprises at least one of atmospheric reading selected from: a barometric pressure, an air temperature, and a humidity level. The total emissions quantification method may further include transmitting the first measured substance concentration to a first server, transmitting the first set of individual atmospheric readings to the first server, and procuring a regional atmospheric parameter for the site from a second server. The total emissions quantification method may further include training a prediction model associated with the first air quality monitor and obtaining a plurality of first predicted substance concentrations of the target substance corresponding to the first air quality monitor from the prediction model, with at least: the first set of individual atmospheric readings and the regional atmospheric parameter for the site. The plurality of first predicted substance concentrations is obtained over a predefined period at a predefined frequency.

The total emissions quantification method may further include generating a mapping of a weighted mean of the plurality of first predicted substance concentrations grouped in each wind-direction bucket of a predetermined number of wind-direction buckets. The predetermined number of wind-direction buckets together are representative of wind directions in a full circle. Generating the mapping may include comparing a plurality of first measured substance concentrations with the plurality of first predicted substance concentrations of the target substance to create at least one adjustment factor, and obtaining from the prediction model, a wind-direction contribution value representative of a contribution of a wind-direction in each of the plurality of first predicted substance concentrations as predicted by the prediction model. Generating the mapping may further include adjusting a plurality of wind-direction contribution values corresponding to the plurality of first predicted substance concentrations, using the at least one adjustment factor to obtain a plurality of adjusted wind-direction contribution values, and grouping the plurality of adjusted wind-direction contribution values into the predetermined number of wind-direction buckets. Generating the mapping may further include determining, for each of the predetermined number of wind-direction buckets, a weighted mean of the plurality of first predicted substance concentrations grouped in each wind-direction bucket of a predetermined number of wind-direction buckets, and generating the mapping of the weighted mean of the plurality of first predicted substance concentrations grouped in each group of the predetermined number of wind-direction buckets, for wind directions in a full circle.

The total emissions quantification method may further include obtaining a location map of a plurality of emission sources at the site, the location map comprising a location and an identity associated with each of the plurality of emission sources, and generating a simulated plume model for each emission source of the plurality of emission sources for each emission source of the plurality of emission sources, based on the wind-direction. The total emissions quantification method may further include calculating a plurality of representative circular normal distributions for each air quality monitor, using the simulated plume model, by setting a plurality of presumed flux values to the simulated plume model, and analyzing the plurality of representative circular normal distributions in relation with the mapping to identify a relevant representative circular normal distribution from the plurality of representative circular normal distributions. The relevant representative circular normal distribution is indicative of a target emission source. The total emissions quantification method may further include quantifying a total emission of the target substance at the site by aggregating the plurality of emission sources.

In yet another configuration, an operating emissions quantification method for quantifying emissions of a target substance from operating devices at a site is disclosed. The operating emissions quantification method may include providing a first air quality monitor comprising: a first sensor responsive to the target substance and a first location at which the first air quality monitor is located on the site. The operating emissions quantification method may further include measuring a first set of onsite parameters with the first air quality monitor over a period of time to obtain a plurality of individual measurements of each parameter of the first set of onsite parameters. The plurality of individual measurements of the first set of onsite parameters may include a first measured substance concentration of the target substance measured with the first air quality monitor and a first set of individual atmospheric readings. The operating emissions quantification method may further include transmitting the first measured substance concentration to a first server, transmitting the first set of individual atmospheric readings to the first server, and procuring a height of planetary boundary layer (hPBL) data for the site from a second server. The operating emissions quantification method may further include training a prediction model associated with the first air quality monitor, and obtaining a plurality of first predicted substance concentrations of the target substance corresponding to the first air quality monitor from the prediction model, with at least: the first set of individual atmospheric readings; and the hPBL data for the site. The plurality of first predicted substance concentrations is obtained over a predefined period at a predefined frequency.

The operating emissions quantification method may further include generating a mapping of a weighted mean of the plurality of first predicted substance concentrations grouped in each feature group of a predetermined number of feature groups. The predetermined number of feature groups together are representative of feature values over a predetermined range. The operating emissions quantification method may further include obtaining a location map of a plurality of emission sources at the site, the location map comprising a location and an identity associated with each of the plurality of emission sources. The operating emissions quantification method may further include, for each emission source of the plurality of emission sources, generating a simulated plume model, based on a wind-direction and calculating a plurality of representative circular normal distributions for each air quality monitor, using the simulated plume model, by setting a plurality of presumed flux values to the simulated plume model. The operating emissions quantification method may further include performing an analysis of the plurality of representative circular normal distributions in relation with the mapping to identify a relevant representative circular normal distribution from the plurality of representative circular normal distributions. The relevant representative circular normal distribution is indicative of a target emission source. The operating emissions quantification method may further include determining the target emission source, based on the analysis and the location map.

In another configuration, an asset appraisal method for tagging equipment handling a target substance at a site is disclosed. The asset appraisal method may include obtaining a plurality of two-dimensional images of the site and extracting three-dimensional measurements corresponding to the plurality of two-dimensional images to create a three-dimensional model. Extracting the three-dimensional measurements may include calculating a distance between two points lying on a plane parallel to a photographic image plane, corresponding to measured associated distances on the plurality of two-dimensional images, using a scale associated with the plurality of two-dimensional images and determining at least one site-parameter associated with the site, based on the three-dimensional model.

In yet another configuration, an alert calibration method for training a prediction model is disclosed. The alert calibration method may include obtaining a plurality of first predicted substance concentrations of a target substance corresponding to a first air quality monitor, from the prediction model, with at least: a first set of individual atmospheric readings, and a regional atmospheric parameter for a site. The prediction model is trained using training dataset. The alert calibration method may further include, upon obtaining the plurality of first predicted substance concentrations of the target substance, comparing each of the plurality of first predicted substance concentrations of the target substance with a respective manually verified substance concentrations of the target substance. The alert calibration method may further include validating the plurality of first predicted substance concentrations of the target substance, based on the comparison, to obtain validated first predicted substance concentrations of the target substance, and logging the validated first predicted substance concentrations of the target substance in the training dataset.

In another configuration, a communications method for improving transmission of onsite parameters measured at a site is disclosed. The communications method may include averaging a plurality of individual measurements of each parameter of a set of onsite parameters obtained by an air quality monitor over a period of time, to obtain time-averaged set of individual atmospheric readings. The plurality of individual measurements of the set of onsite parameters may include a first measured substance concentration of a target substance measured with the air quality monitor and a first set of individual atmospheric readings. The communications method may further include transmitting the time-averaged set of individual atmospheric readings to a first server, over a wireless network, and increasing a power of transmission, when the first measured substance concentration is intermittently transmitting to the first server.

In another configuration, a server for locating an emission source of a target substance at a site is disclosed. The server includes a processor and a memory communicatively coupled to the processor. The memory stores instructions, which on execution by the processor, cause the processor to: receive, from a first air quality monitor, a plurality of individual measurements of each parameter of the first set of onsite parameters, measured over a period of time. The plurality of individual measurements of the first set of onsite atmospheric parameters comprises: a first measured substance concentration of the target substance measured with the first air quality monitor, and a first set of individual atmospheric readings. The first set of individual atmospheric readings comprises at least one of atmospheric reading selected from: a barometric pressure, an air temperature, and a humidity level. The instructions further cause the processor to procure a regional atmospheric parameter for the site from a second server, train a prediction model associated with the first air quality monitor, and obtain a plurality of first predicted substance concentrations of the target substance corresponding to the first air quality monitor from the prediction model, with at least: the first set of individual atmospheric readings and the regional atmospheric parameter for the site. The plurality of first predicted substance concentrations is obtained over a predefined period at a predefined frequency. The instructions further cause the processor to generate a mapping of a weighted mean of the plurality of first predicted substance concentrations grouped in each feature group of a predetermined number of feature groups. The predetermined number of feature groups together are representative of feature values over a predetermined range. The instructions further cause the processor to receive a location map of a plurality of emission sources at the site, the location map comprising a location and an identity associated with each of the plurality of emission sources. The instructions further cause the processor to, for each emission source of the plurality of emission sources, generate a simulated plume model, based on a wind-direction and calculate a plurality of representative circular normal distributions for each air quality monitor, using the simulated plume model, by setting a plurality of presumed flux values to the simulated plume model. The instructions further cause the processor to perform an analysis of the plurality of representative circular normal distributions in relation with the mapping to identify a relevant representative circular normal distribution from the plurality of representative circular normal distributions. The relevant representative circular normal distribution is indicative of a target emission source. The instructions further cause the processor to determine the target emission source, based on the analysis and the location map.

Further areas of applicability of the present disclosure will become apparent from the detailed description provided hereinafter. It should be understood that the detailed description and specific examples, while indicating various configuration, are intended for purposes of illustration only and are not intended to necessarily limit the scope of the disclosure.

BRIEF DESCRIPTION OF DRAWINGS

The accompanying figures of the drawing, which are included to provide a further understanding of general aspects of the system/method, are incorporated in and constitute a part of this specification. These illustrative aspects of the system/method, and together with the detailed description, explain the principles of the system. No attempt is made to show structural details in more detail than is necessary for a fundamental understanding of the system and various ways in which it is practiced. The following figures of the drawing include:

FIG. 9B illustrates a graph related to the number of observations and average emission rates, in accordance with an illustrative configuration of the present disclosure;

FIGS. 40-42 illustrate a flowchart of a total emissions quantification method for quantifying emissions of a target substance at a site, in accordance some configurations of the present subject matter;

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label. Where the reference label is used in the specification, the description is applicable to any one of the similar components having the same reference label.

DETAILED DESCRIPTION

Illustrative configurations are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed configurations. It is intended that the following detailed description be considered as exemplary only, with the true scope and spirit being indicated by the following claims.

Figure 1:
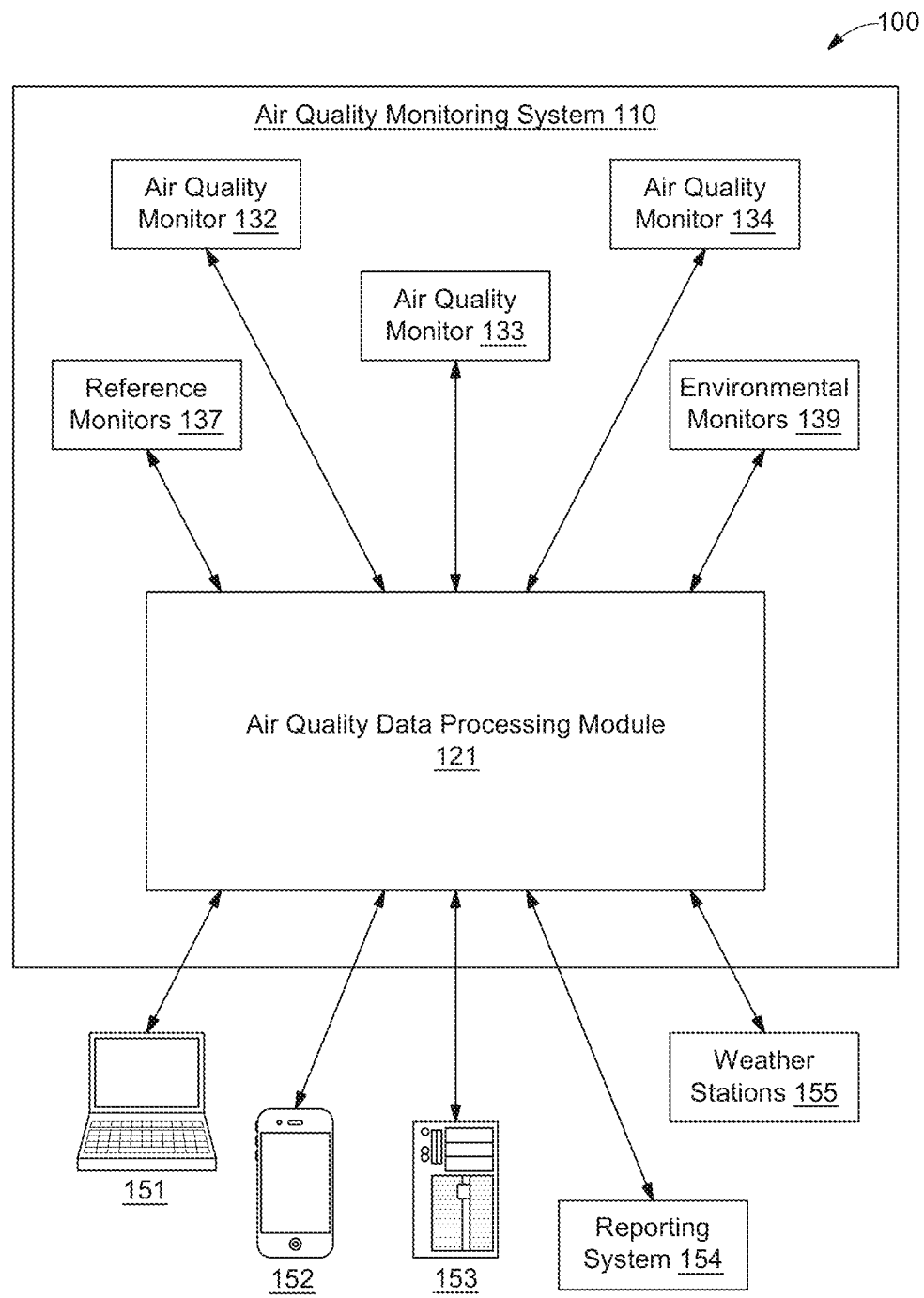
FIG. 1 illustrates an example of an air quality monitoring system, in accordance with an illustrative configuration of the present disclosure.

FIG. 1 shows an example of an air quality monitoring system 110, which handles air quality data from different sources. As illustrated in FIG. 1, air quality monitoring system 110 may include an air quality data processing module 121, a plurality of air quality monitors 132-134, reference monitors 137 and environmental monitors 139. Air quality monitors 132-134 can include one or more chemical sensors configured to detect and measure chemicals, such as ozone, nitrogen oxide, carbon dioxide, sulfur dioxide, volatile organic compounds, methane or other hydrocarbons, and other chemicals in gaseous state (these are herein being described as gaseous chemicals), as well as one or more particle sensors configured to detect and measure the presence of suspended particles in air such as dust, smoke, pollen, or soot (these are herein described as particulate matter or PM). Air quality monitors 132-134 may include an enhanced gaseous chemical sensor having a multi-pass cell for light rays, as will be described in more detail below. Air quality monitors 132-134 may be located at multiple different locations. For example, multiple monitors may be located around a sizable area, such as a county, a city, or a neighborhood. Several instruments may also be located within a building or a dwelling.

Reference monitors 137 include precision gaseous chemical sensors and are configured to provide measurements for use in calibrating the gaseous chemical sensors in air quality monitors 132-134. Environmental monitors 139 are configured to measure environmental conditions, such as humidity, temperature, atmospheric pressure, air density, ambient light, geographic location, wind speed and direction, and the like.

Air quality data processing module 121 is configured to communicate with air quality monitors 132-134, reference monitors 137, and environmental monitors 139. For example, air quality data processing module 121 may receive data from these monitors, such as measurements. Air quality data processing module 121 may also transmit data to these monitors, such as providing calibration data. Air quality data processing module 121 can correct measurements from air quality monitors 132-134 using cross-calibration factors, as will be explained below. Air quality data processing module 121 is also configured to process the data from monitors and perform analyses to calculate or infer additional air quality data such as the amount of various gaseous chemicals in various locations, sources of those gaseous chemicals, and recommendations based on elicited requirements or preferences of end users. Air quality data processing module 121 is configured to communicate with mobile devices 152, computing devices 151 and server devices 153 to receive data and provide received, calculated, and inferred air quality data. For example, air quality data processing module 121 may receive user-input data and use that data to derive additional air quality data relevant to the area of analysis. Air quality data processing module 121 is also configured to communicate with other sources of data such as reporting system 154 and weather stations 155. Air quality data processing module 121 may be implemented in any appropriate physical or virtual computing platform (such as a networked server) and may operate and act through any suitable interface (such as a cloud computing platform).

Air quality monitoring system 110 may also be configured to process incoming data to provide a variety of outputs. For example, air quality monitoring system 110 may analyze measurements from air quality monitors 132-134 to determine sources of the gaseous chemicals being detected. Air quality monitoring system 110 may provide actionable steps to affect the chemical sources, such as ways to reduce the release of those chemicals or ways to minimize exposure to those chemicals, making use of stated preferences or user requirements, and/or ancillary (e.g., topological, geological, meteorological, demographic) datasets relevant to the area of investigation. The air quality monitoring system 110 can be used to quantify, qualify and/or localize sources, as discussed in connection with FIGS. 7-11.

Figure 2:
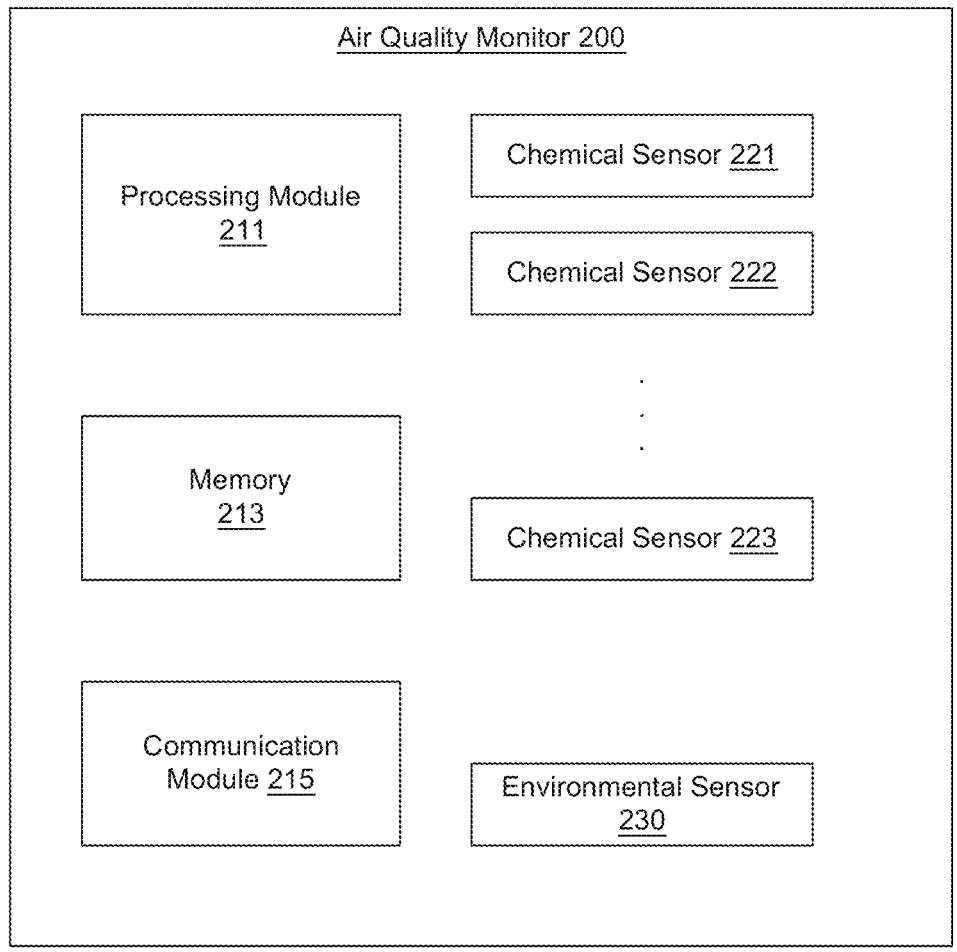
FIG. 2 illustrates an example air quality monitor and select example components that may be included, in accordance with an illustrative configuration of the present disclosure.

FIG. 2 shows an example air quality monitor 200 (such as air quality monitors 132-134 in FIG. 1) and some example components that may be included therein. Air quality monitor 200 may include processing module 211, memory 213, communication module 215, and one or more gaseous chemical sensors, such as chemical sensors 221-223, and environmental sensor 230. Processing module 211 processes computing tasks and controls other components. The computing tasks may include calibration. Memory 213 stores data, such as measurement data from gaseous chemical sensors 221-223 and calibration data such as cross-calibration factors. Chemical sensors 221-223 are configured to measure gaseous chemicals and particulates in analyte gas, such as gas under sampling by air quality monitor 200. Environmental sensor 230 measures environment conditions, such as temperature, pressure, humidity, location, wind speed, and the like. Communication module 215 handles communication with other devices. For example, communication module 215 may handle communication between air quality monitor 200 and air quality data processing module 121 of FIG. 1, other air quality monitors, user-devices such as mobile devices 152 and computing devices 151 and 153, and the like. Communication module 215 may communicate through any of a variety of wired and wireless mechanisms, such as Wi-Fi, Bluetooth, mobile networks, long-range radio, satellite, and the like. Air quality monitor 200 may also be configured to measure time, position, and other relevant information for computing devices. The components, functionality, and configuration of the sensor can be selected based on desired monitoring capabilities.

Figure 3:
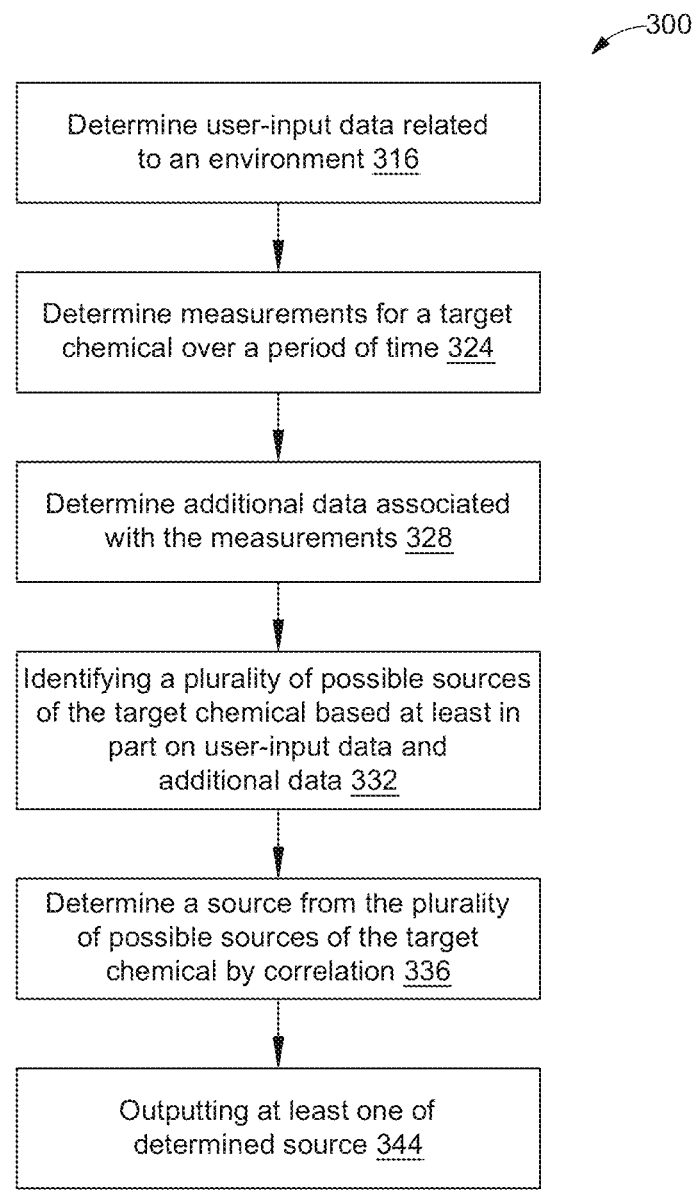
FIG. 3 illustrates a flow chart of an example source determination method, in accordance with an illustrative configuration of the present disclosure.

Source Determination and Action Recommendation Process: Air quality monitoring system 110 can be configured to determine sources of gas that are detected by air quality monitors. An example source determination method 300 is shown in FIG. 3. At step 316, user-input data related to an environment is determined. The user-input data may include any type of input about the environment, as such conditions associated with one or more air quality monitors deployed around a location. User-input data can include any of a variety of types of data such as:
1. type and location of objects, such as newly installed carpet that can out-gas chemicals;
2. events that can cause chemical emissions in the air, such as cleaning using chemical products;
3. layout of the location of concern, such as the placement of vents, windows, and doors; and
4. users' personal data, such as allergies, medical conditions, health concerns, daily routines, travel plans, and the like.

Air quality monitoring system (e.g., air quality monitoring system 110 of FIG. 1) may receive this data in any of a variety of way, such as through a website, an application installed on a mobile device, automatically from home sensors or mobile devices, information from other systems and services, and the like.

At step 324, the source determination method 300 determines measurements for a target gaseous chemical over a period. These measurements may be provided by air quality monitors of air quality monitoring system 110. At step 328, additional data associated with the measurements are determined. The additional data may include data from a variety of sources that are relevant to determining sources of gaseous chemicals measured by air quality monitoring system 110. The additional data may come from any of a variety of sources, such as weather data from weather stations, traffic data from traffic management administration, chemical emission events data such as from government reporting agencies, online services such as social networks, and the like.

At step 332, a plurality of possible sources of the target chemical are identified based at least in part on the user-input data and additional data. At step 336, one or more sources from the plurality of possible sources of the target chemical are identified by correlation. The correlation may be determined between the measured data from an air quality monitor, user-input data, and additional data. For example, the presence and amount of a gaseous chemical may correlate to an event or an object at the proximate location and at around the same time. The correlation process may be implemented in any of a variety of ways. An example process is shown below along with example equations that illustrate the methodology. Artificial intelligence algorithms and cloud-based data analytics may be employed as part of the correlation process.

At step 344, at least one determined source is output. The source may be output in many different ways, such as data to a service, a website, a user-interface on a mobile app, and the like. Source determination method 500 may also provide recommendations, such as to reduce the gaseous chemical from the source, reduce exposure to the gaseous chemical, and the like. Examples are provided in the source determination examples below.

Correlation Process and Calculations: An example of correlation steps and calculations are provided below:

1) Sort training data into categories using a clustering algorithm, such as a k-means clustering approach. Given a set of d parameters and n observations of each parameter, the present disclosure solved the following minimization equation to cluster the data into k sets S. This is done by finding means mu (μ):

$$\arg\min_S \sum_{i=1}^k \sum_{x \in S_i} \|x - \mu\|^2 = \arg\min_S \sum_{i=1}^k |S_i|\sigma^2 S_i \quad \text{Equation 1.1}$$

2) In real-time, feed in data. Using the categorization established in (1), determine which category Si variable x is most likely to fit by solving for i:

$$\min \sum_{i=1}^k \sum_{x \in S_i} \|x - \mu_i\|^2 \quad \text{Equation 1.2}$$

3) Map the categorization S to solutions S' using scientific literature reviews, best practices from experts, and clinical guidelines
3) Map the categorization S to solutions S' using scientific literature reviews, best practices from experts, and clinical guidelines.

Source Determination and Action Recommendation Examples: The below examples illustrate some possible implementation scenarios of the chemical source differentiation process and example capabilities of the air quality monitoring system.

Source Determination and Action Recommendation Example 1: A volatile organic compound (VOC) sensor detects a large, quick increase in VOC concentration that quickly dissipates. By considering the concentration, change of concentration over time, and time of the signal, the process determines that the source is most likely to be a consumer cleaning product.

Source Determination and Action Recommendation Example 2: Detecting high VOC concentrations in an indoor environment, the air quality monitoring system recommends that individuals open a window to increase airflow and reduce their exposure.

Source Determination and Action Recommendation Example 3: The air quality monitoring system detects high temperature, pressure, and ozone levels outdoors characteristic of a stationary pressure weather system during the summertime on the East Coast. The system determines that the high ozone levels are most likely due to high levels of ozone being blown into the area, coupled with high levels of traffic. The system recommends that the city increase carpooling and public transportation use.

Source Determination and Action Recommendation Example 4: The air quality monitoring system detects moisture, pressure, and high levels of particulate matter during an early fall cold spell in the Pacific Northwest. It deduces that an inversion layer is responsible for the buildup in pollution and suggests that the city reduce biomass burning to reduce pollution (e.g., what is colloquially referred to as a 'burn ban').

Source Determination and Action Recommendation Example 5: The air quality monitoring system detects high levels of particles and nitrogen dioxide in India in the winter. The system recommends that users wear a protective mask to lower their health exposure to pollution.

Figure 4A:
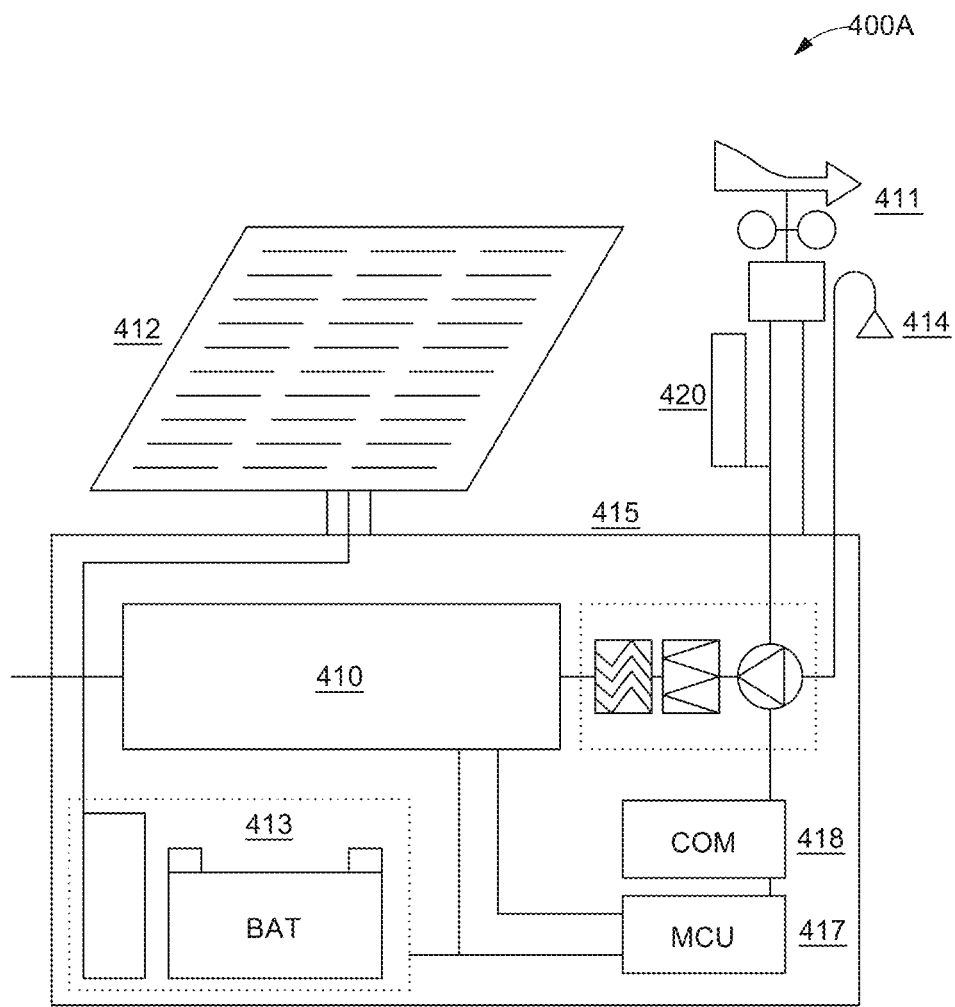
FIG. 4A illustrates an embodiment of the sensor system, which is deployed in the field, in accordance with an illustrative configuration of the present disclosure.

FIG. 4A presents a particular embodiment of a sensor system 400A capable of measuring a target compound and one or more environmental parameters (e.g., weather conditions) in a collocated and contemporaneous manner. The compound measurement function of the sensory system of FIG. 4A is performed by the compound sensor or sensors 410. These sensor(s) are point sensors, which means that their function is to measure a particular physico-chemical property of the target compounds to distinguish them from background atmospheric composition (targeted compounds include, but are not limited to: one or more gases and aerosols that are emitted by one or more industrial, anthropogenic, or natural activities). In particular, one embodiment focuses on hydrocarbons and other greenhouse gases that absorb in the mid-IR region of the electromagnetic (EM) spectrum, in particular wavelengths between 1 um and 5 um. In one embodiment, compound sensor 410 is an absorption spectrophotometer that can measure mid-infrared absorption in the 3 um to 5 um range of the EM spectrum. Without loss of generality, compound sensor 410 may comprise other sensor technologies that may be similarly used for the measurement of target compounds.

In order to capture a sample for analysis, a sampling cane 414 may be used to pump an air sample at a specific height and avoid sampling water in the case of precipitation or other foreign agents of large size. The sample may be pumped and conditioned by a sample pumping and conditioning system 419. The system depicted 419 may include a pump for sampling the air for the compound sensor 410, a filter for the removal of particulate matter and a coalescent filter for the removal of water. The system may further include desiccant filters, temperature and pressure adjustment systems, valves, and additional drain pumps to facilitate moisture removal, temperature conditioning of the sample, or for flushing and other filter regeneration tasks. The purpose of this is to provide a properly conditioned sample based on the sensor system requirements, while limiting the necessary maintenance of the pumping and conditioning system 419.

In some embodiments, the compound sensor 410 may use an open path in order to avoid the necessity of pumping or conditioning samples. The sample may then be naturally transported into the sensing area by weather patterns without the use of a cane 414 or sampling pumping and conditioning system 419.

The sensor system of FIG. 4A further includes a weather sensor system 411 collocated with the sampling point of the compound sensor 410 around the sampling cane 414. The weather sensor system should at least include sensing elements to measure wind speed and direction. Further sensing about temperature, pressure, hygrometry, insolation, and precipitation may also be used to refine the subsequent modeling effort. The wind speed and direction may be measured by a combination of a wind vane and an anemometer, or by an anemometer alone such as in the case of using an ultrasonic anemometer. The wind direction measurement may be made in two or three dimensions. Temperature may be measured using MEMS sensors, thermistors, or other suitable sensing technology. Pressure may be measured using a barometer sensor and hygrometry by a moisture sensor. The sensors for temperature, pressure and moisture may be connected for improvement of each of the measures as they are interdependent. Insolation may be measured using a photodiode or any other appropriate light-sensitive sensor. Precipitation may be measured using a precipitation sensor with auto-draining capability. While collocating the weather measurement with the sampling point is important for the purpose of accurately characterizing emissions, it is not absolutely necessary for performing the method as long as weather measurements are collected in close proximity to the sensor system (e.g., within 100 m). This conformation, i.e., being collocated, minimizes the measurement error and is the one illustrative configuration of the present disclosure.

The data collected by the compound sensor 410 and weather sensor system 411 may be collected and processed by a local computing unit 417. The local computing unit may also control the execution of the main sampling and measurement program and the actuation and controlling of any subsystem of the sensor system 400A. The local computing unit 417 runs the main firmware, which schedules and collects data from compound sensor 410 and weather sensor system 411, conditions the sensor signals into a rational format, performs data preprocessing, locally stores data, formats, and prepares messages, and generates diagnostic and metadata pertaining to the identification, time stamping and operational diagnostics of the sensor system and supporting circuitry. The messages may be encrypted and transferred to a communication unit 418 and messages may be received from remote assets. The communication unit 418 includes a modem or other interface that conditions the message to the right protocol for communication or receives external messages to be communicated to the computing unit 417. The communication protocol may be wired, such as a SCADA system or wireless, such as Bluetooth®, Wi-Fi, LoRa, cellular or satellite or any other radiofrequency, optical line of sight, or other wireless data-transmission protocol. If a wireless protocol is employed, the data may be relayed using a communication antenna 420, if appropriate. In general, a communication system, which may consist of a communication antenna 420 and communication unit 418, has a role that includes the communication of the measurement to a remote or centralized node and the receipt of communications related to settings and operations changes or firmware updates. The communication system may be used to relay messages to and from other sensor systems such as in a daisy chain, star, or mesh configuration in order to reduce the communication cost when relying on external communication infrastructure such as cellular or satellite communication networks. In case of communication error, or other cases that warrant it, the messages may be stored by the computing unit 417 to communicate at a later more opportune time. For example, when communication services may be interrupted, multiple channels of communication (such as multiple wireless data-transmission protocols) may be used to attempt to alert the computing unit 417 to changes of operating conditions and to receive instructions.

The deployment of sensors in the field may require the exposure of the equipment to harsh outdoor conditions with no external support such as power access and communication infrastructure. The sensing system is housed in an enclosure 415 to protect the system from the environment and from tampering. This may include, but is not limited to: precipitation, moisture, surface water and flooding, high temperature and insolation, low temperatures, high winds, storms, hurricanes, typhoons, tornadoes, lightning, external impacts and vibrations, robbery, defacement, damage, earthquakes, light or electromagnetic interference, foreign agents or fauna and flora disturbance or intrusion. The enclosure 415 may also be highly visible by day and reflective at night to avoid accidental damage. The enclosure 415 may be directly on the ground, mounted on a foundation, or pole-mounted.

The sensor system in FIG. 4A may produce and manage its own power. In one embodiment, the sensor system may include a solar power system 412 and a power conversion and storage system 413. The solar power system 412 and power conversion and storage system 413 are designed to provide sufficient power to the various other subsystems with sufficient reserves and capacity to ensure proper functioning of the sensor system in most environmental conditions present in the field. Solar power system 412 may be replaced by wind- or gas-based power generation, or any other form of compact power generation system if the conditions warrant it. For instance, at high latitudes wind-based power generation may be preferable to solar on account of low insolation. The power conversion and storage system 413 may include a battery storage bank and a charge controller. The power conversion and storage system 413 may further include power converters for providing appropriate power to the various systems, relays, fuses, and breakers, and switches appropriate for the power protection, function, and physical interfacing required by a particular embodiment of the sensor system. The battery storage bank may include lithium-ion (such as LiFePO4 cells), lead acid (such as a deep-cycle sealed battery) or any other appropriate battery technology that can operate nominally in conditions that may include high and low temperatures and irregular charging profiles. The charge controller may use Pulse-Width Modulation (PWM) or Maximum Power Point Tracking (MPPT) or other technology appropriate to convert the raw energy from the solar power system 412 to the battery storage bank charging requirements. All subsystems of FIG. 4A may be modular in nature to facilitate replacement of subsystems with minimal tools in the case of maintenance.

Figure 4B:
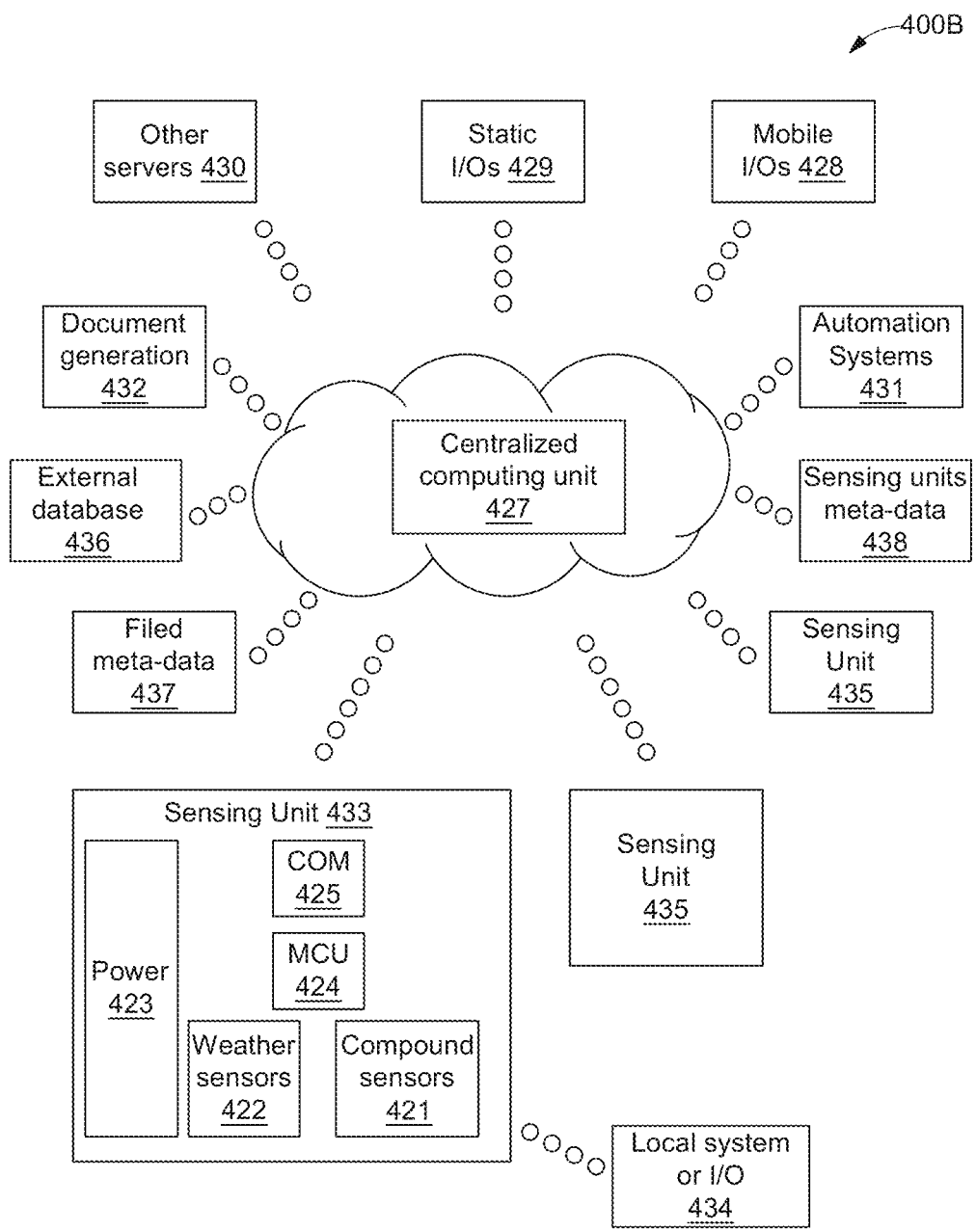
FIG. 4B illustrates an embodiment of a communication architecture of a set of sensor systems, in accordance with an illustrative configuration of the present disclosure.
Figure 4C:
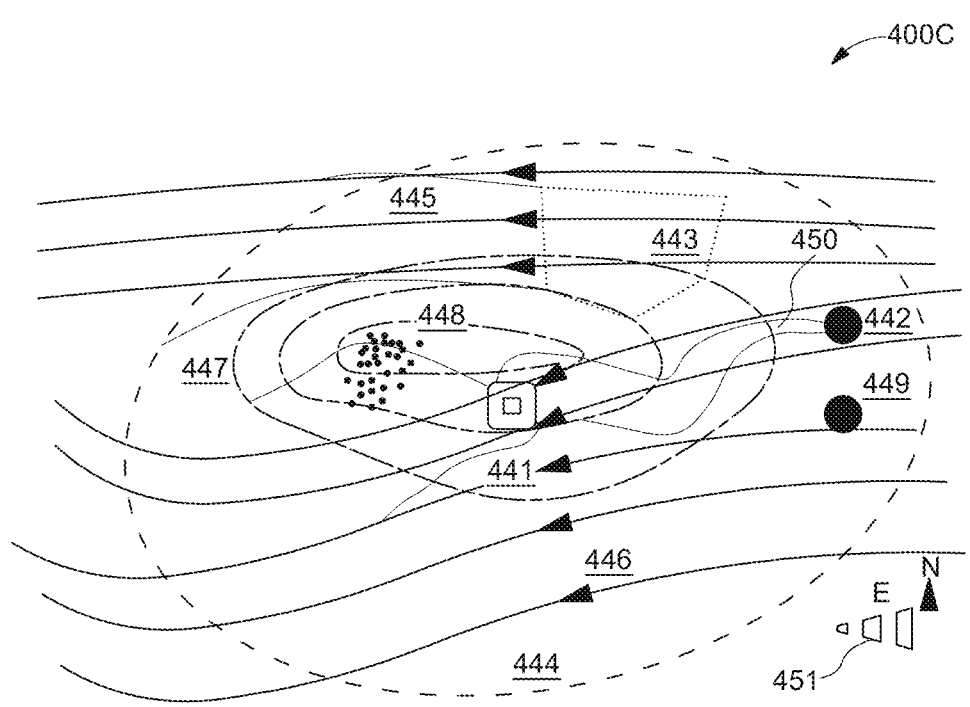
FIG. 4C illustrates a symbolic map representation of a sensor deployment amid the field where sources are present, in accordance with an illustrative configuration of the present disclosure.
Figure 4D:
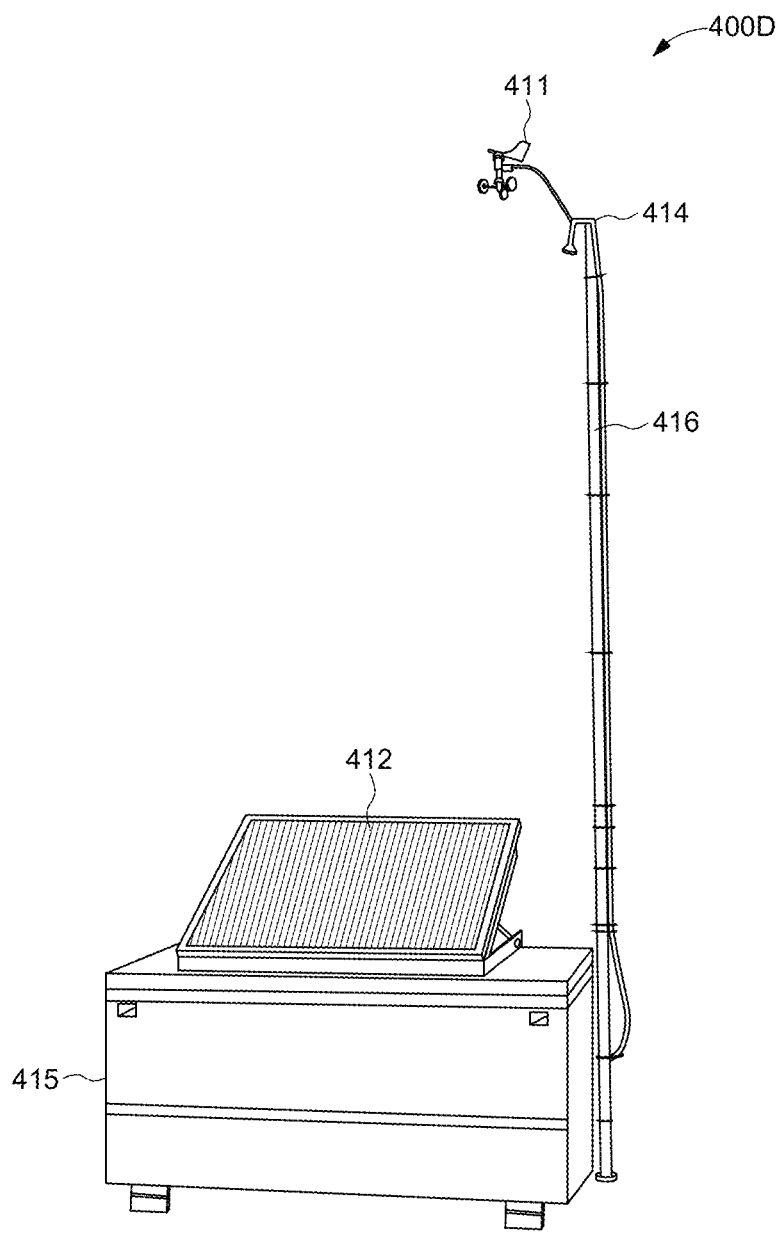
FIG. 4D illustrates another view of the embodiment of the sensor system of FIG. 7A, in accordance with an illustrative configuration of the present disclosure.

FIG. 4D shows another view 400D of the embodiment of the sensor system of FIG. 4A. The system includes enclosure 415, anemometer 411, pole 416, sampling cane 414, and solar power system 412.

Figure 5A:
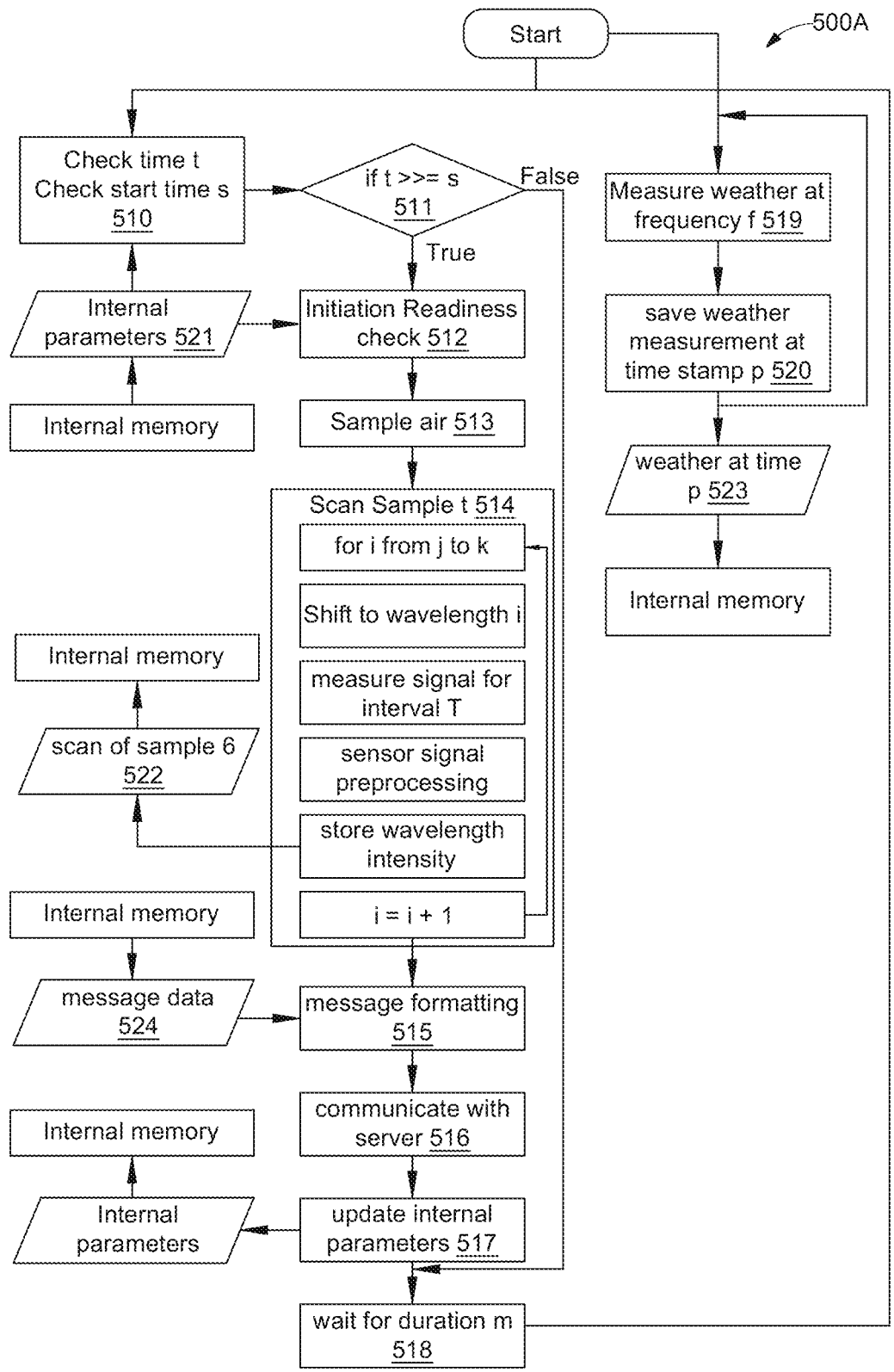
FIG. 5A illustrates an embodiment of a method for compound measurement related to spectroscopy, in accordance with an illustrative configuration of the present disclosure.

With regard to the sensor system disclosed in FIGS. 4A and 4D, certain critical functions may be performed for the collection of sensor data and for relaying sensor data through the communication units. The flowchart 500A displayed in FIG. 5A presents an embodiment of a method for collecting weather data as well as compound measurement data. In particular, a compound sensor is capable of scanning the absorption spectrum of a sample as presented in 514. Step 514 may be generalized to any other compound sensor system embodiments that are sensitive to certain physical or chemical aspects of said compound(s) such that concentration of such compound(s) in the sample can be derived from the measurements of such physical or chemical aspects with a sufficient actionable detection limit for the end user's intended application. FIG. 5A presents an example of a method using a particular embodiment of the sensor. Other embodiments which collect and communicate compound and weather measurement may be also used. For example, the sensor system in FIGS. 4A and 4D may have other operational functions that can facilitate the sensor system operation and the functions described in FIG. 5A.

The sensor system performs measurement of the weather concurrently to the measurement of the compounds of interest. The weather measurement step 519 by the sensors, such as those described in reference to FIG. 4A, is performed continuously at a frequency f In step 520, each weather measurement is time-stamped at time p and saved.

In step 523, the weather measurement at time p is stored in the internal memory. The frequency f may be read from an internal parameters table 521 and may be dynamically allocated. The measurement at time p in step 523 may also be obtained as a combination of multiple measurements obtained during step 519. For example, wind direction may be measured every second but stored over 1 minute averages.

The sensor system of FIG. 5A as described above operates on a dynamic schedule for the sampling of air. In step 510 of FIG. 5A, the time stamp t as kept and measured by the device and the scheduled start time s as read in from the internal parameters table 521 as stored in the internal memory may be checked. The device compares times t and s in step 511 to determine if it is time for starting the sample sequence. If too early (false; t<s), the device waits for the duration m in step 518 and restarts the loop from step 510. The duration m may be selected as the time difference between t and s minus the process time to loop from step 518 to step 511. If step 511 instead finds that it is time to sample (true; t>=s), the function proceeds forward to step 512.

In step 512, initiation and readiness checks are performed. This may involve diagnostic functions for all the subsystems, the communication unit pinging the server, and readying of the compound sensor such as reaching a target temperature or any other necessary state for operations. Step 512 may trigger the operation of a subsystem dedicated to enforcing nominal conditions. For example, the temperature of the sensor may be found out of bounds for optimal operation and a thermal regulation subsystem may be triggered to raise or lower the sensor temperature. Step 512 may result in delaying the sensor measurement, aborting the sensor measurement in the case where critical issues are found that inhibit measurement, delaying or aborting communication of the message if communication can't be performed, or fully aborting the performance of the sampling sequence. For example, a battery voltage may be found to be under a critical voltage that would reduce the sensor system's life expectancy between maintenance cycles, and the sample sequence may be aborted to avoid damaging the battery. Another example may be that the server link may not be possible at this time and the measurement may be stored for subsequent communication. The diagnostic result may be stored in step 512 for the purpose of communication to the server and for storage in the internal logs for subsequent maintenance check. When all the diagnostic functions are performed in step 512 and if all the diagnostics point toward a nominal state, the firmware may progress to step 513.

In step 513, a sample acquisition mechanism may be triggered. In the case of a short open path, the sample collection may be achieved naturally by the force of the wind without any actuator. Other systems may trigger a pumping mechanism that transfers the air sample to a sampling chamber. The step 513 may further involve the trigger of active subsystems for the conditioning of the sample, such as pneumatic systems for the removal of water or particulate matter or other undesirable contaminants. For example, a subsystem may involve, prior to sampling, a regeneration mechanism for adsorption or absorption-based desiccation. The conditioning of the air sample in step 513 may be fully passive, for example, when the pumping pressure differential is used for actuation in the case of an auto-draining coalescing filter.

When the sample of air is in a sample cell where the compound- or compounds-sensitive sensor operates, the measurement may be performed in step 514. The specific sensor technology embodiment presented in step 514 of FIG. 5A may operate, for example, by scanning absorption spectroscopy. In this case, the sensor measurement is operated by observing sequentially a set of target wavelengths from j to k. For a specific wavelength i, the sensor or source proceeds to shift in order to observe the spectrum centered on wavelength i. The sensor's analog signal is then measured for a time interval T and converted into a digital signal at a certain sampling rate. The digital signal is then preprocessed to identify the sensor's response intensity associated with the measurement centered at wavelength i. This wavelength intensity is stored as part of the scan 522 of the sample measured at time stamp t, which is completed when all the intensities associated with wavelengths j to k are measured.

When the sample scan is performed in step 514, the sensor system proceeds to message preparation and formatting in step 515. The message formatting involves message data 524 gathered from the internal memory. This may involve the current sample t measurement. This may include a set of weather measurements at time p measured before and during sampling. Diagnostic information as well as sensor metadata identifying the sensor and its subsystem, operation, and such may also be added to the message. Furthermore, previously captured, and stored sample and wind measurements may be added to the message data, for example when communication was unsuccessful at the previous sampling schedule time. Finally, relayed messages from other sensor systems deployed in the field may be added to the message data 524, for example when the sensor systems are networked to reduce the cost of communication to the central computing unit. The formatting in step 515 may involve encryption of the message. The message in step 515 may be further formatted into packets suitable for transmission by the communication unit.

In step 516, the message is transmitted to the server in suitable packets. Packet integrity may be evaluated to ensure that any data transfer or communication failure may trigger retrying transmission or the storage of the message for subsequent transmission. The sensor system may further query for an update of internal or operational parameters in step 517. This step may involve a general firmware update that would alter the operation of the device to a new modality or may simply influence critical parameters, such as the schedule for sample measurements, weather measurement frequency and storage or other parameters that pertain to the operation of the critical and non-critical functions. In some embodiments, step 517 may be triggered by dynamically analyzing the latest measurements. For example, the schedule of subsequent measurements may be shifted as a response to changes in recent past measurements. For instance, if a large concentration of a target compound is detected, the frequency of measurements may be augmented to increase the response speed in case of a critical emission. In another instance, wind measurement may trigger an immediate sample sequence in order to capture an emission from a critical direction. The critical direction may be, for example, the direction from which a source emission is likely to be observed. This dynamic scheduling may be decided by a sensor system control unit using edge computing resources, or by query from the centralized computing unit 427 of FIG. 4B for scheduling decisions requiring human intervention or larger computing resources. The sensor system firmware may loop in step 517 for dynamic scheduling until the time for the next scheduled sample approaches. The device may then proceed to step 518 until time s is near and repeat the main sample loop starting at step 510.

In some configurations, a cloud server (for example, "Amazon Web Services" or simply "AWS") may be provided. Further, each of the sensor systems (i.e., the plurality of air quality monitors) may include control unit which may be using edge computing resources. The edge computing resources may further include a processor (for example, processing module 211), and an averaging routine operatively associated with the processor. The processor may be configured to average a series of the actual emissions measurements obtained by the each of the plurality of air quality monitors to generate an averaged actual emissions measurement. The averaged actual emissions measurement may be generated by the processor at each of the plurality of air quality monitors, according to the averaging routine. The processor may be further configured to transmit the averaged actual emissions measurement to the cloud server. It may be noted that the each of the plurality of air quality monitors may be communicatively coupled to the cloud server. As such, the data received from all the plurality of air quality monitors may be received and analyzed at the cloud server.

In some configurations, the averaging to generate the averaged actual emissions measurement may be dependent on either the wind speed or the wind direction. Further, the averaging to generate the averaged actual emissions measurement may be increased when the wind speed decreases below a diffusion-only speed. The diffusion-only speed may refer to the wind speed when the speed of wind is insufficient to cause considerable movement of emission gases along with the wind. As such, the emission gases only tend to diffuse in the surrounding air (i.e., move from region of high concentration to lower concentration). Additionally, or alternately, the averaging to generate the averaged actual emissions measurement may be increased when the wind direction indicates delivery of dry air (i.e., the air when the concentration of target compound/emission on the air is minimal or absent) to a predominate air quality monitor 3804(1) of the plurality of air quality monitors. As will be appreciated, increasing the averaging allows for more accurate detection of emissions, if any, in the above situations.

Further, in some embodiments, the edge computing resource of the air quality monitor may include a memory (for example, memory 213). The air quality monitor may further include emissions sensors (for example, chemical sensors 221-223) configured to obtain sensor data at a predefined frequency. The memory may be configured to store sensor data obtained by the emissions sensors. The air quality monitor may transmit the sensor data to a cloud-base database (for example, "AWS"). Further, the edge computing resources (or processing module 211) may detect a low-connectivity condition. The low connectivity condition may be as a result of network downtime/failure, power failure, etc. Upon detecting the low-connectivity condition, the air quality monitor may start storing the sensor data in the memory. Further, upon detecting a normal-connectivity condition, the air quality monitor may start transmitting the sensor data stored in the memory to the cloud-based database.

Further, the air quality monitor may detect a threshold condition. The threshold condition may be one of a large concentration of a target compound, or a wind measurement from a threshold direction. It may be noted that the threshold direction may be a direction from which a source of emission is likely to be observed. In such a threshold condition, the air quality monitor may augment the frequency of obtaining sensor data by the emissions sensor, based on the detection of the threshold condition. The processor (e.g., processing module 211) may further procure the sensor data from the emissions sensor, and average the sensor data to obtain averaged data. The averaged data may be obtained according to one of a time-based criterion, or an event-based criteria. For example, the time-based criteria may define a time period (e.g., 60 seconds) after which the averaging of the sensors data obtained during that period may be performed. The event-based criteria may define an event (e.g., a low wind condition or high wind condition based on a windspeed threshold) on occurrence of which the averaging may be performed. The air quality monitor may further include a transmitter communicatively coupled to the processor. The transmitter may transmit the averaged data to the cloud-based database. In some embodiments, the air quality monitor (i.e., the processor) may sequentially combine the averaged of the sensor data into a data packet, and transmit the averaged data to the cloud-based database via a receiver. The receiver may be one of a cellular networks, a wired network, a satellite, a shortwave radio, a CDMA network, or a GSM networks.

The embodiment of the system as in FIGS. 4A and 4D or any other sensor system embodiment capable of measuring target gas and weather measurements in a collocated manner may be deployed in a field where prospective emission sources are present. A symbolic map 400C of a prospective field deployment is presented in FIG. 4C. In FIG. 4C, a sensor system 441, as depicted by a rounded-corner square, is deployed in the field to detect emissions plumes 445, 450 of target compounds, depicted by color gradients. These emissions plumes 445, 450 may be emitted by point sources 442, 449 depicted by circles, or by area source 443 depicted by a filled polygon. The plumes 445, 450 are transported by advection by an air flow as denoted by streamline arrows 446, and by buoyancy and diffusion of the compound in air. Typically, the air flow is of a complex three-dimensional geometry and depends on many parameters including, but not limited to, terrain, surface roughness and obstacles, temperature and pressure differential, insolation and inversion layer position, turbulence, and atmospheric boundary conditions or other atmospheric conditions forced by large-scale weather patterns. The streamlines 446 are a simplified view of the average transport (where turbulence is approached as an average) of air parcels during the sampling time. Note that the streamlines 446 are influenced by the effect of a terrain 447, as noted by isoclines, and by the presence of obstacles 448 (e.g., trees) represented by the small black dots. In this specific snapshot, the point source 442 is emitting the target gas, thereby producing plume 450 which is transported by the air flow 446 to the sensor system 441. Note that the cross section of the plume 450 increases when further from the source 442 due to diffusion and turbulent mixing. Plume 450 can also appear to have a tortuosity due to the dynamic change in wind speed and direction during the transport. In this example, point source 449 is not emitting and area source 443 is emitting but its plume 445 does not intersect the position of the sensor system 441 in this particular snapshot. Note that plumes are typically three dimensional and may vary in vertical cross sections, though this is not displayed in this figure.

It may therefore be necessary to have precise wind measurement collocated at the sensor system as well as a modeling of the emission transport that considers terrain, obstacles, rugosity, and other field parameters that can affect transport. For instance, in the specific snapshot presented in FIG. 4C, local wind pattern 451 at long distance comes approximately from the East direction before entering the field of interest. The wind measurement collocated at sensor system 441 is approximately Northeast as denoted with streamline 446 intersecting sensor system 441. From the perspective of sensor system 441, diffusing area source 443 is located in the northeast sector, point source 442 is located in the east-northeast sector, and point source 449 is in the east sector. Only plume 450 from point source 442 is measured by sensor 441 in this particular snapshot.

If a model only accounted for a wind direction and/or speed from a local weather pattern, such as that for a distant wind measurement of local wind pattern 451, the perceived source for plume 450 detected by sensor system 441 would be in the East sector, thereby leading to the incorrect guess that point source 449 is the source that is emitting plume 450. However, if the collocated measurement of wind direction at sensor system 441 is considered, plume 450 appears to be coming from area source 443, which is also incorrect. Note that a simple, linear local back-tracing of the wind parcel from the perspective of the wind sensor in sensor system 441 would have led to the same bad conclusion that area source 443 is the source since the terrain is the main source of the non-linear wind flux geometry. What this example shows is that identification of sources from wind speed and direction measurements alone is difficult without large numbers of wind measurements.

In one embodiment, fine measurements of wind around the site would be taken to properly measure the complex wind pattern responsible for the plume transport. Using multiple wind measurements can be cost-prohibitive. In another embodiment, a simulation of the emission transport using a digital twin of the site is performed. Such a digital twin can reconstruct an estimation of the actual flux responsible for the transport and consider the effect of terrain 447, obstacles 448, source geometry 443, 442, 449, as well as other parameters relevant for the turbulent advection/diffusion of the target emitted compounds. With that simulation, the accuracy of the flux in the site is enhanced and closer to the actual flux of air flow 446. Because of this, attributing the plume 450 to point source 442 with a single deployed point sensor is possible.

The same model may allow for reconstructing a detection limit 444 of the sensor system 441. Detection limit 444 denotes the limit for which the smallest leak size is only detected 50% of the time. Other criteria for detection limit 444 may be specified for different leak size or different confidences of detection. In a perfectly flat model with a uniform chance of wind in any direction, the detection limit at a constant altitude is circular (approximated by a cardioid in three dimensions). In practical cases, the shape of the detection limit may be very complex and may change based on wind pattern, temperature and pressure, terrain and other parameters impacting the transport of the compounds as well as detection limits of the sensor itself. FIG. 4C gives an approximation of the detection limit at constant altitude as an ellipse. In this case, sensor system 441 is adequately positioned to detect emissions from sources 443, 442, and 449 as these potential sources are within a range of the detection limit 444 of the sensor system 441. Note that other positions may lead to higher sensitivity to sources 443, 442, and 449 but the position of sensor system 441 may be dependent on other factors, such as land usage authorization, better line of sight for communications, or network optimization positioning for a deployment with more than one sensor system.

Multiple sensor systems as described in FIGS. 4A, 4C, and 4D may be deployed in a field for the acquisition of weather measurement and compound measurements. The sensor system takes these measurements and relays messages related to these measurements with timestamps, identifiers, and other metadata regarding sensor operations to a centralized computing unit 427 in FIG. 4B. The communication of data and commands is represented in FIG. 4B. Sensing unit 433, which may or may not be the same as that described in FIG. 4A, can incorporate components such as a power system 423, weather sensors 422, compound sensors 421, a computing unit 424, and a communication unit 425. Sensing unit 433 can relay messages, as described above, to centralized computing unit 427 using network layer. The network layer may rely on existing communication infrastructure such as cellular or satellite, or dedicated infrastructure such as custom wired or wireless systems, including but not limited to, Wi-Fi, Bluetooth, SCADA systems, LoRa, and other telemetry and data transmission systems. The data transmission may rely on other network infrastructure, such as the internet or on dedicated networks such as intranet or LAN. Sensing unit 433 may also directly transmit messages to non-networked systems or local systems 434 as may be the case for a local interface used by the sensor system user. The message from sensing unit 433 may be relayed through other sensor units as in daisy-chained or starred sensor system networks or through a dedicated unit for the local storage, scheduling and packaging of messages from various sensing systems 433, 435, deployed in the vicinity of each other. This may be done to amortize the cost of expensive transmission technology such as satellite links.

Once in centralized computing unit 427, message processing is performed to transform raw data into actionable data. This may include simple operations such as data formatting or more complex operations such as creating a maintenance tracking system for the operator. In one embodiment, the data processing is the conversion of weather and compound measurements into detection, localization, quantification, and qualification of target compound emissions. To transform the raw compound measurement into speciation and concentrations, an external database 436 such as the HiTRAN database may be queried for reference spectra, or internal databases of calibration measurements taken with the specific sensing unit 433 during calibration runs. Other information such as sensor units' metadata 438 may be used for the specific instrument characteristics to enhance speciation and concentration measurements.

In order to perform localization, quantification and qualification, centralized computing unit 427 may reference field metadata 437 collected by field operators such as, but not limited to, topological maps of the field deployment, images of site, the potential sources and equipment, equipment inventory and GPS coordinates of features of interest, for the purpose of creating a digital twin of the site for the purpose of atmospheric transport modeling and simulation. Other field metadata may include previous local weather information and the external weather databases 436 are queried.

Centralized computing unit 427 may use other messages from another sensing unit 435 for enhanced localization, quantification, and qualification of the emissions. Sensing unit 435 may include multiple sensing units and may be of the same type as sensing unit 433 or any other sensing units present on the sites. For example, sensing unit 435 may be a flare lighting sensor used as an indicator to help attribute an emission detected by sensing unit 433 to a flare misfiring.

Actuator commands may be used as a sensor feed as well. For example, the actuation of pneumatic equipment at oil sites may result in a predictable emission; therefore, command signals from actuators may be used to help predict expected emissions from an oil site. An example in the landfill industry may be variation in the pressure head of wells which may be correlated with a local emission hotspot.

This concept can be extended to all existing command signals and process sensors already present in equipment associated with potential emissions sources.

Once detection, quantification, qualification, and localization of sources is obtained by the processes in the centralized computing unit 427, actionable data may be generated. Actionable data may mean the data necessary to take a corrective action, including, but not limited to, emission reports, maintenance lists, maintenance tracking and emissions-reduction tracking tools. The actionable data may further be used as commands or scripts for automation systems 431. For example, actuators on a site may be automatically put in a safe position if an explosive concentration of a flammable compound is detected. Another example would be the operation of alert equipment such as sirens or visual cues triggered to alert operators to perform emergency evacuation if a toxic compound is detected. At times, robotic or automated inspection and repair or maintenance of equipment may be deployed as a response to a command. For example, a drone may be deployed to perform precise automated inspection of a certain area identified by sensing unit 433 to perform fine-scale equipment leakage detection. Another example would be automated excavation equipment which can be deployed for placing additional ground cover on a detected emission hotspot at a landfill. A third example would be triggering an automated self-diagnostic system in a continuous production environment which may require large computation power for distinguishing problems in the process.

Actionable data may be used to generate automated reports in document generation task 432. For example, the sensor data may be used to generate regulation-mandated emission inventory reporting and edit auto-completed reports to be physically or digitally sent to the concerned agency with or without operator intervention.

Actionable data, emission data and raw data may be transmitted to other servers 430, that may be internal or external. The purpose of this may be to relate raw data for archiving or post-processing, or to send data to servers behind a firewall in specific user instances where proprietary data is collected and require different levels of encryption. In that case raw encrypted data may not be decrypted in the centralized computing unit 427 for data safety reasons and may only be safely decrypted behind a client's firewall.

Actionable data such as triage information, reports, maintenance, and abatement data may be communicated through emails, text messages, dashboards, or dynamic notebooks, to static I/Os 429 and mobile I/Os 428. Static I/Os 429 can include PC and other fixed computing units such as in the office of the field manager. Mobile I/Os 428s can include pagers, PDAs, phones, tablets or laptop computing units and equivalents such as the phone of a field operator such as a pumper or a field foreman for oil and gas applications.

As seen in FIG. 4B, the centralized computing unit 427 processes the messages received by the sensing unit 433. Now referring to FIG. 5B, an embodiment of a method 500B executed in the central computing unit for converting the information received in messages 540 originating from the sensing system described in FIG. 4A is described. The message generation process described in FIG. 5B converts messages 540 into actionable data in the form of emission detection, localization, quantification, and qualification as well as other actionable data generated by an actionability engine 537.

First, in step 530, message 540, which may be stored in a server database 570 after reception, is routed to the server instance that is responsible for message processing. Message 540 includes the information formatted by the sensor system of FIG. 4A and may be constituted of spectral or concentration information as measured for a certain sample t (which is taken at the time t) as well as weather information and sensor metadata (such as, but not limited to, diagnostic parameters, GPS location and sensor ID). The message is first decrypted and decoded in step 531.

Figure 5B:
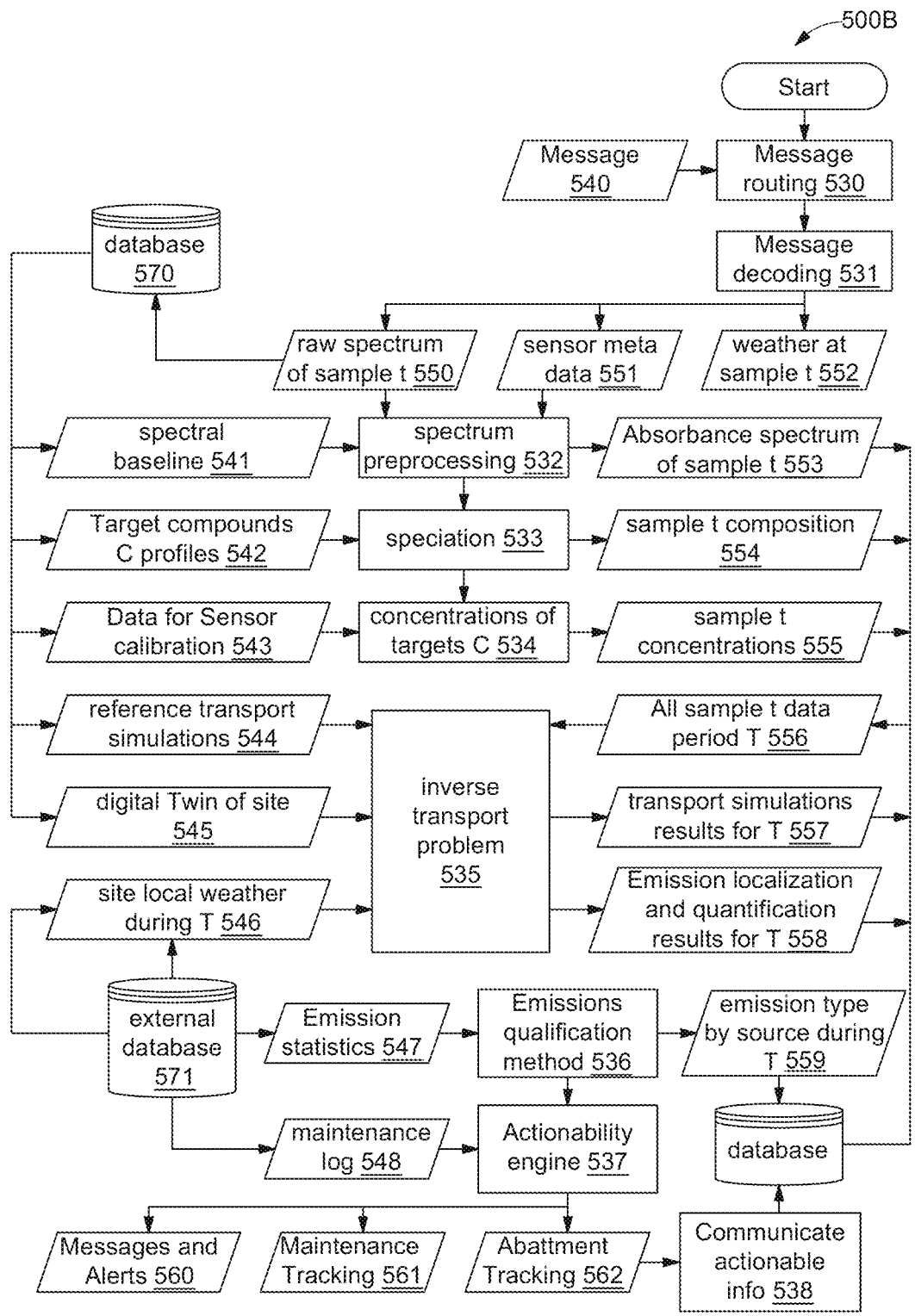
FIG. 5B illustrates an embodiment of a method for converting messages from the sensor systems via cloud implementation, in accordance with an illustrative configuration of the present disclosure.

Step 531 of FIG. 5B first uses a decryption protocol associated with the encryption method employed in step 515 of the message formatting as described in FIG. 5A. Message 540 may be parsed into three datasets: (1) raw spectrum 550, which may contain an absorption spectrum measured at sample t; (2) sensor metadata 551, which may contain sensor diagnostic, ID, GPS location and such; and (3) weather data 552 that may be taken around the time of the sample t. Raw spectrum data 550, sensor metadata 551, and weather data 552 may be stored in database 570 for future reference or for recalculation if new computation methods are later available. Note that raw spectrum data 550 is specific to an embodiment of the sensing technology and could be any other type of raw data associated with measuring the concentration of a target compound.

In step 532, the data of step 550 associated with the sensing of the target compounds is preprocessed. In an embodiment of step 532 for the specific case of spectroscopy sensor technologies, a raw spectrum is processed. The preprocessing includes denoising the data, peak alignment and bias shifting and computing an absorbance spectrum of sample t 553 from the transmission spectrum by using a spectral baseline 541 as a reference transmission. This step may involve sensor metadata for sensor-specific preprocessing, for example for accounting for light source power shifts, using sensor-specific information stored in database 570. Generally, regardless of the sensing technology embodiment used, step 532 may involve denoising, debiasing, or otherwise calibrating and enhancing the raw signal with preprocessing strategies that may involve sensor-specific information such that the preprocessed sensor signal may be analyzed.

Figure 5C:
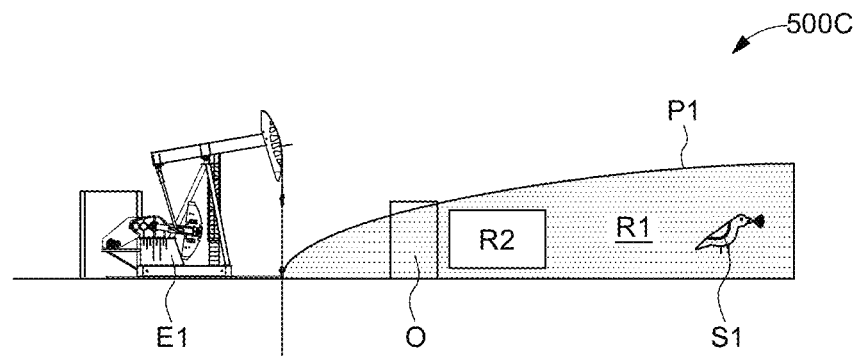
FIGS. 5C-5D illustrate a front view and a top view, respectively, of an example site that includes an emission source, in accordance with an illustrative configuration of the present disclosure
Figure 5D:
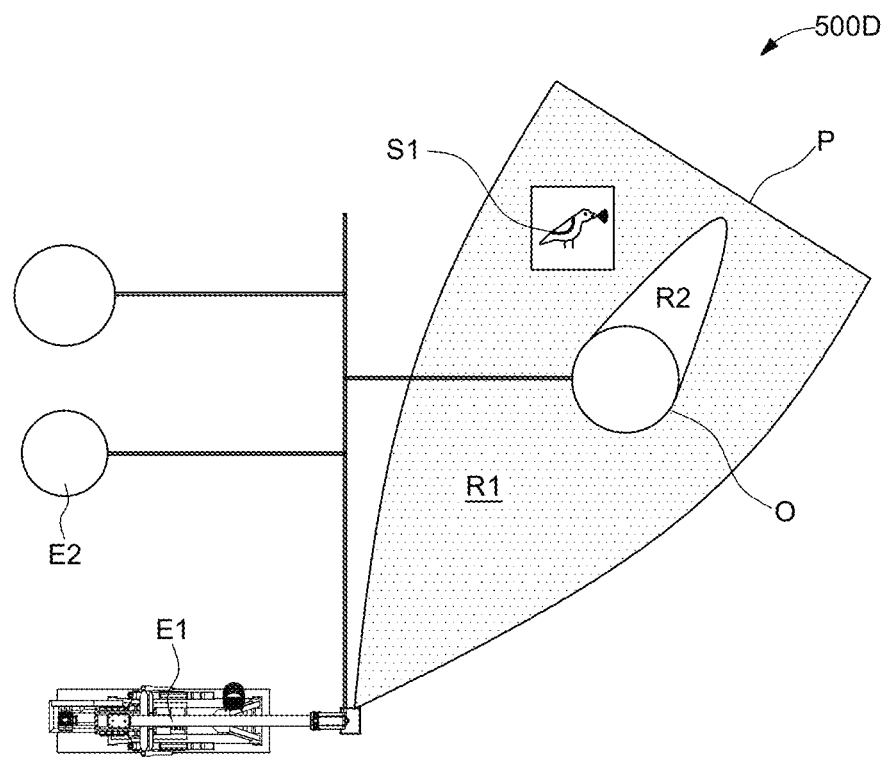

In step 533, the preprocessed sensor signal may be analyzed for speciation. The process of speciation involves the identification of various compounds from a raw signal. For example, FIGS. 5C-5D illustrate a front view 500C and a top view 500D, respectively of an example site. The site may include multiple potential emission sources E1, E2, etc. Further, the site may include a sensor S1. In the scenario depicted in the FIGS. 5C-5D, a target compound C1 is emitted from the source E1 and forms a plume P1 covering a region R1. Further, an obstruction O is present which may obstruct the plume P1. As such, the obstruction may result in a region R2 within the region R1 where the target compound C1 is not present or is minimally present. The sensor S1 which may be lying within the region R1 but outside the region R2 may detect the target compound C1.

Figure 5E:
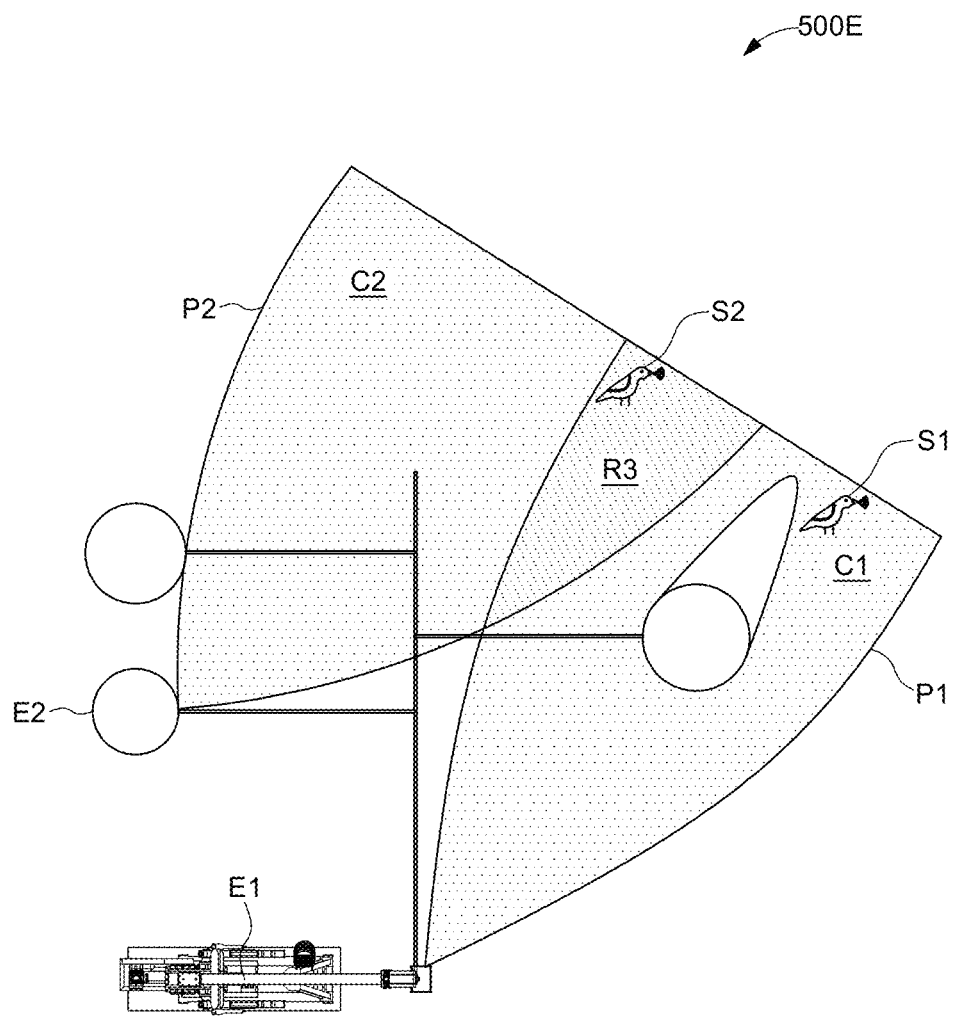
FIG. 5E illustrates a top view of a scenario with respect to an example site that includes multiple emission sources, in accordance with an illustrative configuration of the present disclosure

Referring now to FIG. 5E, a top view 500E of another scenario with respect to an example site is shown where mixing of multiple target compounds takes place. As shown in the FIG. 5E, the site may include multiple potential emission sources E1, E2, etc. Further, the site may include the sensor S1 and S2. Target compound C1 is emitted from the source E1 and forms the plume P1. Further, a target compound C2 is emitted from the source E2 and forms a plume P2. The plumes P1 and P2 merge in a region R3. As such, the region R3 includes both the target compound C1 and the target compound C2. The sensor S1 which may be lying outside the region R3 may detect only the target compound C2. The sensor S2 lying in the region R3 detects both the target compounds C1 and C2 and therefore generates a confounding signal.

Referring back to FIG. 5B, the process of speciation therefore involves may involve identifying the contribution of one or multiple target compounds and separating them from confounding signals. This step may not be necessary for single-compound sensor signals that have no confounding elements. For the specific embodiment of a spectrometer absorbance signal, the identification may involve using reference target compounds spectral profiles 542 and minimization, inverse, or inference methods to decompose the spectrum into its component spectral signatures associated with target compounds. The target compounds profiles 542 may originate from the database 570 or from external spectral databases 571, for instance a HiTRAN database. A residual spectrum may be left over that may contain noise, non-linear contributions from light source and sensor bias over time and a spectrum of non-target compounds that may or may not be known.

A sample composition 554 for the sample t taken at time t is generated and stored in the database for the target compounds. This may further contain a residual signal for further analysis. Once the composition is identified, the concentration of each target compound in this composition may be obtained in step 534. For certain embodiments of the sensor technology, the concentrations may be obtained directly from steps 532 and/or 533. In one embodiment related to spectroscopy, the composition may be identified for normalized target compound profiles in step 533; the purpose of step 534 is then to associate the normalized profiles to a certain concentration. This may be achieved by using data from a specific sensor calibration data 543 as stored in the database 570. This calibration data 543 may be obtained by testing the specific sensor that has taken the sample t, or a reference sensor of the same type, with a multiple point test against a calibrated compound mixture. For example, when measuring methane, a five-point calibration in the range of concentration of interest such as 0 ppm to 100 ppm may be taken. The calibration data 543 associates a known concentration to spectral profile intensity, which may be nonlinear and can use the composition of spectated spectra from steps 533 to derive the concentration of each species of the composition. The sample t concentration data for the target compounds 555 is stored in the database 570.

Once the sample composition and concentration with respect to target compounds are found for a certain sample t, the localization, qualification, and some of the quantification is performed in steps 535 and 536. Step 535 focuses on solving an inverse transport problem. That may include a representative fluid mechanics model and models of the geometry, topology and other characteristics of the site surrounding the sensor system responsible for a set of measurement samples t. The model is created to recreate the condition in which the compounds of interest may be transported from the prospective sources and other confounding sources to the sensor system. The direct problem creates the relations between causes, such as source location and emissions flux for each source, weather at the sources, and consequences, such as sensor concentrations measurements and weather at the sensor.

The inverse model identifies the inverse relation; that is, finding the sources of emissions and emission intensities knowing the sensor system's measurements. This may be done explicitly by running a set of reference transport simulations 544 that may be stored in the database 570 for reuse and creating an inverse relation matrix to relate measurements with sources. Two inverse problems may also be run by first solving the flux inverse problem, i.e., finding the weather conditions at boundaries of a simulated domain that would result in the observed weather measurements by the sensor system, and then solving for the transport inverse system, i.e., what source's emissions would have resulted in the observed compound concentrations in the weather conditions found in the first inverse problem. The inverse problem may also be solved by modifying the transport equations such that they may run backward in time. Furthermore, local weather during the period of interest T 546 from external databases 571 may be used to enhance the selection of appropriate initial and boundary conditions in the solving of the direct or inverse problems. Together with this inverse problem solving, uncertainty quantification may be used to enhance the result and/or reduce the burden of large simulation sets by rewriting the problem as a function of probability distribution functions of the input parameters, formulating prior probabilities, and using statistical inferences such as Bayesian methods. This can help in source identification by explicitly solving for the probability that a prospective source is an actual source given the sensor system measurements and may reduce the number of direct simulations to an acceptable minimum based on known error distributions. Results of the transport simulations for a certain period T 557 may be stored.

In order to improve the inverse transport problem in step 535, all the samples t in a data period T 556 may be used by a solver algorithm. This is important because each sample t constitutes only a snapshot of the site for a given weather pattern. Therefore, in order to both build accuracy through repeated observations and in order to increase coverage of the site, a certain number of samples t are used, all within a contiguous period T. The period T is selected based upon the expected detection speed, the time necessary for the weather pattern, in particular the wind direction and speed, to change sufficiently such that the detection of potential emission for the observed sources is possible and based on the expected accuracy of reporting. The period T can shift from 1 minute, for example for the detection of critically dangerous compounds where emergency protocol may be engaged, to multiple months, for example at remote sites where intervention may not be possible or of concern for long periods of time. The period T may be dynamically, manually, or automatically allocated based on the sample t concentration 555 and composition 554, operator requirements, maintenance schedule, hazard, duration of emission and such.

Without loss of generality, the longer the period T, the higher the accuracy of the inverse transport problem in identifying average emissions over the duration T and with higher spatial resolution. However, in case of the identification of transient emissions, that is, emissions that may be intermittent rather than continuous, it may be better to select a duration T that matches the expected time characteristics of such emissions. In the embodiments related to upstream oil and gas, a judicious period T may be 1 to 2 weeks for emission monitoring purposes and shorter for safety purposes. In the embodiments related to solid waste, such as solid waste landfills and composting operations, a judicious period T may be from 5 days to a month when identifying cover hotspots and shorter for diagnosing well failures and for safety purposes.

The inverse transport problem 535 may be solved for various periods T using the same dataset in order to achieve different objectives. Once the inverse problem is solved, both the emissions probable sources and emissions flow rates for the selected period T, 558, are identified and stored in the database 570. This allows both the quantification (by identifying emission fluxes) and localization (by associating the probable sources with the site's equipment or areas). Then, emissions are to be qualified in step 536. The qualification allows further refinements of the understanding of the emissions. Indeed, emissions can come from different elements within an equipment but more importantly, emissions from the same equipment may be separated into categories of expected emissions from normal operation and spurious emissions from leaks or abnormal operations. For example, in the upstream and midstream oil and gas industry, equipment such as compressors and pneumatic actuators may emit methane in normal operation. In another example, landfills may have diffuse emissions depending on the presence or type of cover. This means that successfully detecting, localizing, and quantifying an emission may not mean that a leak has been detected, and may in fact indicate that the site is operating as designed.

One embodiment of step 536 uses statistical inference together with emission statistics 547 to identify the type of normal emission or leaks by distinguishing their intensity, frequency, and composition over time during a period of interest. Each emission type indeed has a specific signature in terms of intensity, frequency, and composition over time. Matching these signatures with the observations allows for the identification of emission profiles or outliers. The emission statistics 547 can be generated as a composite from equipment characteristics, for instance by accessing external databases 571 such as the Environmental Protection Agency (EPA) expected average emission by equipment type, by in situ statistical quantification by observing the emission profile of a site under normal operation, or by any other suitable experimental or theoretical methods to create such emission statistics. Statistical inference may be used to classify the emission type by source 559 which may be saved in the database.

The accuracy of the statistical inference can be improved by integrating a feedback loop, such as using operator data and/or maintenance logs 548. Indeed, these logs may be used to positively identify that a certain footprint was really indicative of a certain emission type. An alternative method to this qualification method embodiment may be to use artificial intelligence, machine learning, or neural networks. In this case, a training set is first created to identify the signatures of the emissions. The artificial intelligence method may learn over time by accumulating validation information from the type of emission through the site operator maintenance log 548. Over time, emission types may be more and more accurately qualified by a learning algorithm.

Once emissions are detected, qualified, quantified, and localized, this data needs to be provided in an actionable form to the end user. An actionability engine 537 provides this additional layer of intelligence by matching the characteristics of the emission to the needs and objectives of the end user. The actionability engine 537 may interpret the emission data, together with the maintenance logs 548, to provide three categories of actionable information. Some additional categories may be extracted from the data as well, may the need arise.

The first category is messages and alerts 560. The purpose of these is to relate the relevant information to the operator, to provide either a call to action or a status update. The messages may be, but aren't limited to, an indication of the current state of emissions in all the covered sites, a triaged list of emission flags ranked by intensity or gravity for maintenance intervention, and alerts in case of critical or emergency conditions due to the emitted compounds. For example, in the upstream oil and gas industry, a ranking of notifications or virtual "flags" for potential fugitive emissions may be sent to a field foreman in order to prioritize sites for inspection and maintenance. In another example, an alert for high concentrations of hydrogen sulfide may be sent to all field operators or pumpers in the vicinity of a dangerous hydrogen sulfide leak at a specific well pad. In yet another example, the emission inventory for a specific site for a quarter may be summarized for an operational field manager to track emission inventory objectives. This first category of actionable insights provides one-way, summary information that may be used for metrics tracking, safety alerts, or maintenance scheduling. Fundamentally, this first category does not have a feedback loop.

The second category generated by the actionability engine 537 may be a maintenance tracking system 561, where information from the operator may be used, for example as maintenance log 548, to actively update the maintenance strategy. In the oil and gas industry, the maintenance tracking system 561 could be used to track and schedule maintenance efforts based on available resources and to flag resolutions. For example, the maintenance tracking system 561 could limit the number of flags by avoiding notifying the operator multiple times for the same emissions until the emission is marked as fixed. For example, in the landfill industry, the flag associated with a particular hotspot may be suspended until the site manager confirms that cover remediation was attempted by adding more cover around the hotspot. In effect, the maintenance tracking system 561 can help ascertain that remediation for a particular emission was successful. The maintenance tracking system 561 may also suggest the most likely faulty component to look for based on a site's known equipment inventory. The maintenance tracking system 561 may directly allocate works to various maintenance teams based on availability of tools, human resources, and time. The maintenance tracking system 561 may suggest replacement parts when repeated leaks are detected from certain components, for example a particular actuator being known as faulty may be replaced by a better model to avoid the repeat maintenance cost. The maintenance tracking system 561 may send a triage list of unwanted emissions by intensity and suggest intervention speeds for each considering the likely maintenance cost, lost gas, and resource intensity requirements. For example, in upstream oil and gas, an open thief hatch identified as the likely emission source from a liquid tank would be rated as a high priority, as it is a high emitter, does not require specialized equipment to address or find, does not require large amounts of human resources to address, and is easy to verify. The maintenance tracking system 561 therefore does balance practical requirements with emission reporting for maintenance purposes and make use of operator feedback in its updating.

A third category of actionable information lies in abatement or emission reduction tracking 562. For this category, information over a longer time trend is analyzed. By collecting maintenance information and emission over long periods of time, emission inventories and repeat equipment failures may be compared across many sites. This may allow ranking sites which are attempting emission reductions by various strategies. For example, one site may use compressed air actuators in one oil field and low-bleed actuators in another and compare emission intensities of both technologies in real life conditions. This may lead to better decision making when implementing pilots for new, lower emission technologies. In particular, the cost per avoided ton of CO2 equivalent may be compared when using an embodiment technology which tracks greenhouse compounds. Emission inventory trends may be used to evaluate the efficacy of practice or equipment change using the abatement tracking system 562.

In general, the actionability engine 537 may involve a set of rules, algorithms, and artificial intelligence to generate actionable data for the messages and alerts 560, maintenance tracking 561, and abatement tracking 562. This actionable data may be stored in the database 570 and may be communicated to stakeholders in step 538.

FIGS. 5A and 5B have detailed an embodiment of a process for the conversion of weather and compound sensor measurements for emission detection, qualification, quantification, and localization, and for the generation of actionable data, insights, and maintenance and emission reduction tracking. The described method is not limited with respect to the type of sensor technology. The following presents the particularities associated with signal treatment in the near to mid-infrared region for an embodiment of the sensing technology which utilizes absorption spectroscopy. This region of the spectrum is of particular interest for detecting greenhouse gases, which are gases that absorb electromagnetic radiation in the infrared part of the spectrum and contribute to the trapping of heat when present in the atmosphere.

FIG. 4C presents how a sensor system may be deployed in the field in a manner accounting for terrain, potential source location, transport obstacles and wind pattern. The underlying principle for uncovering a source is to sample from the plume of said source when the wind direction and speed point (in an average sense) form a line from the emission source to the sensor system.

Figure 6A:
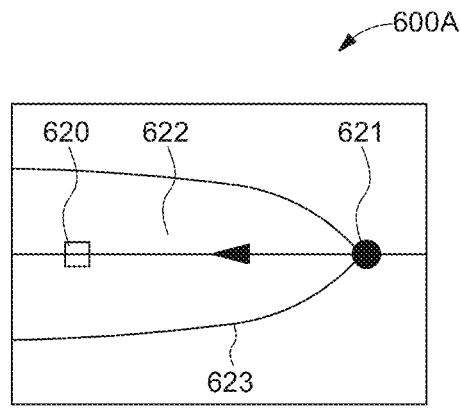
FIGS. 6A-6D illustrate multiple cases of the transport of a compound from a source to a sensor, based on wind direction, wind speed, and dynamic wind effect, in accordance with an illustrative configuration of the present disclosure.
Figure 6D:
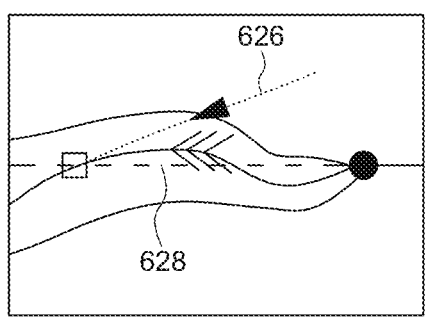
Figure 6B:
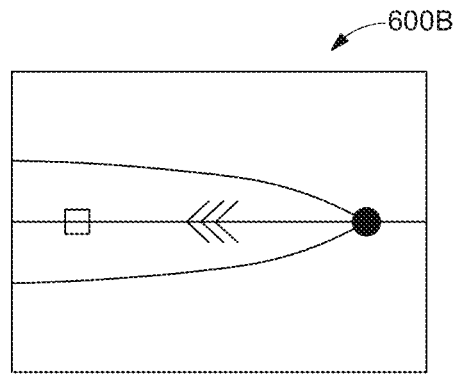
Figure 6E:
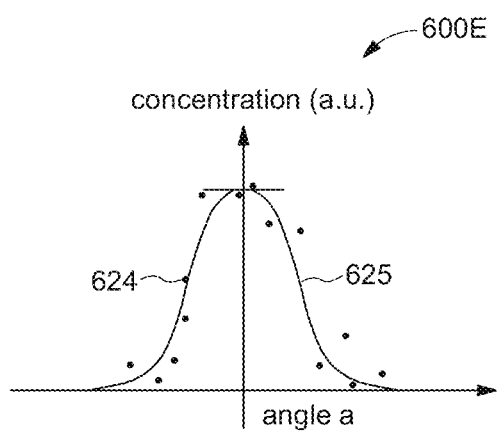
FIG. 6E illustrates a graph related to the concentration across the cross section of an emission plume, in accordance with an illustrative configuration of the present disclosure.
Figure 6C:
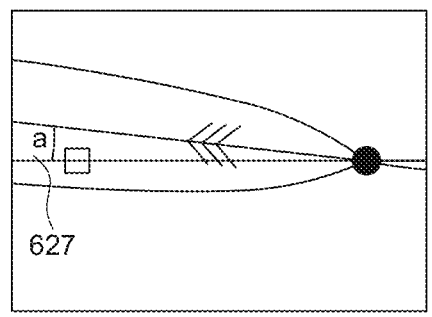

The fundamental principles of this plume detection are detailed in FIGS. 6A-6E. FIG. 6A presents a symbolic top view 600A of the transport of an emission plume 623 from a source 621 to a sensor system 620 via transport denoted by streamline 622. In reality, the plume 623 may not be contiguous and may have a complex three-dimensional shape. FIG. 6A presents the transport in the case of a steady medium-speed wind pointing directly to the sensor system 620. FIG. 6B illustrates a similar symbolic top view 600B but with a faster wind speed. FIG. 6C illustrates another symbolic top view 600C showing effect of a change in wind direction. FIG. 6D yet another symbolic top view 600D showing the effect of a tortuous streamline. FIG. 6E illustrates a symbolic representation 600E of construction of a plume cross-section using the wind direction to 'scan' across the plume.

Comparing FIGS. 6A to 6B, it can be observed that an increase in speed may result in a narrower plume extent since the plume spread is determined by a balance between diffusion and turbulent mixing, and advection, and at higher wind speeds, horizontal advection becomes the dominant force. This results in a change in an observed concentration at the sensor system 620, namely that a maximum concentration observed across the plume may be higher in the case of higher wind speeds. However, higher wind speed can also result in more turbulent mixing in some conditions which may influence this result, particularly resulting in a large spread of measurements of maximum concentrations. This change from low speed to high speed clearly denotes the importance of wind speed in transport, and therefore the necessity to measure wind speed when measuring concentrations of the emitted compounds.

In FIG. 6C, the average wind transport is shifted angularly compared to the direct line from the source to the sensor as in 6A and 6B. Angle 627 is denoted "a". In idealized conditions, an increase in "a" may result in a reduction of the observed plume concentration. The concentration in an idealized plume is maximum at the center. In practice, due to turbulence, the plume may be branched, and its cross-section profile may not follow a regular pattern like the one shown in FIG. 6E. FIG. 6E presents an idealized profile of the cross section of the plume as measured by the sensor system 620. The sensor system 620 may sample the plume at different angles and register an associated concentration point 624. When sufficient numbers are obtained, a fit of a point cloud 625 can be obtained. If the measurements occur in idealized conditions when the wind speed, temperature and other parameters beside wind direction are stable, the plume flux may be calculated using a simple mass conservation equation by multiplying the area concentration of the plume cross section by its normal speed and by estimating the plume concentration in the height direction. This approach may be taken using plume theory for the estimation of the plume geometry and using a mobile sensor across the plume cross section to estimate the average plume concentration.

One illustrative configuration instead uses shifts in wind direction to estimate the plume average concentration, as depicted in FIG. 6E. Another, more precise embodiment is given in the description of the inverse model used to estimate emission source and flux. The wind may change dynamically during transport from the source to the sensor system 620, as shown in FIG. 6D. FIG. 6D shows a case where the transport from source to sensor is on average direct as denoted by an average flow direction 628 but may have a dynamically tortuous path. Moreover, a wind direction as sensed by the sensor system 620 is shown as vector 626. This exemplifies that in case of dynamic wind or when the topology influences the actual path taken by air flow, the source position may not be given by the wind direction measurement at the sensor system or at the source. This exemplifies the need for modeling of the air flow in the vicinity of the sensor to better understand the transport of the emission from a source to a sensor system when dynamic effects, obstructions, topology, or other effects may influence the transport.

Figure 7:
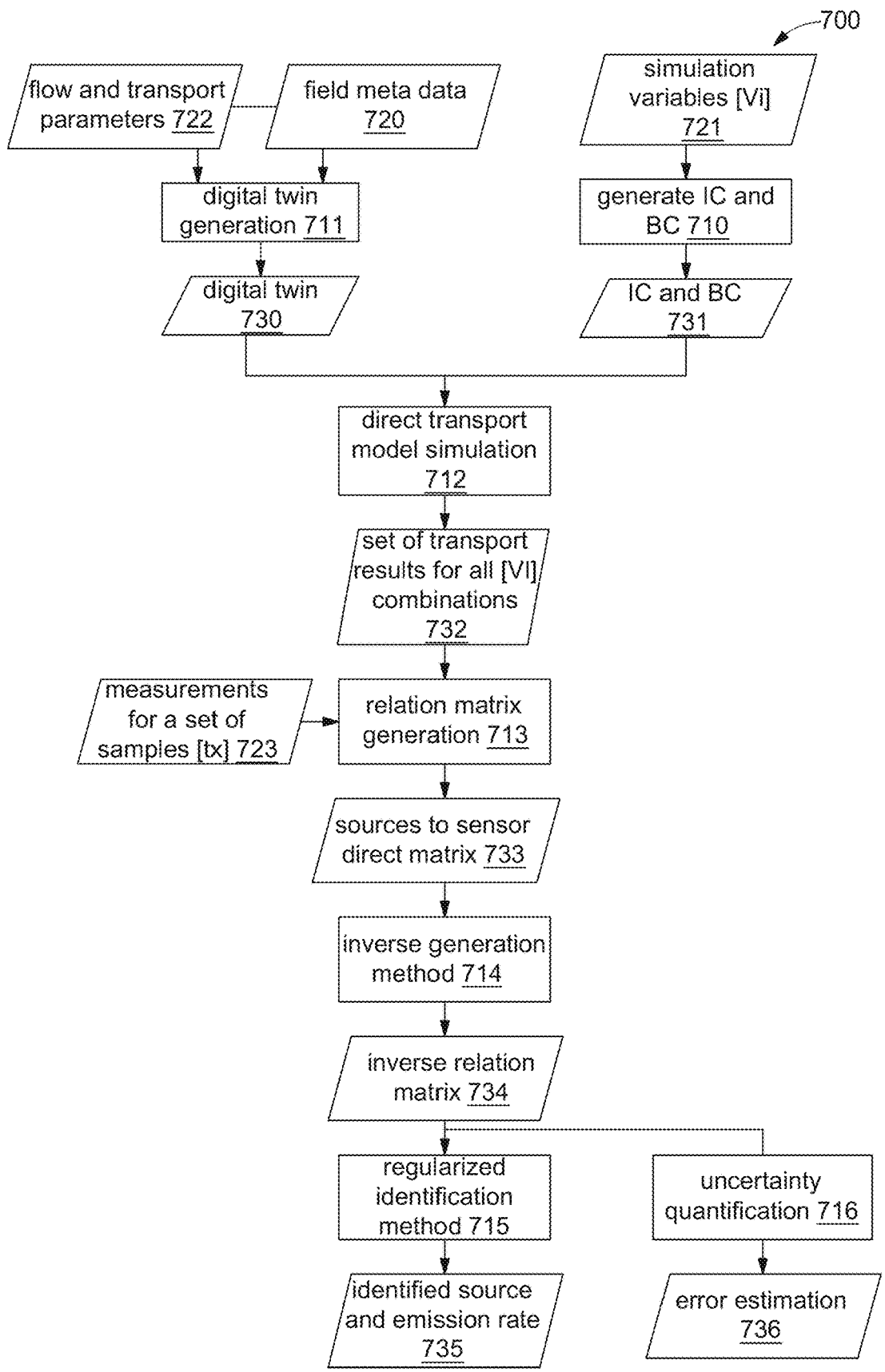
FIG. 7 illustrates an embodiment of a method to quantify, qualify and localize sources relying on transport simulation and a source identification strategy relying on solving an inverse problem, in accordance with an illustrative configuration of the present disclosure.

An embodiment of processes 700 and 800 for transport modeling including an inverse solver to identify source location and emission flux is given in FIGS. 7 and 8, respectively. In both of these models, a digital twin of the site where the sensor system is placed is modeled and may include, without limitation, topology, obstacles, equipment on site, potential emission sources and a model of the sensor system itself. FIG. 8 proposes a complete solving of the problem with two distinct inverse problems being solved, one to identify the flow over the site and a second to identify the sources and emission flux. In FIG. 7, a single inverse problem is solved for localizing the sources while the weather over the site is found by matching the weather measured at the sensor location of a pre-simulated set of weather conditions. The method 700 depicted in FIG. 7 may be used when the flux is easier to define such as when the wind is constant during sampling, with the advantage that most of the direct simulations can be carried out in advance and reused for subsequent source and flow identification. The method 800 in FIG. 8 may be suitable when the wind conditions are shifting during sampling and in complex transport cases. The method 800 in FIG. 8 may take longer to compute as it may be necessary to run direct simulations for the data processing every time a sample is analyzed. In both methods in FIGS. 7 and 8, a probabilistic approach such as prescribed in uncertainty quantification or statistical inference methods may be used, in which case the simulation variables may be described as probability density functions in order to propagate an error estimator to the results such as a probability of positive source identification and error estimation on the predicted emission fluxes. The advantage of such a probabilistic method is that the number of pre-simulated models may be reduced or tailored to the precision requirement, thus limiting the computational cost of the methods.

Further, a method of identifying a target emission at a site is disclosed. The method may include creating at least one simulation model for the site based on simulation parameters. The simulation parameters may include a wind direction, a wind speed, an air pressure, an air temperature, a number of potential emission sources, a location of each of the potential emission sources, a source flux associated with each of the potential emission sources, a surface concentration, a weather condition, a hygrometry data, and an altitude. According to the method, actual parameters for the site corresponding to the simulation parameters may be received, receiving actual emissions measurements from a plurality of air quality monitors deployed at the site associated with the actual parameters for the site may be received. The plurality of air quality monitors may be deployed at predefined locations at the site. The method may include identifying a relevant simulation model from the at least one simulation model. It may be noted that the simulation parameters associated with the relevant simulation model match with the actual parameters. The method may further include extracting virtual emissions measurements generated by the relevant simulation model, and receiving actual emissions measurements from the plurality air quality monitors deployed at the site associated with the actual parameters for the site, correlating the virtual emissions measurements with the actual emissions measurements from the plurality air quality monitors, and determining configuration of at least one emission source based on the correlation. The configuration of emission sources may include a location of the emission source at the site and a concentration of emissions from the emission source.

In particular, with respect to FIG. 7, a digital twin (also, referred to as simulation model in this disclosure) is first constructed in step 711. To construct the digital twin, field meta data 720 (part of simulation parameters) is collected. The field metadata 720 includes all the relevant information about the site in the vicinity of the sensor system at least containing the detection range of the sensor system. The field metadata 720 may use satellite images, altitude, and topographic data to reconstruct the terrain, location of equipment, type of ground cover and so on. Furthermore, field metadata 720 may be collected by an operator to ascertain the relative position of the equipment and sources relative to the sensor system, GPS coordinates of the sensor, list of potential obstacles, actual covers such as grass, earth, and trees, as well as a series of pictures of the site. These can be used to properly identify a geometry of the site and surface properties that may influence the simulation. Additionally, a three-dimension cloudpoint of the site may be obtained by one or more scans, such as a LIDAR or radar scan. A numerical mesh or simulation grid is then constructed to represent a section of the atmosphere around the site that includes ground topology, large surface covers like trees, as well as discretization of equipment, obstacles, and the sensor system. Atmospheric borders of that mesh are defined as boundaries for the simulation and properties such as friction and slip may be attributed to surfaces associated with ground, cover, equipment, and other topological features. Sources are located in the mesh and identified as potential boundaries to specify emissions. The simulated volume may be as small as 100 by 100 by 100 meters (m) and as big as necessary to include a large field network, and the characteristic mesh size may be as small as 10 cm and as big as 100 m.

For example, consider the case of an upstream natural gas well pad. The well pad may be 100 m by 100 m. A sensor system is positioned on this site. Assume for this example that the sensor system is configured to detect methane and is accurate enough to detect leaks within 200 m in the conditions encountered at this pad. Satellite images give an accurate view of the pad, containing wells, separator groups and liquid tanks. The pad surface is identified by the operator pictures as gravel and the pad is surrounded by hilly grassland. The altitude is given as 500 m with a continental climate. A patch of pine trees lies to the north. Topological survey maps of the site are obtained in a national database. The sensor is positioned in the north corner of the pad and angular position and distance of the different equipment group is measured by an operator for validating the satellite images. From all this information a three-dimensional numerical mesh may be generated by an engineer. The mesh is a box roughly 300 m long by 300 m wide by 200 m high for this example with a mesh size of 1 m. The terrain is first created using point cloud extraction from the topological map. The equipment position is marked and three-dimensional models of the equipment group, generated with a 3d modeling software, are positioned. The patch of trees may be added as individual trees or as a forest block with an appropriate diffusion model attached. The different terrain rugosity is attributed to the appropriate mesh elements. Boundaries of the 300×300×200 m box are specified for boundary and initial conditions. The surface of the potential sources, here the equipment groups including the well heads, separators, and tanks are identified as sources boundaries.

Consider another example, in the case of a landfill. The landfill may be 400 by 400 m and includes a 35 m high mound. Four sensor systems are positioned on the landfill. The landfill is surrounded by forested areas and the surrounding terrain is more or less flat. A service building lies to the north along an access road and a flare with a collection pond to the east. The landfill operator provides an up-to-date topological survey of the landfill. In this case, the mesh is 1200×1200×500 m with a mesh grid size of 5 m. The building and flare are 3d rendered as obstacles and the dense forest is represented as a diffuse cover group. The surface of the landfill is denoted as a source and divided into sectors of interest based on the landfill cover type and based on the location of the sensors. Each sector's emission may be evaluated individually in order to determine the presence of emission hotspots. The flare is also noted as a potential point source as are the individual wells over the landfill.

Parallel to the task of generating the geometry of the mesh and mesh surface classification in step 711 (digital twin generation), simulation flow and transport parameters 722 may be introduced. These parameters may facilitate the simulation by providing values for internal parameters such as diffusion of the target compounds in air, buoyancy of the compounds and boundary parameters such as typical atmospheric wind profile at the site's altitude and location, frictional parameters associated with cover type and such. These parameters 722 may be collected from scientific studies, external databases, or experimental data. These parameters 722 may be added to a generated digital twin 730 to constrain and bound the digital twin 730. Note that FIG.

8 has the same process for generation 811 of a digital twin 840, from field metadata 830 and flow and transport parameters 833.

Now with respect to FIG. 7, consider a generation of initial and boundary conditions in step 710. As stated earlier, FIG. 7 denotes an embodiment of the method where a set of reference simulations is conducted a priori to identify the relation between the virtual sources, their emission flux and the concentration measured virtually at the location of the sensor system in the digital twin simulation under simulated weather conditions. To do so, this set of reference simulations may need to include a large dataset to encompass weather conditions likely to be observed at the site as well as a combination of emitting sources at likely emission rates. A set of simulation variables [Vi] (i.e. simulation parameters) 721 may include, but is not limited to, the wind direction (varying from 0 to 360 degrees, at 1 to 45 degree resolution), the wind speed (from 0 to 50 m/s, at 0.5 to 5 m/s resolution), the air pressure (+−150 mbar around the predicted nominal pressure at the altitude of the site, at 1 to 20 mbar resolution), air and soil temperature (+70-90C, at 1 to 20C resolution), potential emission sources (their location and number is specified by the equipment or sector to be monitored), source flux (from 0.01 g/s to 500 g/s, with resolutions from 0.01 g/s to 100 g/s), surface concentrations (in the case of diffuse sources, from 0 ppm to 10%, with resolutions of 0.01 ppm to 100 ppm), hygrometry (0 to 100%, from 1% to 20% resolution) or boundary layers altitude, if necessary. The number of simulations may therefore be high due to the dimensionality of the variable space and the resolution at which these simulations may be taken and may be carefully selected based on the site's specifics. For example, it may be unnecessary to run a reference direct simulation using temperatures under −15C if the site's lowest recorded temperature is −15C. Furthermore, some parameters can be ignored if their variation does not fundamentally affect the transport result.

Each of the simulation variable combinations selected is used to generate the initial conditions (IC) and boundary conditions (BC) of a single reference simulation in step 710. This step is repeated for each available variable combination. The initial conditions may include setting the sites temperature and pressure and initial turbulence pattern within the simulation domain. The active sources and their emission flux may be specified on the appropriate boundaries, and the wind conditions may be set on the simulation mesh external boundaries. The simulation of the digital twin 730 under these conditions 731 may be executed in step 712.

In step 712, a transport simulation is performed. Flux over the site is simulated by an appropriate closure of the Navier-Stokes function, for example, using a Large Eddy Simulation (LES) model which may be static or dynamic, and the transport is ruled by an advection-diffusion model. Simpler or more complex simulation models may be used here as long as the fidelity of that model is sufficient for the appropriate source allocation and emission flux quantification within the site operator requirements. The effect of gravity and earth's rotation may be considered when appropriate, that is, when the size of the simulated site calls for it. In other words, simulation parameters may also include effect of gravity and earth's rotation. The result of the simulation is a series of fields (i.e., virtual emissions measurements), static or over time, which describe the evolution or the steady-state of the concentration of the target compound across the site and in particular at the location of the virtual sensing system, as well as other flux and transport parameters. These results 732 are accumulated for all the combinations of simulation parameters.

In particular, in step 713, the weather conditions and the concentrations of target gases can be extracted from these simulations and directly related to the simulation variables related to sources and emissions flux. That creates a set of relationships between the potential emission sources and sensor (It may be noted that the term sensor and air quality monitor may have been used interchangeable in this disclosure) for certain weather conditions observed at the sensor location. A subset of these may be selected based on a set of measurements 723 collected on the basis of real samples. In particular, the weather conditions measured from the site in a period of interest may be compared to the simulated weather conditions. For example, three samples may have been taken at 25, 24 and 25C, and with wind speeds of 1, 3, 5 m/s and wind directions of 12 degrees, 24 degrees and 15 degrees respectively. It may be therefore possible to not consider other combinations of temperature, wind direction and wind speed from the reference set of simulations. Then, it may be possible that the resolution of the reference set does not match the exact condition monitored, in which case, the results may be interpolated across multiple reference simulations. For example, the sample at 24C, 3 m/s and 24 degrees may not have been simulated, but a case at 24C, 4 m/s and 24 degrees and one at 24C, 2 m/s and 24 degrees were. The results in terms of concentrations may then be interpolated (i.e. correlated) to get a composite relationship between potential emissions sources, emission flux or surface concentrations (for diffuse sources) and sensors at 3 m/s. Additionally, multiple samples may occur in the same weather conditions, in which case, the sample concentrations may be averaged over the various observations in the same weather conditions, or any other appropriate weighed associative or multiplicative combination.

This process allows the creation of a set of relationships between virtual sources, prescribed emission fluxes or surface concentrations, and compound concentration measurements at the virtual sensor in weather conditions that matches the set of sample measurements [tx] of the real sensor over a period of interest. This relationship may be stored in a direct matrix 733. The purpose of the inverse method is to identify the inverse relationship between source and sensor; namely, given certain weather conditions measured at the sensor, this method predicts the configuration of emitting sources and source flux/surface concentration from the measured concentration at the sensor during a period of interest. The direct matrix 733 then needs to be inverted. In general, the matrix 733 is an injection and may be ill-posed (generally due to rank deficiency); as a result, an inverse generation method may be necessary to inverse the matrix in step 714. The most trivial method is to use the Moore-Penrose generalized inverse, which pads the relationship with zero eigenvalues, but any suitable inversion method may be used, in particular methods that specify more complex eigenvalue estimates; for instance, by complementing the solution space by appropriate fits that may minimize various norms or by constitutive-based approaches based on the nature of the equations used to calculate the transport problem. Regularized generalized inverse strategies may also be taken.

The end result of that inversion process is an inverse relation matrix 734 that predicts the sources and their emissions or surface concentrations from a certain concentration observed at the sensor and given certain weather conditions. The inverse matrix may be evaluated for quality using its conditioning number as an error indicator or any relevant matrix invariant. In case of a bad condition number or equivalent error indicator, the condition number may be improved by varying the dimensionality of either the image space or the initial domain. In practice, this means that a larger number of observations may be chosen or that potential sources may be eliminated from the search in the hope of improving the well-posedness of the problem. For example, if the wind direction does not shift enough during the inspected period to observe all the potential sources of emissions, it makes sense to either eliminate from the relation matrix the sources that have no chance to be detected by the sensor (a source north of the sensor may not have a plume detected by the sensor if the wind is predominantly from the east in the sampling period), or by adding additional samples from an extended testing period where a sufficient number of wind directions are sampled to detect plume from all the potential sources of emissions.

A follow-up method for improving the quality of the inverse may also arise from regularized or tailored padding inverse generation methods, where the regularization or padding parameters may be explored in order to minimize the error indicator associated with the inverse matrix 734, thereby improving the prediction accuracy of the method. Once a satisfactory inverse relation matrix 734 is obtained, a regularized identification method 715 may be attempted. The trivial operation is to perform a matrix vector operation where the matrix is the relation matrix 734 and the vector is the set of concentration or concentration averages as observed by the sensor in the sample period of interest. If both the model and the detection instrument were perfect, this method could be applied straight away. However, the model and instrument are subject to error, which is generally greatly amplified by inverse methods. It may be therefore advantageous to regularize the inversion method. This may be done by adding constraints to the matrix operation, akin to a minimization, where the weight of the constraints may be tailored to optimize the result. For example, one potential constraint is to force values to remain close to the mean. Other methods may introduce ad hoc information about the error bounds of the instrument. Other strategies may be used for regularization for that purpose.

The weight of the regularization may be obtained using tools such as an L-curve optimization. In general, one may use similar inverse methods as the ones used for MRI image generation or seismic mapping. The result of the regularized identification method 715 is a prediction of the sources that are actually emitting the target compound and an estimation 735 of their emission rates for both point and diffuse sources and/or their surface concentration in the case of diffuse sources. Parallel to this process is an uncertainty quantification process 716 which may provide an error estimation 736 on both source identification and emission flux/surface concentration. The initial way to generate such error estimation is the estimated errors associated with the inversion matrix (through the intermediary of its condition number) and the upper bound of the measurement error (given by the sensor system accuracy and precision in both gas concentration and weather measurements). This error upper bound can be propagated to the result and used as a tolerance in the final result. For example, if the sensor system has a 1 ppm precision and accuracy, the surface concentration at the source is estimated at plus or minus 2 ppm at best. Furthermore, if the coupling is weak, say if a 10 ppm concentration at the source results in a 1 ppm concentration at the sensor for some particular transport conditions, the error at the source surface concentration is at best of plus or minus 20 ppm for the same sensor precision and accuracy. Similar error estimation may be given to propagate the transport model error on the end result.

Another strategy for uncertainty quantification 716 is to use statistical or Bayesian inference throughout the process. That is, rather than solving the problem for a set of deterministic variables, probability distribution functions are used for these variables to indicate uncertainty; this results in a propagated uncertainty throughout the process which can then be used for error estimation. One advantage of this is that bottlenecks in the method may be identified through this approach such that they can be addressed either by improving the model or sensor system, or inversely by limiting computational or experimental efforts. For example, it may be unnecessary to simulate cases with wind direction at a resolution of 1 degree if the wind vane is only precise at 3 degrees. The uncertainty propagation can be tailored such that the uncertainty remains uniform across the solution space. Another advantage is that the probability of identifying a source may be extracted from that uncertainty quantification, and a percentage of source identification accuracy may be given.

Figure 8A:
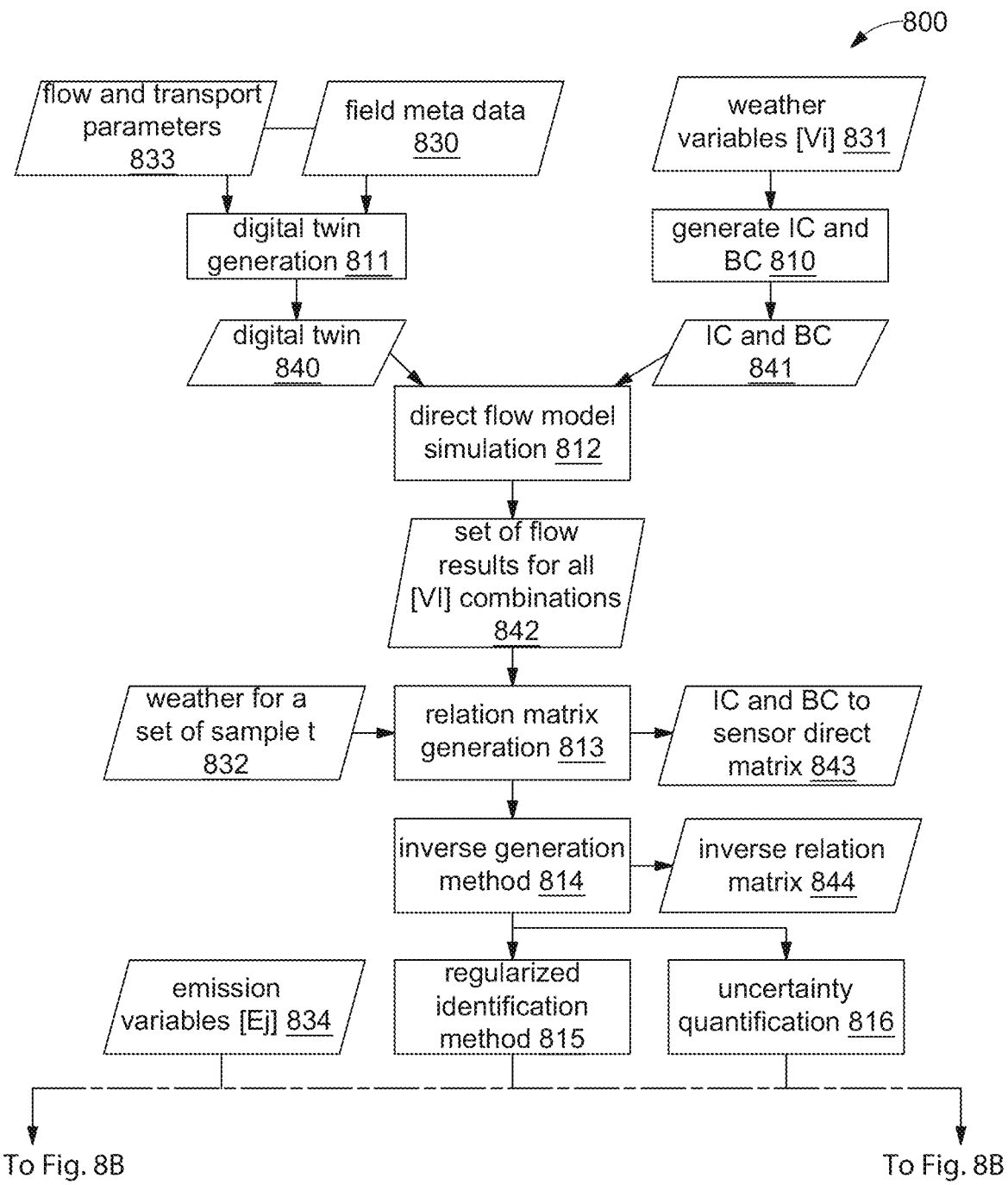
FIG. 8A-8B illustrates another embodiment of a method to quantify, qualify and localize sources, in accordance with an illustrative configuration of the present disclosure.
Figure 8B:
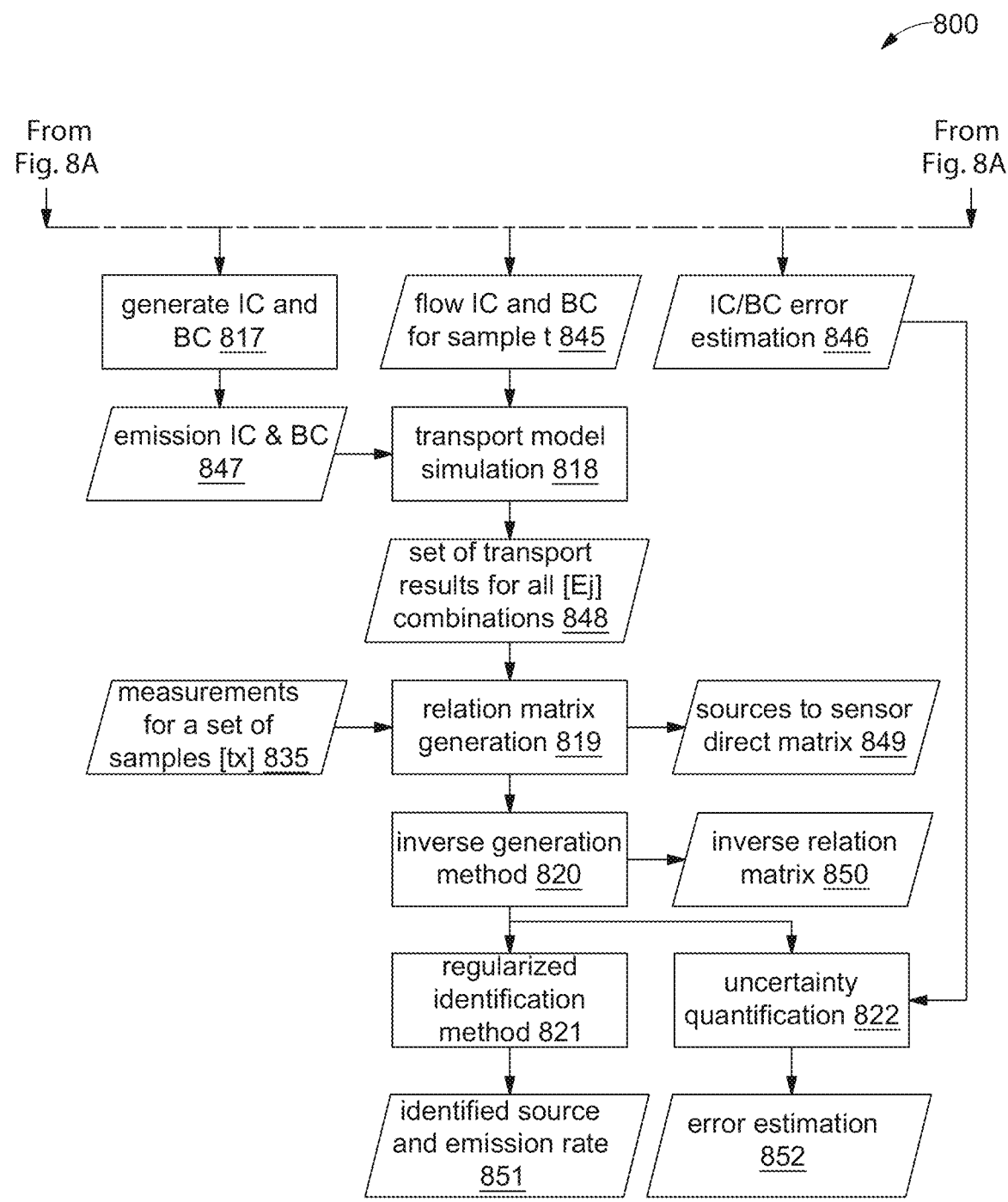

Fundamentally, the method in FIGS. 8A and 8B (generically referred to as FIG. 8) is similar to the one given in FIG. 7. In particular, steps 819, 820, 821 and 822 as well as data 835, 849, 850, 851 and 852 have similar description to steps 713, 714, 715 and 716 as well as data 723, 733, 734, 735 and 736, respectively. The principal difference between the method of FIG. 7 and FIG. 8 is that two distinct inverse methods are solved in the method of FIG. 8, namely that the weather conditions are first matched with an inverse problem and then the transport problem is solved, rather than a single inverse problem as in FIG. 7. This may be of interest when more complex weather conditions need to be simulated for accuracy purposes; for example, in a case where the wind is dynamic and not static during the sampling. In this case, it may be computationally intractable to simulate all the potential weather conditions, such that an inverse problem may be solved to identify the weather initial and boundary conditions that match the observed weather pattern during and preceding the air sample.

In the step 810 a set of initial and boundary conditions is constructed from weather variables [Wk] 831. These variables may be defined by first processing similarly to in FIG. 7, by using an interpolation of the average weather conditions at the sensor to derive the average weather condition at the boundary of the domain. This may provide a restricted domain to identify the dynamics of the weather condition around this average. The weather variables may be formed as a time basis over the duration of a particular sample. For example, the wind speed may be decomposed over time into a set of test functions that span the time domain such that wind speed variations during the sample may be accounted for. This may be done for all the weather variables and a set of initial conditions and boundary conditions is found 841. This set is used, together with the digital twin 840 to perform a direct flow simulation in step 812.

These direct simulations may be dynamic simulations over the time preceding and during a sample such as the flow of all the air parcels contributing to the sample are represented. The result 842 is given as a flow field over the domain, in particular at the location of the sensor. A direct relation matrix is then generated in step 813 from this which relates the initial and boundary conditions of the domain and the observed flow and weather conditions at the sensor 843. An inverse generation method 814 may be used to form an inverse relation matrix 844 which relates the weather measurements at the sensor with the initial and boundary conditions. A regularized identification method 815, similar to the one described in step 815, as well as an uncertainty quantification method 816, similar to 716 of FIG. 7, is then performed to identify the initial and boundary conditions that led to the weather measurement of the sample t 845, as well as error estimation 846 on the quality of that boundary identification.

A set of direct transport simulations 818 can then be run for that sample t. Initial and boundary conditions of the sample t 845 are used together with source initial and boundary condition 847 for these simulations. Indeed, a set of emission variables [Ej] 834 is formed to test all the potential sources, their emission flux and surface source concentrations that may contribute to the concentration of the target compound at the location of the virtual sensor in the model under flow conditions 845. Sources and emissions are used to generate the initial conditions and boundary conditions associated with a certain source distribution in 817. The emission initial and boundary conditions 847 are then used in the transport model simulation in step 818.

Step 818 is repeated until all the simulations associated with each set of combinations of the emission variables are completed. This process (813-818) is repeated for each sample t of a certain period of interest. The sets of all transport results for all combinations of [Ej] for each estimated boundary conditions for obtaining the weather measurements at sample tin a set of interest [tx] is given in 848. The process in steps 819 to 822 is then similar to steps 713 to 716 in FIG. 7, namely that the relationship between source, emissions, and sensor concentrations for that time period of interest is obtained (819,849), that relation matrix is then inverted (820, 850), and an identification method 821 and uncertainty quantification 822 are performed to identify sources, their emission flux or surface concentrations 851 and their error bounds 852. Note that the uncertainty quantification 822 of FIG. 8 has the specificity of being propagated from the error estimation 846 evaluated for the specified boundary conditions.

Note that the methods described in FIGS. 7 and 8 may also be used in multiple target gas identification methods. In these cases, not only the source identification, their flux and or surface concentrations are sought, but as well their compositions with respect to the target gases. For instance, it may be possible to track both methane and propane at an oil and gas site, and different potential sources may emit different composition ratios, for example, the liquid tank emissions may contain a much larger fraction of propane than methane, when compared with a wellhead emission.

Figure 9A:
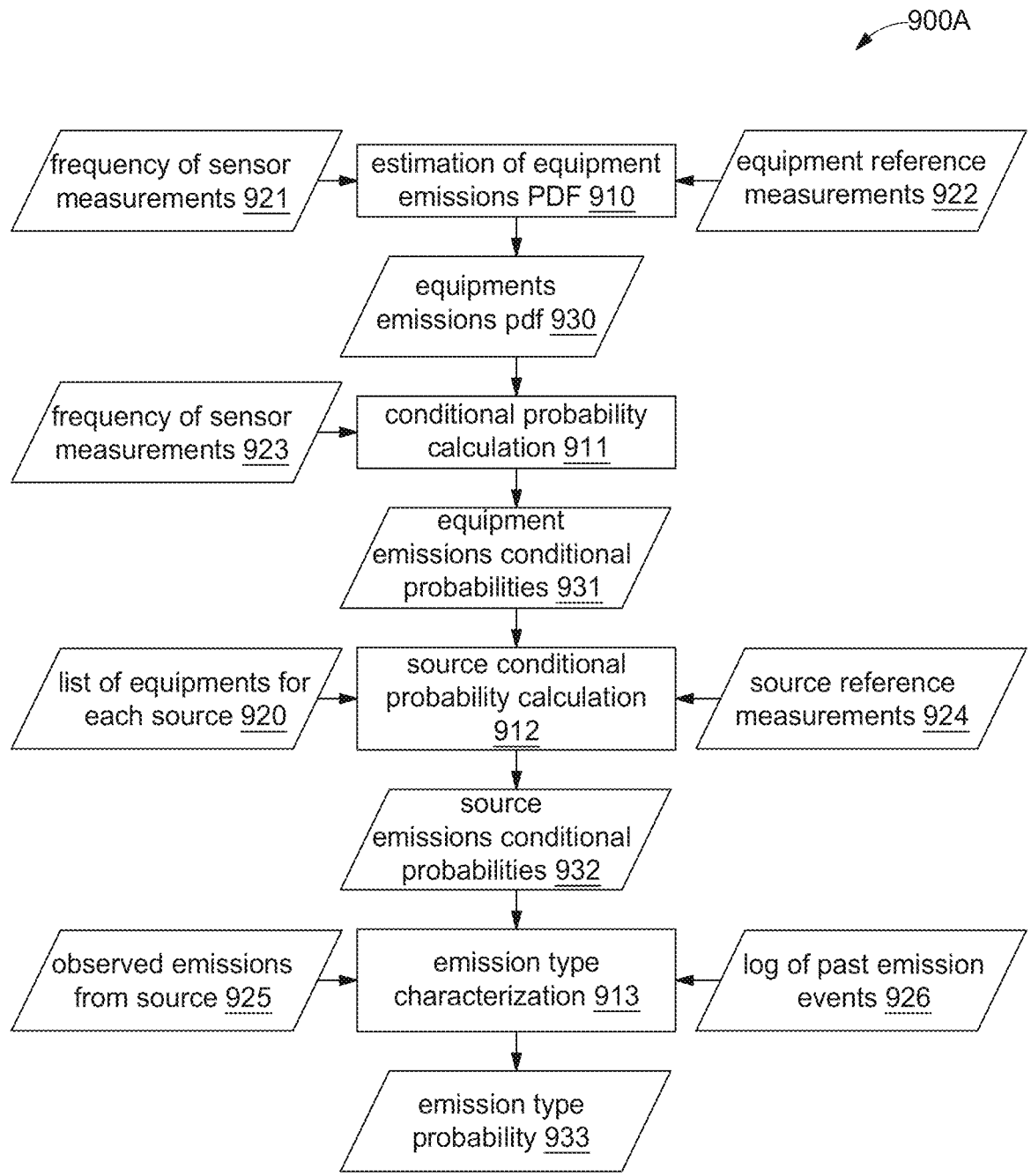
FIG. 9A illustrates an embodiment of an operational flowchart for the qualification of emission type using statistical inference, in accordance with an illustrative configuration of the present disclosure.

The methods presented in FIGS. 7 and 8 are possible embodiments to localize and quantify the emissions and their sources. Possible embodiments for the qualification of source with respect to their type is presented in FIGS. 9A and 9B. FIG. 9A presents a flowchart 900A for construction of a statistical inference method where the emission type is distinguished from another by their characteristics in terms of composition, frequency or duration and intensity. This is particularly important to distinguish between allowed emissions and leaks since some equipment or activities may emit the target compounds as part of their normal operating process. One potential first step may be to create an estimation of the probability density functions of equipment emissions 910. This can be done by collecting detailed descriptions of the equipment behavior currently deployed at a site 921, which may include information or estimations about the emission frequency, intensity, and composition in normal operating conditions. This may be obtained from the site operator or from direct observation of the equipment type and using manufacturer- or industry-specific information to aggregate the emission frequency, composition, and intensity for the deployed equipment. Another source of information may be equipment reference measurements 922, either for each type of equipment for a period of time or for the whole site to be observed, when the operations are supposed nominal (i.e., no leaks). This may be done, for instance, just after installing the monitoring equipment by first completing a full maintenance of the equipment for nominal operations and by observing the subsequent equipment reference behavior using the sensor system described herein in order to generate a set of reference measurements 922. These measurements are then analyzed using appropriate statistical methods to extract the expected equipment emission frequency, intensity, and composition in normal operations. Similarly, specific failure modes resulting in fugitive emission may also be qualified if at all possible. For example, a stuck open valve may be voluntarily simulated to evaluate its emission profile if such an event did happen by accident. The result of this analysis is a set of statistical data characterized by probability density functions for the emission frequency, duration, intensity, and compositions 930.

The characteristics of the sensor measurement 923 are considered in step 911 by the computation of conditional probabilities. Indeed, based on the sensor system placement, frequency of measurement of a certain equipment group, accuracy and precision of emission intensity, duration of sample and so on, the conditional probability of the observation of an emission given the characteristics and limitations of the sensor system is calculated from each equipment probability distribution function 930. The conditional probabilities of equipment emissions 931 may be used to generate composite conditional probabilities for each source in step 912.

Figure 9B:
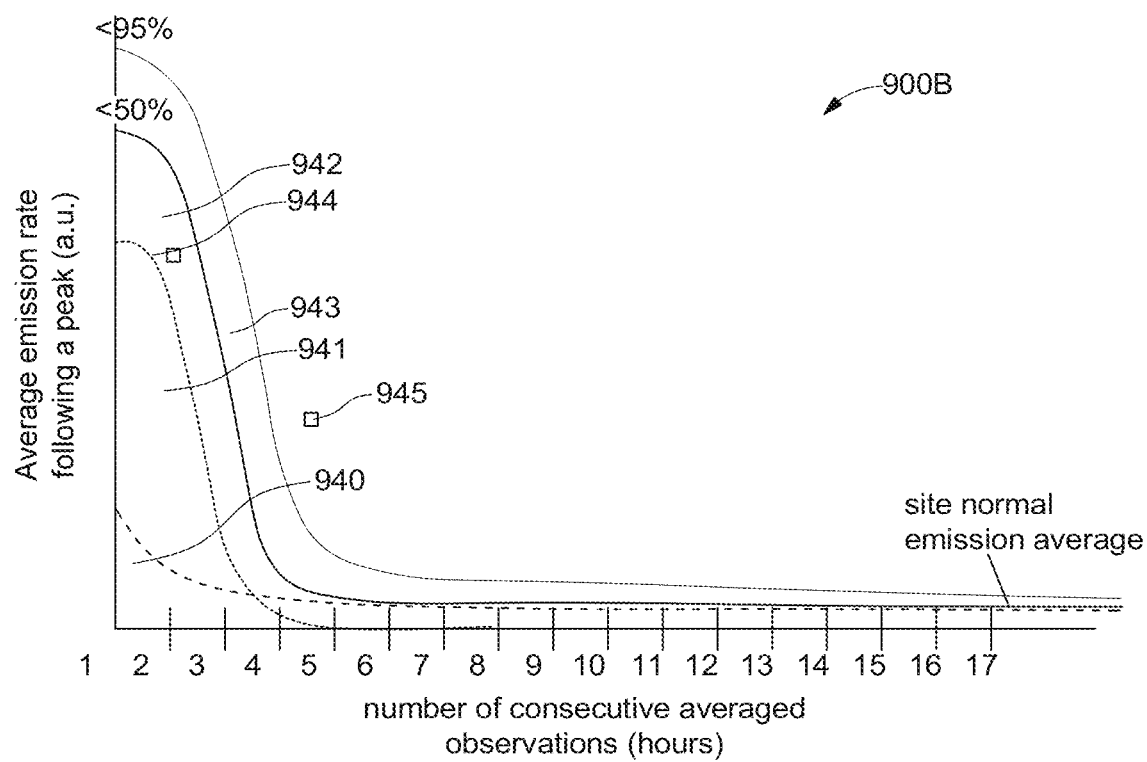
FIG. 9B illustrates an embodiment of a certain unqualified fugitive leak identification method through a graph, in accordance with an illustrative configuration of the present disclosure.

Indeed, a source may contain multiple equipment types. This may be generated as a composite of the equipment emissions conditional probabilities if a list of equipment for each source 920 is obtained, or it can be constructed directly through the process 910-911 if source reference measurements as a whole 924 are given. This leads to source emission conditional probabilities 932 as observable by the sensor system. In step 913, these probabilities may be used to qualify the emission types of various observed emissions from the source 925, obtained by the sensor system. The conditional probability could be less adequate over time due to a plurality of factors such as weather conditions, seasonal changes, and operational changes at the well and shall be considered in a differential manner; that is, the record of past emissions events 926 from that source may be used to continuously refine and update the initial conditional probabilities such that the number of false positives are minimized. In practice, the probability of an emission as observed by the source over a period of time is calculated from these conditional probabilities 933. For example, in a natural gas upstream onshore site, a liquid unloading event may be identified when a high intensity, short duration and low frequency event involving mostly liquefiable hydrocarbons occurs; this may be distinguished from high frequency, short duration low intensity events such as methane puffs from pneumatic controllers. The probabilities obtained 933 are analyzed and ranked based on likelihood. Emission events with high probabilities to be identified as a specific event or equipment type are sorted. Unsortable events which are unlikely to be normal equipment emissions may be identified as outliers. If such outliers have high intensities, these may be identified as fugitive leaks. An embodiment of a certain unqualified fugitive leak identification method through a graph 900B is illustrated in FIG. 9B. In FIG. 9B, consecutive measurement averages as observed from a particular source are compared after a specific peak event is detected. The curve 942 denotes the limit under which 50% of the nominal emissions are typically observed. Note that on small time intervals, the emission intensity average may be high, because it is dominated by normal high-intensity low-frequency events, noted by 941, which may occur, such as liquid unloading. At long average periods, the curve 942 tends toward the site long term nominal emission average. 940 denotes the contributions from equipment that emits at low intensity but at high frequency, as exemplified by their large contribution to the site overall average over time. The curve 943 denotes the limit at 95%, for which 95% of the observed normal emissions are under the curve. Thus, these curves may be used to identify the outliers. For instance, note that 944 is under the 50th percentile and may likely be a normal emission. Furthermore, its high intensity makes it a likely contender for a high-intensity, low-frequency event of the type depicted by 941. On the other hand, measurement average 945 is outside the 95 percentile range, it may therefore be a fugitive emission, even if 945 intensity average is lower than 944. This method may be used to qualify the leaks. Note that the probability of some low-frequency event may collapse. For example, if only liquid unloading are responsible for 941, and if a liquid unloading occurred the week prior, the probability of a new liquid unloading this week is extremely low, which would make curve 941 collapse and reduce the intensity of 942 and 943. In this case, 944 may be considered to be a fugitive emission. It is therefore important to keep track of infrequent events in order to adapt the conditional probability to the specifics of a certain site's activity. Note that in general, leaks are either continuous or intermittent and can be generally identified in outlying deviations of the long term average, but early detection may be of interest as well. The embodiment of FIG. 9B may be supplemented with deviation estimates such as the calculation of a weighted integral of the evolution of observations averages over time and comparison of this metric to the 95% average.

Beside the detection, localization, quantification, and qualification of the emissions of a site for certain target compounds, specific metrics of interest may be considered such as total site emissions. A method of computation of such emissions is proposed herein.

Assume that detection, localization, quantification, and qualification of emission has been performed and that emissions are characterized for the site over contiguous time periods where both emission and weather have been measured and calculated.

In the case of point source and diffuse sources where the emission flux is known, this may take the form of average emission flux for all the emitting sources on the site over periods T, following each other. The average total emission of a site may simply be calculated as the sum of each emission flux for all point sources, which may be weighted by the estimated start time of each source emission, interpreted based on their probability of intermittency and smoothed over time. This process may provide a total emission estimation from one period to the next. Interpolation considering diurnal effects and seasonality may be used for padding the total flux estimate when measurements were unavailable, and total emission flux for periods of interest such as a week, a month, a quarter, a year or so on may be evaluated.

In the case of some diffuse sources, the emission flux may not be known directly, and surface concentrations may be known instead. This may be the case for sources at low pressure and high reservoir, where the emission flux actually depends on the transport rate. Assume that the surface concentration of a diffuse source across multiple sectors is known as an average for a certain time period and that weather conditions are known in its vicinity. A direct transport simulation of the digital twin of the site may be performed using part of the method described in FIGS. 7 and 8. This simulation may be run with boundary conditions that match the weather conditions measured during the time period as well as the surface concentration as measured on the source surface. The direct simulation is then conducted for all the weather conditions as measured during the sample period and the outbound emission flux is calculated at virtual surfaces enclosing the source. Indeed, the flux may be calculated this way by measuring the concentration and area of all the virtual surfaces enclosing the source and multiplying it by the normal to the surface component of the local velocity field. This is equivalent to the mass conservation method employed for plume cross-sectional computation of flux but is conducted on the simulated digital twin. As a result, the flux of emissions may be known over time for a diffuse source from ground concentrations and wind measurements using a simulation model. Note that this method may be applied with measurements of the ground concentrations of the source, rather than calculated by an inverse method as in FIGS. 7 and 8. Indeed, this may be a practical methodology for landfill total emission estimation as landfill surface concentration measurements are routinely conducted to identify hot spots. The further use of wind measurement can then complement the measurement of surface concentrations, together with a digital twin, to provide a novel method for total landfill emission calculation.

One particularity associated with the use of a static sensor system for the detection of a particular emission is that the detection threshold of an emission may vary greatly based on external factors related to the transport of that emission from the source to the sensor. For example, a source hundreds of meters away from the sensor may be easily detected if a direct path and frequent weather pattern lead to the transport of the emission plume to the sensor, while a source of equivalent intensity, mere meters away, may never be detectable due to an impassable obstacle. Source interference may also be at play, for example when two sources are not separable from each other for being too close together or from presenting a similar angle of view from the perspective of the sensor, the closer source thereby partially occulting the more distant source. These considerations are schematically approached in FIGS. 10A-10D, representing in turn an idealized sensor 1020 and its detection limit 1021, the effect of local wind as exemplified by a wind rose 1023, the effect of topology as depicted by the isocline 1022 and the effect of occlusion by an undesirable source 1024, respectively.

Figure 10A:
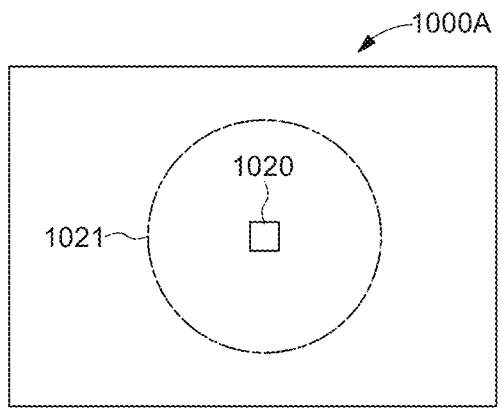
FIGS. 10A-10D illustrates a set of figures representing the effect of terrain, usual wind pattern and source separation on the detection area of a sensor deployed in the field, in accordance with an illustrative configuration of the present disclosure.

In FIG. 10A, a view of a schematic map of a sensor system 1020 is given. In this example, the topology is supposed to be flat, with no rheological effect from the ground. If the sensor detection limit is supposed constant and the weather uniform with wind direction equiprobable, the intersection of the detection limit of a source with a plan parallel to the ground is a circle. If the wind has no altitude term (normal to the ground), then the three-dimensional view of that limit is akin to a cardioid centered on the sensor. In practice, the detection limit may take complex form due to external factors; some of them are presented in FIGS. 10A-10D.

Figure 10C:
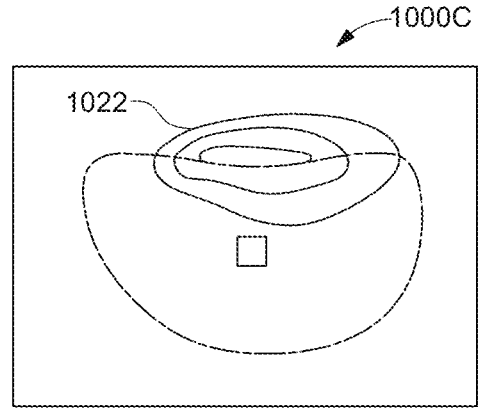
Figure 10B:
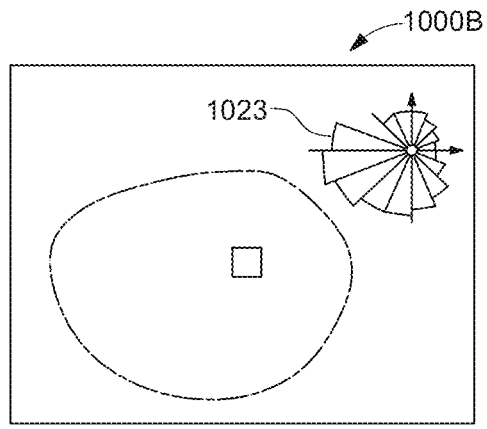

In FIG. 10B for instance, an average wind rose diagram 1023 related to wind speed for a period of interest is given.

This deforms the detection threshold of the sensor system, allowing for detecting emission further away in the direction of faster and recurring wind. This is because of the relative weight of diffusion and advection on the transport of the emission, and faster wind increasing the distance at which a high concentration may be observed. Similarly, repeated observation in the same wind direction may reduce the effect of the noise of the sensing by averaging and decreasing the detection threshold of the system. The result is a non-uniform detection threshold curve.

Figure 10D:
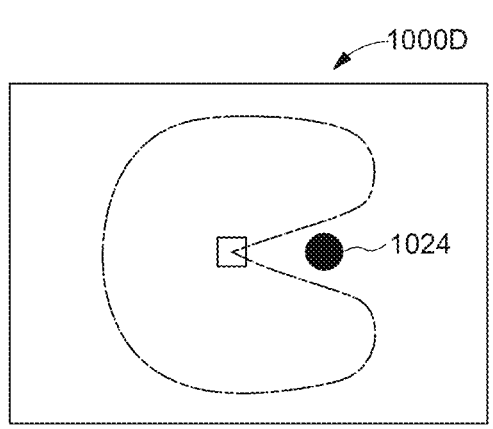

The effect of terrain and topography 1022 on transport is evaluated in FIG. 10C. As mentioned earlier in this disclosure, wind patterns may avoid obstacles which give rise to curved streamlines. If a topological feature 1022 lies in the detection area of a sensor system, this detection limit may follow the weather pattern topology and likewise shape itself following average streamlines. Further, in FIG. 10D, source 1024 may cause obstruction that limits the detection threshold in its vicinity. This can occur when one observed source blocks the detection of another source of interest in the same angular region, when two sources are not distinguishable because of being too close to each other, or when undesirable sources are interacting with the sensor. In FIG. 10D, an undesirable source 1024 is located within the detection area of the sensor. The detection area is then sharply reduced in the vicinity of that source because a source in the vicinity of source 1024 may be confused for source 1024.

Such consideration as presented in FIGS. 10A-10D may be taken into consideration when selecting placement of the sensor within a site and optimization of sensor networks which maximize detection while minimizing the overlap of sensor detection areas. Note that while one may use the concepts presented in FIGS. 10A-10D and other adjacent concepts to create ad hoc rules for sensor system positioning, this may only be performed in a qualitative manner. In order to effectively evaluate the practical detection area of a sensor, one may use an experimental or modeling approach. The experimental approach optimizes the positioning of the sensor by comparing expectations in detection to actual detection in the field, therefore effectively measuring the position of the detection threshold. This may be done using the potential sources themselves to generate data or by using a tracer correlation method. Another method relies on simulation to provide adequate information and estimation of the shape and size of the detection threshold. To employ such a method, one may use the direct transport model over a digital twin of the prospective site. The detection threshold may be found by testing the source-to-sensor coupling virtually by providing simulated test sources at various positions and distances from the sensor, therefore fully characterizing the detection area. Another simulation technique may only use the sources of interest and verifies that each potential source is located within the detection area of the sensor by simulating virtual leaks from each source at the wanted flux or surface concentration threshold. This may also be conducted at the network level, which is for large sites which may require more than one sensor.

Using this strategy, the detection area of a sensor may be described and fully utilized to the limit of the sensor system, thereby reducing the number of sensor systems to be deployed and maximizing coverage. In some embodiments, detection speed is also of interest, in which case redundancy of coverage from multiple sensors may be used to maximize the speed of detection. Indeed, wind direction may shift during observation and every detection that should occur faster than the characteristic time necessary for the wind to cover most directions may require more than one sensor in order to be detected in time. This requirement may be added to an optimizing network algorithm running the direct transport simulation. The positioning of the sensor may be adjusted in this simulation to provide maximized coverage at the necessary detection threshold and detection speed. This optimization may be performed by a random search (e.g., Monte Carlo method) of the space of positions for the sensor in which a minimum is sought that reduces the number of sensors and increases coverage. Other directed algorithms may be used, such as genetic algorithms or gradient-based algorithms to identify configurational minima. Machine learning, neural networks and other AI-based approaches may be used to provide adequate initial guesses to accelerate this optimization. Human experience may also be used for an initial guess.

The objective function that governs this optimization may be defined in success/failure metrics or by progressive scores such as measurement over detection thresholds and detection speed over desired detection speed. Measurement over detection threshold ratio may be optimized to be superior to 1 and detection speed over desired detection speed may be optimized to be inferior to 1. A minimum-maximum optimization is then performed to maximize the realization of the objective function while minimizing the number of sensor systems used.

The number of sensors and their position can then be chosen for the site by selecting the best optimization result with a sufficient margin of safety to guarantee operation over time.

Figure 11A:
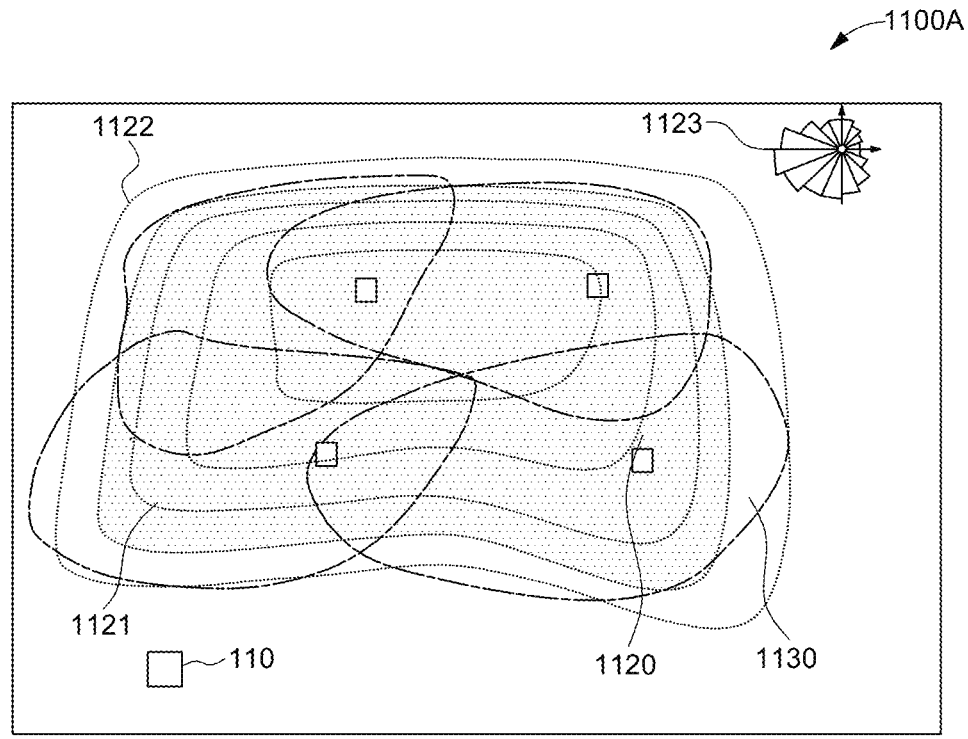
FIGS. 11A-11B show two symbolic maps of sensor network deployments for a diffuse source area and for point sources, respectively, in accordance with an illustrative configuration of the present disclosure.
Figure 11B:
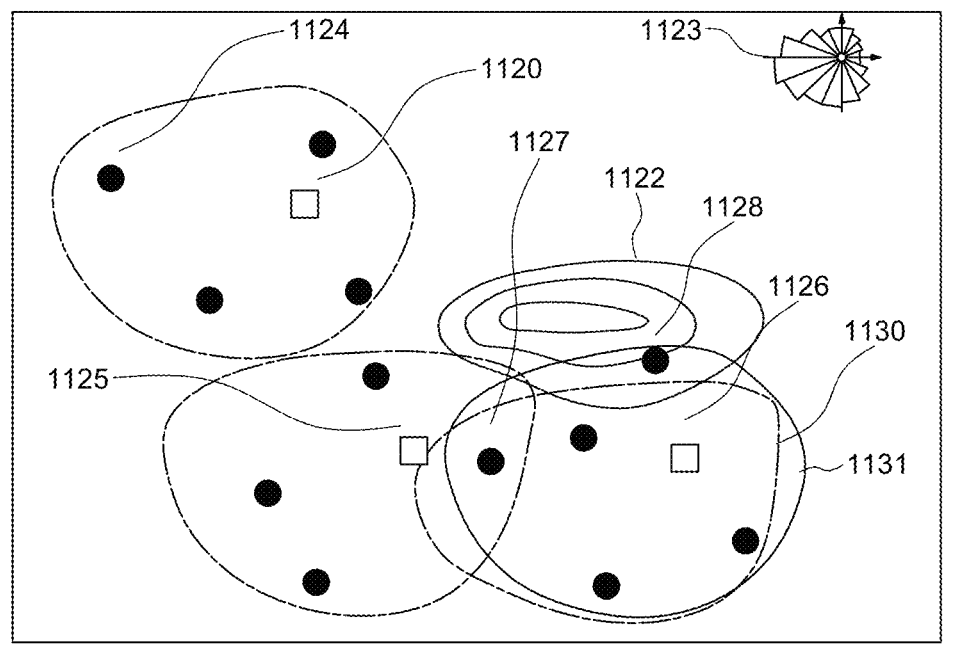

FIGS. 11A-11B illustrate symbolic maps 1100A and 1100B of sensor network deployments for a diffuse source area and for point sources, respectively. The symbolic map 1100A of FIG. 11A is constituted of two sensor networks, for a large diffuse source akin to a landfill. The symbolic map 1100B of FIG. 11B is for a site with multiple point sources, akin to an onshore natural gas field with multiple well pads. In both cases the wind speed and direction distribution are given by the wind speed rose 123.

FIG. 11A shows four sensors 1120 deployed on a mound that is akin to a landfill. The isoclines 1122 denote the altitude change and the greyed area 1121 the diffuse sources. The dotted line 1130 indicates the detection threshold of the sensor 1120. It should be noted that a quasi-total coverage of the diffuse source is realized by the sensor placement choice and that the area of detection of each sensor is influenced by both the wind pattern and the topography of the land. Such a complex detection area may not be easy to define without a digital twin simulation without redundant coverage necessitating more sensor systems to be deployed. The diffuse source may further be divided into sectors that have equivalent emission contribution to each sensor and consider sensor area detection overlap.

FIG. 11B illustrates the deployment of sensors in a field with many sources (indicated by solid black circles) 1124 and three sensors (indicated by white hollow squares) 1120, 1125, 1126. Sensor 1120 detection area (dash-dot line surrounding 1120) is mainly influenced by the wind pattern, while sensors 115 and 1126 are also influenced by the topology noted by the isocline 1122. The grey line 1131 denotes the hypothetical detection area of the sensor 1126 if the topology was not considered. Note that the source 1128 is not actually contained in the detection area of any sensor even though 1126 could hypothetically detect source 1128 were topology 1122 not present. Similarly, source 1127 may be detected by either of the two sensors; in practice, 1127 may be partially occulted by another source from the point of view of sensor system 1126. The coverage of the source 1127 by the sensor system 1625 provides distinguishable coverage of 1127.

The examples of FIGS. 11A and 11B exemplify the need for optimization in the deployment of a sensor network and the need for a fine understanding of the effect of external variables on the behavior of emission transport. The methods presented herein cover both conceptual, experimental and simulation approaches to optimize a network of deployed sensors that monitor emissions in real time. In some embodiments, the systems can include an air quality monitoring system and/or other systems or components disclosed herein. FIG. 11A illustrates the system including the air quality monitoring system 110 discussed in connection with FIG. 1 and can be programmed to receive output from the sensors 1120, 1125, 1126 via wireless, wired, and/or optical connections.

One embodiment of the disclosure concerns a method to generate emission predictions, preventative maintenance predictions, and targeted equipment and process replacement from existing data streams that may be interpreted to quantify, qualify, localize, and reduce emissions. Another embodiment of the technology can be a hybrid inspection method that may involve additional sensing modalities beyond static, real-time sensors, namely, fence-line monitoring, operator-based, drone-based, plane-based, or satellite-based systems that may or may not be used in conjunction with stationary sensing.

Another embodiment of the technology is a method for the monetization of emission reduction by taking advantage of financial markets. The systems can be programmed to identify emissions, track emissions (e.g., track for emissions credits/compliance), and manage emissions by controlling equipment, generating schedules (e.g., operation schedules), etc. For example, the system of FIG. 11 can be programmed to monetize emission reductions based on one or more monetization algorithms. Sensor deployment techniques discussed in connection with FIG. 4C can be used to select the number of sensors, sensor position, etc.

The quality of the information obtained by existing datastream analysis may be enhanced by increased inspection frequency such as through the static monitoring device described herein and may justify the usage of static monitoring for some sites. However, real-time monitoring may not be the most cost-effective method for inspection for all the sites or at all times. A method for dynamically selecting the most effective inspection method based on the datastream described above is presented herein. Other inspection methods such as operator-based, drone-based, plane-based, satellite-based or fence line monitoring may be used together with continuous monitoring from static sensors to provide a holistic approach to monitoring. Indeed, some sites may have topological, environmental, technical and/or economic criteria that would make a particular embodiment of a compound monitoring system more worthwhile from an emission reduction perspective at a certain time. For example, densely packed oil and gas production sites that produce large volumes, as well as compressor stations, tank batteries or other concentrated sites with a large number of potentially emitting sources, may be ideal for continuous or close to continuous monitoring; while remote, sparsely located, low production volume sites may gain from being monitored less frequently by aerial inspection. Similarly, the emission risk over the life of the equipment may change significantly and as a result the optimal inspection strategy may change over time. Finally, the overlay of different inspection methodologies may change the inspection requirements of a site based on the availability of information about emission at a certain time and the rapidity with which a particular inspection embodiment can be deployed.

The technology can dynamically blend different data-sensing methodologies to provide a hybrid method which may utilize more of the advantages of multiple embodiments of disparate systems for the measurement, quantification, localization, qualification of emission of certain compounds as well as for the reduction of such emissions, all while optimizing for capital utilization. Different types of sensors can be used on a site. The number of sensors, sensor functionalities, and/or sensor configurations can be selected based on the sensor locations.

In particular, the analysis from the existing datastream informs about which sites are large emitters and which sites are emitting less. If an operator has many sites, such as in the upstream oil and gas industry, having different approaches for different sites may be a cost-effective emissions reduction strategy. For example, in the oil and gas upstream market, approximately 20% of sites may be responsible for 80% of the leaks by volume. This would suggest that the budget dedicated for monitoring, as well as the frequency of monitoring, should be highest in this 20% of sites. These sites may be identified through the data streams presented herein. Prevalence of failure points also influences the necessity of monitoring. An oil and gas site, for instance, with numerous wells and other systems such as separation units, tanks, injection pumps and so on will have more emissions and more leaks than a site with lower equipment counts. The average number of failures or leaks per equipment type may be predicted from a maintenance report, and the combined number of failures or leaks per year for a site may be calculated from these equipment failures or leaks or extracted from the maintenance or leaks report data streams. In particular, frequency of monitoring may be set in relation to the frequency of failure or leaks of a certain site. In some cases, the frequency of monitoring may be predicted as lower than the mandated inspection frequency, in which case no additional monitoring may be required. In other cases, the frequency of monitoring needed may be higher than the mandated inspection frequency in which case additional monitoring may be prescribed. The schedule of that additional monitoring may be selected to minimize the uncertainty associated with the state of the equipment from the site. For instance, for a site mandated to be monitored once a year, it may be necessary to add the additional monitoring step at the six-month mark such that monitoring inspections are equally spaced in time. This scheduling may be influenced by other factors such as seasonality, operational state of the site, density of neighboring site or other factors. For instance, monitoring for butane gas leaks in Alberta during wintertime may not be sensible because butane does not vaporize at low temperatures. Another factor of interest is the intensity of the leaks. Scientific literature suggests that the emission of typical airborne compounds of interest (e.g., methane or other compound) can generally follow the 80/20 rule, meaning that 20% of the largest leaks emit 80% of the compound. This means that this larger type of leak, while less common, emits more than an average-sized leak. Other rules can be determined and used. Identifying the sites or equipment with the highest probability of large leaks can inform the order or priority of inspection, maintenance, etc. A third factor of interest is the intermittency of leaks. Some leaks are intermittent at a certain frequency, and this informs the frequency at which the measurement needs to be performed. A fourth factor is the response time of the operator.

Indeed, certain sites are inaccessible, and the operator may not be able to respond rapidly to a leak, in which case the rapidity of measurement may matter less than the certainty of it. A fifth factor is the possibility of overlapping inspection methodologies. For example, one may use satellites at the field level to inform of leaks sufficiently large to be detectable from space, which may dynamically trigger inspection visits to target sites, reducing the cost of monitoring a large area. A sixth factor is the proximity of various sites. Indeed, sites sufficiently close together may be inspected by a single static monitor, therefore amortizing the instrument cost over multiple sites.

Leaks are not the only type of emission that may be observed, identified, and/or analyzed at a site. A large fraction of emissions can result primarily from the activity or from the operation of the equipment. If the total emission is of importance from an inspection standpoint, real-time (continued or periodic) or frequent inspection methods may be of interest.

Externalities such as weather and remoteness of the site may influence the best method to be used. High cloud cover can for instance block observation from space and harsh weather conditions and low communication infrastructure can influence the cost of deployed sensors.

The return on investment for a certain inspection method may reduce with frequency: once initial leaks are repaired, a long period of time may elapse before new leaks occur, meaning that the probability of leaks is dependent on the history of the site and may widely vary. Thus, the use of datastream and statistical inference of the conditional probabilities of leaks is tremendous for the prediction of potential leaks and appropriate inspection schedules and methods. The proposed method weights these various factors to select the most appropriate inspection embodiment.

The advantage of each inspection method is described herein. Static monitoring through a single sensor or through a network of sensors may provide high-frequency measurements, with tailored detection thresholds based on the distance of the sensor to the potential source, and address at least equipment identification, as presented in the disclosure. Because the sensor is static, the cost of the inspection is determined by the number of potential leak points observable in the detection area, site size, and the cost of ownership of the sensor system, which may be higher than a mobile solution on a per-year basis. The advantage of a mobile solution could be the possibility of amortizing the measurement price on a larger number of potential sources to the cost of lower frequency and/or lower detection limit. For instance, drones may be used once per quarter and have a low detection limit, while satellites may have a 24-days frequency and cover large swaths of land but only detect the largest leaks. Monitoring by plane falls in between the satellite and the drone, and thus could offer a balance of price, inspection frequency, and detection limit. Manual site inspections or operator-based inspections are driven by the cost of labor and a variable measurement quality depending on operator competency, but these inspections can generally pinpoint the leak location and partially assess their size. Similarly, a larger firm could amortize labor costs across many sites, whereas smaller firms may pay more in labor costs per site.

In certain embodiments, methods can identify the best method or methods for site inspection at a given time by calculating the advantages and disadvantages as a function of the expected site emissions volume and frequency and the externalities associated with the measurements in order to maximize a measured emission volume while minimizing the cost. The higher volume of measured emission may then be used to provide a higher volume of reduced emissions.

One embodiment of the technology involves using monitoring information and data streams to enhance product recovery and emission reduction and to generate income by emissions reduction credits, such as carbon credits or added value at the sale of the product via product labeling or certification. For example, this technology could be employed to certify low-emission natural gas or biogas, or some other certification or labeling of interest, in the case that the measured compound is a greenhouse gas, valuable gas, or commoditized product.

Indeed, the detection of greenhouse gases emitted during operations may be used as a quantification of carbon-equivalent intensity. In general, carbon credits in a cap-and-trade market may be allocated based on the carbon emission offset compared to competitors for a certain product intensity. For example, a certain number of carbon allocations may be provided for a certain number of MMBtu produced in a gas field. An operator that emits fewer greenhouse gases and can demonstrate that fact through emissions quantification may demonstrate emitting less per MMBtu produced, and thereby earning carbon credits which may be sold on the carbon market for a profit. In another embodiment, in the case of an open carbon market, the measurement of carbon equivalent emissions through the use of the method proposed herein may be presented as a carbon offset method directly by quantifying the amount of carbon equivalent reduced through the application of the method and may be sold as such. For instance, the use of a static sensor may lead to the reduction of methane emissions that if related to the cost of operation of the sensor, may lead to a significantly lower cost per carbon ton equivalent than the spot price. The reduction of the carbon footprint may be evaluated, and the difference may be sold as a carbon offset on the carbon market.

The other path to revenue that commoditizes emission monitoring and reduction resides in the certification of the product being produced by the monitored equipment. Indeed, the environmental impact of the condition in which the product is produced may impact the certification of the product to certain standards, which in turn can be sold at a higher price than a product that does not meet the standard. For example, the emissions due to the production of natural gas may reach levels that make the greenhouse gas impact of natural gas on par with burning coal, negating its value proposition of being a more environmentally friendly fuel. Some certified natural gas products attain a price that is up to 1% to 10% higher than the non-certified commodity. The monitoring of emissions and reduction of emission disclosed herein can help producers meet the strict rules and burden of proof associated with certification.

In all or some embodiments, the method can include the quantification of emissions and emission offsets obtained by a hybrid/dynamic inspection, preventative maintenance, and operational optimization for the generation of low emission certified products, carbon offsets, or the reduction of carbon credit consumption through emissions reductions and total emission reporting.

The construction and arrangement of the elements of the systems and methods as shown in the embodiments are illustrative only. Although a number of embodiments of the present disclosure have been described in detail, those skilled in the art who review this disclosure will readily appreciate that many modifications are possible (e.g., variations in number of sensors, sensor position, removal and addition of sensors, weather detection elements, etc.) without materially departing from the novel teachings and advantages of the subject matter recited. For example, elements shown as integrally formed may be constructed of multiple parts or elements. Any embodiment or design described herein is not necessarily to be construed as beneficial or advantageous over other embodiments or designs. Accordingly, all such modifications are intended to be included within the scope of the present disclosure. The order or sequence of any process or method steps, including the steps discussed in connection with the algorithms discussed herein may be varied or re-sequenced according to alternative embodiments. Other substitutions, modifications, changes, and omissions may be made in the design, operating conditions, and arrangement of the embodiments without departing from scope of the present disclosure or from the spirit of the appended claims. For example, the techniques disclosed herein can be used to monitor other locations, including inside factories, warehouses, shipping centers, homes, apartments, or the like.

The present disclosure contemplates systems and methods which may be implemented or controlled by one or more controllers to perform the actions as described in the disclosure. For example, in some embodiments, the controller, whether part of a sensor, computing device, etc., may be configured to process data from sensors, users, or operators and model, calculate, and perform one or more simulations within different data sets, tables or maps described, perform any or all described algorithms and any others similarly suitable, and control operation of any disclosed parts or components in a manner necessary or appropriate for proper function, operation, and/or performance of any disclosed systems or methods.

1—Gaussian Plume Model: An aspect of the system may use a reduced order model rather than a full dispersion advection transport model for the simulation of transport of the trace gas of interest. In particular, Gaussian Plume modeling may be used. The Gaussian plume model uses a gaussian approximation of the plume geometry to approximate dispersion. This model assumes a flat terrain and a well-mixed dispersion process. The gaussian Plume is a reduction of a steady state solution of the flow equations in this simple geometry of the terrain. Therefore, only a few parameters are sufficient to describe the model, such as: the source to sensor distance and direction, the wind direction, the height of the source and the height of the sensor. Internal parameters include the dispersion width in the horizontal and vertical directions through the intermediary of the standard deviation of the gaussian shape. A simple reduction consists in taking an identical standard deviation for both vertical and horizontal terms. Some approximation of the dispersion width can be obtained using Pasquill curves which may depend on the atmospheric stability class at the time of transport and distance between source and sensor. One configuration of the present disclosure is directly estimating the stability class and or the dispersion standard deviation using the measured standard deviation of the wind at the sensor location on a time scale that is corresponding to the time of transport from the sensor to the source. This standard deviation is calculated over many samples using the wind direction change during a period of interest, for example using 1 sample per second over a period of a minute to calculate the wind standard deviation. It is then possible to use the horizontal wind standard deviation to calculate the stability class and then use this to calculate the dispersion standard deviation. Alternatively, the standard deviation of horizontal wind can be used to directly approximate the plume dispersion width.

When the internal dispersion terms are obtained, the other inputs such as concentration at the sensor, position of source and sensor and average direction of wind during the observation period can be used to solve the gaussian plume equation. Note that the direct gaussian plume equation relates flux at the source to a concentration at a selected point. The inverse gaussian plume equation permits to relate the concentration at a point to the flux at the evaluated source. Because the position of source and measurements at the site setup can be determined, and wind speed, wind direction and concentration may have been measured continuously, the flux of a source by using the inverse gaussian equation may be estimated.

The gaussian plume model and its inverse model can be used in the methods described in FIGS. 7 and 8 as an alternative to the more complete dispersion advection transport model as a lower computational cost alternative. This is to the cost of ignoring the effects of topology and obstacles that are considered in the dispersion advection transport model.

Quantification Algorithm: A quantification algorithm may be used to quantify and detect leaks from the use of continuously monitored concentration and wind data. There are four major steps in the road map of this algorithm: localization, event detection, background calculation, and atmospheric stability. The localization uses the location of the sources and detectors to calculate the probability of a detector seeing an event or leak from each sensor. Emission plumes, for example methane plumes of equivalent size are compared along with the peak events at each sensor. The most probable source will be identified, and the source will collapse if there is no event identified. The probabilities from each detector then provide a weighted average of the flux rate at each source.

During event detection, the methane plumes "seen" by the detectors are individually isolated, so that each event can be identified. The background calculation involves estimating the background concentration for each detector when no event is detected. The background concentration is used as a baseline to determine the significance of an event when there is a spike in methane readings. In the last step, the atmospheric stability is predicted from wind speed and direction to account for spreading of the plume.

Localization and Atmospheric Stability: The Gaussian plume model is the foundation of the quantification algorithm and attributable to some of the major assumptions during modeling, e.g., multivariate normal distribution of concentration and radial basis coordinate system. The effects of wind speed and direction, mixing, and atmospheric stability are accounted for in the Gaussian plume model.

Figure 12:
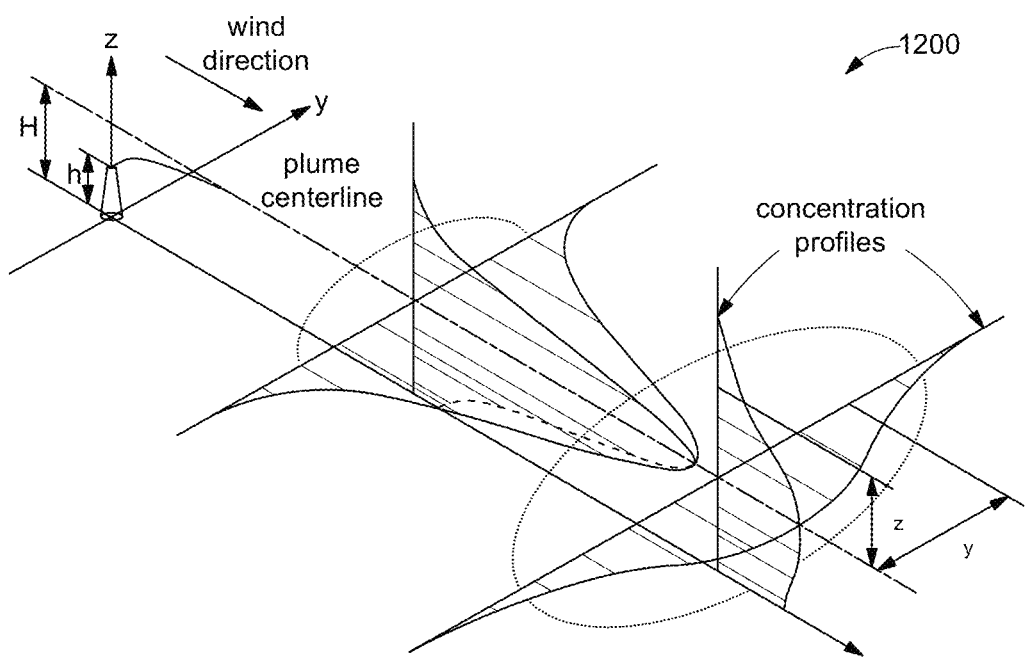
FIG. 12 illustrates an example Gaussian plume model that includes a plume modeled as radially extending with horizontal and vertical spreading, in accordance with an illustrative configuration of the present disclosure.

With reference to FIG. 12, a representation 1200 of a Gaussian plume model (adapted from J. M. Stockie (2011)) is illustrated. As shown in the FIG. 12, a plume (for example, of methane gas) is modeled as radially extending with horizontal and vertical spreading. For an emission rate Q g/s and wind velocity of u m/s, the concentration distribution profile is known as the Gaussian plume solution for some sensor height of z meters and source height of H meters, as provided in the below equations:

$$C(r, y, z) = \frac{Q}{4\pi u r}\exp\left(-\frac{y^2}{4r}\right)\left(\exp\left(-\frac{(z-H)^2}{4r}\right) + \exp\left(-\frac{(z+H)^2}{4r}\right)\right) \quad (2.1)$$

$$r = \frac{1}{2}\sigma^2(x) \quad (2.2)$$

$$\sigma^2(x) = ax^b \quad (2.3)$$

$$x = R\cos(\theta - \theta_0), \ y = R\sin(\theta - \theta_0) \quad (2.4)$$

In the equation (2.1), the first term $Q/4\pi u r$ is the initial condition or initial flux; and the second term $\exp(-y^2/4r)$ is the spreading of the plume off the y-axis. The third and fourth terms $\exp-(z-H)^2 + \exp-(z+H)^2/4r$ 4r are the change in the plume as a function of height. The parameter $\sigma$ is the standard deviation of the concentration distribution and r represents its variability; y, z are the Cartesian coordinates; a, b are the diffusion parameters related to the atmospheric stability class. Depending on the hour of the day, a relationship between the time of day, Pasquill-Gifford stability class, and the diffusion parameters can be determined. In the equation (2.1), the concentration distribution profile is projected to radial basis coordinates.

A function T dependent on wind direction may be defined using equation below:

$$T_1 = \frac{1}{2\pi u (aR^b)^2}, \tag{2.5}$$

$$T_2 = \exp\left(-\frac{R^2 \sin^2\left(\frac{\pi(\theta - \theta_0)}{180}\right)}{2(aR^b)^2}\right), \tag{2.6}$$

$$T_3 = \exp\left(-\frac{(z-H)^2}{2(aR^b)^2}\right), \tag{2.7}$$

$$T_4 = \exp\left(-\frac{(z+H)^2}{2(aR^b)^2}\right) \tag{2.8}$$

Figure 13:
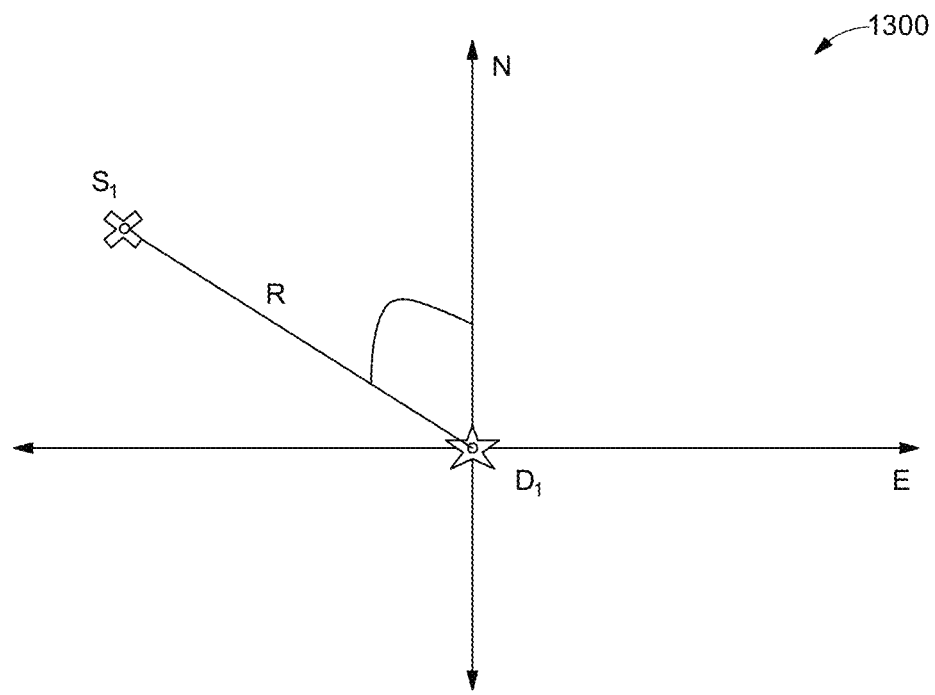
FIG. 13 illustrates a graphical representation illustrating radial distance and angle between a source and a detector, in accordance with an illustrative configuration of the present disclosure.

During localization, there is a probability pn,m that a detector n=1, 2, ..., N can "see" a source m=1, 2, ... M at a given time as a function of wind speed and direction. The angle $\theta_0$ and radial distance R between the source and detector is first measured and then the flux from source m is computed using concentration data from detector n. FIG. 13 is a graphical representation 1300 illustrating radial distance and angle between source S1 and detector D1. The conditional probability is then given by (2.9)

$$P(S_m|D_n, t_k) = pn,m, n=1,2,\ldots,N, m=1,2,\ldots M, k=1,2,\ldots J, \tag{2.9}$$

The probability P(Sm|Dn,tk) in (2.9) is the probability source m emits given readings from detector n. Essentially, it is the probability of seeing a leak at the source. The probability curves are given for all possible paths of the Gaussian plume in radial coordinates. The input parameter $\theta_0^{n,m}$ is the angle between the specific source m and detector n. The function T is dependent on wind direction, such that $$T(\theta_j^{n,m}) = \frac{T_1 \times T_2(\theta_j^{n,m}) \times (T_3 + T_4)}{\rho_{gas}}, j = 1, 2, \ldots, J, \tag{2.10}$$

$$\theta^{n,m} = (-89 + \theta_0^{n,m}, 89 + \theta_0^{n,m}), m = 1, 2, \ldots, M, n = 1, 2, \ldots, N, \tag{2.11}$$

In addition, the condition is set that if $\theta_j^{n,m} > 360$, j=1, 2, ..., J, then $\theta_j^{n,m} > 360 - \theta_j^{n,m}$. The constant 6.56×10−4 is for the conversion of units between parts per million volume and g/m³.

The next step is to normalize (2.10) at time $t_k$, k=1, 2, ..., J given some wind direction $\theta_j^{n,m}$ and wind speed $u_k$. The sum of probabilities for the sources $S_m$ and the residual probability or background B is 1, where, $$P(S_m | D_n, t_k) = (\hat{T}(\theta_1^{n,m}), \ldots, \hat{T}(\theta_J^{n,m})), \text{ at time } t_k \text{ for} \tag{2.12}$$

$$k = 1, 2, \ldots, J; m = 1, 2, \ldots, M, n = 1, 2, \ldots, N,$$

$$P(B | D_n, t_k) = 1 - \sum_{m=1}^{M} P(S_m | D_n, t_k), \tag{2.13}$$

$$\hat{T}(\theta_i^{n,m}) = \frac{T(\theta_i^{n,m})}{\sum_{j=1}^{J} T(\theta_j^{n,m})}, i = 1, 2, \ldots, J. \tag{2.14}$$

Figure 14:
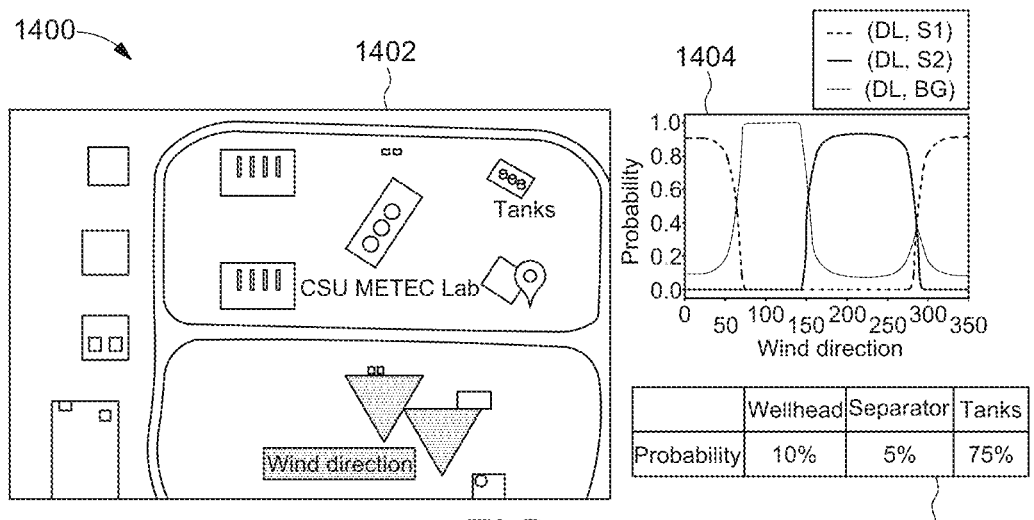
FIG. 14 illustrates an example of analysis performing localization of a site (e.g., Colorado State University's METEC Lab experimental site) with the probability curves given as a function of wind direction, in accordance with an illustrative configuration of the present disclosure.

FIG. 14 shows a schematic representation 1400 an example of analysis performing localization of a site 1402 (e.g., Colorado State University's METEC Lab experimental site) with the probability curves 1404 given as a function of wind direction and graph 1406.

The associated functions for localization and atmospheric stability may be the following: radial gaussian, flux, return BNL dispersion coefficients, compute geometry, site probability.

The next phase of the quantification algorithm is to detect events from each set of concentration data corresponding to its respective detector. A preliminary analysis was developed to look at 3-minute intervals of 1-minute data to see if there is a peak in concentration during this period of time. The peak in concentration is analyzed by using the difference formula to approximate the gradient or slope of the concentration curve. If it exceeds a threshold of 0.75, then the time period is classified as an "event" with a nonzero flux rate; otherwise, it is classified as "no event" with a negligible flux rate. The start and end time of the event must also be specified. The event is said to start if the change in concentration is greater than some δt, and the event ends when it is less than −δt. In this way, the event is assumed to be like a symmetric curve with about the same slope for the start and ending of the event.

Figure 15A:
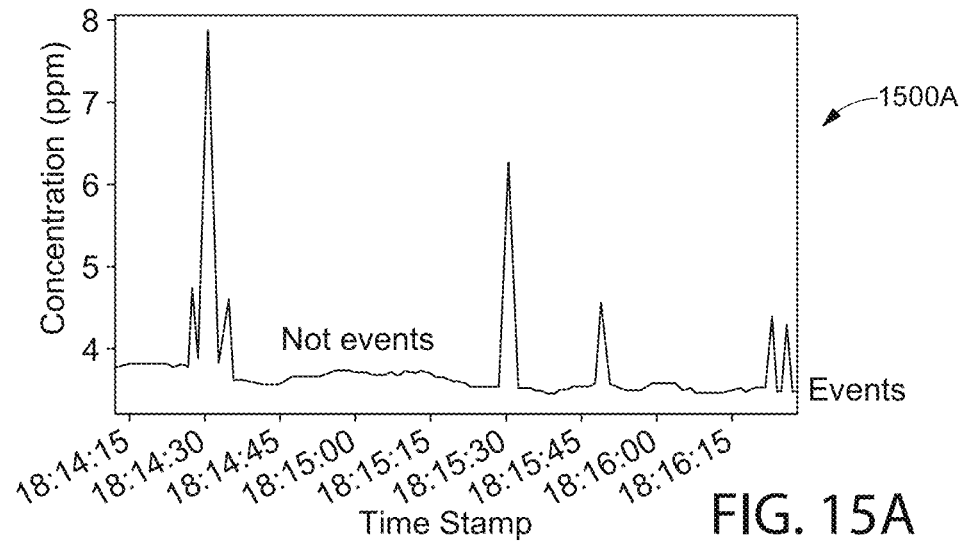
FIGS. 15A-15B illustrate graphical representations illustrating example of five events detected along with background concentration, in accordance with an illustrative configuration of the present disclosure.
Figure 15B:
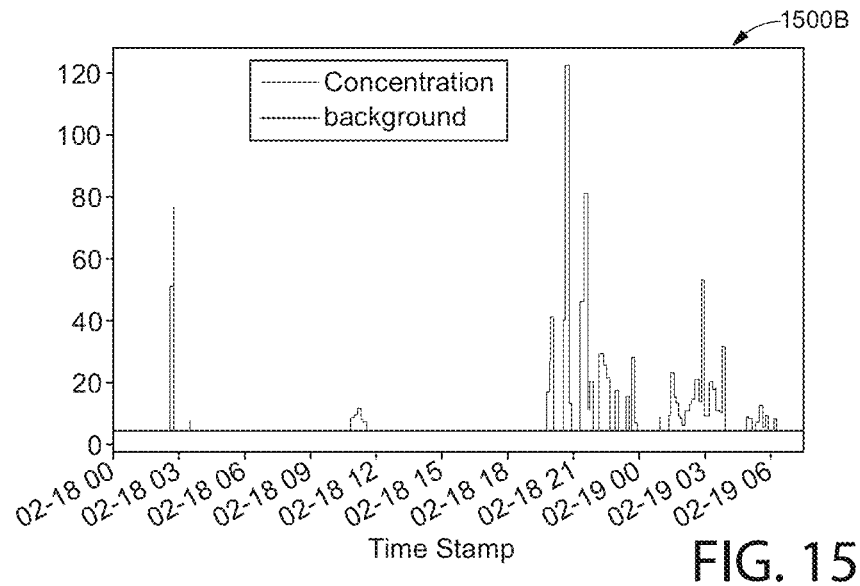
Figure 16:
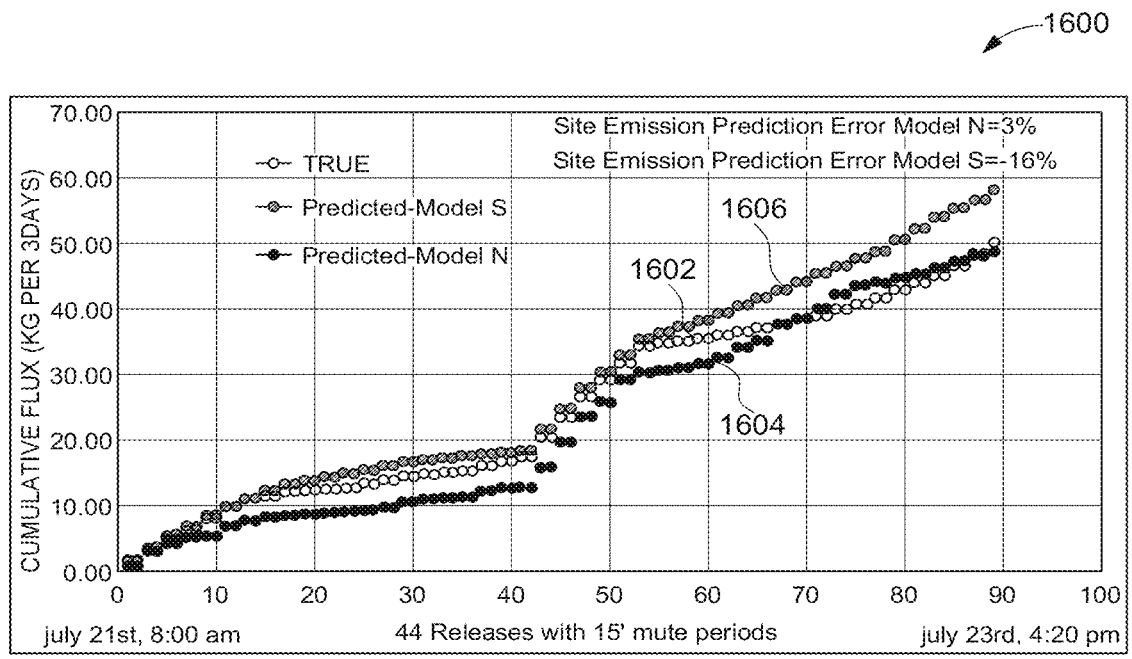
FIG. 16 illustrates a graphical representation of cumulative predictive emissions for a site (METEC Site Emissions) over the course of three days as compared to true emissions, in accordance with an illustrative configuration of the present disclosure.

The baseline concentration must first be specified as a continuous line. To do so, the background concentration is calculated using the data corresponding to wind direction between +25 degrees from θ0. Outside of the events, the data is removed 15 minutes before and after an event from the background concentration. Then, a continuous 5-minute rolling average is taken over designated background concentration. If there is no concentration data moving forward, the backward fill is applied to populate missing values forward in time; and the forward fill is applied to propagate the last observation forward. Then, the wind speed was filtered, so that it cannot drop below 0.5 m/s and exceed 10 m/s. FIGS. 15A and 15B highlights an example of five events detected along with the background concentration.

With reference to FIGS. 15A and 15B, graphical representations 1500A, 1500B of results from (a) event detection and (b) background concentration are depicted. The associated functions for event detection and background calculation may be the following: quantify_and_detect_leaks, and quantify.

In some configurations, total hourly flow rate may be determined using either (i) maximum probability based method or the (ii) total weighted average method. For method (i) in Equation (3.1), the total hourly flow rate is displayed as the average of hourly sensor based flow rate for the most probable source. This average is restricted to sensors with conditional probabilities higher than 75% or attributable to the sensor with the highest probability reading sensor if no other sensors have a probability reading higher than 75%. This method works best if only one source is active and the rest are inactive with negligible or no emissions. The maximum and minimum flow rates at each sensor are provided if it has a specific flow rate over 75%. For method (ii) in Equation (3.2), the flow rate of each source is the weighted average as the average of all partial flow rates of the sensors weighted by the hourly conditional probabilities for each sensor with probabilities higher than 100/M (100 per million). The flow rate for all sources is then summed to form a total flow rate for sources that have a total probability of leak over 100/M. This method is more efficient at accounting for multiple sources but less so for a single emitting source.

Method (i): $\bar{Q}_m = Q_m(P_{>0.75}(S_m | t_{60}))$, $m = 1, 2, \ldots, M$,  Equation (3.1)

Method (ii): $\hat{Q} = \sum_{m=1}^{M} P_{>\frac{100}{M}}(S_m | t_{60}) Q_m$,  Equation (3.2)

$$P(S_m | t_{60}) = \frac{\sum_{n=1}^{N} C(D_n, T) P(S_m | D_n, T)}{\sum_{n=1}^{N} C(D_n, T)}$$  Equation (3.3)

METEC Round 2 Testing and Validation Findings and Results of MVP1 Quantification Model: In a field-testing campaign in real world environment at a site (for example, Methane Emissions Technology Evaluation Center (METEC) at Colorado State University), illustrative results from developing, testing, and implementing methods for quantification of methane emissions from oil and gas facilities using sensor nodes and analytics platform are presented. This platform integrates detector data, meteorological conditions, and cloud analytics to detect and quantify methane emissions for remote locations. This first minimum viable product for quantification (MVP1) has, or will be, updated by subsequent tests.

An illustrative installation of the present disclosure performed three days of around the clock live methane emissions tests including daytime, nighttime and in between to investigate the diurnal effect on quantification methods. The design of experiment included a total of forty-four test conditions (experiments) where programmed methane releases were introduced from actual natural gas site structure including gas processing units, well heads, and storage tank batteries. A total of eight sensor nodes forming a larger sensor network were deployed at the fence line of the 200 ft×280 ft site with a detector to source distance ranging from 69 to 230 ft. The duration of each test was 60 minutes followed by 15 minutes of no methane release to establish baseline for the next new test and so on. Each test was repeated three times to examine various quantification models for reproducibility of consistent results. Methane release rates ranged from low, 0.05 to high, 0.84 g/s which is a wide range that represents average well pad emissions. Wind speed and direction may be measured using ultrasonic wind sensors installed in some of the sensor nodes.

Figure 17:
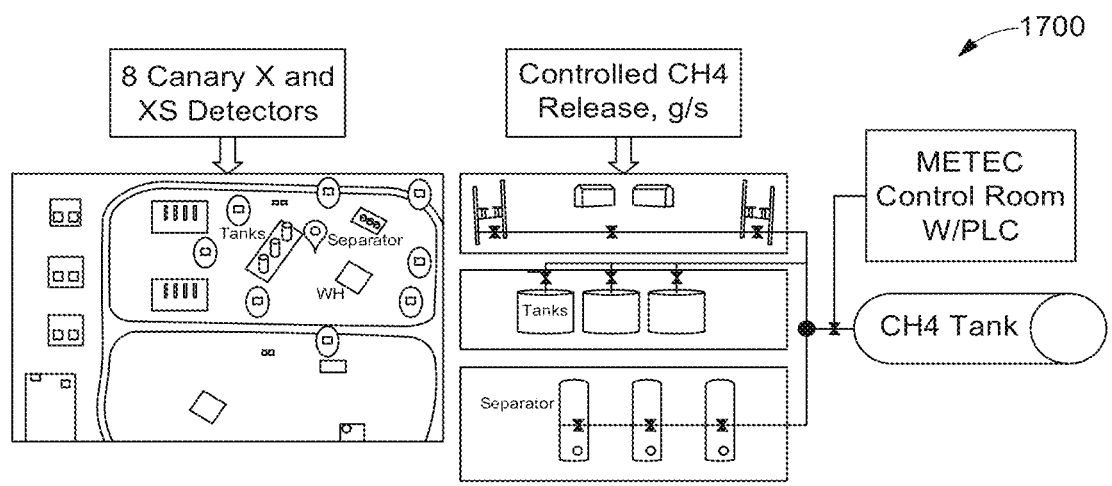
FIG. 17 illustrates a workflow diagram showing a framework of quantification, in accordance with an illustrative configuration of the present disclosure.

FIG. 17 illustrates a workflow diagram 1700 depicting a framework of quantification. As shown in, the quantification workflow diagram of FIG. 17, as field testing progresses, time series data from individual detectors are streamed to Amazon Web Servers (AWS) in real time. The data is comprised of signals from the sensing element as it responds to local methane concentrations, at the location of the detector in addition to wind speed in m/s and wind direction measurements (0o to 360o). Detector data are pushed to AWS for pre-processing before being passed on to the developed model for emission rate and source location prediction. When the data is downloaded into local servers, it is passed on to an extraction, transformation, and loading (ETL) computational pipeline before being ready for the prediction algorithm. The concentration data (ppm) is augmented by GPS coordinates of the individual sensors and a single file encompassing the experimental time of a given test (typically one hour) before being ingested by the model.

Figure 18:
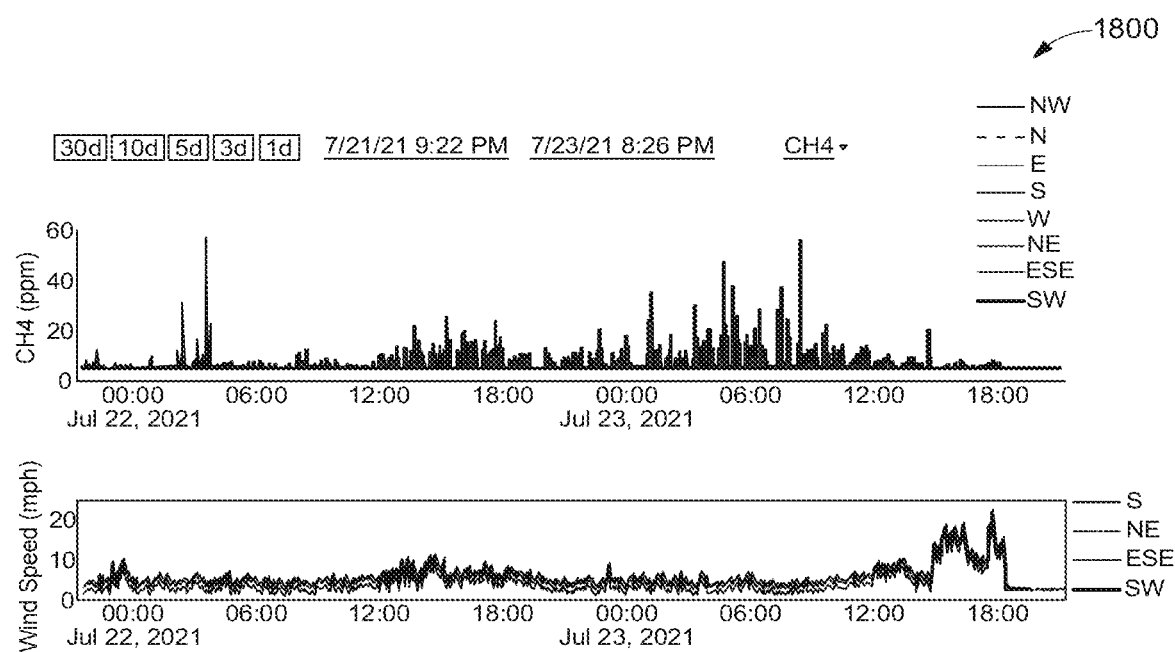
FIG. 18 illustrates an example wind rose diagram defined by a weather data for a site (e.g., METEC site), in accordance with an illustrative configuration of the present disclosure.
Figure 19:
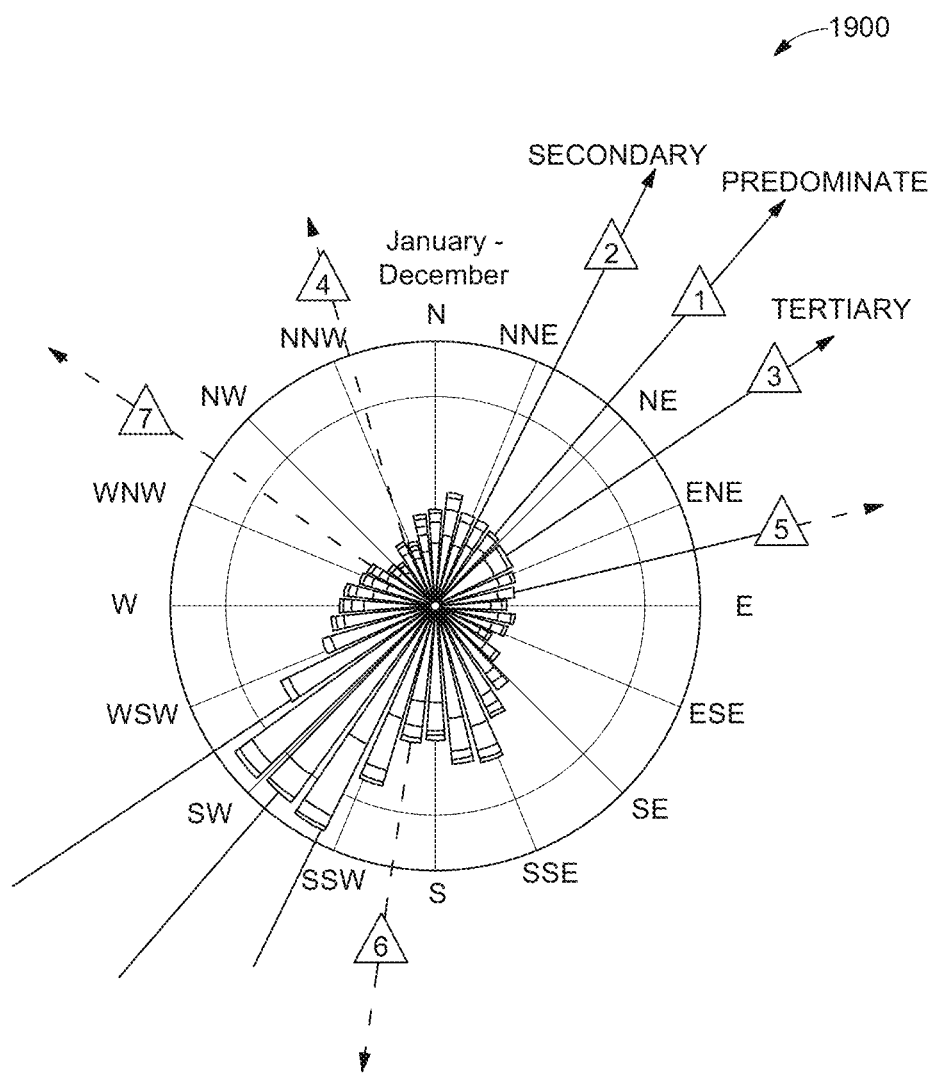
FIG. 19 illustrates another example wind rose diagram including a predominate wind direction, a secondary wind direction, and a tertiary wind direction over a period of time (e.g., a year), in accordance with an illustrative configuration of the present disclosure.
Figures 20A, 20B, 20C:
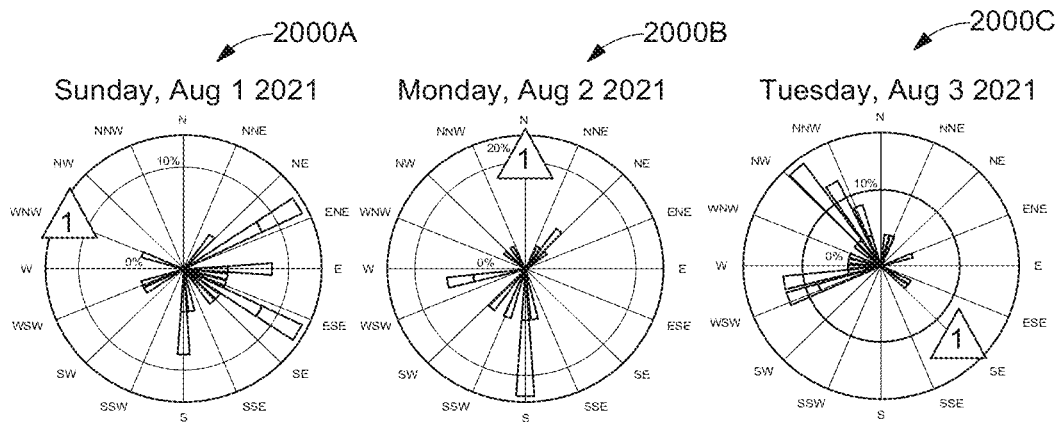
FIGS. 20A-20G illustrate a wind rose diagram for each of a week including a predominate wind direction (shown as "1") during that day, in accordance with an illustrative configuration of the present disclosure.
Figures 20D, 20E, 20F:
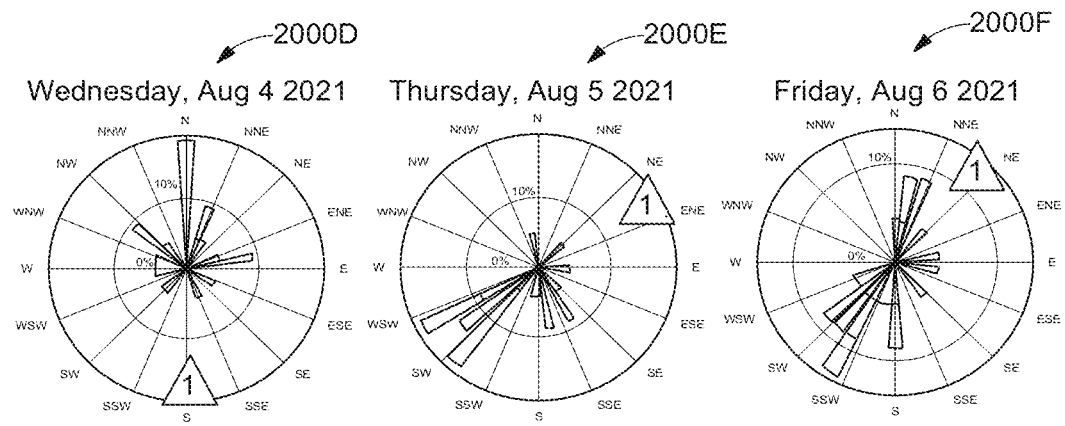
Figure 20G:
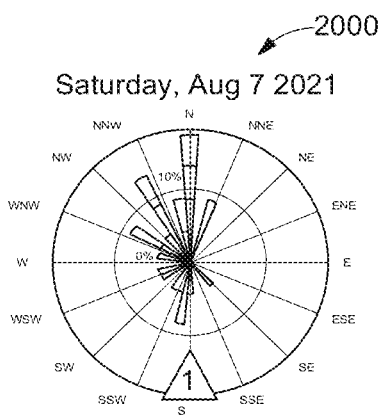

Detector placement is initially decided prior to the testing campaign by studying multiple wind rose diagrams from historical weather stations data and identifying the most likely dominant wind directions around the location of the testing. Visualization of time series and hourly aggregated statistics of concentration, wind speed, and wind direction from all detectors and weather sensors enable the user to assess node engagement and to adjust the experimental setup, if necessary, to maximize alignment of sensors with the dominant methane dispersion directions by the prevailing wind. FIG. 18 illustrates an example wind rose diagram 1800 defined by a weather data for a site (e.g., the METEC site). As will be appreciated, wind rose diagrams are graphical charts that characterize the speed and direction of winds at a location. FIG. 19 illustrates another wind rose diagram 1900 including a predominate wind direction (shown as "1"), a secondary wind direction (shown as "2"), and a tertiary wind direction (shown as "3") over a period of time (e.g., a year). FIGS. 20A-20G illustrates a wind rose diagram for each of a week, respectively including a predominate wind direction (shown as "1") during that day. In other words, a wind rose diagram 2000A for Sunday (Aug. 1, 2021), a wind rose diagram 2000B for Monday (Aug. 2, 2021), a wind rose diagram 2000C for Tuesday (Aug. 3, 2021), a wind rose diagram 2000D for Wednesday (Aug. 4, 2021), a wind rose diagram 2000E for Thursday (Aug. 5, 2021), a wind rose diagram 2000F for Friday (Aug. 6, 2021), and a wind rose diagram 2000G for Saturday (Aug. 7, 2021).

Plume Dispersion Model for Quantification of Methane Emissions: In a real environment, an industrial plume may propagate and diffuse from the moment an emission is released from a point source as shown in FIG. 12. This transport process is the combination of diffusion (due to turbulent eddy motion) and advection (due to the wind) that defines the term, dispersion (Stockie 2011). The concentration of a contaminant release will be transported through the air in an axisymmetric pattern (idealized case). A method used in modeling this phenomenon may be derived from the advection-diffusion equation and results in decaying Gaussian distribution profiles with distance. A dispersion model is essentially a computational procedure for predicting concentrations downwind of a pollutant source, based on knowledge of the emissions characteristics (stack exit velocity, plume temperature, stack diameter, etc.), terrain (surface roughness, local topography, nearby buildings), and state of the atmosphere (wind speed, stability, mixing height, etc.) (MacDonald 2003).

The complexity of the plume source inversion arises from the need to recover information about the source emission rate(s) and location using concentration signatures from a few detectors. These emissions are related through a highly nonlinear and high-dimensional turbulent dynamic that pervades the near surface atmosphere. A number of analytical and approximate solutions for atmospheric dispersion may be derived under a wide range of assumptions, boundary conditions, and parameter dependencies. One of these solutions is the Gaussian plume solution, which is an approximate solution for single point-source emissions:

$$C(x, y, z) = \frac{Q}{2\pi U \sigma_y \sigma_z} * \exp\left(-\frac{y^2}{2\sigma_y^2}\right) * \left[\exp\left(-\frac{(z-H)^2}{2\sigma_z^2}\right) + \exp\left(-\frac{(z+H)^2}{2\sigma_z^2}\right)\right]$$  Equation (4.1)

Where:
$\sigma_y$=S.D. of horizontal distribution of plume concentration=axb (m)
$\sigma_z$=S.D. of vertical distribution of plume concentration=cxd (m)
C=Concentration at the detector (kg/m3)

H=Effective height of emission source (m)
U=Wind speed along x-axis, assuming invariable with height (m/s)
Z=Detector height above ground (m)

Data Post-Processing: The plume model outputs may include predicted release rates (or instantaneous fluxes) at each detector. The predicted release rates from each detector may be grouped together to form a big sample of flux data called the population. After obtaining a full timeseries flux for each detector, bootstrap resampling may be performed to quantify the random errors and provide a confidence range for the statistics reported. The mean flux for each detector may be calculated and added to the population. Further, summary statistics and estimated the precision of the reported statistics may be reported using bootstrap resampling described immediately below.

As already explained in conjunction with FIGS. 6A-6E, the plume flux of the plume of emissions at the site may be determined by receiving a predetermined number of samples of the plume at a plurality of angles of the plume by the plurality of air quality monitors (i.e., sensors systems 620) installed at the site. Further, an associated concentration point may be registered based on the plurality of angles. A fit of a point cloud may be obtained. When the measurements occur in idealized conditions of the site parameters, the plume flux may be calculated using a mass conservation equation by multiplying an area concentration of the plume cross section by its normal speed and by estimating the plume concentration in the height direction. The site parameters may include wind speed, wind direction, temperature, and other parameters associated with the site.

Figure 21:
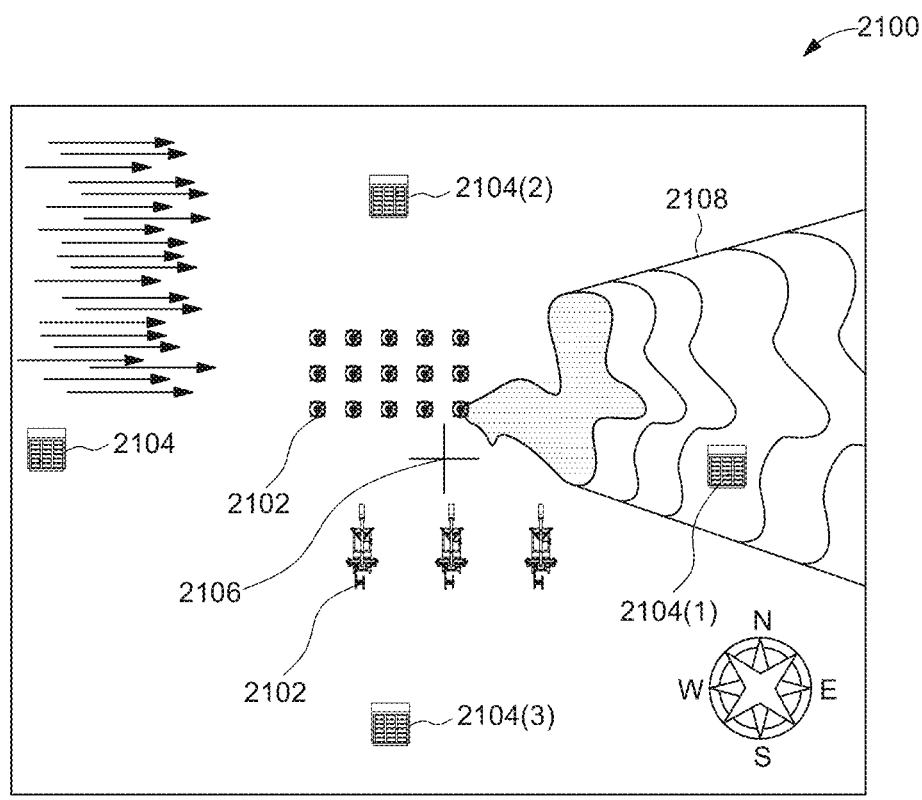
FIG. 21 illustrates a plan of an example site under monitoring, in accordance with an illustrative configuration of the present disclosure.

Referring now to FIG. 21, a plan 2100 of an example site under monitoring is illustrated. The site may include equipment 2102, and a plurality of air quality monitors 2104 (as mentioned before, air quality monitors may also be referred to as sensors, sensors systems, sensing system, detectors in this disclosure). Further, a method of installing an air quality monitor system at the site may be performed. The method may include surveying the site by procuring: an equipment log of a plurality of leak-prone equipment 2102 at the site, a centroid 2106 of the leak-prone equipment, and a wind-rose diagram representative of wind at the site. Surveying the site may further include procuring a 3D point cloud of topography of the site and procuring a 3D point cloud of the leak-prone equipment 2102 of the site. Upon surveying, the wind-rose diagram may attached to be the site.

The wind rose diagram is already illustrated in the FIG. 19. As shown in the FIG. 19, the wind-rose diagram may include the predominate downwind direction ("1"), the secondary downwind direction ("2") angularly offset from the predominate downwind direction ("1"), and a tertiary downwind direction ("3") angularly offset from the predominate downwind direction ("1") and oppositely disposed from the secondary downwind direction ("2").

A predominate air quality monitor 2104(1) may be installed at the site in the predominate downwind direction ("1") from the centroid 2106 at a location where the predominate air quality monitor 2104(1) has a maximal angular separation between the leak-prone equipment 2102. Before installing the predominate air quality monitor 2104(1), a site operator may be instructed to install a first vertical object (for example, a post, a pole, or any vertically aligned shaft) where the predominate air quality monitor 2104(1) will be installed. The predominate air quality monitor 3504(1) may be installed to the first vertical object. Further, a secondary air quality monitor 2104(2) may be installed in the secondary downwind direction ("2") from the centroid 2106 where the secondary air quality monitor 2104(2) has minimal observational overlap with the predominate air quality monitor 2104(1). Before installing the secondary air quality monitor 2104(2), the site operator may be instructed to install a second vertical object where the secondary air quality monitor 2104(2) will be installed. The secondary air quality monitor 2104(2) may be attached to the second vertical object. Furthermore, a tertiary air quality monitor 2104(3) may be installed in the tertiary downwind direction ("3") from the centroid 2106 where the tertiary air quality monitor 2104(3) has minimal observational overlap with the predominate air quality monitor 2104(1) and with the secondary air quality monitor 2104(2). Before installing the tertiary air quality monitor 2104(3), the site operator may be instructed to install a third vertical object where the tertiary air quality monitor 2104(3) will be installed. The tertiary air quality monitor 2104(3) may be attached to the third vertical object.

The predominate air quality monitor 2104(1), the secondary air quality monitor 2104(2), and the tertiary air quality monitor 2104(3) may be configured to obtain the first weather reading of local weather from a weather station and modify transmission of an emission data according to the weather reading obtained from the weather station. This is already explained in conjunction with FIG. 4A. As mentioned before, the sensor system (or the air quality monitor) may include a weather sensor system 411 (also referred to as weather station 411). The weather sensor system 411 may include sensing elements to measure wind speed and direction. The wind speed and direction may be measured by a combination of a wind vane and an anemometer or by an anemometer alone, such as in the case of using an ultrasonic anemometer.

Further, a predominate connector may be communicatively coupled to the predominate air quality monitor 2104(1). Further, a predominate weather station may be communicatively coupled to the predominate air quality monitor 2104(1) at the predominate connector. Similarly, a secondary connector may be communicatively coupled to the secondary air quality monitor 2104(2). Further, a secondary weather station may be communicatively coupled to the secondary air quality monitor 2104(2) at the secondary connector. In the same way, a tertiary connector may be communicatively coupled to the tertiary air quality monitor 2104(3), and a tertiary weather station may be communicatively coupled to the tertiary air quality monitor 2104(3) at the tertiary connector.

The weather data from each of the predominate weather station, the secondary weather station, and the tertiary weather station may be transmitted to a cloud computing device (for example, "Amazon Web Services" or simply "AWS"). This weather data may be analyzed to determine redundant or non-contributing weather data. Further, at least one of the predominate weather station, the secondary weather station, and tertiary weather station may be removed. As will be appreciated, all the weather stations (i.e., the predominate weather station, the secondary weather station, and the tertiary weather station) may not contribute to the analysis, and therefore, the non-contributing weather station may be discarded.

In some embodiments, a ground temperature probe may be communicatively coupled to at least one of the predominate air quality monitor 2104(1), the secondary air quality monitor 2104(2), and the tertiary air quality monitor 2104(3). This ground temperature probe may provide a ground temperature. One of the predominate air quality monitor 2104(1), the secondary air quality monitor 2104(2), and the tertiary air quality monitor 2104(3) may transmit the ground temperature (for example to the "AWS"). Based on the ground temperature, a diffusion-area of emissions may be estimated. It may be noted the ground temperature, or the diffusion-area of emissions may be fed to the plume model for analysis.

In an illustrative configuration of the system, the environmental sensors are not collocated to the target gas sampling point. As explained in this disclosure, the collocation of environmental sensors such as the anemometer with the gas analysis sensor intake may improve the interpretation of the data because of the effect of topology and obstacles on the transport of the target gas. To this end, as mentioned above, the weather station may include the anemometer which may further include a due-North indicia. The weather station may be communicatively coupled to the predominate air quality monitor 2104(1) at the connector. The due-North indicia of the anemometer may be aligned to North of the Earth. A first weather reading of local weather may be transmitted from the weather station. The weather reading of local weather may include a wind speed and a wind direction.

In some embodiments, multiple sensors, for example, three sensors (i.e., the predominate air quality monitor 2104(1), the secondary air quality monitor 2104(2), and the tertiary air quality monitor 2104(3)) may be deployed at the site, for example, a gas pad. If the topology and obstacles configuration allows the environmental variables such as wind direction and wind speed are only marginally variable from the perspective of the different sensors deployed at the site. It may then be possible to reduce the number of environmental sensors, such as anemometers, by only positioning a single environmental sensor for multiple gas sensors. For example, on the site with three gas sensors, only one anemometer may be collocated with one of the three gas sensors, while no anemometer is used with the remaining two gas sensors. This allows for a reduction of the cost of deployment with only a marginal reduction of the efficacy of localizing, quantifying or qualifying emissions.

One illustrative configuration of the disclosure concerns the deployment of sensor to a site and the collection of site metadata. As mentioned above, once a site is selected for continuous monitoring, information about the site (i.e., surveying) is first collected in order to identify the best deployment locations. First site boundary and topologies are obtained. This may be offered by the site owner, or by consulting a satellite map databank. For example, in the case of a natural gas pad, the edge of the 50×75 m pad may be identified, and the terrain may be obtained using lidar maps from google earth. Then, the emplacement of equipment groups that are to be observed are identified. This may be done by inspection of the site, LIDAR mapping or by satellite image analysis. The equipment groups type, geometries and location are collected to establish the geometry and location of sources in the predictive simulations. For example, a trained operator may identify the equipment group and their size from satellite image and add then to the site topology of the digital twin. Additional local topology information about the terrain surrounding the site may also be added to the digital twin to improve simulations, for example by adding obstacles like trees and buildings, following a process similar to the identification of equipment groups. The next step or concurrent step is to identify local weather patterns. Historical wind conditions of the site may be extrapolated from the wind conditions at a proximate weather station, in particular the identification of the primary and secondary wind directions. For example, the cli-MATE tool from the Midwestern Regional Climate Center database may be used to construct historical wind rose from reference weather stations in the proximity of the site. Once the historical weather data is obtained, the position of the sensors may be decided. The sensors may follow deployment rules that are site dependent. In general, the objective is to maximize separate observations of the observed equipment groups or areas of interest. This means that the angular separation of the centroid of each equipment group from the perspective of the sensor should be maximized to enhance plume differentiation. Second, the sensor may only be deployed in an allowed area of the site. In the case of oil and gas pads, the site boundary is generally allowable as it is part of the site and far enough away from the hazard zone around the equipment groups. Third, the position of the sensor shall maximize the number of plume observations, this means that sensor shall be placed downwind of the observed equipment groups. With a limited number of sensors, this means that sensors shall be placed with regard to the principal (i.e., predominate) and secondary wind directions extracted from the historical weather data. If additional sensors are allowed, these shall be placed to maximize angular coverage of the equipment groups.

The first sensor (or predominate air quality monitor) is therefore placed close to the downwind direction of the principal (or, predominate) historical wind direction from the centroid of the equipment groups in a position that maximizes angular separation of the equipment groups. Assuming a secondary wind direction exists, a second sensor (or secondary air quality monitor) shall be placed downwind of the secondary historical wind direction in front the centroid of the equipment groups in a position that maximizes separation of the equipment groups and minimizes observational overlap with the first sensor. Subsequent sensors shall follow equivalent rules if additional secondary wind direction exists or maximize angular coverage of the site. For example, in a three-sensor deployment on an oil and gas site, the first sensor position may be selected north of the site because of the south principal wind direction. The second sensor may be positioned southwest because of the secondary northeast wind direction and the third sensor (or tertiary air quality monitor) location may be set east of the site to maximize coverage. The exact position of the sensor may be shifted by few degrees based on local conditions and angular coverage. In the precedent example. The third sensor location may be shifted to southeast because this would give it a better angular position for observing all the equipment groups.

Once the prospective sensor position is established, the map of potential sensor location is shared with the operator of the site for approval and for site preparation. The operator may move or object to certain locations due to risk, need of access or future development project. The position may then either be corrected to accommodate this or the alternate location provided by the operator accepted. The operator may then proceed to the site preparation. For anchored sensors, this means the position of an anchor (e.g., a T-post) for the fastening of the sensor. Once the site preparation is over, the sensor systems may be deployed at the specified location of the site.

Optionally, the position of the sensor may further be shifted. This may happen if the operators plan requires the sensor to be removed (e.g., the site may be modified) or if the observation data from the continuous monitoring of the site is suboptimal (e.g., the historical wind data from a proximate weather station was not applicable to the site). A new plan from the data acquired by the deployed sensors may then be conceived to relocate the sensor to more favorable locations.

As explained in conjunction with FIGS. 7 and 8, methods for the reduction of real time simulation cost by simulating many representative conditions in advance and using inverse methods for identifying matching conditions and predicting flux and source localization are provided. One alternative embodiment is the simulation in real time of the transport problem using real time experimental data, such as weather conditions, stability class and so on. While this may result in additional computational cost, this would reduce some of the modeling error by having more accurate specification of the boundary conditions. In some instances where dynamics is of importance, i.e., when the wind conditions are shifting during transport, this may yield more accurate results. It should be noted that for direct real time simulations, one may use a fully resolved advection diffusion transport model with appropriate closure of the turbulence flow (i.e., LES, RAS, etc) or use a reduced order model such as the gaussian plume model.

An optional computational cost saving approach may be adopted to sub-select periods of interest to simulate, rather than simulate the entire time sequence. For example, in a 24-hour period, only smaller periods within that 24 h period may be simulated, rather than the entire period, say 1 hour. The selection of the appropriate period may be derived directly from the data. For example, emissions may only be detected by the sensor systems when the wind direction is appropriate. In that case, only when the wind direction is within a certain range would the simulation be run. Another discriminant may be the concentration intensity detected by the sensor systems. In this case, only when an outlying concentration enhancement is detected that the simulation be run. An outlying concentration even would be indicative of an emission plume being detected.

An additional computational cost saving approach may lay in the choice of model. A reduced order model, such as the Gaussian Plume Model may first be run in real time for all selected periods of interest. This may allow for a first pass at quantification, localization, and qualification of emission. Then in a second step, a fully resolved advection diffusion transport model may be run to confirm or reduce the uncertainty of quantification, localization, and quantification on selected time periods of interest where the uncertainty of the reduced order model is higher than the uncertainty of the fully resolved model.

Referring back once again to FIG. 8B, the flowchart related to the execution of a real time model is illustrated. Fundamentally, the method in FIG. 8B is similar to the one given in FIG. 7 and FIG. 8A. In particular, the intermediary result of a relational matrix relating emission flux to emission concentration is shared by all method, which then requires an inverse method to solve. The initial problem to be simulated is slightly different, however. While the digital twin model and parameters are similar, and the search space for emission sources and flux amount is the same, the simulation uses weather measurements for the generation of initial and boundary conditions. In particular, temperature, pressure, hygrometry, and wind information may be used. Derived variables such as stability class, updraft, turbulent energy, standard deviation of wind and other input parameters may also be measured and calculated. In particular, the measurement of wind direction and speed at different points of the digital twin may be used to generate boundary conditions that mimic the boundary conditions of the real site during a period of interest. A direct simulation may then be conducted to identify the transport of the target compound by assuming variable sources and flux rates (together emission variables) [Ej]. This can be done using multiple simulations using different emission variables, or by simulating the transport from multiple sources and or multiple target gas in a single simulation over the period of interest. Many models may be used for the direct simulation, for example a full field advection diffusion transport model using an LES closure, or reduced order models such as the gaussian plume model. From the results of the direct simulation(s), the concentration of the target analytes at various time stamps of the simulated periods can be evaluated at the positions of the deployed sensor systems within the digital twin simulation. It is then possible to form the relational matrix that relates emission variables to concentrations of analytes. The inverse relation can then be obtained with an inversion method as presented in FIGS. 7 and 8.

Figure 22:
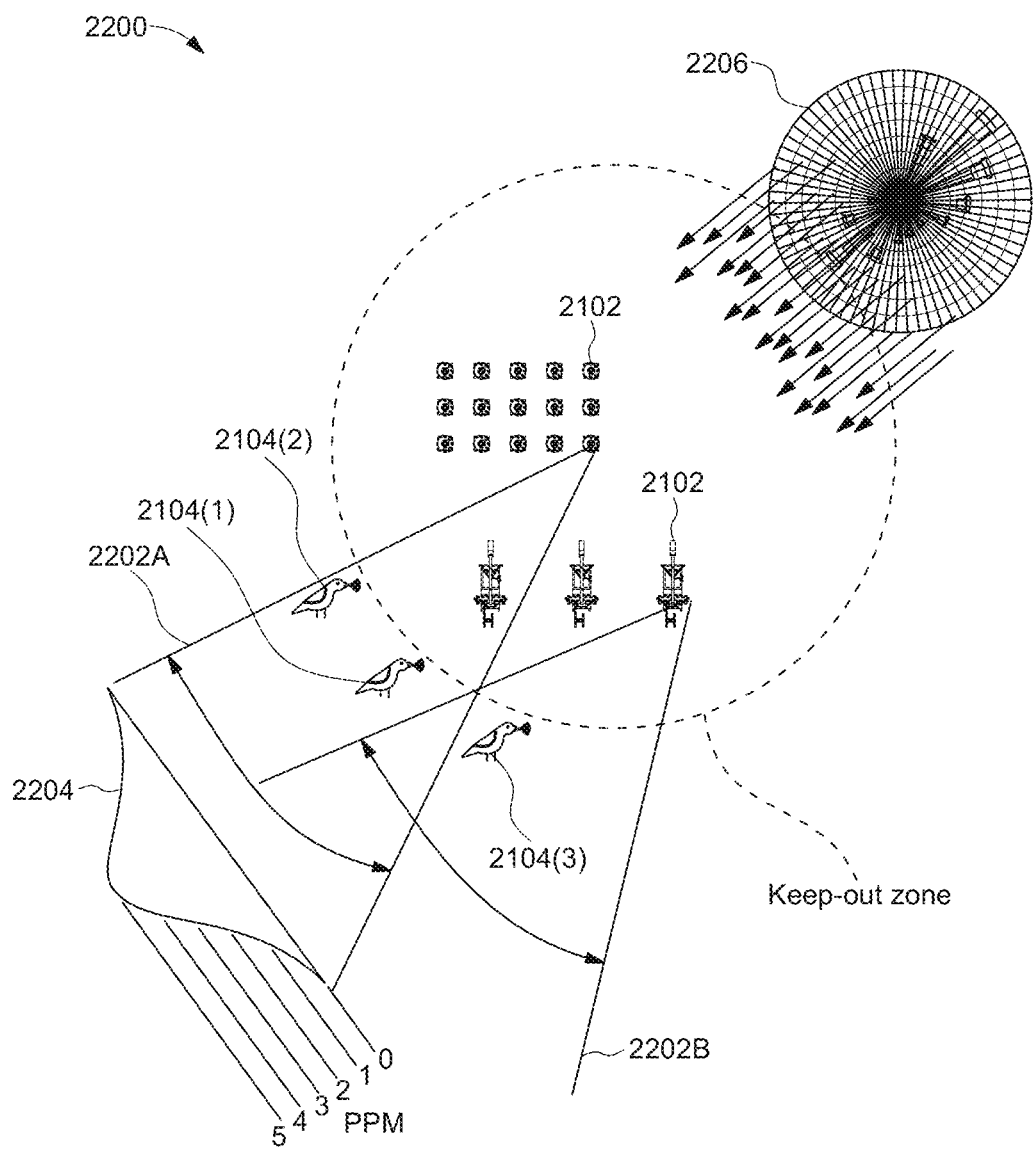
FIG. 22 illustrates another plan of an example site under monitoring, in accordance with an illustrative configuration of the present disclosure.

In particular, in order to identify a source of a target chemical at a site, a computer-implemented method may be performed. Referring now to FIG. 22, a plan 2200 of an example site under monitoring is illustrated. The site may include equipment 2102, the plurality of air quality monitors 2104 (as mentioned before, air quality monitors may also be referred to as sensors, sensors systems, detectors in this disclosure). According to the method, the predominate air quality monitor 2104(1) may be provided which may include a first sensor responsive to the target chemical and a first location information at which the predominate air quality monitor 2104(1) is located at the site. Further, a first concentration of the target chemical at the predominate air quality monitor 2104(1) may be measured as a function of a wind speed and a wind direction. It may be noted that other factors (for, example air temperature, air pressure, etc.) other than the wind speed and the wind direction may be taken into consideration as well. The wind speed and the wind direction may be measured using a wind sensor (e.g., an anemometer) which may be provided at the air quality monitor (as shown in FIG. 4C). The wind sensor may be located at the first location at the predominate air quality monitor 2104(1) or the second location at the secondary air quality monitor 2104(2). In case of an emission, a plume 2108 of the emission (i.e., the target chemical) may occur at the site. Further, the wind speed and the wind direction may be obtained from a wind rose diagram 2206.

In some configurations, the predominate air quality monitor 2104(1) may include a second sensor responsive to a second chemical that is different than the target chemical. Further, the method may include creating a containment table defined as a composition of liquid contained at each of the plurality of sources. The composition may include at least the target chemical or the second chemical. A second concentration of the second chemical at the predominate air quality monitor 2104(1) may be measured, and the measurements of each of the target chemical and the second chemical to the containment table may be compared. The source of the target chemical or the second chemical may be determined according to the containment table, and the identified source may be outputted to a computer device (for example, the mobile device 152).

As mentioned earlier, the air quality monitors (i.e., the predominate air quality monitor 2104(1), the secondary air quality monitor 2104(2), etc.) may obtain measurements of the concentration of air samples at regular intervals (i.e., a predetermined frequency/cadence). Further, under some conditions, the frequency/cadence of obtaining the measurements may be automatically increased or decreased for more accurate emission detection. To this end, in some configurations, a wind-speed-threshold algorithm indicative of improved confidence of sensor readings by the predominate air quality monitor 2104(1) and the secondary air quality monitor 2104(2) may be predetermined. As such, the wind speed may be monitored, and the wind speed may be compared to the wind-speed-threshold. At the wind-speed-threshold, cadence of the measuring of the first concentration may be increased.

In some configurations, a population of the actual emissions measurements may be transmitted to the cloud server (e.g., "AWS"). As mentioned above, some measurements may have noise, and therefore, may not be suitable for performing the plume analysis and may be discarded. To this end, a highest first concentration of the population of emissions measurements may be identified. Further, a lowest first concentration of the population of emissions measurements may be identified. Furthermore, an SNR threshold may be determined. For example, an SNR ratio may be determined by dividing the first concentration by a difference between the highest first concentration and the lowest first concentration. The individual readings of the first concentration that have an SNR ratio below the SNR threshold may be discarded.

Figure 23:
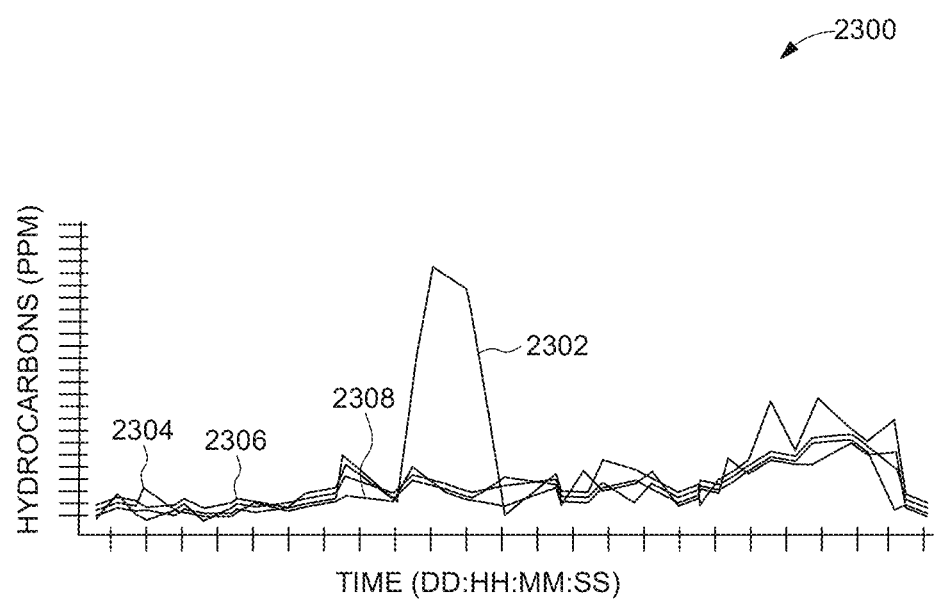
FIG. 23 illustrates a graphical representation of example SNRs associated with different sensors deployed at a site, in accordance with an illustrative configuration of the present disclosure.

FIG. 23 illustrates a graphical representation 2300 of example SNRs associated with different sensors (air quality monitors 2104). For example, an SNR for the predominate air quality monitor 2104(1) may be depicted by a curve 2302, an SNR for the secondary air quality monitor 2104(2) may be depicted by a curve 2304, an SNR for the tertiary air quality monitor 2104(3) may be depicted by a curve 2306, and an SNR for another air quality monitor 2104 may be depicted by a curve 2308. Further, a threshold SNR of 0.7 may be selected. Based on this SNR, the air quality monitors with SNR<0.7 may be discarded.

According to the method, a horizontal distribution deviation defined as a standard deviation of a horizontal distribution of a plume concentration may be obtained. Similarly, a vertical distribution deviation defined as a standard deviation of a vertical distribution of the plume concentration may be obtained. Further, according to the method, at least one simulation model may be created for the site based on simulation parameters. As mentioned above, the simulation parameters may include at least two of a wind directions, a wind speed, an air pressure, an air temperature, a number of potential emission sources, a location of each of the potential emission source, a source flux associated with each of the potential emission sources, a surface concentration, a weather condition, a hygrometry data, an altitude, etc.

For example, as shown in the FIG. 22, a first plume model 2202A and a second plume model 2202B may be generated corresponding to two different potential emission sources, based on the various simulation parameters including wind direction and wind speed (as provided by the wind rose diagram 2206). Further, for example, the plume model 2202A may have a configuration 2204 (along y-plane).

An emission rate of the target chemical at the source may be identified using the simulation model functionally which may be operated by the standard deviation of horizontal distribution, the standard deviation of vertical distribution, the first concentration at the predominate air quality monitor 2104(1), and the wind speed. The identified source may be outputted to a computer device and displayed for a user.

Additionally, in some configurations, the secondary air quality monitor 2104(2) may be provided that may include a second sensor responsive to the target chemical, and a second location information at which the secondary air quality monitor 2104(2) is located. A second concentration of the target chemical at the secondary air quality monitor 2104(2) may be measured as a function of the wind speed and the wind direction. According to the method, a first bearing of the source relative to the predominate air quality monitor 2104(1) may be identified using the simulation model. Further, a second bearing of the source relative to the secondary air quality monitor 2104(2) may be identified using the simulation model. Thereafter, in some configurations, coordinates of the location of source of the target chemical may be identified using the first bearing and the second bearing. Further, the source may be identified from a plurality of possible sources of the target chemical by correlating the identified coordinates of the source with the emission rate. The coordinates and the emission rate of the identified source may be outputted to the computing device.

According to the method, a concentration profile may be built according to a plurality of inputs. The plurality of inputs may include concentration of emission and the wind direction. Further, a wind speed dependent variable may be created according to the concentration profile sourced as the wind speed fluctuates. The location of the emission source may be determined according to the plurality of concentration profiles effected by the wind speed.

Further, in some configurations, a maximum of the first concentration of the target chemical at the predominant air quality monitor along with the wind direction may be logged. Further, a plume centerline may be established as the wind direction less 180 degrees from the location of the predominant air quality monitor, to thereby identify a direction of the source of the target chemical from the predominant air quality monitor.

In one embodiment, the composition of the emission may be an indicator for refining the localization of emission. Emissions may contain different compounds based on their origin in the site. Indeed, the product may be separated or transformed at the site. If multiple target compounds are monitored, the ratio of these may indicate different processes.

For example, in natural gas extraction, natural gas from the well may contain various compounds such as methane, heavier hydrocarbons such as ethane, propane and butane, trace VOC such as H2S, Toluene, additives such as methanol (for preventing hydrate formation) and additional gas and liquids such as CO2 and water. This multiphase flow is then separated in the separator, and liquids are stored in tanks. As a result, emission prior to separation, during separation, after separation and from the tanks may have different ratios and composition of these compounds. If the sensor system can detect more than one compound, or group of compounds, refinement can be obtained in process step identification. For example, a VOC sensor may be used in conjunction with a methane sensor to differentiate emission within the process. Methane emissions with less VOC may come from post separation methane gas while emission with more VOC may come from the tanks.

In one configuration, virtual emissions and/or simulation models created by a mathematical model may be utilized. One illustrative mathematical model is the Navier-Stokes function in fluid mechanics that describes the flow of fluids (such as, for example, the flow of air). The Navier-Stokes function may be derived from an equation devised by Swiss mathematician Leonhard Euler to describe the flow of incompressible and frictionless fluids. Other physicists and mathematicians (e.g., Sir George Gabriel Stokes) have evolved the model to improve both two-degree and three-degree models. Complex vortices and turbulence, often referred to as chaos, which occur in three-dimensional fluid (including gas) flows as velocities increase have proven intractable to any but approximate numerical analysis methods. Examples of methods include Euler's original equation, Guglielmo Marconi wireless communications models, Laplace's equation, Gaussian Plume Model (GPM), Large Eddy Simulation (LES), and the like. Navier-Stokes equations may be found and incorporated, such as those—for example—found at https://en.wikipedia.org/wiki/Navier%E2%80%93Stokes_equations which is specifically incorporated by reference for all that is disclosed and taught therein.

Figure 24:
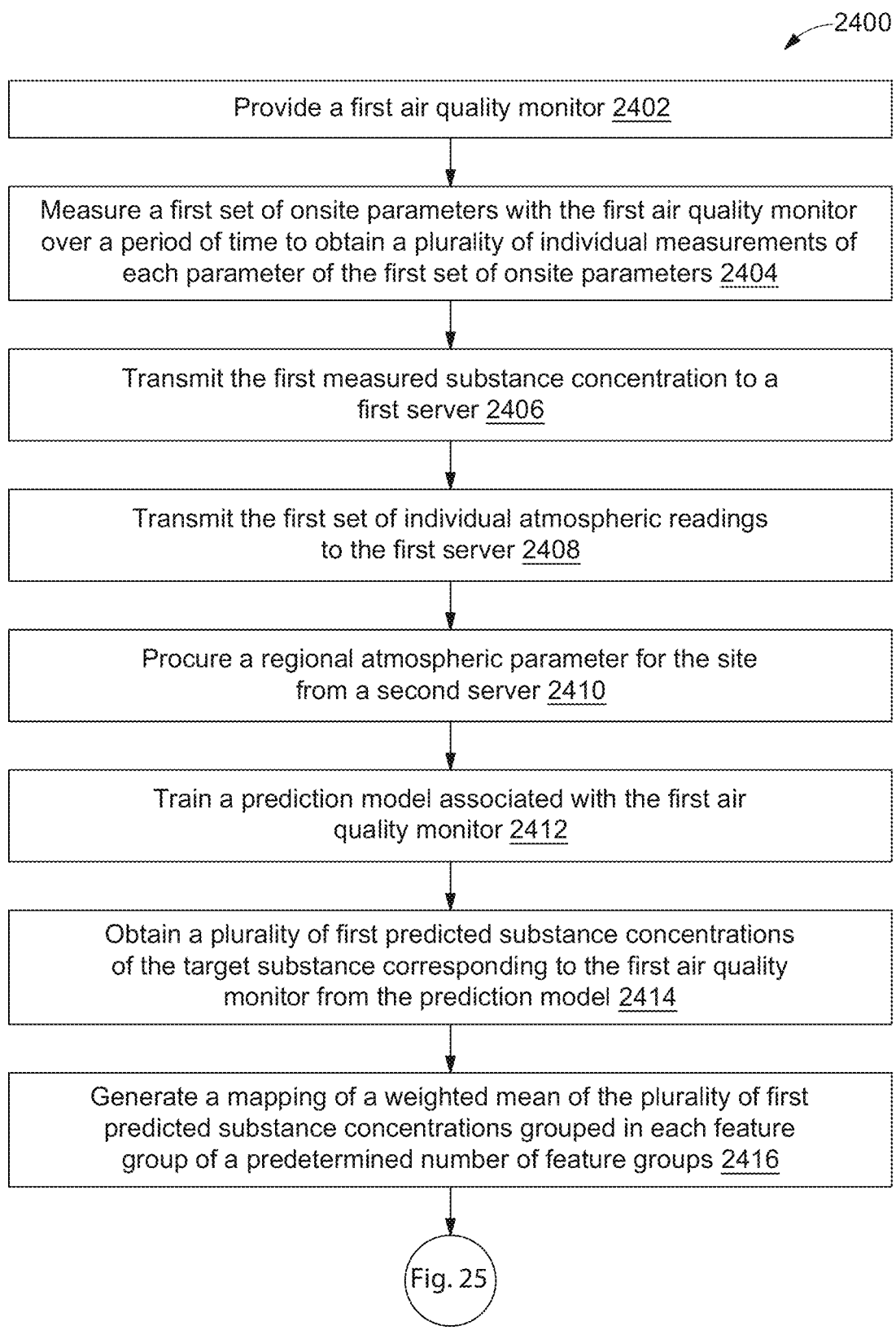
FIGS. 24-25 illustrate a flowchart of a location method of locating an emission source of a target substance at a site, in accordance with some configurations of the present disclosure.
Figure 25:
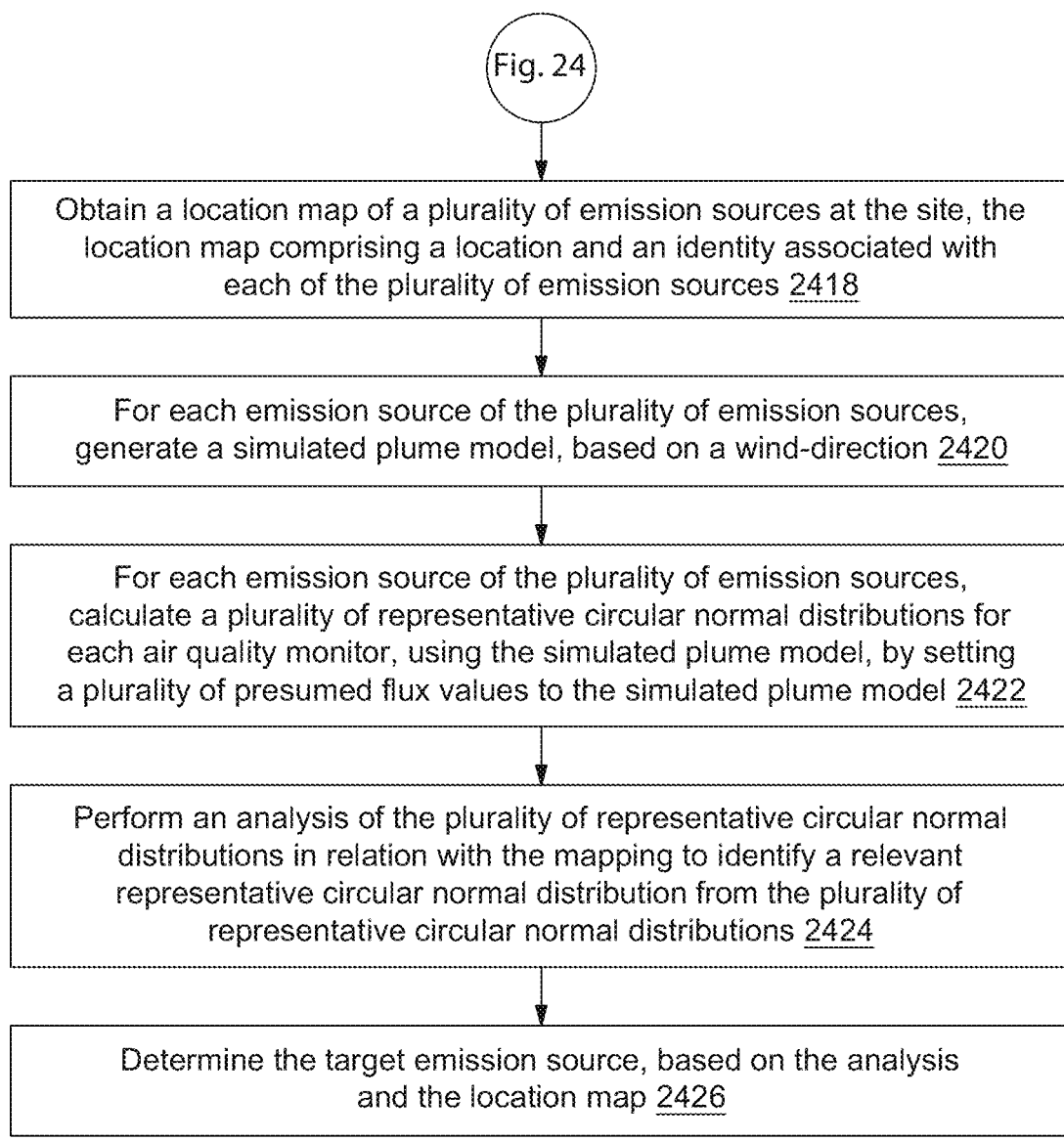

Referring now to FIGS. 24-25, a flowchart of a location method of locating an emission source of a target substance at a site is disclosed, in accordance with some configurations of the present disclosure. At step 2402, a first air quality monitor may be provided. As it will be understood, a plurality of first air quality monitors may be provided at the site. In one example, three air quality monitors may be provided at the site, and in another example, four air quality monitors may be provided at the site. Further, by way of an example, the target substance may be a chemical, and in particular, methane (CH4) gas which is emitted or leaked from one or more emission sources present at the site. The emission sources are already discussed in detail in the above sections of this disclosure. The first air quality monitor may include a first sensor responsive to the target substance. Further, the first air quality monitor may store information about a first location at which the first air quality monitor is located on the site. The information about the first location may include coordinate as per the geographic coordinate system (GCS), or alternatively, reference coordinates with respect to the site.

At step 2404, a first set of onsite parameters may be measured with the first air quality monitor over a period of time to obtain a plurality of individual measurements of each parameter of the first set of onsite parameters. The plurality of individual measurements of the first set of onsite atmospheric parameters may include a first measured substance concentration of the target substance measured with the first air quality monitor. Further, the plurality of individual measurements of the first set of onsite atmospheric parameters may include a first set of individual atmospheric readings. The first set of individual atmospheric readings may include at least one of atmospheric reading selected from a barometric pressure, an air temperature, and a humidity level. These atmospheric readings may be obtained using one or more atmospheric (weather) sensors provide within the first air quality monitor. In some configurations, the first set of individual atmospheric readings may additionally include wind-speed and wind-direction. It should be noted that these readings associated with the wind-speed and wind-direction may be obtained from at least one anemometer installed at the site. As will be understood, in some embodiments, the anemometer may be provided within the first air quality monitor as well.

At step 2406, the first measured substance concentration may be transmitted to a first server. By way of an example, the first server may be a third-party server for carrying out computations, based on the data extracted from the site. As such, for example, the first server may be Amazon Web Services (AWS) server, or Google Cloud server, etc. At step 2408, the first set of individual atmospheric readings may be transmitted to the first server. The above parameters (i.e., the first measured substance concentration and the first set of individual atmospheric readings) may be transmitted to the first server for archiving, transforming, and/or processing, and may be stored there for a short period of time or archived for long-term utilization depending on the application. The location-specific atmospheric parameters may be transformed/processed and sent to a different location for processing, or processed locally, depending on the server characteristics, size of the data set, cost of transmitting data from location to location (e.g., transfer over internet protocol), etc.

In some configurations, transmitting the first measured substance concentration to the first server may include increasing a power of transmission, when the first air quality monitor is intermittently transmitting the first measured substance concentration to the first server. Further, in some configurations, a battery level may be obtained from a battery powering the air quality monitor. Based on the battery level, the rate of transmission of the first measured substance concentration may be modified based on the battery level. In particular, when the battery level is low, the rate of rate of transmission may be reduced to maximize the output from the battery. Further, in some configurations, a ticket may be generated and transmitted to the first server, when the battery level is below a predetermined battery level. Further, in some configurations, transmitting the first measured substance concentration to the first server may include boosting a rate of transmission, when the first measured substance concentration is indicative of an emission. It should be noted that the boosting may include transmitting at high frequency.

In some configurations, one or more Maximum Power Point Tracking (MPPT) controller may be included, for example, in the air quality monitor with a roll-over procedure. In case of a failure of one of the MPPT controllers, one of the MPPT controllers may send a ticket to the operator to replace the failed MPPT controller. Further, in some embodiments, the battery voltage may be connected to the to an interface (input/output (I/O)) pin of a microcontroller to enable transmission of the battery health data to the operator. Moreover, a change in the energy levels of the battery may be signaled. For example, if the air quality monitor system deployed with a signal-booster with a power status level, it could sense the low power status of the battery and therefore decrease or altogether turn off the signal boosting. In some example configurations, a cellular booster may be used that be provided by any of a variety of vendors, such as Wilson Electronics, Llc of Cottonwood Heights, Utah USA. One example of an illustrative system manufactured by Wilson Electronics, Llc is the WeBoost® model 'Drive Sleek' recorded in the Federal Communications Commission ID PWO460035. Illustrative patents specifically incorporated by reference herein include: U.S. Pat. Nos. 7,221,967; 7,729,669; 7,486,929; 7,409,186; 7,783,318; 8,583,034; 8,583,033; 8,874,030 B2; 8,874,029 B2; 8,755,399; 8,849,187 B2; 8,639,180; 9,537,455; and, 10,148,341

At step 2410, a regional atmospheric parameter for the site may be procured from a second server. In some configurations, the regional atmospheric parameter for the site may be a height of planetary boundary layer (hPBL). As such, the hPBL may be procured from the second server which may be High Resolution Rapid Refresh (HRRR) maintained by National Oceanic and Atmospheric Administration (NOAA). As will be appreciated by those skilled in the art, a planetary boundary layer (PBL)—also known as the atmospheric boundary layer (ABL) or peplosphere—is the lowest part of the atmosphere. The National Oceanic and Atmospheric Administration (NOAA), which has an improved observation model for land surface, works on a combination of satellite, radar, commercial airplanes, weather balloons combined observations that enable update of the HRRR.

Procuring interpolated atmospheric parameters from numerical weather prediction (NWP) models operating on actual/interpolated data procured from a variety of observing systems and instruments (e.g. radar, lidar, sonar, remote stations, flight data, satellite images/data, etc). Examples of the procured predicated atmospheric parameters include, for example: time of day, date, physical measurement or indirect calculation of: total cloud, dew point temperature, wind speed/max-speed/time-average/at-height, height of planetary boundary layer hPBL, surface visibility, precipitation types snow/ice-pellets/freezing-rain/rain, vertical velocity/mean-velocity/, surface pressure, best 4-layers lifted index, snow depth, water equivalent accumulated snow depth, temperature, component of wind, component of wind shea low-level/deep-level, surface lifted index, radar reflectivity maximum/composite/echo-top, radar vertically-integrated liquid water, cloud fraction high-level/mid-level/low-level cloud, lightning, storm relative helicty, maximum of updraft helicity over layer 2 to 5 km AGL, maximum updraft/downdraft velocity, total column integrate graupel, etc.).

In one illustrative example, the numerical weather prediction model may be the High Resolution Rapid Refresh (HRRR) model processed/supplied by the National Oceanic and Atmospheric Administration (NOAA). The HRRR is an interval-updated (e.g. hourly updated) assimilation and model of atmospheric parameters and weather-related reporting. The HRRR (and other systems) are used for various applications including aviation (and transportation in general), severe weather, and energy. Details of the HRRR and other atmospheric modeling are available for download from the International DOI Foundation at: https://doi.org/10.1175/MWR-D-15-0242.1 and specifically incorporated by reference for all that is disclosed therein. Depending on deployment location or other factors, other numerical weather prediction models may be utilized alone or in combination. While numerical weather prediction models report/calculate/estimate/provide different atmospheric parameters, one particularly useful atmospheric parameter is the height of planetary boundary layer (hPBL), through ongoing research other variables may be incorporated to improve agreement between the predicted and the actual results. Data from a zero-hour analysis data set is procured for each numerical weather prediction NWP model run (hourly for the HRRR model). The procured data set may consist of three-dimensional data at, in one example, a three kilometer per-node resolution.

The HRRR is updated every hour and gives detailed forecast weather and conditions for 3 kilometer (km) spatial resolution. The processing power required to create the HRRR is substantial and housed on supercomputers of whose main output is available via web-lookup or presentation. For instance, 95 million points are processed in the United States that are computed and reported on an hourly basis. Further, various data points can be obtained from National Weather Service (NWS). These data points may include: total cloud, dew point temperature, wind-speed at 10 meters (m) above ground-level, percent of frozen precipitation, total precipitation, precipitable water, height, height of cloud top, lifted condensation level, planetary boundary layer height, model terrain height, surface visibility, categorical precipitation types (snow, ice pellets, freezing rain and rain), wind gust speed, vertical velocity, mean vertical velocity, pressure mean sea level, surface pressure, Pressure of level from which parcel was lifted, best 4 layers lifted index, Snow depth, Water equivalent accumulated snow depth, temperature, component of wind, component of wind sheaLow Level, component of wind sheaDeep Layer, component of wind, component of wind sheaLow Level, component of wind sheaDeep Layer, surface lifted index, radar reflectivity, maximum radar reflectivity, composite radar reflectivity, echo top, radar vertically-integrated liquid water, high-level cloud fraction, mid-level cloud fraction, low-level cloud fraction, lightning, storm relative helicity, maximum of updraft helicity over layer 2 to 5 km above ground level, maximum updraft velocity, maximum downdraft velocity, total column integrate graupel.

As will be further appreciated, the behavior of the planetary boundary layer (PBL) is directly influenced by its contact with a planetary surface. For example, the planetary boundary layer (PBL) usually responds to changes in surface radiative forcing in an hour or less. In this layer physical quantities such as flow velocity, temperature, and moisture display rapid fluctuations (turbulence) and vertical mixing are strong. It should be noted that above the PBL is the "free atmosphere", the wind is approximately geostrophic (parallel to the isobars), whereas within the PBL, the wind is affected by surface drag and turns across the isobars. The hPBL therefore signifies the height above the sea-level until which the planetary boundary layer (PBL) exists. The hPBL has proven to be useful in monitoring operating emissions at a site. For example, when the hPBL is at a relatively low elevation, emission accumulate at the site. In some instances when very low hPBL and stagnation conditions exist, the concentration level of a compound accumulate constantly. In other words, the time:concentration ratio is linear. Because global average methane levels are about 1.876 parts per million, the nominal leakage from operating devices (e.g. pneumatics operating on well-provided gases that include methane ($CH_4$)), the leakage of methane over time into the right conditions can be utilized to establish and/or confirm operating emissions. The height of planetary boundary layer (hPBL) is further explained in detail in conjunction with FIGS. 26-29.

As mentioned above, the first measured substance concentration and the first set of individual atmospheric readings (also, referred to as on-site atmospheric parameters) may be transmitted to the first server. The on-site atmospheric parameters may include physical measurement or indirect calculation of: wind-speed, wind-direction, air-pressure, air-temperature, humidity, etc. The first measured substance concentration may be in parts per million of the substance such as methane, nitrogen, nitrogen oxides, oxygen, ozone, carbon oxides, argon, sulfur oxides, water vapor, etc. In some configurations, the first measured substance concentration and the first set of individual atmospheric readings may be transmitted by the air quality monitor to the first server at an interval (e.g., 1 second interval). Further, in some configurations, the first measured substance concentration and the first set of individual atmospheric readings may be first averaged before transmitting to the first server. The averaging may be performed over an averaging-time, for example, 1 minute interval. It should be noted that the averaging may be performed to create at least one time-averaged measured on-site atmospheric parameter. Some examples of time-average measured on-site atmospheric examples include, but are not limited to: air temperature, relative humidity, barometric pressure, wind-direction, wind stability class, circular standard deviation of past (e.g. 10 minutes) of wind-direction, current wind-speed, time-average wind-speed (5-minute/10-minute/30-minute), the hPBL, etc.). This averaging may, in some situations, occur on-site at an air quality monitor before transmission. Alternatively, the raw data may be directly transmitted. In both the cases, the averaging of the measured on-site atmospheric parameters may be useful for efficiently utilizing resources, for example, available energy, transmission capacity/bandwidth, etc. The time-averaged measured on-site atmospheric parameters may be transmitted over a cellular network to the first server (e.g. a cloud-attached server, such as Amazon Web Services (AWS) server) for storage, transforming, and/or processing. In one configuration, the raw data of the measured on-site atmospheric parameters may be sent to and stored on a Postgres database (a free and open-source relational database management system emphasizing extensibility and SQL compliance).

Figure 26:
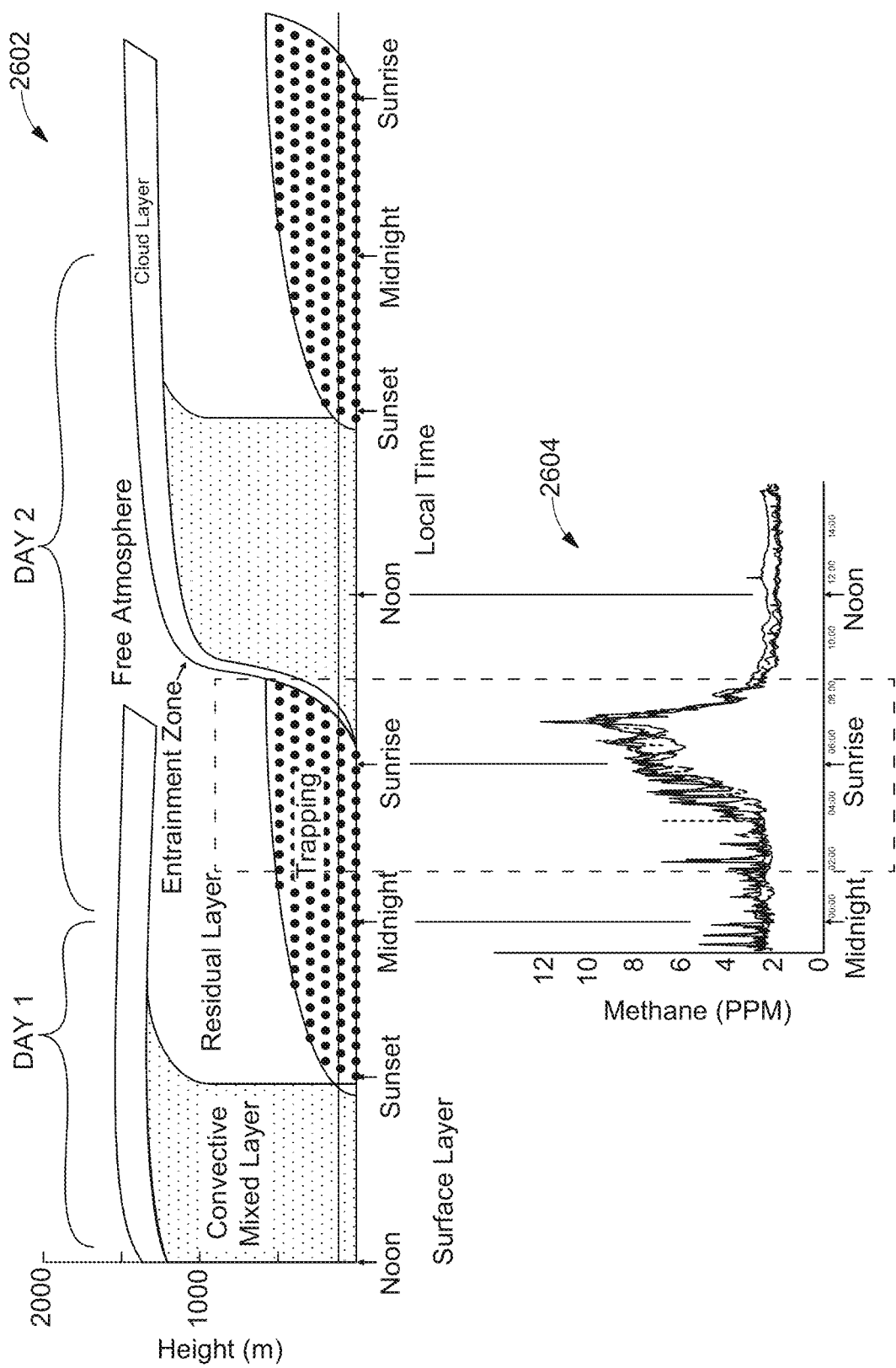
FIG. 26 illustrates a first example graphical representation and a second example graphical representation of a planetary boundary layer (PBL) for a site, in accordance with some configurations of the present disclosure.

Referring now to FIG. 26, a first example graphical representation 2602 of a planetary boundary layer (PBL) for a site are illustrated, in accordance with some configurations. The first example graphical representation 2602 represents a plot of time-of-day 2606 (along X-axis) and a height of planetary boundary layer (hPBL) 2608 (along y-axis). As can be seen in FIG. 26, the height of planetary boundary layer (PBL) varies as the day progresses. For instance, the hPBL is low between midnight until morning, and is relatively higher during the day, i.e. from sunrise until sunset. As it will appreciated, the variation in the hPBL in a 24-hour period is due to variation in the speed of winds at the site. Since the wind speed is relatively higher during the period between the sunrise until sunset, the hPBL during this period is observed to be higher.

As a result of the variations in the hPBL, a concentration of a substance mixed in the atmospheric air, for example, due to emission/leakage from an emission source present at the site, may also vary. As will be further appreciated, the concentration of the substance may be lower during a period when an average wind speed during that period is high, and the concentration may be higher during a period when an average wind speed during that period is relatively lower. FIG. 26 further shows a second example graphical representation 2604 showing a graphical plot between a substance concentration (along y-axis) in the atmospheric air of the site and a time of the time (along x-axis). For example, the substance may be Methane (CH4) gas. As shown in the second example graphical representation 2604, during the period between midnight and sunrise, i.e., when the wind speed is low and the hPBL is also observed to be low, there is a gradual (almost linear) increase in the concentration of the Methane (CH4) gas in the atmospheric air surrounding the site. This condition may be referred to as trapping condition which may occur due to wind stagnation. During emission of the substance from an emission source, under the trapping condition, there is a gradual accumulation of the substance in an atmosphere surrounding the site and a higher first measured substance concentration of the target substance measured with the first air quality monitor. Therefore, for accurate predictions, it is important to take the trapping condition into consideration. Further, the hPBL data may indicate a specific time period during a 24-hour period, during which such trapping conditions may be observed. As will be appreciated, the measured concentration of the emission under the trapping conditions may not provide accurate representation of the total average emissions, since the measured concentration might be higher than the usual measurements owing to the emission trapping or trapping condition. This is further explained in detail in conjunction with FIGS. 27-28.

Figure 27:
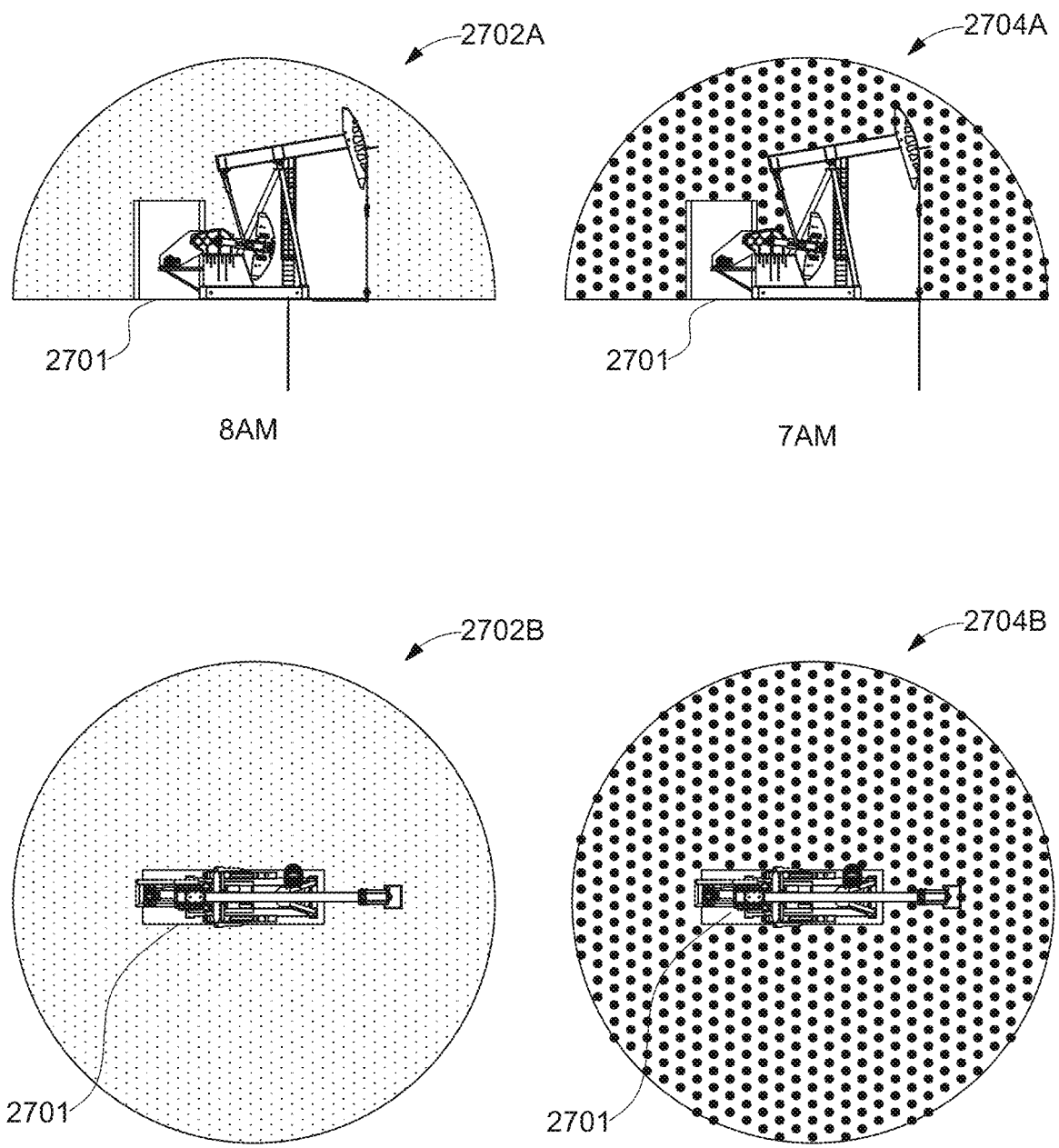
FIGS. 27-28 illustrate two example scenarios (also referred to a trapping conditions) of a consistently leaking emissions source at two different times of the day, in accordance with some embodiments of the present disclosure.
Figure 28:
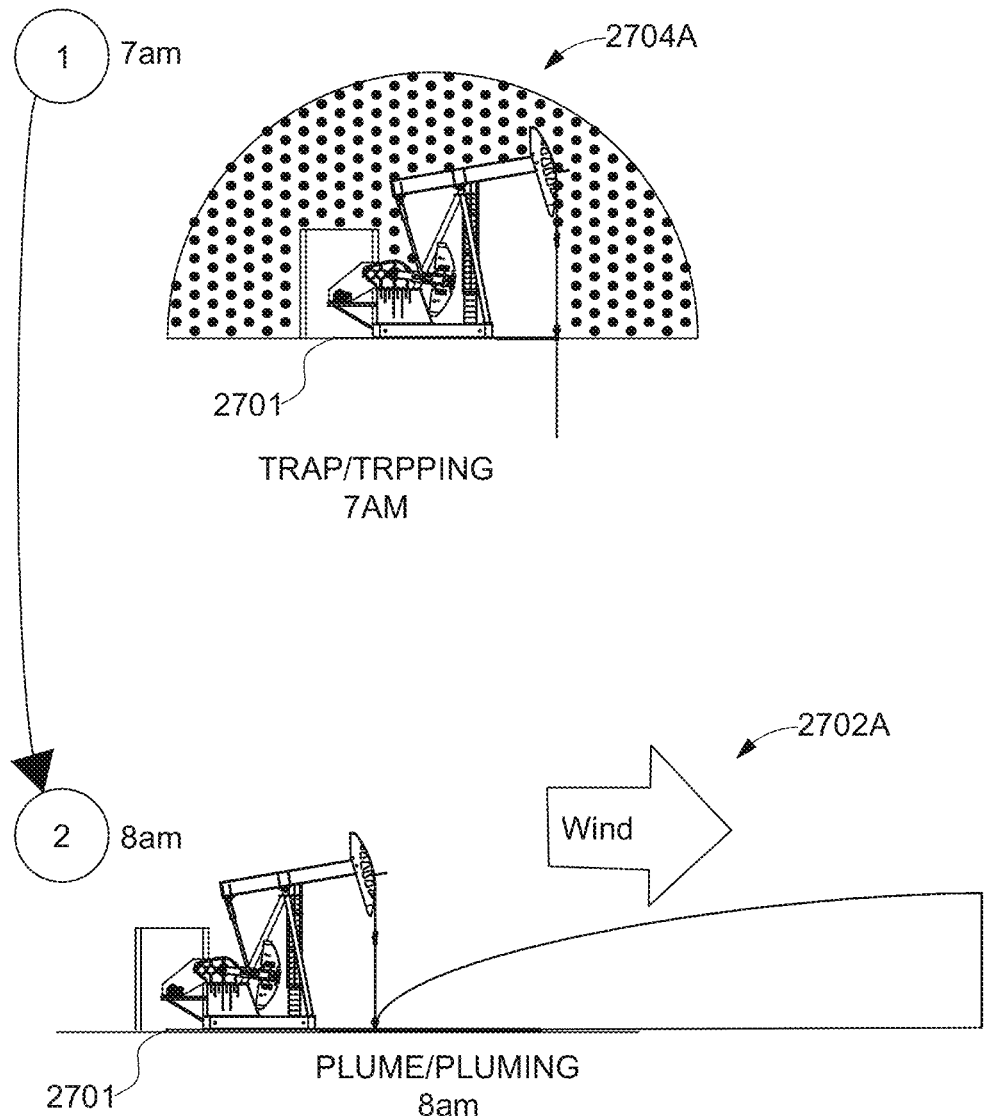

Referring now to FIGS. 27-28, two example scenarios (also referred to a trapping conditions), respectively of a consistently leaking emissions source 2701 at two different times of the day are illustrated, in accordance with some embodiments. FIG. 27 shows a schematic front view 2702A of the emission source 2701 along with its immediate surroundings and a schematic top view 2702B of the emission source 2701 along with its immediate surroundings at a first time (8 AM) of the day. FIG. 27 further shows a schematic front view 2704A of the emission source 2701 along with its immediate surroundings and a schematic top view 2704B of the emission source 2701 along with its immediate surroundings at a second time (8 AM) of the day. It should be noted that the hPBL at the first time (8 AM) of the day is higher than the hPBL at the second time (7 AM) of the day. This may be due to lower wind speeds towards the sunrise at the first time (7 AM) of the day as compared to the second time (8 AM) of the day. As such, the concentration of the substance in the immediate surroundings of the emission source 2701 is lower during the first time (8 AM) as compared to the second time (7 AM). Further, FIG. 27 shows the above two scenarios (also referred to a trapping conditions) in different views. FIG. 28 a schematic front view 2704A of the emission source 2701 along with its immediate surrounding at the second time (7 AM) and the schematic front view 2702A of the emission source 2701 along with its immediate surrounding at the first time (8 AM) of the day. As it can be seen, due to higher winds-speeds at the first time (8 AM), the hPBL is raised, due to which the concentration of the substance reduces, as compared to the second time (7 AM) of the day.

The height of pressure boundary layer (hPBL) has proven to be useful in monitoring operating emissions at a site. For example, when the hPBL is at a relatively low elevation, emission accumulate at the site. In some instances when very low hPBL and stagnation conditions exist, the concentration level of a compound accumulate constantly. In other words, the time:concentration ratio is linear. Because global average methane levels are about 1.876 parts per million, the nominal leakage from operating devices (e.g., pneumatics operating on well-provided gases that include methane), the leakage of methane over time into the right conditions can be utilized to establish and/or confirm operating emissions.

Returning to FIGS. 24-25, at step 2412, a prediction model associated with the first air quality monitor may be trained. In other words, a trained prediction model may be obtained for carrying out the computations for the location method. The prediction model may be trained specific to each of one or more air quality monitors provided at the site, or may be trained specific to the site, based on on-site atmospheric parameters and the procured atmospheric parameters (either as raw data or transformed/processed data). By way of an example, the prediction model or the machine learning regression model may be based on a gradient tree-boosting algorithm. In particular, the machine learning regression model may utilize a FastTreeTweedie algorithm in ML.NET framework. The prediction model may be used for identifying the emission sources and the also for isolating correlation between elevated concentrations and atmospheric variables. For example, a prediction model (machine learning model) configured as a tree-based model and a gradient tree-boosting algorithm, may be trained with 10 leaves and 300 trees. The prediction model may be trained daily for each air quality monitor for up to 90 days of data. The trained prediction model may be used to generate a predicted pollutant concentration for each minute using the device measurements.

For example, the gradient tree-boosting algorithm used in one of the algorithms may be configured based on the information available at the source: //arxiv org/pdf/1508.06378.pdf, specifically incorporated by reference for all that is disclosed therein. This reference discloses a tweedie generalized linear model for performing the prediction. It should however be noted that other versions of the gradient tree-boosting algorithms that may or may not apply tweedie compound Poisson models may be utilized as well. In utilizing the tweedie generalized linear model, a profile likelihood approach to estimate the index and dispersion parameters may be used. As such, the model may be capable of capturing complex interactions among predictions. Alternative machine learning regression models, such as, a simple-stress regression model could be used, however, the gradient tree-boosting algorithm (decision tree) ensembles may provide better performance and may therefore be preferred. Further, other alternative machine learning regression models may include: Common Regression Models, Linear Regression Models (e.g. Ordinary least squares, Gradient descent, Regularization), Decision trees and tree ensembles (e.g. random forest, bagging, boosting), Generalized Additive Model, Support Vector Machine, Artificial Neural Network, etc.

As it will be appreciated by those skilled in the art, the gradient tree-boosting algorithm may be used for predicting continuous target variable (as a Regressor, using cost function Mean Square Error (MSE). In order to apply the gradient tree-boosting algorithm, an average of the target label may be calculated, using a leaf that is an average value of the variable to be predicted. This leaf may then be used as a baseline. Further, for every sample, the residual may be calculated, for example, using the formula: (residual=actual value−predicted value). Thereafter, a tree may be constructed with the goal of predicting the residuals. Every leaf contains a prediction as to the value of the residual (not the desired label). In the event there are more residuals than leaves, some residuals may end up inside the same leaf. In such cases, their average is calculated and placed that inside the leaf. Thereafter, the target label may be predicted using all of the trees within the ensemble. Each sample passes through the decision nodes of the newly formed tree until it reaches a given lead. The residual in said leaf may be used to predict the house price. A new set of residuals may be calculated by subtracting the actual house prices from the predictions (made in the previous step). The residuals may then be used for the leaves of the next decision tree. The above steps may be repeated until the number of iterations matches the number specified by the hyperparameter (i.e., number of estimators) Once the model is trained, all the trees may be used in the ensemble to make a final prediction as to the value of the target variable. The final prediction will be equal to the mean computed initially, in addition to the residuals predicted by the trees that make up the forest multiplied by the learning rate.

At step 2414, a plurality of first predicted substance concentrations of the target substance corresponding to the first air quality monitor may be obtained from the prediction model. The first predicted substance concentrations may be obtained using at least the first set of individual atmospheric readings and the regional atmospheric parameter for the site. It should be noted that the plurality of first predicted substance concentrations may be obtained over a predefined period at a predefined frequency. For example, the plurality of first predicted substance concentrations may be obtained at a frequency of 1 minute, i.e., the prediction may be obtained every one minute from the prediction model. Further, the plurality of first predicted substance concentrations may be obtained during a training period extending to 10 days.

In one of the configurations of the present disclosure, methane (Ch4) concentration may also be used in the training the prediction model as the "correct answer". The decision trees are designed and created to try and get as close to the training methane concentration as much as possible. Once a best set of trees is obtained, the same can be used to predict the methane concentration, at the time of testing.

It should be noted that the prediction model may be trained before carrying out the predictions. The prediction model may be trained using measured on-site atmospheric parameters and procured atmospheric parameters. The measured on-site atmospheric parameters and procured atmospheric parameters also referred to as 'independent variables' or 'features' may be utilized to obtain 'dependent variable' or the 'predictions.' By way of an example, the prediction model may be a Machine Learning model, and in particular, a regression models (e.g., trained regression model). As will be appreciated, the longer period of time the prediction model is trained, the more robust the AQM-specific model becomes. As such, for example, the prediction model may be trained for 5 to 180 days. It has been observed that the prediction model trained for a 90-day period has proven capable of utilizing the measured on-site atmospheric parameters with procured atmospheric parameters to accurately perform the predictions. The prediction, for example, may include pollutant concentrations, such as, in parts per million of methane (CH4) in the atmosphere.

Figure 29:
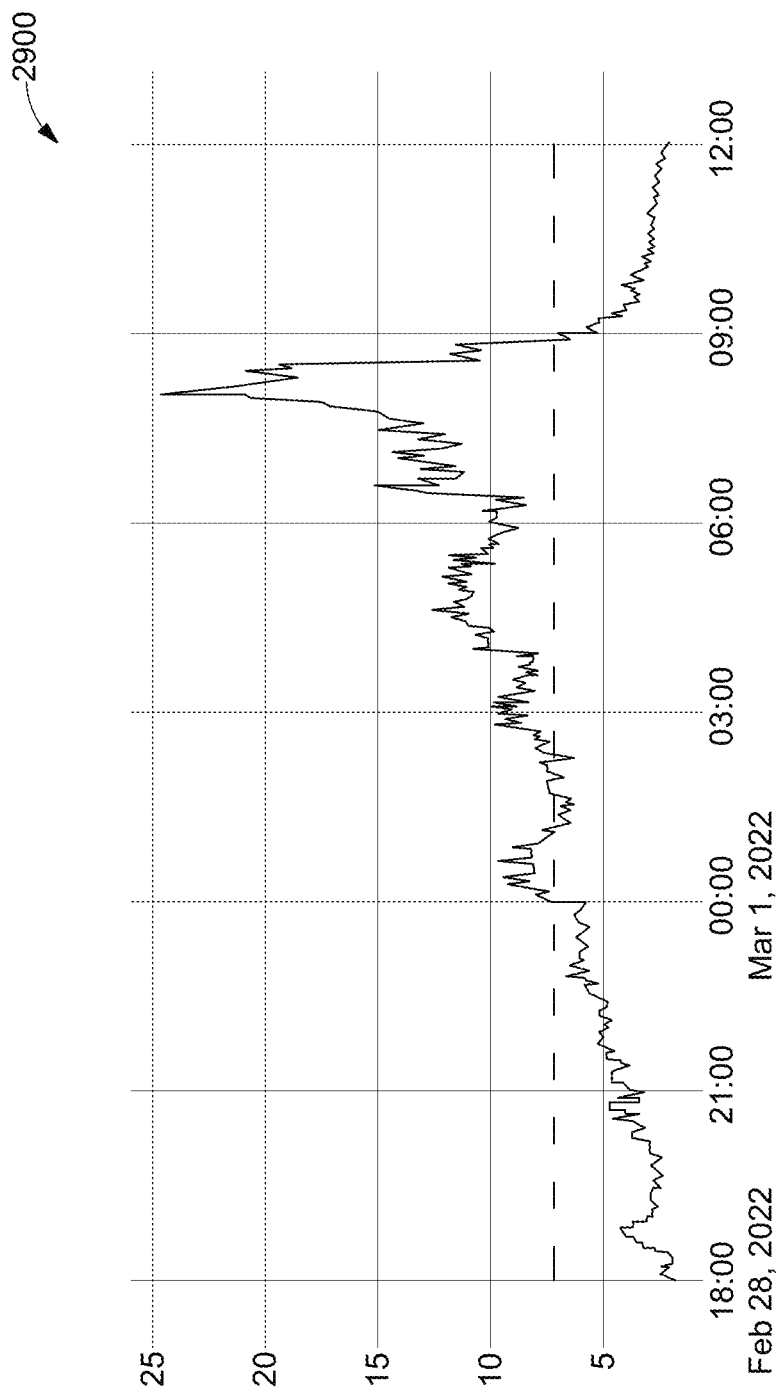
FIG. 29 illustrates a graphical plot of the first predicted substance concentrations obtained from the prediction model over a period on a particular day of a year, in accordance with some embodiments of the present disclosure.

Once trained, the prediction model may be used to obtain first predicted substance concentrations in real-time, or according to an interval (for example, each minute) using the measured on-site atmospheric measurements at the air quality monitor (AQM) and other procured atmospheric parameters (for example, the variables obtained from hourly-supplied variables by the numerical weather prediction models). By way of an example, FIG. 29 shows a graphical plot 2900 of the first predicted substance concentrations obtained from the prediction model over a period of 18 hours on a particular day of a year (e.g., Feb. 28, 2022). The graphical plot may be generated based on the first predicted substance concentrations obtained at one-minute intervals from the prediction model. It should be noted that the trained prediction model may be used for performing one or more functionalities including locating an emission source of a target substance at the site, quantifying emissions of the target substance at the site, etc., as will be discussed in detail hereinafter.

Figure 30:
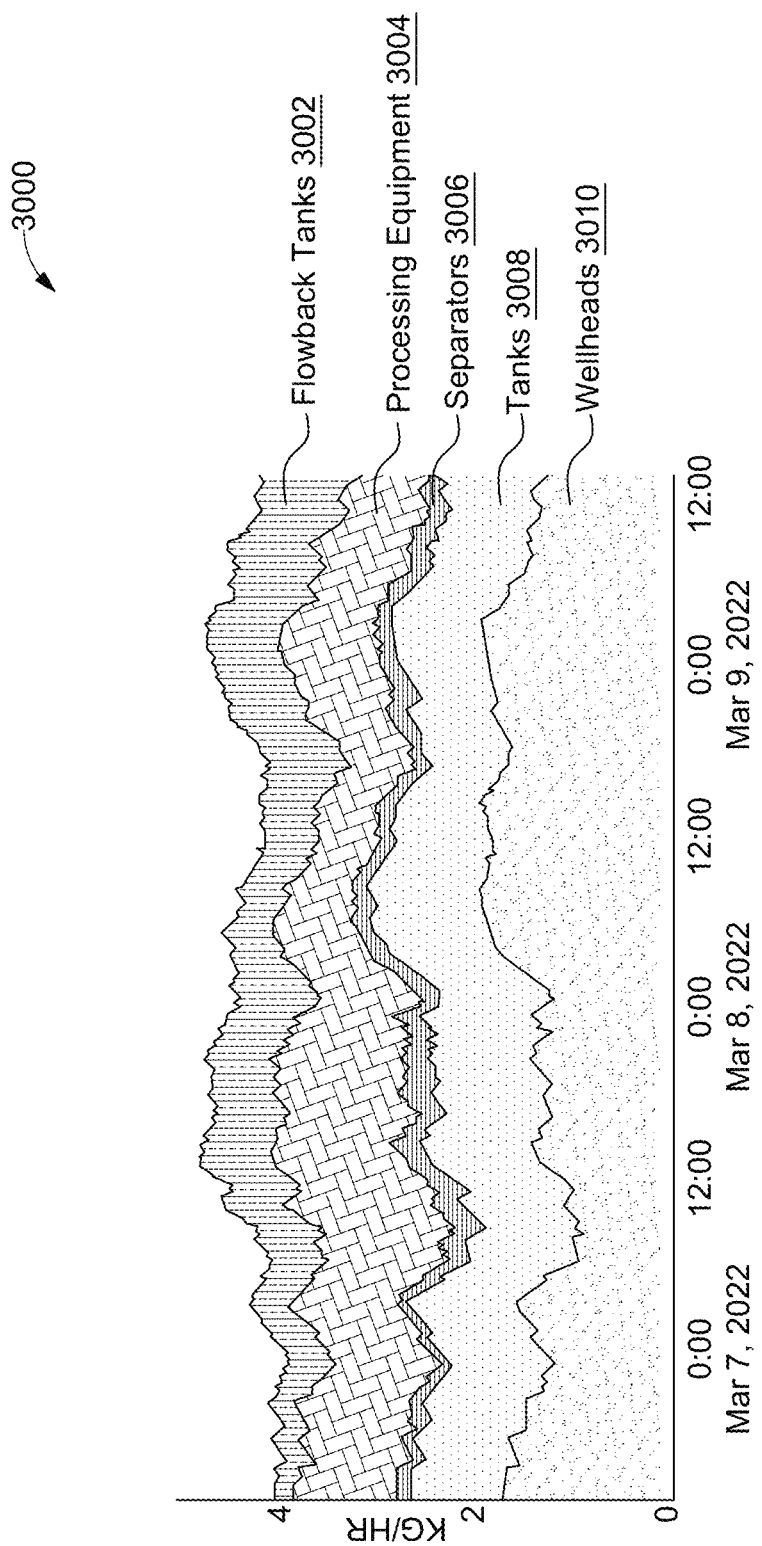
FIG. 30 illustrates another graphical representation of the predicted substance concentrations obtained from the prediction model over a period of time, in accordance with some embodiments of the present disclosure.

As will be understood, the total emissions at a site (e.g., an oilwell) may be a combination of operating emissions and fugitive emissions. The operating emissions and fugitive emissions at the site may include: wellheads, tanks, separators, processing equipment, flowback tanks, etc. FIG. 30 illustrates another graphical representation 3000 of the predicted substance concentrations obtained from the prediction model over a period of 72 hours (e.g., from Mar. 7, 2022 to Mar. 9, 2022). The graphical representation 3000 may be generated based on the first predicted substance concentrations obtained at one-minute intervals from the prediction model. Further, the graphical representation 3000 shows a contribution to the overall predicted substance concentrations of each of the different types of emissions sources. The different types of emissions sources may include flowback tanks 3002, processing equipment 3004, separators 3006, tanks 3006, and wellheads 3010. Further, as plotted along y-axis of the graphical representation 3000, the contribution of each of the different types of emissions sources is represented in kilogram/hour (kg/hr). The on-site emissions are often difficult to ascertain because there are offsite sources such as global atmospheric levels (e.g., 1.9 parts per billion of methane), nearby tanks, nearby wells, passing locomotives, nearby painting facilities, etc. As will be further understood, in most situations, an emissions source generates a plume (largely based on wind-direction wind speed- and) and the distribution of the plume is complicated. In order to determine the location of the emission source at the site, one or more air quality monitors may be placed at various different locations at the site. The one or more air quality monitors measure various onsite atmospheric parameters, including measured substance concentration of the target substance, along with a set of individual atmospheric readings. The set of individual atmospheric readings may include at least one of atmospheric reading selected from: a barometric pressure, an air temperature, and a humidity level.

At step 2416, a mapping of a weighted mean of the plurality of first predicted substance concentrations grouped in each feature group of a predetermined number of feature groups may be generated. The predetermined number of feature groups together may be representative of feature values over a predetermined range. In some configurations, each feature group may be associated with a wind-direction bucket. As such, a predetermined number of wind-direction buckets together may be representative of wind-directions over a full circle, i.e., wind-directions over 360 degrees. As such, in some embodiments, the mapping may be generated of a weighted mean of the plurality of first predicted substance concentrations grouped in each of a predetermined number of wind-direction buckets together are representative of wind-directions over the full circle. This step of generating the mapping is further explained in the conjunction with FIG. 31.

Figure 31:
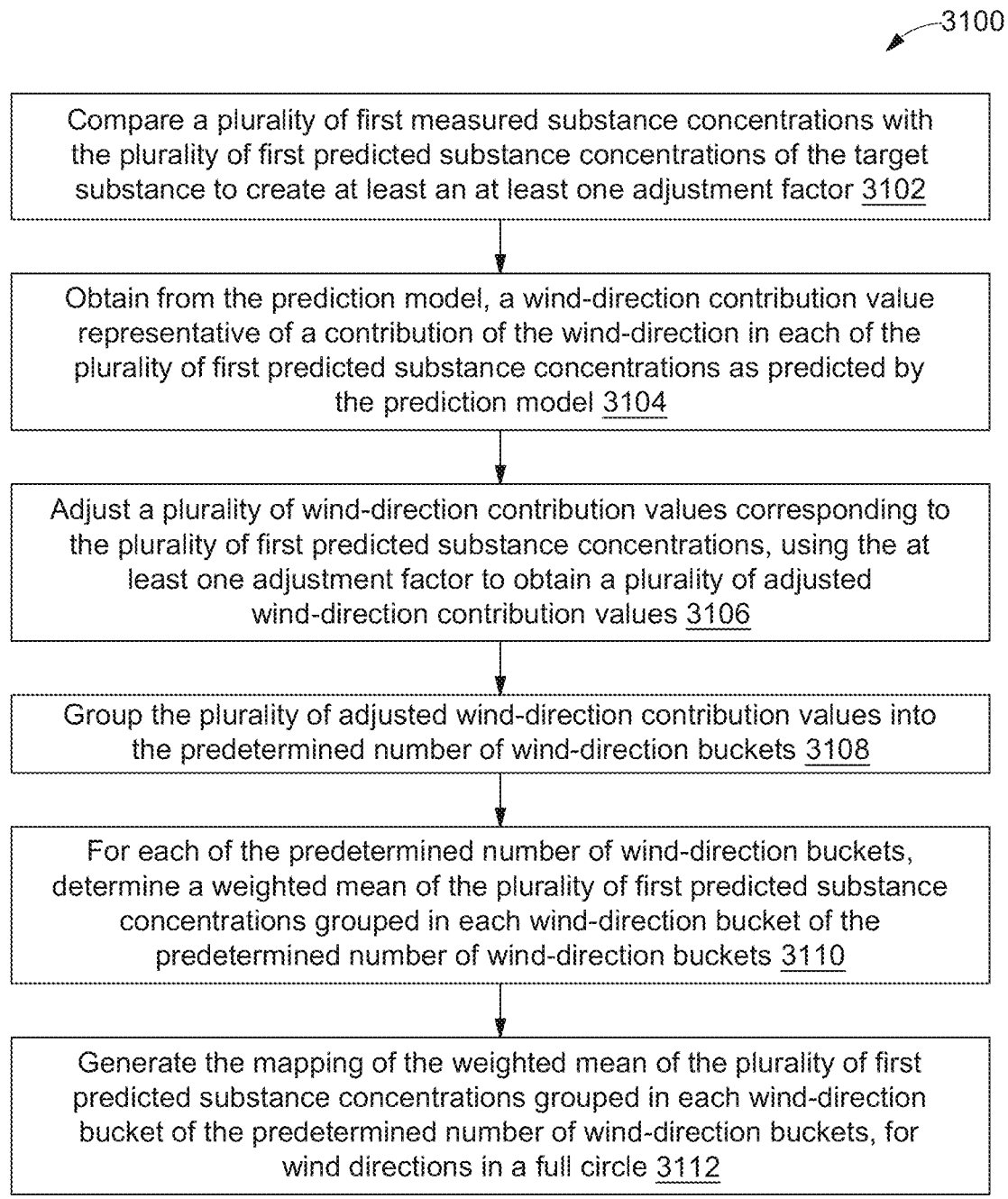
FIG. 31 illustrates a flowchart of a method of generating a mapping of a weighted mean of the plurality of first predicted substance concentrations grouped in each feature group of a predetermined number of wind-direction buckets, in accordance with some embodiments of the present disclosure.

Referring now to FIG. 31, a flowchart of a method 3100 of generating a mapping of a weighted mean of the plurality of first predicted substance concentrations grouped in each feature group of a predetermined number of wind-direction buckets, is illustrated, in accordance with some embodiments.

Figure 32:
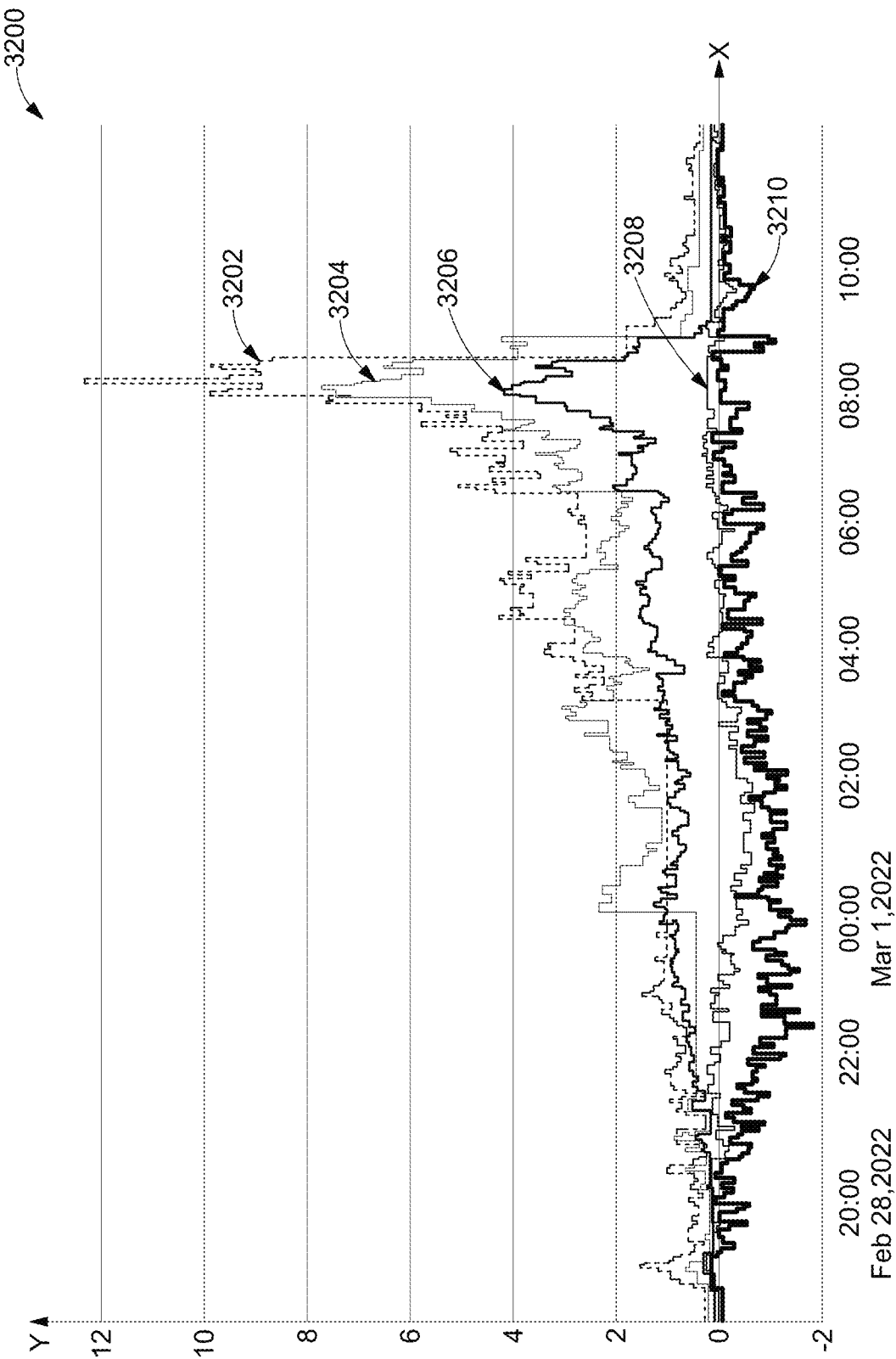
FIG. 32 illustrates a graphical representation of contribution of the six features with respect to time of the day, in accordance with some embodiments of the present disclosure.

It should be noted that mapping may be created for various different feature groups, including the wind-direction buckets. As will be understood, each feature group may have some contribution in the plurality of first predicted substance concentrations as predicted by the prediction model. For example, FIG. 32 illustrates a graphical representation 3200 of contribution of the six features (along y-axis) with respect to time of the day (x-axis). As shown in FIG. 32, the graphical representation 3200 shows the predicted substance concentrations as predicted by the prediction model. And further, the graphical representation 3200 shows the contribution of each of as many five features in arriving at a prediction at any time in the prediction model. Further, as can be seen in FIG. 32, some of the features may have a higher contribution at any given time of the day. For example, the five features may include a feature-1 of wind direction (shown by line 3202), a feature-2 of wind speed (shown by line 3204), a feature-3 of barometric pressure (shown by line 3206), a feature-4 of air temperature (shown by line 3208), and a feature-5 of humidity level (shown by line 3210).

As will be further appreciated, isolating wind-direction effect on the predicted pollutant concentration leverages statistical methods used in the training of the regression model to isolate the contribution of (only) wind-direction on the observed pollutant concentration. This allows removal of the effects of: 1) ambient atmospheric concentrations of the targeted pollutant, and 2) removal of the effects of height pressure boundary layer (hPBL), wind-speed, temperature, humidity, etc. without understanding and modeling the factors behind the phenomena of atmospheric concentration and/or effects of hPBL, wind-speed, temperature, humidity, etc. Instead, the model relies on statistical analysis of large amounts of data to train the prediction model (e.g., a trained regression model) that can accurately predict the measured pollutant concentration based on the values of other known parameters, and then examine that model to determine what portion of the predicted concentration can be attributed to only the wind-direction.

For machine learning regression models configured as a tree-based model, the contribution of a feature may be determined by exploring the opposite sub-tree for each decision node containing the given feature, i.e., comparing the results when making the "wrong" decision at each node containing the feature compared to the results when making the "right" decision. Some alternative configurations include fixing values of all-but-one feature and incrementing the wind-direction feature around the full circle, i.e., 360 degrees, thereby generating a new prediction for each wind-direction. The value predicted at the actual measured wind-direction is then compared to the predicted values at all other directions to determine the wind-direction contribution.

Referring to FIG. 31, at step 3102, a plurality of first measured substance concentrations may be compared with the plurality of first predicted substance concentrations of the target substance to create at least an at least one adjustment factor. As it will be appreciated, the predicted substance concentrations may have been predicted by the prediction model based on the training that has been provided to the prediction model, using training data over a period of time (e.g., 90 days). However, the predictions performed by the prediction model may vary from the actual or measured substance concentrations measured by the air quality monitor. This variation may be influenced by the factor of the current wind-direction. In order to carry out the calculations accurately, the contribution of the wind-direction may be determined.

As such, at step 3104, a wind-direction contribution value may be obtained from the prediction model. The wind-direction contribution value is representative of a contribution of the wind-direction in each of the plurality of first predicted substance concentrations as predicted by the prediction model. For example, the wind-direction contribution value may be obtained from the prediction model by analyzing an opposite sub-tree for each decision node associated with the wind-direction within the prediction model. In particular, obtaining the wind-direction contribution values may include varying a value associated with a wind-direction, when values associated with remaining readings of the first set of individual atmospheric readings are fixed. Further, obtaining the wind-direction contribution values may include obtaining, from the prediction model, a first predicted substance concentrations of the target substance, for each variation of the value associated with the wind-direction. Furthermore, obtaining the wind-direction contribution values may include comparing the first predicted substance concentrations with the first measured substance concentration of the target substance measured with the first air quality monitor, and determining the wind-direction contribution values, based on the comparison.

As will be understood, since the wind-direction contribution is calculated relative to the regression model's predicted concentration, it will not be representative of conditions that did not exist in the data that was used to train the model, such as a new leak or fugitive emission. To account for this, the wind-direction contribution is adjusted by adding (or in some instances subtracting) the difference between the measured and predicted concentrations.

Returning to FIG. 31, at step 3106, a plurality of wind-direction contribution values may be adjusted corresponding to the plurality of first predicted substance concentrations, using the at least one adjustment factor to obtain a plurality of adjusted wind-direction contribution values. Further, at step 3108, the plurality of adjusted wind-direction contribution values may be grouped into the predetermined number of wind-direction buckets. For example, the predetermined number of wind-direction buckets may include 72 wind-buckets. Therefore, each of the predetermined number of wind-direction buckets is representative of the wind directions in a segment of 5 degrees of the full circle. In other words, average wind-directions at the site over a specific period of time may be grouped into 72 wind-buckets, with each bucket being representative of the wind directions in a segment of 5 degrees of the full circle i.e., 360 degrees.

In one configuration, a predetermined number of days (e.g., 10 days) of data is utilized to ensure that sufficient data for all wind-direction bins is evaluated. In another configuration, the number of days may be reduced by improving processing of wind-direction bins to accommodate for wind-direction bins with limited (or no) data. Further, in another configuration, an exponentially time-weighted arithmetic mean may be used to calculate the average concentration for each (wind-direction) bin. The weighting factor is calculated as $(dt\_max-dt)^p$, where dt_max is the window size, dt is the time difference between the measurement time and window end time, and p is the weighting power. The weighting power can be adjusted to change the sensitivity of the distribution to new measurements at the expense of increased noise. A weighting power of zero would result in an unweighted mean. Further, a power of one would apply a weight of zero to measurements taken exactly at the start of the window, linearly increasing to a maximum weight at the end of the window. Similarly, higher weighting powers would result in exponentially greater weight being applied to more recent measurements.

At step 3110, for each of the predetermined number of wind-direction buckets, a weighted mean of the plurality of first predicted substance concentrations grouped in each wind-direction bucket of the predetermined number of wind-direction buckets may be determined. At step 3112, the mapping may be generated of the weighted mean of the plurality of first predicted substance concentrations grouped in each wind-direction bucket of the predetermined number of wind-direction buckets, for wind directions in a full circle. An example mapping is shown in and explained via FIG. 30.

Figure 33:
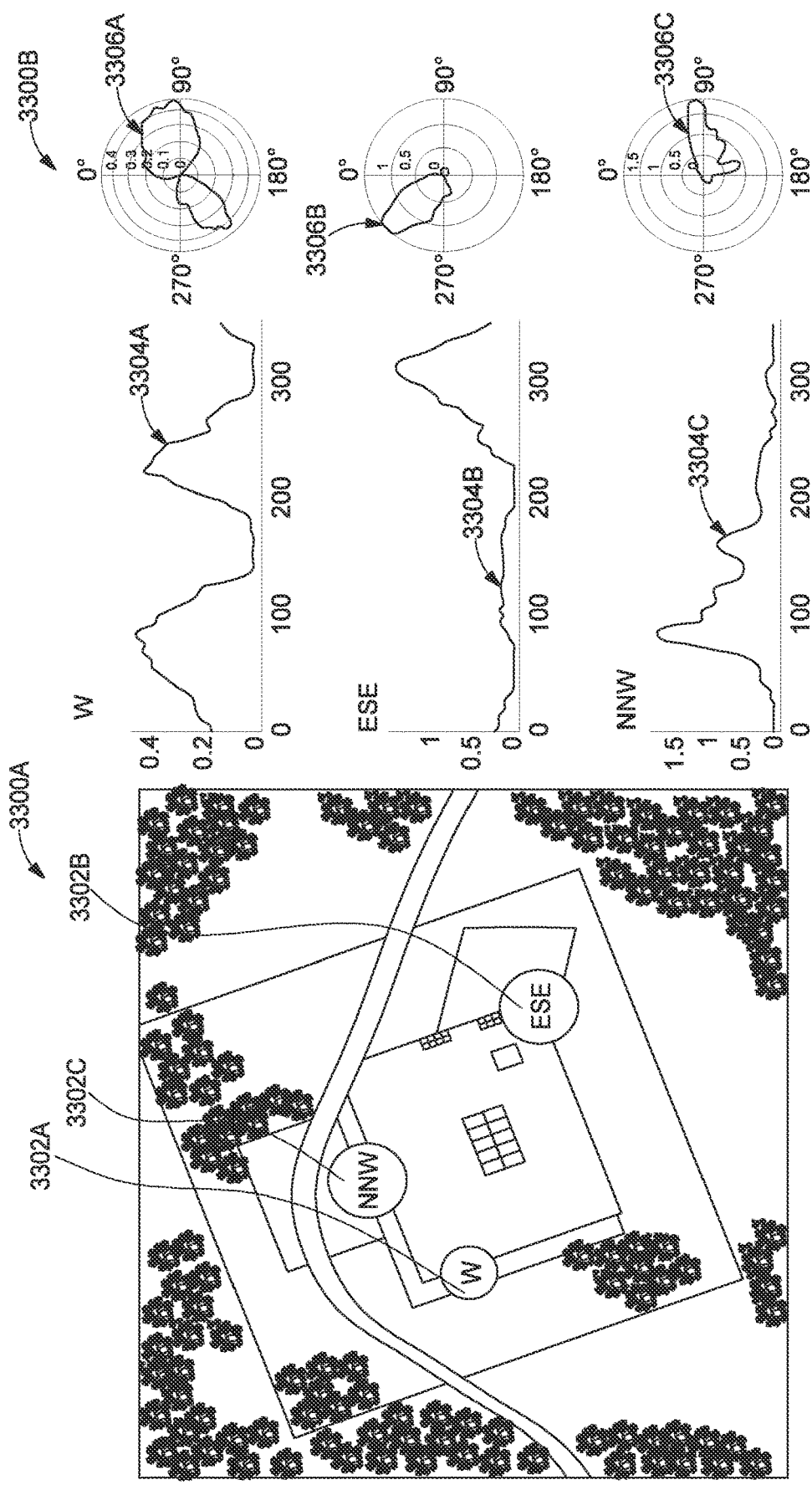
FIG. 33 illustrates a topological view of a site, and mappings charts associated with mapping of weighted mean of first predicted substance concentrations grouped in each of a predetermined of wind-direction buckets are illustrated, in accordance with some configurations of the present disclosure.

Referring now to FIG. 33, a topological view of a site 3300A, and mappings charts 3300B associated with mapping of weighted mean of first predicted substance concentrations grouped in each of a predetermined of wind-direction buckets, are illustrated in accordance with some configurations. As mentioned above, the predetermined number of the wind-direction buckets together are representative of wind-directions over 360 degrees. As shown in FIG. 33, the site includes three air quality monitors 3302A (W), 3302B (ESE), and 3302C (NNW). Corresponding to each air quality monitor, a line chart from 0-360 degrees with the y axis as the elevated concentration (ppm) and a polar chart is shown. In particular, for the air quality monitor 3302A (W), the line chart 3304A and a polar chart 3306A is shown. For the air quality monitors 3302B (ESE), the line chart 3304B and a polar chart 3306B is shown. For the air quality monitor 3302C (NNW), the line chart 3304C and a polar chart 3306C is shown. The mapping charts i.e., the line charts 3304A, 3304B, 3304C and the polar charts 3306A, 3306B, 3306C help to visualize the circular distribution of the wind-direction.

By way of an example, the prediction model (regressor model) may be used to predict the methane concentration for a time period, for example, of the last 10 days. The time period may be selected so as to ensure that data representing the wind blowing in every direction is obtained. Further, the wind-direction contribution value may be calculated for all of the predictions. The wind-direction contribution value may be an amount in parts per million (ppm) that the individual wind-direction affected the predicted ppm. All the predictions may be then grouped into 72 wind buckets (for every 5 degrees of the full circle or 360 degrees) based on the wind direction from the individual measurements. Further, a weighted Methane Mean may be calculated for each 5-degree bucket. A value function may be defined as: FeatureContribution[WindDirection]+ActualCh4−PredictedCh4. It should be noted that the function may be weighted with a recency bias. If no wind data is available for a specific wind bucket, the missing data may be filled in by interpolating it from the surrounding buckets for which data is available. In this way, for each of three air quality monitors, a weightCh4Mean value associated with a 5-degree wind bucket is obtained, that is represented in the line charts 3304A, 3304B, 3304AC and the polar charts 3306A, 3306B, 3306C.

Figure 34:
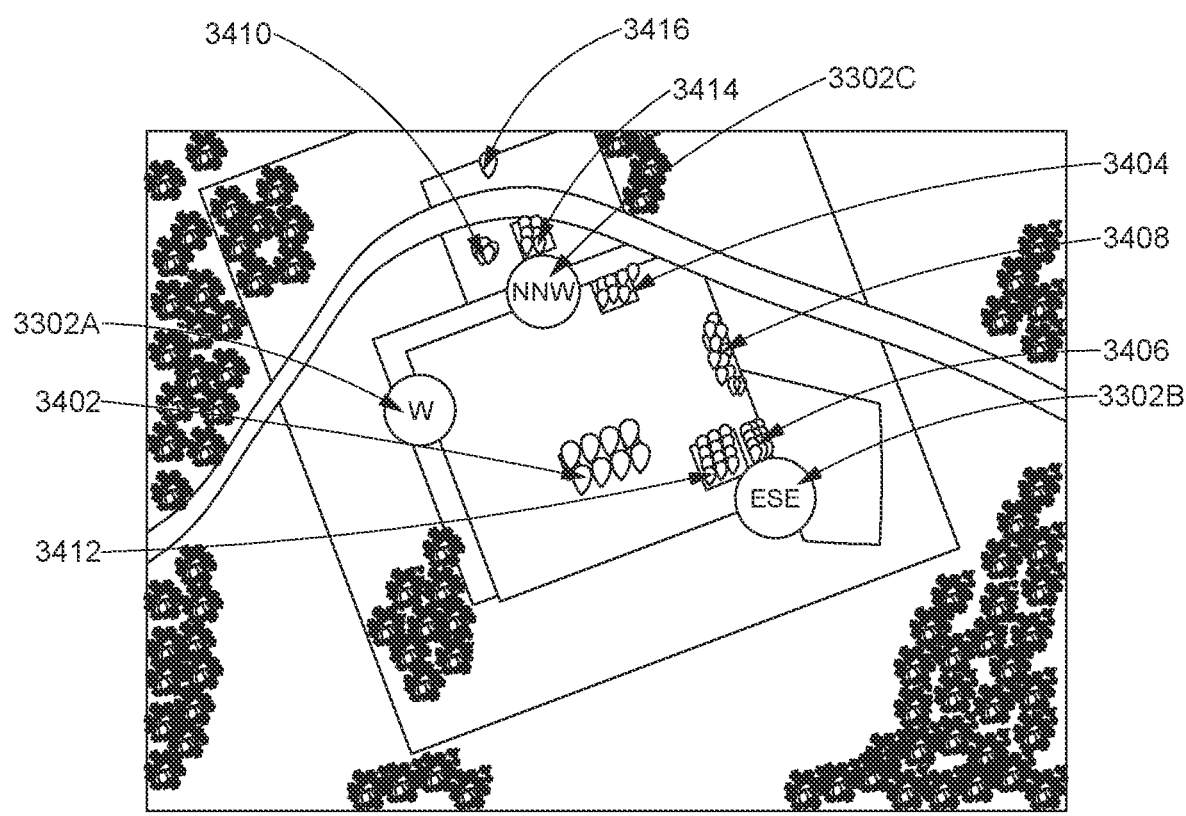
FIG. 34 illustrates an example location map for a site, in accordance with some configurations of the present disclosure.

Referring once again to FIGS. 24-26, at step 2418, a location map of a plurality of emission sources at a site may be obtained. The location map may include a location and an identity associated with each of the plurality of emission sources. An example location map 3400 for a site, for example, an oil rig, is shown in FIG. 34. As shown in FIG. 34, the location map 3400 includes a plurality of tags representative of an identity and a location of the plurality of potential emission sources present at the site. For example, the plurality of emissions sources may include one or more wellheads 3402, tanks 3404, separators 3406, processing equipment 3408, offsite separators 3410, flowback tanks 3412, offsite tanks 3414, and offsite wells 3416. As can be further seen in FIG. 34, some emission sources like offsite wells 3416 may be located outside the periphery of the site, and as such, the emissions from these offsite wells may sometimes also contribute to the total emission values detected at the site. Further, as shown in FIG. 33, the site may include the three air quality monitors 3302A (W), 3302B (ESE), and 3302C (NNW).

Figure 35:
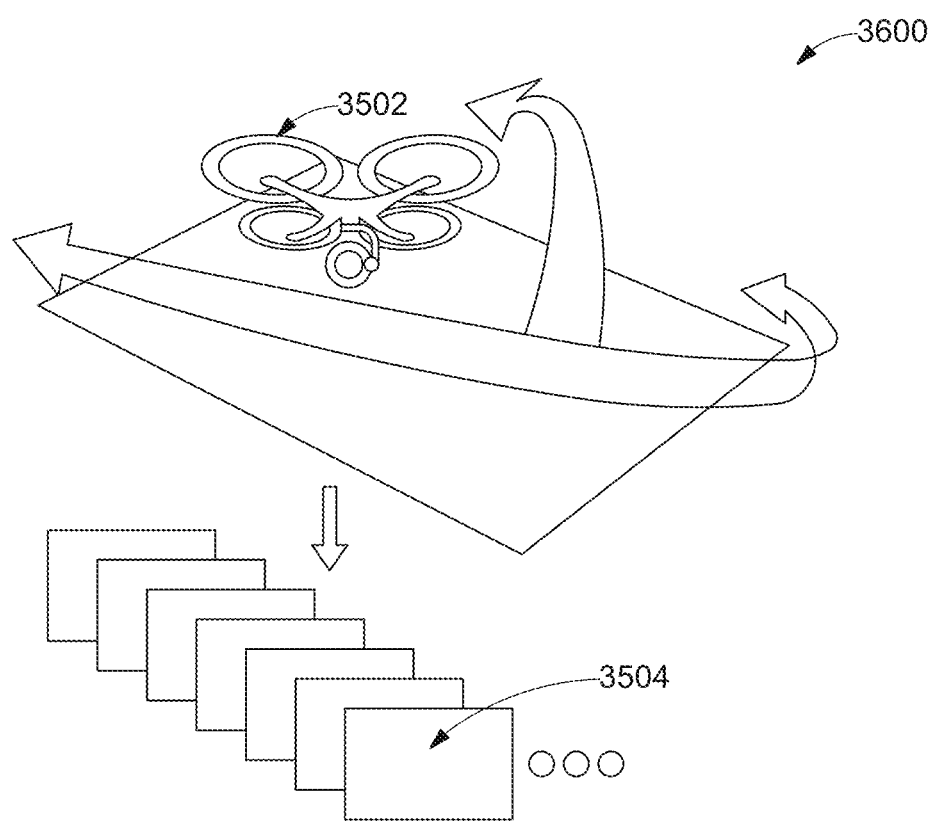
FIG. 35 illustrates a schematic view of a process of obtaining the location map using drone imagery, in accordance with some configurations of the present subject matter.

In some configurations, the location map may be obtained using drone imagery. In such configurations, the location map may be created by obtaining a plurality of two-dimensional images using the drone imagery. FIG. 35 shows a schematic view of a process 3500 of obtaining the location map using drone imagery, in accordance with some configurations of the present subject matter. For example, as shown in FIG. 35, a drone 3502 (i.e., an aerial vehicle implementing one or more still-image or video capturing cameras) may be used for obtaining a plurality of two-dimensional images 3504. As will be appreciated by those skilled in the art, the drone 3502 may be made to traverse across the location region for which the location map is to be obtained.

Once the plurality of two-dimensional images 3504 are obtained, three-dimensional measurements corresponding to the plurality of two-dimensional images 3504 may be extracted. Each of the three-dimensional measurements may include a distance between two points lying on a plane parallel to a photographic image plane, corresponding to measured associated distances on the plurality of two-dimensional images 3504, using a scale. In particular, the location map may be obtained using principles of photogrammetry for the air quality monitors. As will be appreciated, photogrammetry may be used to obtain reliable information about physical environments through the process of recording, measuring and interpreting photographic images. To this end, three-dimensional measurements may be extracted from two-dimensional data (i.e., images). The distance between two points that lie on a plane parallel to the photographic image plane can be determined by measuring their distance on the image, if the scale of the image is known. Further, close-range photogrammetry may be used that may include collection of photography from a lesser distance than traditional aerial (or orbital) photogrammetry. Thereafter, photogrammetric analysis may be applied to one photograph. Alternatively, high-speed photography and remote sensing may be used to detect, measure, and record complex two-dimensional and three-dimensional motion fields by feeding measurements and imagery analysis into computational models, so as to successively estimate, with increasing accuracy, the actual, 3D relative motions. As such, photogrammetry may be used for surveying the above site to accurately mark locations of a boundary line, equipment located on the site, and at least one ground control point to establish a point-of-truth from which the scale and orientation may be set. In one configuration, a single ground control point may be sufficient to establish the point-of-truth. However, some applications may benefit from multiple ground control points. In order to carry out the survey the site based on photogrammetry, some commercial tools may be used, for example, including but not limited to, Photo-Modeler (of Vancouver BC), Pix4D (of Prilly, Switzerland), and Topodrone (of Montreux, Switzerland).

At step 2420, for each emission source of the plurality of emission sources, a simulated plume model may be generated, based on the wind-direction. The generation of the plume model is already discussed in detail in the above-sections of the present disclosure. As will be understood, the simulated plume model may depend on the various atmospheric conditions prevailing at the site. At step 2422, for each emission source of the plurality of emission sources, a plurality of representative circular normal distributions may be calculated for each air quality monitor. The plurality of representative circular normal distributions may be calculated, using the simulated plume model, by setting a plurality of presumed flux values to the simulated plume model.

In some configurations, the plurality of representative circular normal distributions may be derived based on representative Von Mises distributions for all of the plurality of emission sources at the site using the corresponding (Gaussian) plume models. The representative Von Mises distributions represent a linear relationship between the leak flux (the term leak and emission may have been used interchangeable in this disclosure) at a given emission source and the expected measured substance concentration at the air quality monitor for each wind-direction bucket. The Von Mises distributions take into account the distance between the leak source and air quality monitor, the angular distance between wind-direction and source-to-device bearing, and the average wind-speed and atmospheric stability class for each wind-direction bin. this is further explained in conjunction with FIGS. 34-37.

Figure 36:
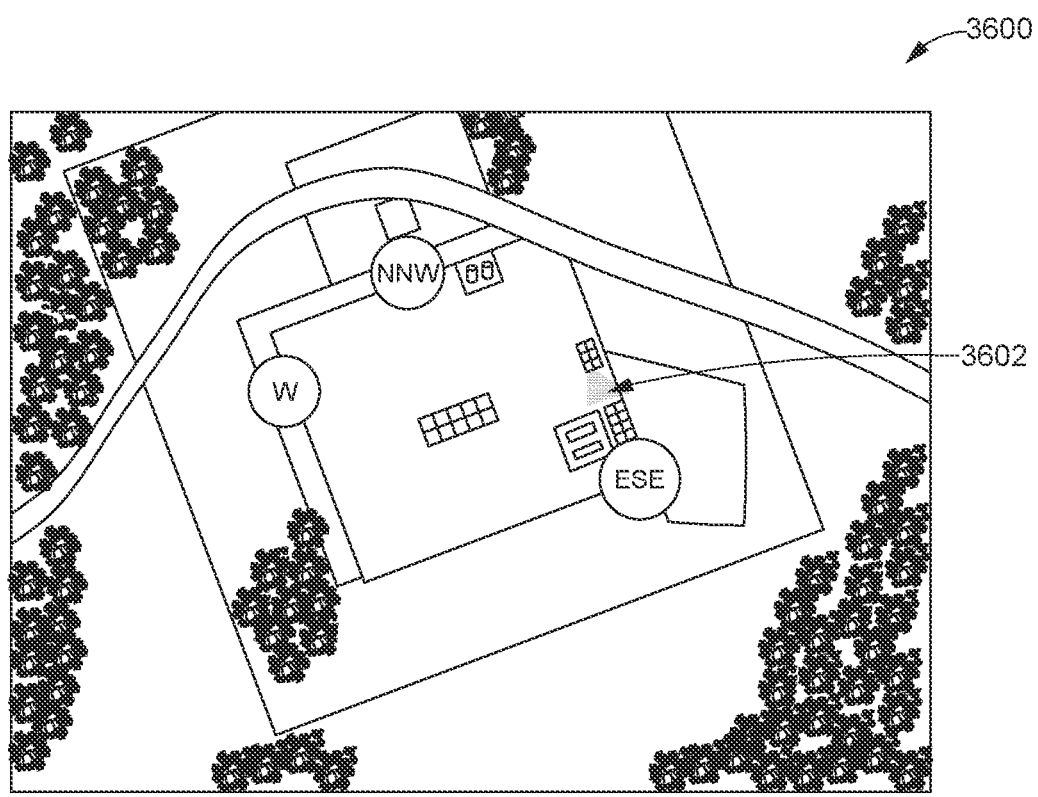
FIG. 36 illustrates a topological view of a site along with a simulated plume model for one of the emission sources, in accordance with some configurations of the present subject matter.
Figure 37:
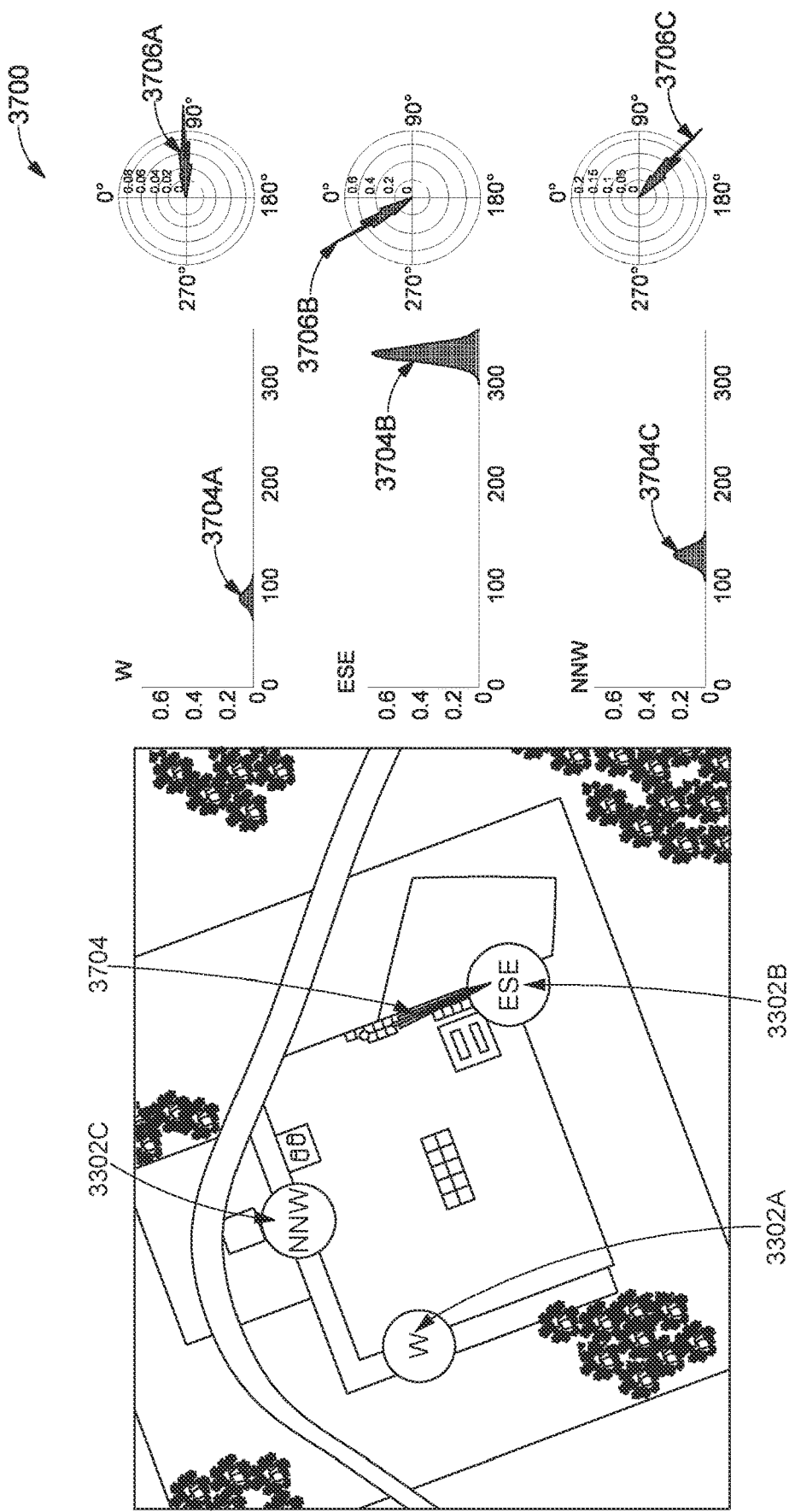
FIG. 37 illustrates a topological view of the site along with a representative Von Mises distribution for the one emission source, in accordance with some configurations of the present subject matter.

As mentioned above, FIG. 34 illustrates the location map 3400 for an example site. FIG. 36 illustrates a topological view 3600 of the site along with a simulated plume model 3602 for one of the emission sources (e.g., 3408). FIG. 37 illustrates a topological view 3700 of the site along with a representative Von Mises distribution 3704 for the one emission source (e.g., 3408). As shown in FIG. 36, the plume model 3602 may be generated using the techniques mentioned in the above-sections. The simulated plume for all the wind directions is use to fit the mapping (i.e. elevated concentration vs wind direction distribution) from the previous steps.

As shown in FIG. 37, the site includes the three air quality monitors 3302A (W), 3302B (ESE), and 3302C (NNW). It should be noted that for each of the emission sources, a representative Von Mises distribution may be generated corresponding to each of the three air quality monitors 3302A (W), 3302B (ESE), and 3302C (NNW). FIG. 37 further shows graphical representations of the Von Mises distributions. For example, the graphical representations of the Von Mises distributions may include a line graph 3704A and a polar graph 3706A for an emission source (e.g. 3408) corresponding to the air quality monitor 3302A. Further the graphical representations of the Von Mises distributions include a line graph 3704B and a polar graph 3706B for the emission source (e.g. 3208) corresponding to the air quality monitor 3302B. Furthermore, the graphical representations of the Von Mises distributions include a line graph 3704C and a polar graph 3706C for the emission source (e.g. 3408) corresponding to the air quality monitor 3302C.

In a nutshell, for each identified emission source, a representative Von Mises distribution (as shown in FIG. 37) for each of three air quality monitors at the site may be determined using the Gaussian plume models. This represents a linear relationship between the leak flux at the given source and the expected measured pollutant concentration at the device for each wind direction bin. Once the plume models are generated, a plume weight may be set to be the ppm value of the plume from the emission source at each of the three air quality monitors' location, for a given flux, for example, of 1 g/s. Further, based on the Von Mises distribution, a bearing of the plume from the emission source to each of the air quality monitors may be determined. Thereafter, the median standard deviation of the wind-direction for the wind-direction bucket may be calculated (also referred to as Stability Class).

Returning once again to FIG. 24, at step 2424, an analysis may be performed of the plurality of representative circular normal distributions in relation with the mapping to identify a relevant representative circular normal distribution from the plurality of representative circular normal distributions. The analysis is further explained in conjunction with FIG. 38.

Figure 38:
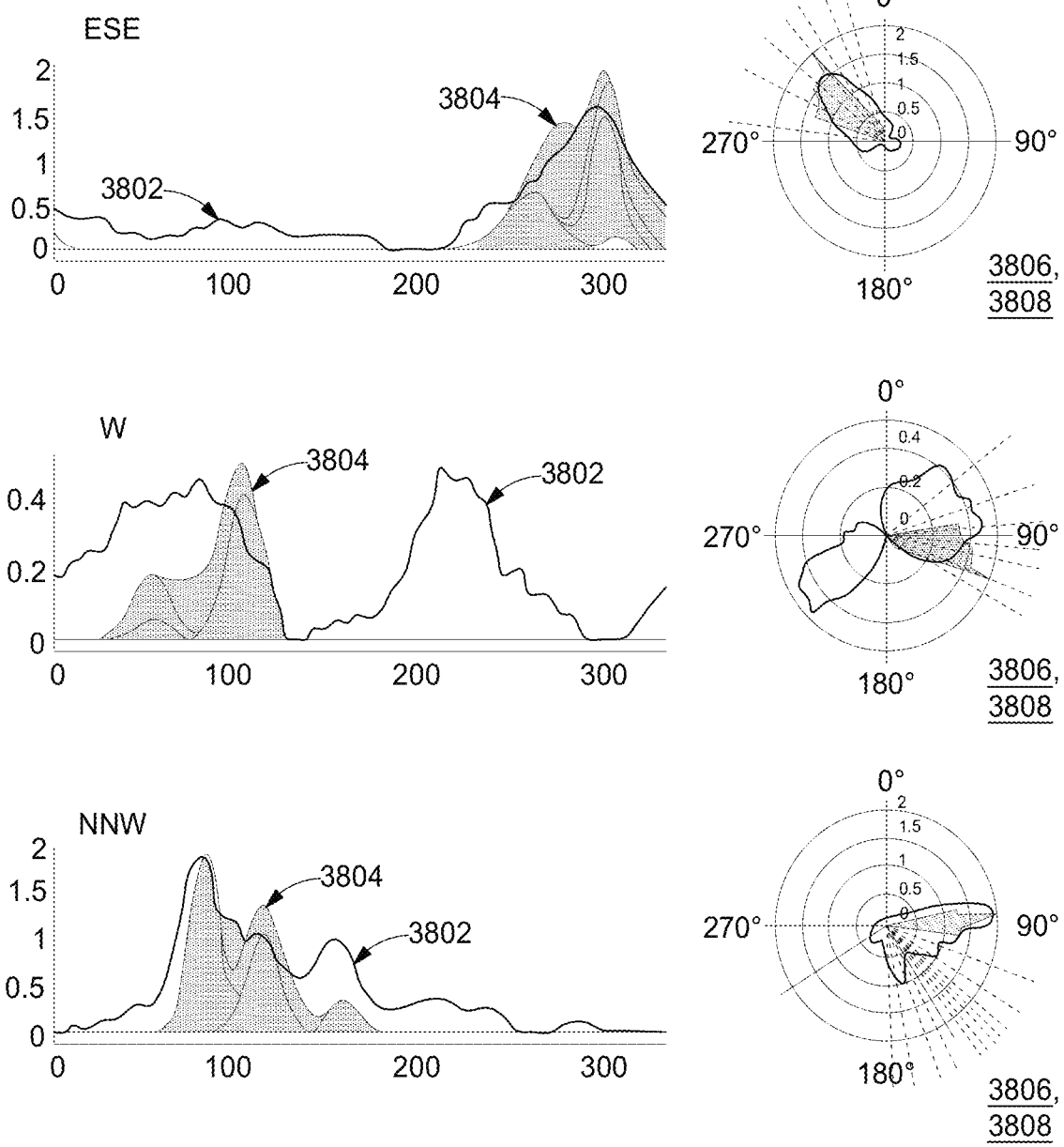
FIG. 38 is a graphical representation of the combination of lines charts and line graphs of the graphical representations of the Von Mises distributions, in accordance with some configurations of the present subject matter.

Referring to FIG. 38, a graphical representation of the combination of lines charts 3802 (corresponding to the line charts 3304A, 3304B, 3304C (of FIG. 33)) and line graphs 3804 of the graphical representations of the Von Mises distributions (corresponding to the line graphs 3704A, 3704B, 3704C of the Von Mises distributions of FIG. 37) is illustrated. FIG. 38 further shows a graphical representation of the combination of polar charts 3804 (corresponding to the polar charts 3306A, 3306B, 3306C (of FIG. 33)) and polar graphs 3808 of the graphical representations of the Von Mises distributions (corresponding to the polar graphs 3706A, 3706B, 3706C of the Von Mises distributions of FIG. 37) is illustrated. In order to perform the analysis, the line charts 3802 (corresponding to the line charts 3304A, 3304B, 3304C) and the line graphs 3804 of the graphical representations of the Von Mises distributions (corresponding to the line graphs 3704A, 3704B, 3704C of the Von Mises distributions) are mapped on to each other to identify the most fitting Von Mises representations with respect to the line charts. The most fitting or a relevant Von Mises representations is identified from all of the Von Mises representations. In other words, the best fit between the Von Mises representations for each of the emission sources and mappings of the weighted mean of the plurality of the first predicted substance concentrations grouped in each wind-direction bucket of the predetermined number of wind-direction bucket, is identified. This Von Mises representation is indicative of the target emission source from the emission or leak is taking place. This process may be performed by trying a plurality (e.g. 1000) of different combinations of plumes and adjusting their weights (fluxes) to find the best fit. As such, the simulated plumes fluxes are adjusted across all emission sources to match the elevated concentrations for each wind-direction. Alternatively, the heights of the Von Mises may be adjusted to fit the line charts.

Returning once again to FIG. 24, at step 2426, the target emission source may be determined, based on the above analysis and the location map.

Figure 39:
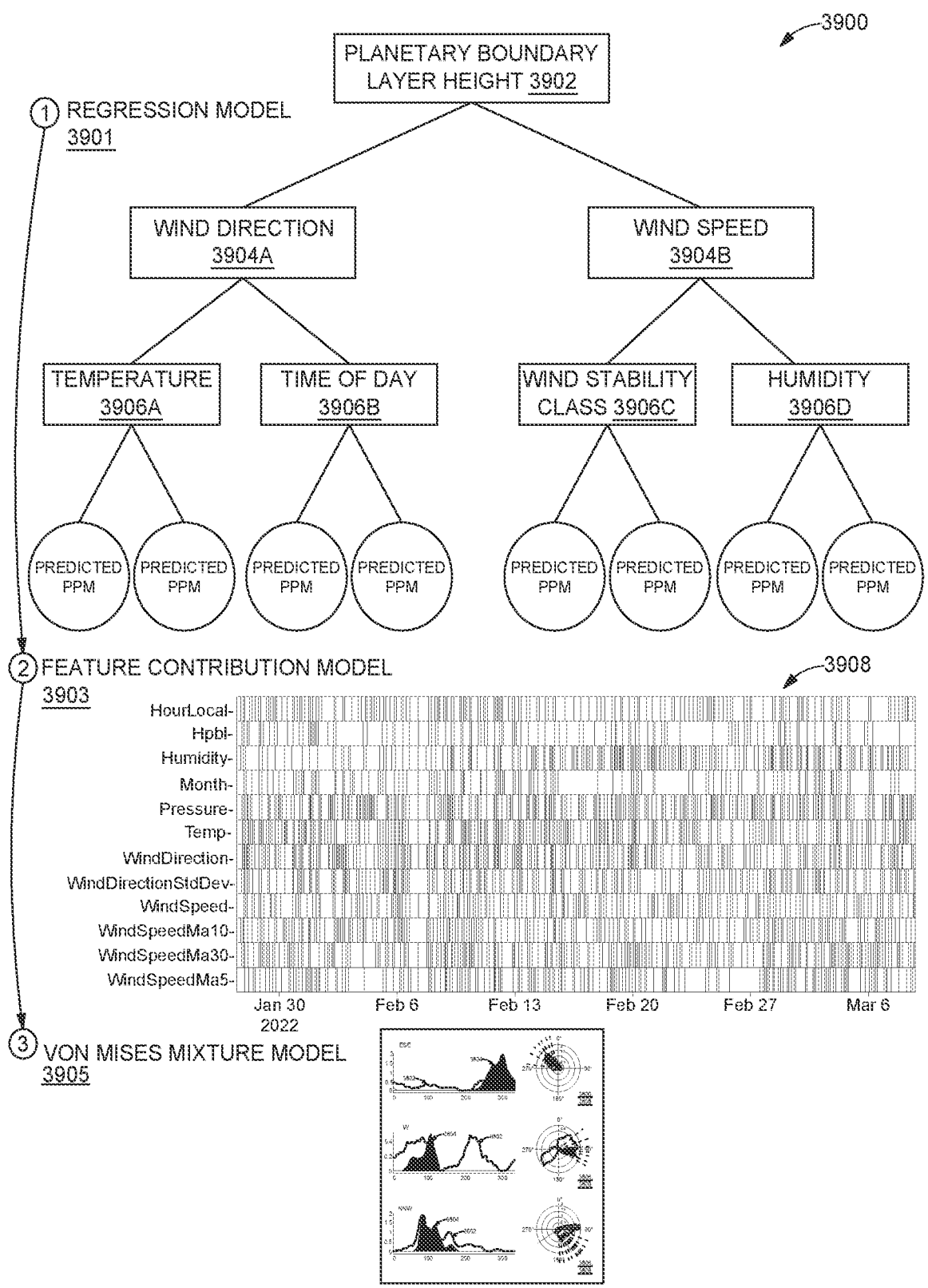
FIG. 39 illustrates a process overview diagram of a process for quantifying emissions of a target substance at a site, in accordance some configurations of the present subject matter.

Referring now to FIG. 39, a process overview diagram of a process 3900 for quantifying emissions of a target substance at a site is illustrated, in accordance some configurations of the present subject matter. As already explained above, a first set of onsite parameters may be measured with the first air quality monitor over a period of time to obtain a plurality of individual measurements of each parameter of the first set of onsite parameters. The plurality of individual measurements of the first set of onsite atmospheric parameters may include a first measured substance concentration of the target substance measured with the first air quality monitor, and a first set of individual atmospheric readings. The first measured substance concentration and the first set of individual atmospheric readings may be transmitted to the first server. Further, a regional atmospheric parameter for the site, for example, a height of planetary boundary layer (hPBL) may be procured from a second server.

As shown in FIG. 39, at a first step 3901, a prediction model associated with the first air quality monitor may be trained, for carrying out the computations for the quantification method. By way of an example, the prediction model or the machine learning regression model may be based on a gradient tree-boosting algorithm. A machine learning regression model may utilize a FastTreeTweedie algorithm in ML.NET framework. The prediction model may be used for identifying the emission sources, quantifying the emissions, and also for isolating correlation between elevated concentrations and atmospheric variables. For example, a prediction model (machine learning model) configured as a tree-based model and a gradient tree-boosting algorithm, may be trained with 10 leaves and 300 trees. Further, the prediction model may be a hierarchy-based model. For example, as shown in FIG. 39, a first hierarchy level may include the parameter hPBL 3902, a second hierarchy level may include the parameters wind direction 3904A and wind direction 3904B, and a third hierarchy level may include the parameters: temperature 3906A, time of the day 3906B, wind stability class 3906C, and humidity 3906D. Using the prediction model, a plurality of first predicted substance concentrations of the target substance corresponding to the first air quality monitor may be obtained, based on the measured on-site atmospheric measurements at the air quality monitor (AQM) and other procured atmospheric parameters.

A mapping of a weighted mean of the plurality of first predicted substance concentrations grouped in each feature group of a predetermined number of feature groups may be generated. The predetermined number of feature groups together may be representative of feature values over a predetermined range. In some configurations, each feature group may be associated with a wind-direction bucket. As such, a predetermined number of wind-direction buckets together may be representative of wind-directions over a full circle, i.e., wind-directions over 360 degrees. As such, in some embodiments, the mapping may be generated of a weighted mean of the plurality of first predicted substance concentrations grouped in each of a predetermined number of wind-direction buckets together are representative of wind-directions over the full circle. The mapping may be created for various different feature groups, including the wind-direction buckets. As will be understood, each feature group may have some contribution in the plurality of first predicted substance concentrations as predicted by the prediction model. Therefore, at step 3903, contribution of each of a plurality of parameters in the first predicted substance concentrations as predicted by the prediction model may be calculated, based on which a graphical representation 3908 may be plotted. For example, the plurality of parameters (as represented on the y-axis of the graphical representation 3908) may include wind speed, wind direction, temperature, pressure, month (i.e., time of the year), humidity, hPBL, and hour (i.e. time of the day). Thus, the graphical representation 3900 of contribution of the parameters (features) with respect to time of the year (x-axis) may be plotted, that represents the predicted substance concentrations as predicted by the prediction model. As can be seen, some of the parameters (features) may have a higher contribution at any of the year/month. By isolating contribution of each parameter on the predicted pollutant concentration and leveraging statistical methods used in the training of the regression model, the effects of ambient atmospheric concentrations of the targeted pollutant may be removed. The prediction model relies on statistical analysis of large amounts of data to train the prediction model (e.g., a trained regression model) that can accurately predict the measured pollutant concentration based on the values of other known parameters, and then examine that model to determine what portion of the predicted concentration can be attributed to only the wind-direction.

The contribution values for each of the parameters may be obtained from the prediction model, by analyzing an opposite sub-tree for each decision node associated with the parameter within the prediction model. For example, obtaining the wind-direction contribution values may include varying a value associated with a wind-direction, when values associated with remaining readings of the first set of individual atmospheric readings are fixed. Further, obtaining the wind-direction contribution values may include obtaining, from the prediction model, a first predicted substance concentrations of the target substance, for each variation of the value associated with the wind-direction. Furthermore, obtaining the wind-direction contribution values may include comparing the first predicted substance concentrations with the first measured substance concentration of the target substance measured with the first air quality monitor, and determining the wind-direction contribution values, based on the comparison.

The contribution values of each parameter may be adjusted corresponding to the plurality of first predicted substance concentrations, using the at least one adjustment factor to obtain a plurality of adjusted contribution values.

The plurality of adjusted contribution values may be grouped into the predetermined number of feature groups. For each of the predetermined number of feature groups, a weighted mean of the plurality of first predicted substance concentrations grouped in each feature group may be determined. Further, a mapping may be generated of the weighted mean of the plurality of first predicted substance concentrations grouped in each feature group. Further, for each emission source of the plurality of emission sources in a location map of the site, a simulated plume model may be generated, based on the wind-direction. The simulated plume model may depend on the various atmospheric conditions prevailing at the site. Further, for each emission source of the plurality of emission sources, a plurality of representative circular normal distributions may be calculated for each air quality monitor. The plurality of representative circular normal distributions may be calculated, using the simulated plume model, by setting a plurality of presumed flux values to the simulated plume model. For example, the plurality of representative circular normal distributions may be derived based on representative Von Mises distributions for all of the plurality of emission sources at the site using the corresponding (Gaussian) plume models.

At step 3905, an analysis may be performed of the plurality of representative circular normal distributions in relation with the mapping to identify a relevant representative circular normal distribution from the plurality of representative circular normal distributions. For example, as already explained above, at step 3905, the analysis may be performed based on graphical representation of the combination of lines charts corresponding to the circular distribution of the features (e.g., wind-direction) and line graphs of the graphical representations of the Von Mises distributions. In order to perform the analysis, the line charts and the line graphs are mapped on to each other to identify the most fitting Von Mises representations with respect to the line charts. The most fitting or a relevant Von Mises representations is identified from all of the Von Mises representations. This Von Mises representation is indicative of the target emission source from the emission or leak is taking place. therefore, the target emission source may be determined, based on the above analysis and the location map. Further, a total emission of the target substance at the site may be quantified by aggregating the plurality of emission sources.

Figure 40:
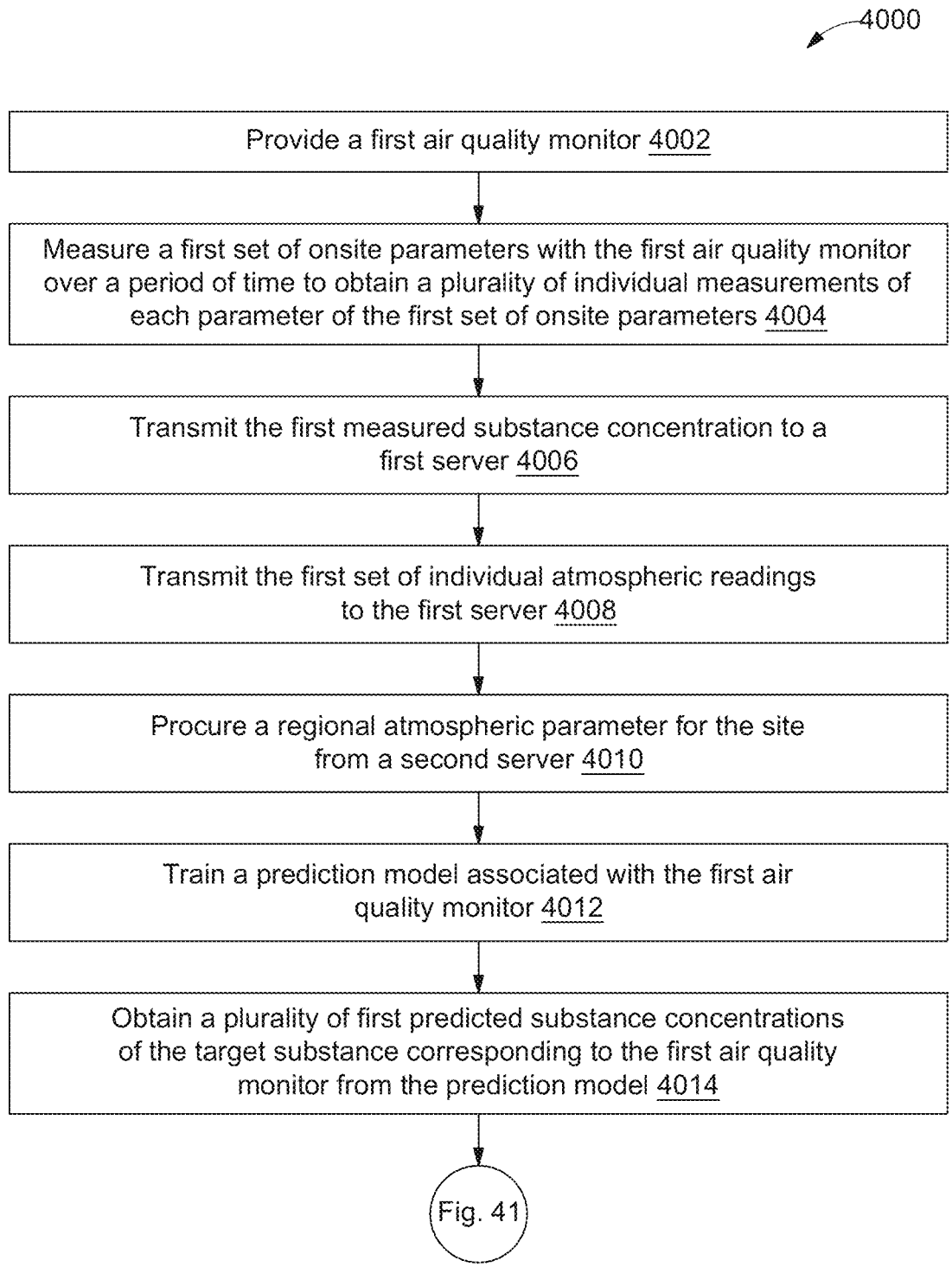

Referring now to FIGS. 40-42, a flowchart of a total emissions quantification method 4000 for quantifying emissions of a target substance at a site is illustrated, in accordance some configurations of the present subject matter. The total emissions quantification method 4000 may be performed based on the measurements of substance concentration of a target substance measured with the one or more air quality monitors provided at the site, and a set of individual atmospheric readings. The measurements of substance concentration of the target substance and the set of individual atmospheric readings are processed using a trained prediction model for quantification of the total emissions at the site, as a result of emission/leakage from one or more emissions sources present at the site.

At step 4002, a first air quality monitor may be provided. The first air quality monitor may include a first sensor responsive to the target substance and a first location at which the first air quality monitor is located on the site. At step 4004, a first set of onsite parameters may be measured with the first air quality monitor over a period of time to obtain a plurality of individual measurements of each parameter of the first set of onsite parameters. The plurality of individual measurements of the first set of onsite parameters may include a first measured substance concentration of the target substance measured with the first air quality monitor. The plurality of individual measurements of the first set of onsite parameters may further include a first set of individual atmospheric readings. The first set of individual atmospheric readings comprises at least one of atmospheric reading selected from: a barometric pressure, an air temperature, a humidity level, a wind-direction, and a wind-speed. For example, the wind-direction and the wind speed may be obtained from an anemometer provided on the site.

At step 4006, the first measured substance concentration may be transmitted to a first server. At step 4008, the first set of individual atmospheric readings may be transmitted to the first server. At step 4010, a regional atmospheric parameter for the site may be procured from a second server. By way of an example, the regional atmospheric parameter for the site is a height of planetary boundary layer (hPBL). The hPBL may be procured from the second server. Further, for example, the second server may be High Resolution Rapid Refresh (HRRR) maintained by National Oceanic and Atmospheric Administration (NOAA). At step 4012, a prediction model associated with the first air quality monitor may be trained. At step 4014, a plurality of first predicted substance concentrations of the target substance corresponding to the first air quality monitor from the prediction model may be obtained. The plurality of the first predicted substance concentrations of the target substance may be obtained, with at least: the first set of individual atmospheric readings, and the regional atmospheric parameter for the site. It should be noted that the plurality of first predicted substance concentrations is obtained over a predefined period at a predefined frequency.

At step 4016, a mapping may be generated of a weighted mean of the plurality of first predicted substance concentrations grouped in each wind-direction bucket of a predetermined number of wind-direction buckets. The predetermined number of wind-direction buckets together may be representative of wind directions in a full circle. For example, the predetermined number of wind-direction buckets include 72 wind-buckets. As such, each of the predetermined number of wind-direction buckets is representative of the wind directions in a segment of 5 degrees of the full circle. It should be noted that for a wind-direction bucket missing wind-direction data, the missing wind-direction data may be filled-in by interpolating the missing wind-direction from one or more of remaining of the predetermined number of wind-direction buckets.

In some embodiments, generating the mapping may include additional steps 4016A-4016F. At step 4016A, a plurality of first measured substance concentrations may be compared with the plurality of first predicted substance concentrations of the target substance to create at least one adjustment factor. At step 4016B, a wind-direction contribution value representative of a contribution of a wind-direction in each of the plurality of first predicted substance concentrations as predicted by the prediction model may be obtained from the prediction model. In some configurations, the wind-direction contribution values may include an amount of concentration of the target substance measured in parts per million (ppm) of the ambient air. At step 4016B, a plurality of wind-direction contribution values may be adjusted corresponding to the plurality of first predicted substance concentrations, using the at least one adjustment factor to obtain a plurality of adjusted wind-direction contribution values. At step 4016D, the plurality of adjusted wind-direction contribution values may be grouped into the predetermined number of wind-direction buckets. At step 4016E, for each of the predetermined number of wind-direction buckets, a weighted mean of the plurality of first predicted substance concentrations grouped in each wind-direction bucket of a predetermined number of wind-direction buckets may be determined. At step 4016F, the mapping may be generated of the weighted mean of the plurality of first predicted substance concentrations grouped in each group of the predetermined number of wind-direction buckets, for wind directions in a full circle. In some configurations, the mapping may be weighted with a recency bias.

At step 4018, a location map of a plurality of emission sources at the site may be obtained. The location map may include a location and an identity associated with each of the plurality of emission sources. At step 4020, for each emission source of the plurality of emission sources, a simulated plume model may be generated, based on the wind-direction. In some embodiments, generating the simulated plume model may include additional steps 4020A-4020C. At step 4020A, a bearing of each of the plurality of emission sources to each air quality monitor at the site may be calculated. At step 4020B, the average wind speed and atmospheric stability class may be retrieved from wind-direction statistics for each bearing. At step 4020C, the simulated plume model may be generated, based on the wind speed and the stability class.

At step 4022, for each emission source of the plurality of emission sources, a plurality of representative circular normal distributions may be calculated for each air quality monitor, using the simulated plume model, by setting a plurality of presumed flux values to the simulated plume model. In some configurations, each of the plurality of representative circular normal distributions for each air quality monitor may be based on: a distance between an emission source and the air quality monitor, an angular distance between the wind directions, a bearing of the air quality monitor relative to the emission source, and an average wind speed and atmospheric stability class for each wind-direction bucket. Further, in some example configurations, the plurality of representative circular normal distributions for each air quality monitor may be generated for 1000 simulated plume models and for a plurality of fluxes.

At step 4024, the plurality of representative circular normal distributions may be analyzed in relation with the mapping to identify a relevant representative circular normal distribution from the plurality of representative circular normal distributions. The relevant representative circular normal distribution is indicative of one or more target emission sources. At step 4026, a total emission of the target substance at the site by aggregating the plurality of emission sources may be quantified. Once the one or more target emission sources are identified, the fluxes associated with all of the one or more target emission sources are summed up, for all the Von Mises distributions. The summation provides the quantification of all the emission sources. The quantification of all the emission sources may then be store in a database and/or displayed on a user interface.

Figure 43:
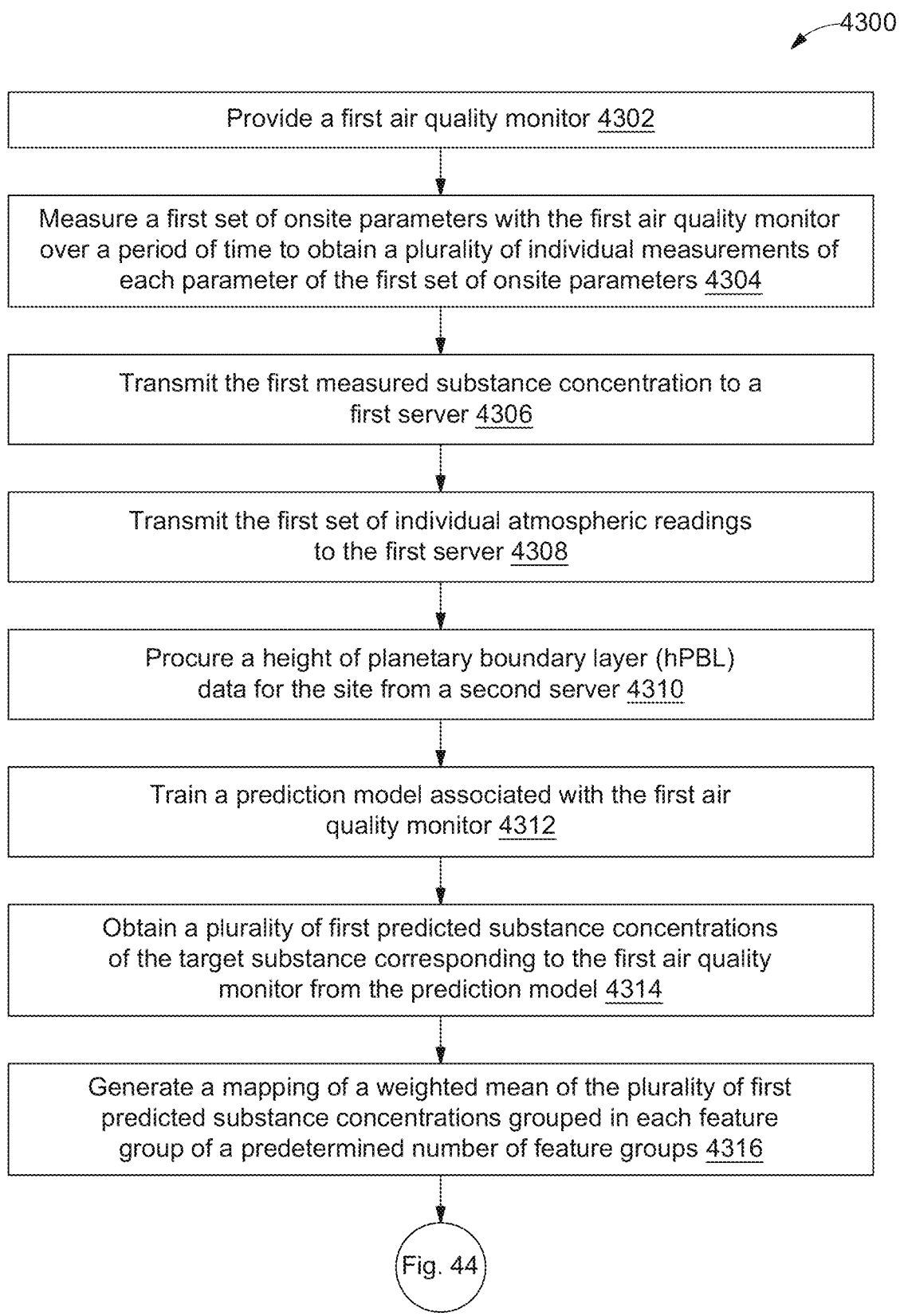
FIGS. 43-44 illustrate a flowchart of an operating emissions quantification method for quantifying emissions of a target substance from operating devices at a site, in accordance some configurations of the present subject matter.
Figure 44:
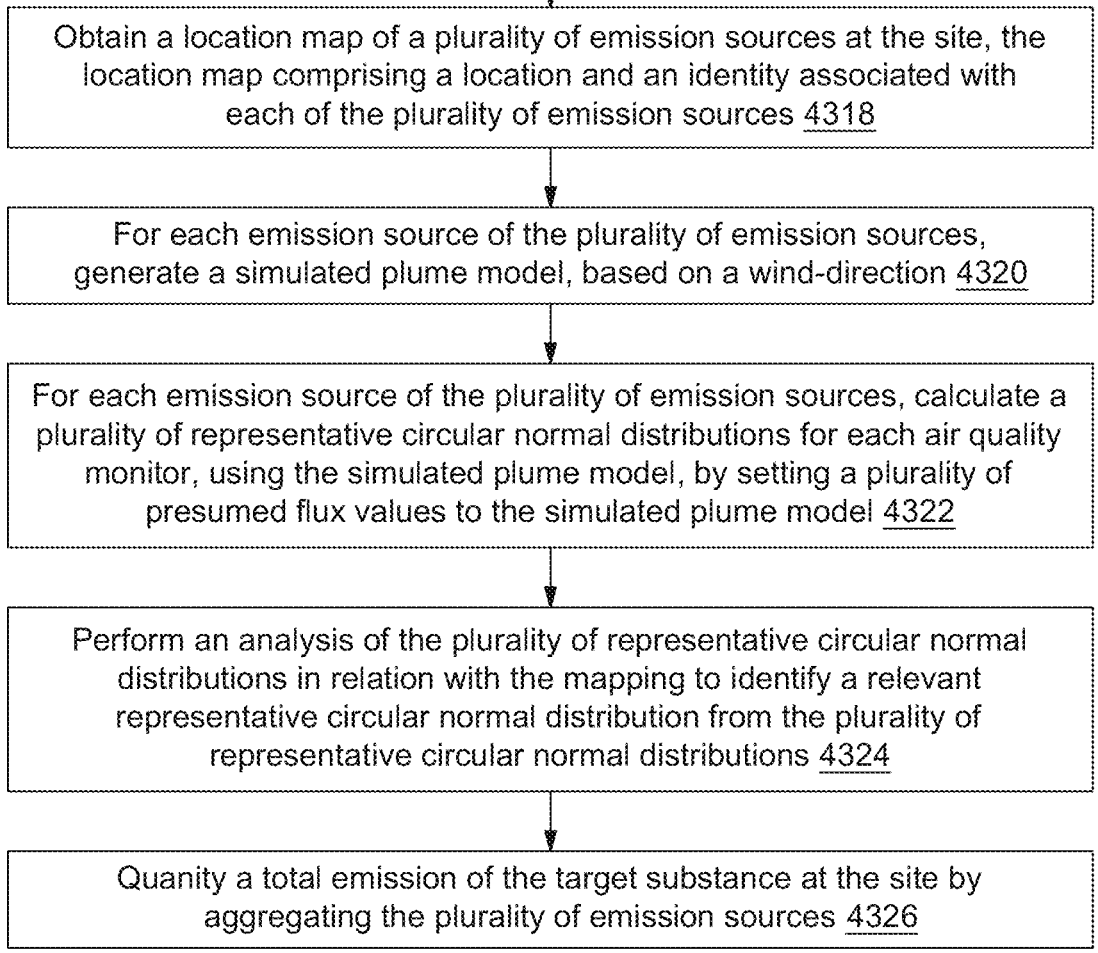

Referring now to FIGS. 43-44, a flowchart of an operating emissions quantification method 4300 for quantifying emissions of a target substance from operating devices at a site is illustrated. At step 4302 of the method 4300, a first air quality monitor may be provided. The first air quality monitor may include a first sensor responsive to the target substance and a first location at which the first air quality monitor is located on the site. At step 4304, a first set of onsite parameters may be measured with the first air quality monitor over a period of time to obtain a plurality of individual measurements of each parameter of the first set of onsite parameters. The plurality of individual measurements of the first set of onsite parameters may include a first measured substance concentration of the target substance measured with the first air quality monitor and a first set of individual atmospheric readings.

At step 4306, the first measured substance concentration may be transmitted to a first server. At step 4308, the first set of individual atmospheric readings may be transmitted to the first server. At step 4310, a height of planetary boundary layer (hPBL) data for the site may be procured from a second server. The hPBL data may include a trapping condition corresponding to wind stagnation. During emission of the substance from an emission source, the trapping condition may be associated with a gradual accumulation of the substance in an atmosphere surrounding the site and a higher first measured substance concentration of the target substance measured with the first air quality monitor. Further, as already explained above, the second server may be the High Resolution Rapid Refresh (HRRR) maintained by National Oceanic and Atmospheric Administration (NOAA). The hPBL data may be procured from the second server periodically at a predetermined frequency. In some cases, the hPBL data may be refreshed on an hourly-basis to a resolution of 3 kilometers. At step 4312, a prediction model associated with the first air quality monitor may be trained. The prediction model associated with the first air quality monitor is trained with the hPBL data continuously procured from the second server periodically at a second predetermined frequency, for at least 24 hours.

At step 4314, a plurality of first predicted substance concentrations of the target substance corresponding to the first air quality monitor may be obtained from the prediction model, with at least: the first set of individual atmospheric readings and the hPBL data for the site. The plurality of first predicted substance concentrations may be obtained over a predefined period at a predefined frequency. At step 4316, a mapping of a weighted mean of the plurality of first predicted substance concentrations grouped in each feature group of a predetermined number of feature groups may be generated. The predetermined number of feature groups together are representative of feature values over a predetermined range. It should be noted that each feature group may be associated with a wind-direction bucket. As such, the predetermined number of wind-direction buckets together are representative of wind-directions over a full circle. The generating of the mapping is already discussed in conjunction with FIG. 29.

At step 4318, a location map of a plurality of emission sources at the site may be obtained. The location map may include a location and an identity associated with each of the plurality of emission sources. At step 4320, for each emission source of the plurality of emission sources, a simulated plume model may be generated, based on a wind-direction. At step 4322, for each emission source of the plurality of emission sources, a plurality of representative circular normal distributions for each air quality monitor may be calculated, using the simulated plume model, by setting a plurality of presumed flux values to the simulated plume model. At step 4324, an analysis of the plurality of representative circular normal distributions may be performed in relation with the mapping to identify a relevant representative circular normal distribution from the plurality of representative circular normal distributions. The relevant representative circular normal distribution may be indicative of a target emission source. At step 4326, a total emission of the target substance at the site may be quantified by aggregating the plurality of emission sources.

Figure 45:
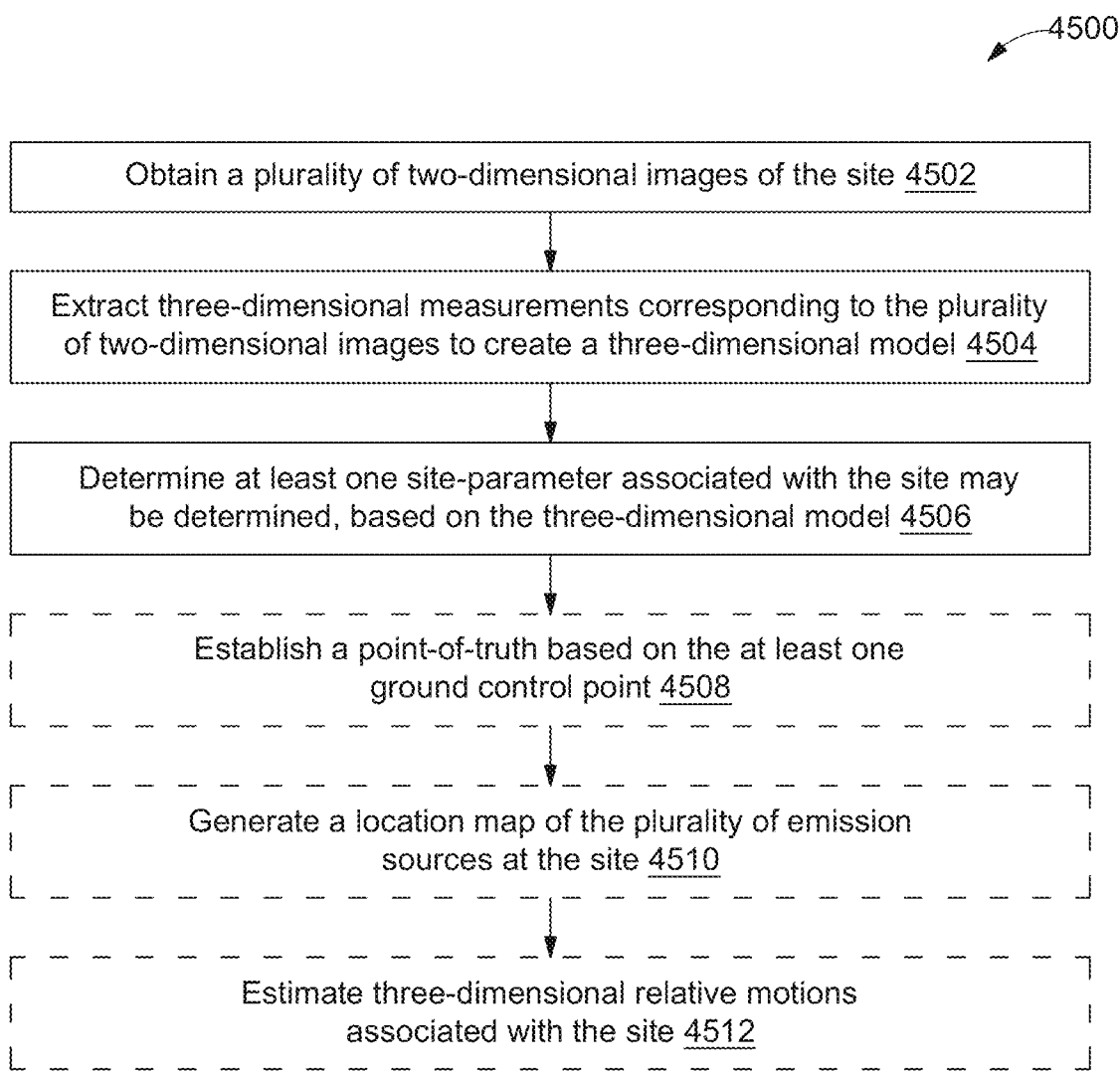
FIG. 45 illustrates a flowchart of an asset appraisal method for tagging equipment handling a target substance at a site, in accordance some configurations of the present subject matter.

Referring now to FIG. 45, a flowchart of an asset appraisal method 4500 for tagging equipment handling a target substance at a site is illustrated. At step 4502, a plurality of two-dimensional images of the site may be obtained. In some embodiments, the plurality of two-dimensional images of the site may be obtained using drone imagery. At step 4504, three-dimensional measurements corresponding to the plurality of two-dimensional images may be extracted to create a three-dimensional model. Extracting the three-dimensional measurements may include calculating a distance between two points lying on a plane parallel to a photographic image plane, corresponding to measured associated distances on the plurality of two-dimensional images, using a scale associated with the plurality of two-dimensional images. At step 4506, at least one site-parameter associated with the site may be determined, based on the three-dimensional model. The at least one site-parameter associated with the site may include locations of a boundary line associated with the site, a location of each of a plurality of emission sources located at the site, and at least one ground control point.

Additionally, in some configurations, at step 4508, a point-of-truth may be established based on the at least one ground control point. A scale associated with the plurality of two-dimensional images may be determined based on the point-of-truth. Further, additionally, at step 4510, a location map of the plurality of emission sources at the site may be generated. The location map may include a location and an identity associated with each of the plurality of emission sources. Further, at step 4512, three-dimensional relative motions associated with the site may be estimated. Estimating the three-dimensional relative motions associated with the site may include obtaining two-dimensional and three-dimensional motion fields associated with the site, and analyzing the two-dimensional and three-dimensional motion fields using a computational model to estimate the three-dimensional relative motions associated with the site. By way of an example, the computational model is selected from PhotoModeler, Pix4D, and Topodrone. Moreover, the two-dimensional and the three-dimensional motion fields associated with the site may be obtained using one of a single photographic image, a high-speed photographic images, or remote sensing.

Figure 46:
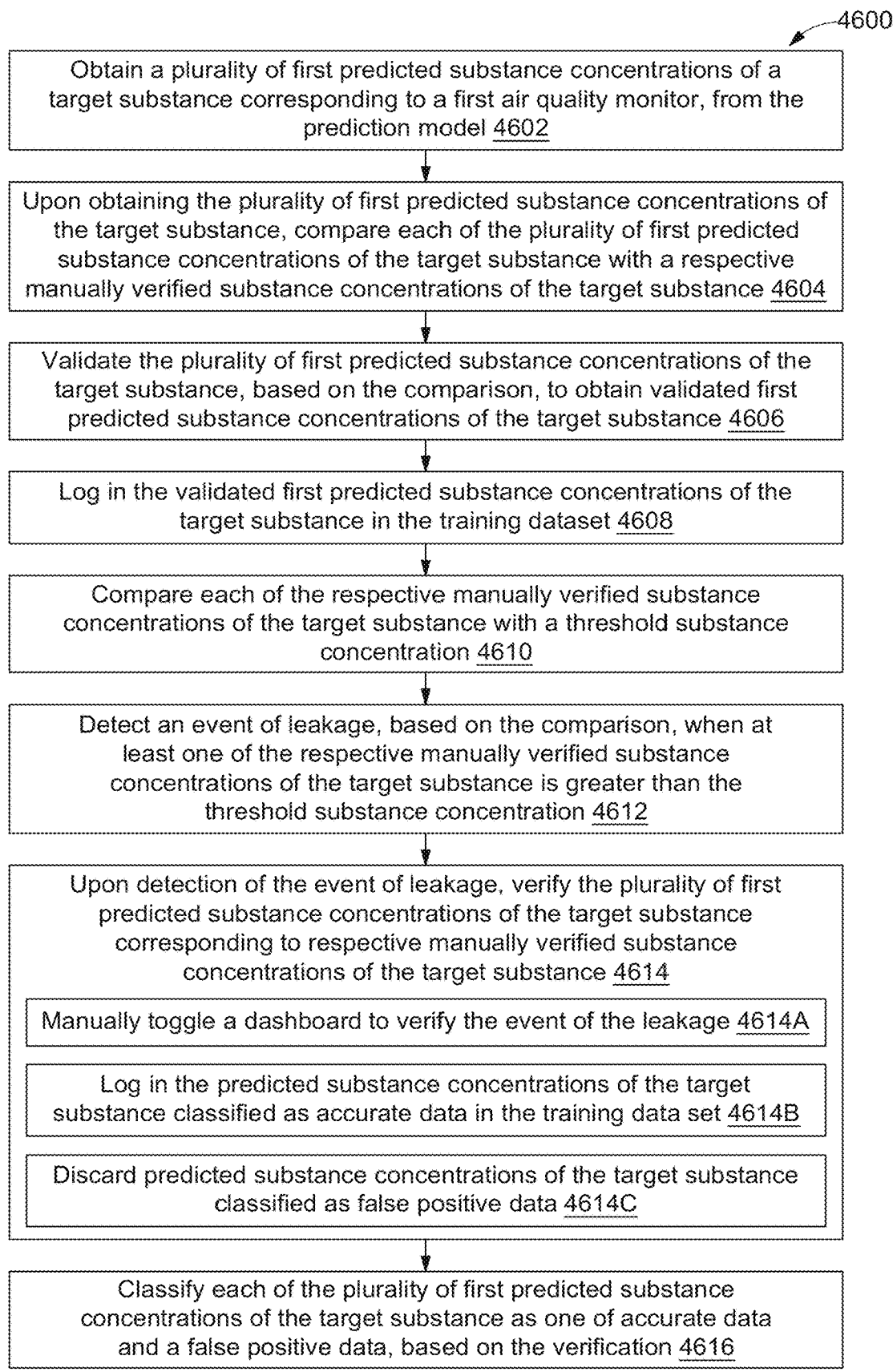
FIG. 46 illustrates a flowchart of an alert calibration method for training a prediction model, in accordance some configurations of the present subject matter.

Referring now to FIG. 46, a flowchart of an alert calibration method 4600 for training a prediction model illustrated. At step 4602, a plurality of first predicted substance concentrations of a target substance may be obtained corresponding to a first air quality monitor, from the prediction model. The plurality of first predicted substance concentrations of the target substance may be obtained, with at least: a first set of individual atmospheric readings, and a regional atmospheric parameter for a site. The prediction model may be trained using a training dataset. For example, the prediction model is trained over a predetermined period, and wherein the predetermined period is 10 days.

At step 4604, upon obtaining the plurality of first predicted substance concentrations of the target substance, each of the plurality of first predicted substance concentrations of the target substance may be compared with a respective manually verified substance concentrations of the target substance. At step 4606, the plurality of first predicted substance concentrations of the target substance may be validated, based on the comparison, to obtain validated first predicted substance concentrations of the target substance. At step 4610, the validated first predicted substance concentrations of the target substance may be logged in the training dataset. Additionally, in some configurations, at step 4612, each of the respective manually verified substance concentrations of the target substance may be compared with a threshold substance concentration. At step 4614, an event of leakage may be detected, based on the comparison, when at least one of the respective manually verified substance concentrations of the target substance is greater than the threshold substance concentration.

Figure 47:
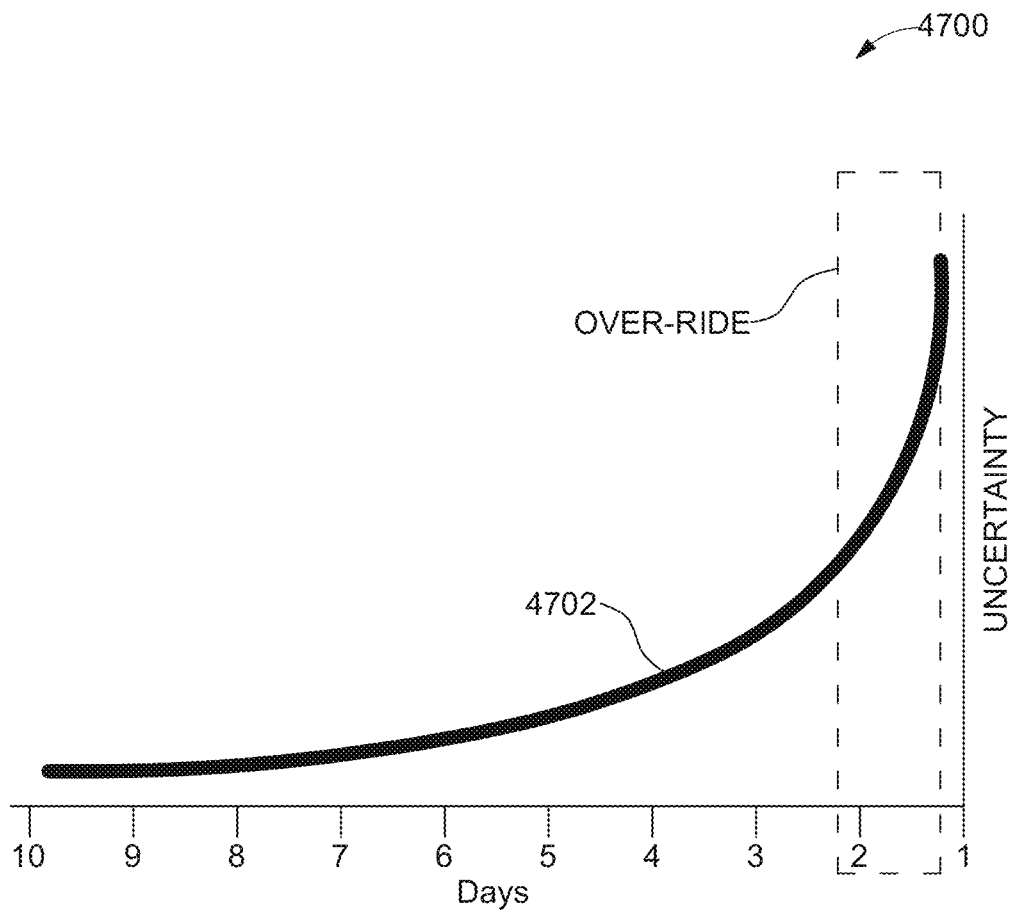
FIG. 47 illustrates a graphical plot of degree of uncertainty of detection of an event over a period, in accordance some configurations of the present subject matter.

In some configurations, a 10-day exponential weighting override may be applied. When 360 degrees of wind-direction data is obtained over a 10-day period, an exponential curve (as shown in FIG. 47) may be plotted that produces a confidence rating. Referring now to FIG. 47, a graphical plot of degree of uncertainty (also y axis) of detection of an event over a period of 10 days (along x-axis) is illustrated. As shown in FIG. 47, an exponential curve 4702 is plotted over the period of 10 days. When the uncertainty of the true detection of the leak/emission is found to be greater than a threshold value, an over-ride may be applied.

When an event is detected, the event is weighted as it is 'new' and requires a truckroll. As such, this event is not averaged into the 10-day rolling average/confidence, since it will take too long to act on the event. As such, when a leak is detected/predicted, an operator during an (on or off-site) inspection, may toggle a checkbox on a dashboard. For example, if the emission/leak from an emission source is confirmed, the operator may toggle the checkbox. However, if the emission/leak is false, the operator does not confirm the event (e.g., by toggling the checkbox). This helps to flag non-events that are false positives. By flagging the false event, the data is denied and suppressed from the total emissions for that site.

Returning to FIG. 46, at step 4616, upon detection of the event of leakage, the plurality of first predicted substance concentrations of the target substance corresponding to respective manually verified substance concentrations of the target substance may be verified. In some configurations, verifying the plurality of first predicted substance concentrations of the target substance may include steps 4616A-4616C. At step 4616A, a dashboard may be manually toggled to verify the event of the leakage. At step 4616B, predicted substance concentrations of the target substance classified as accurate data may be logged in the training dataset. At step 4616C, predicted substance concentrations of the target substance classified as false positive data may be discarded. At step 4618, each of the plurality of first predicted substance concentrations of the target substance may be classified as one of accurate data and a false positive data, based on the verification.

Figure 48:
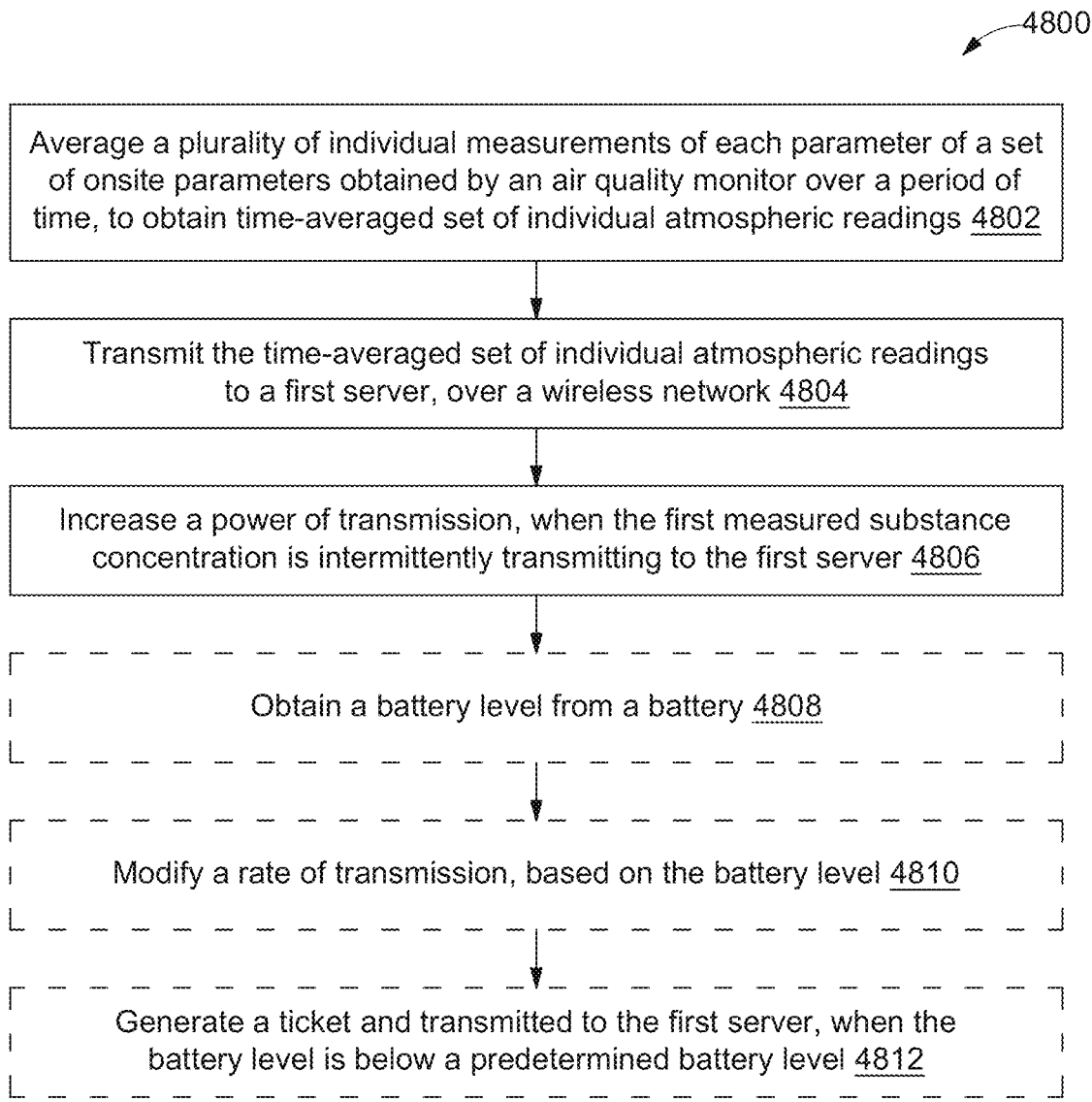
FIG. 48 illustrates a flowchart of a communications method for improving transmission of onsite parameters measured at a site, in accordance some configurations of the present subject matter.

Referring now to FIG. 48, a flowchart of a communications method 4800 for improving transmission of onsite parameters measured at a site is illustrated. At step 4802, a plurality of individual measurements of each parameter of a set of onsite parameters obtained by an air quality monitor may be averaged over a period of time, to obtain time-averaged set of individual atmospheric readings. The set of individual atmospheric readings may include at least one of atmospheric reading selected from: a wind-direction, a wind-speed, a barometric pressure, an air temperature, and a humidity level. The plurality of individual measurements of the set of onsite parameters may include a first measured substance concentration of a target substance measured with the air quality monitor and a first set of individual atmospheric readings.

At step 4804, the time-averaged set of individual atmospheric readings may be transmitted to a first server, over a cellular network. At step 4806, a power of transmission may be increased, when the first measured substance concentration is intermittently transmitting to the first server. At step 4808, a battery level may be obtained from a battery. At step 4810, a rate of transmission may be modified, based on the battery level. Further, additionally, at step 4812, a ticket may be generated and transmitted to the first server, when the battery level is below a predetermined battery level.

Figure 49:
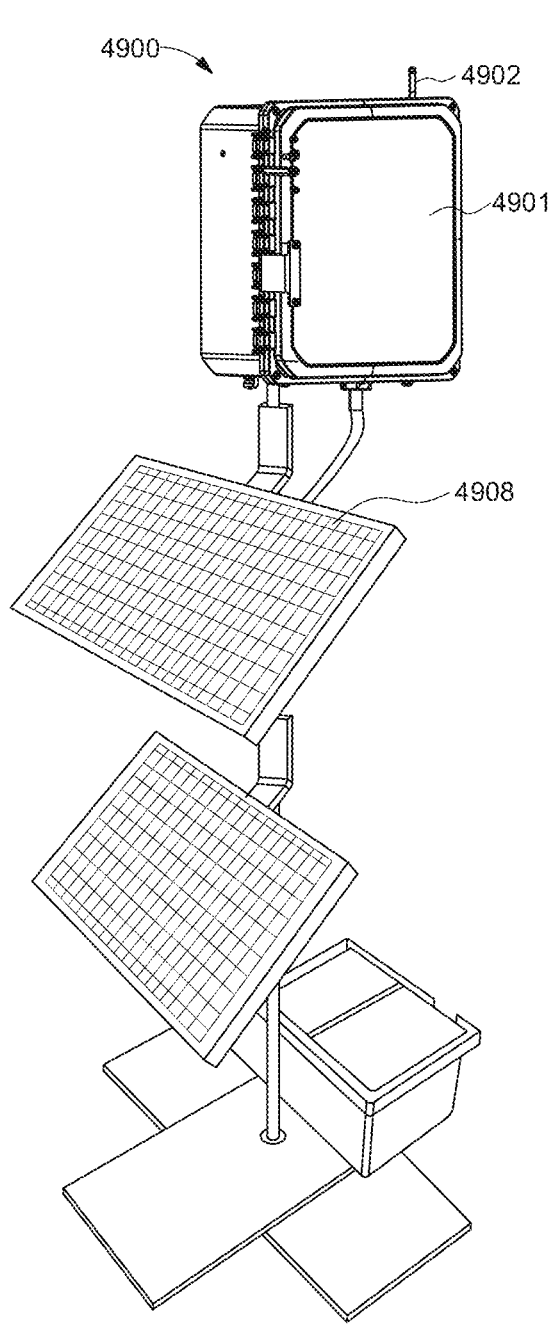
FIGS. 49-50 illustrate perspective views of a system for monitoring air quality, in accordance some configurations of the present subject matter.
Figure 50:
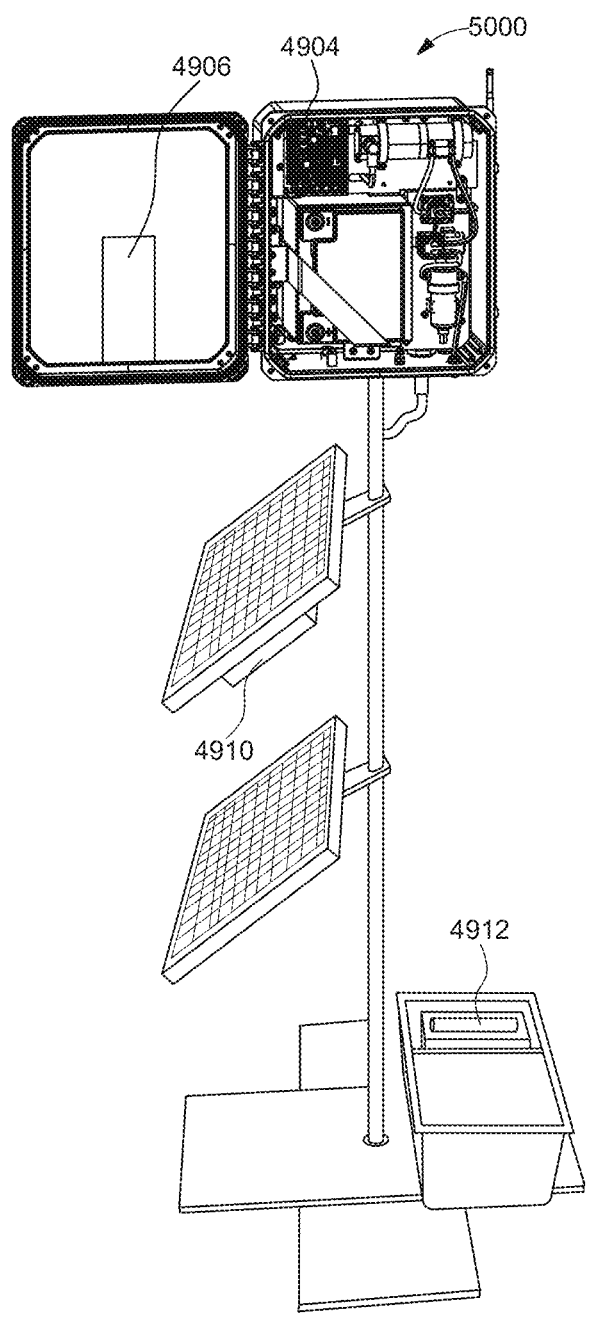

Referring now to FIGS. 49-50, perspective views 4900, 5000 of system for monitoring air quality are illustrated, in accordance with some illustrative configurations. As shown, the system includes an air quality monitor 4901. The air quality monitor 4901 may house a variety of components for sampling air and detecting a concentration of a substance in the air. Further, in some configurations, the air quality monitor 4901 may house a dock 4906 for holding a cellphone which may be used for transmission of data over the cellular network. The system further includes an antenna 4902, and a signal amplifier 4904 for further transmitting and amplifying the signals. The system further includes a solar panel 4908 for charging a battery 4912. The battery 4912 may be configured to power the air quality monitor 4901. The system may further include a MPPT charging controller 4910.

Figure 51:
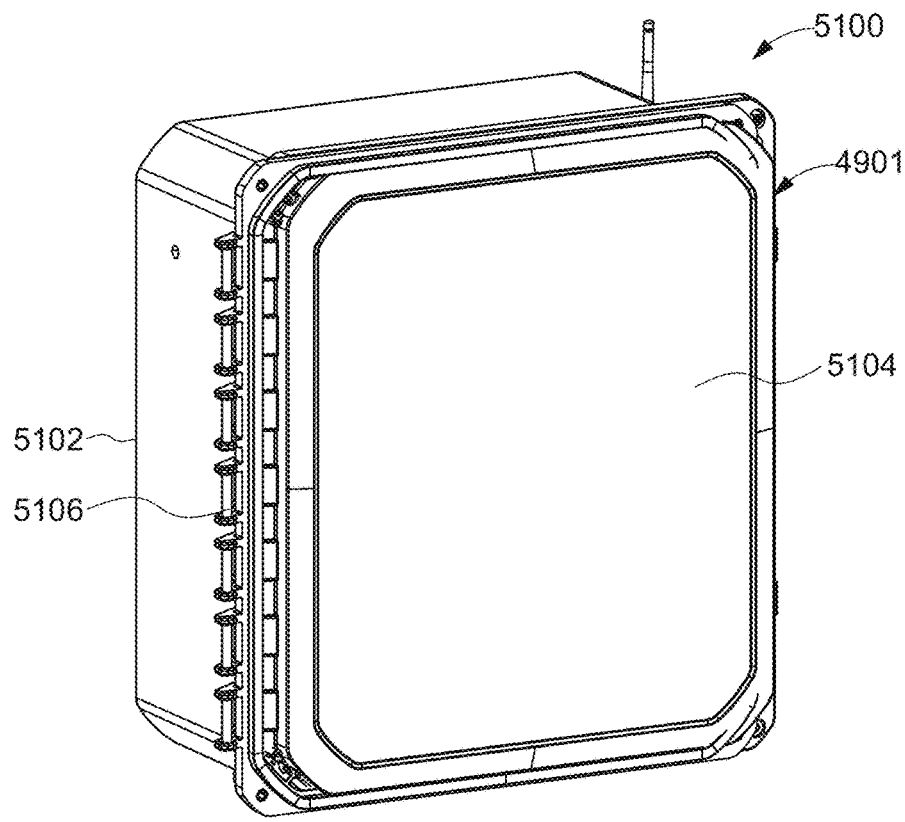
FIGS. 51-53 illustrate various views of an air quality monitor, in accordance with some configurations of the present disclosure.
Figure 52:
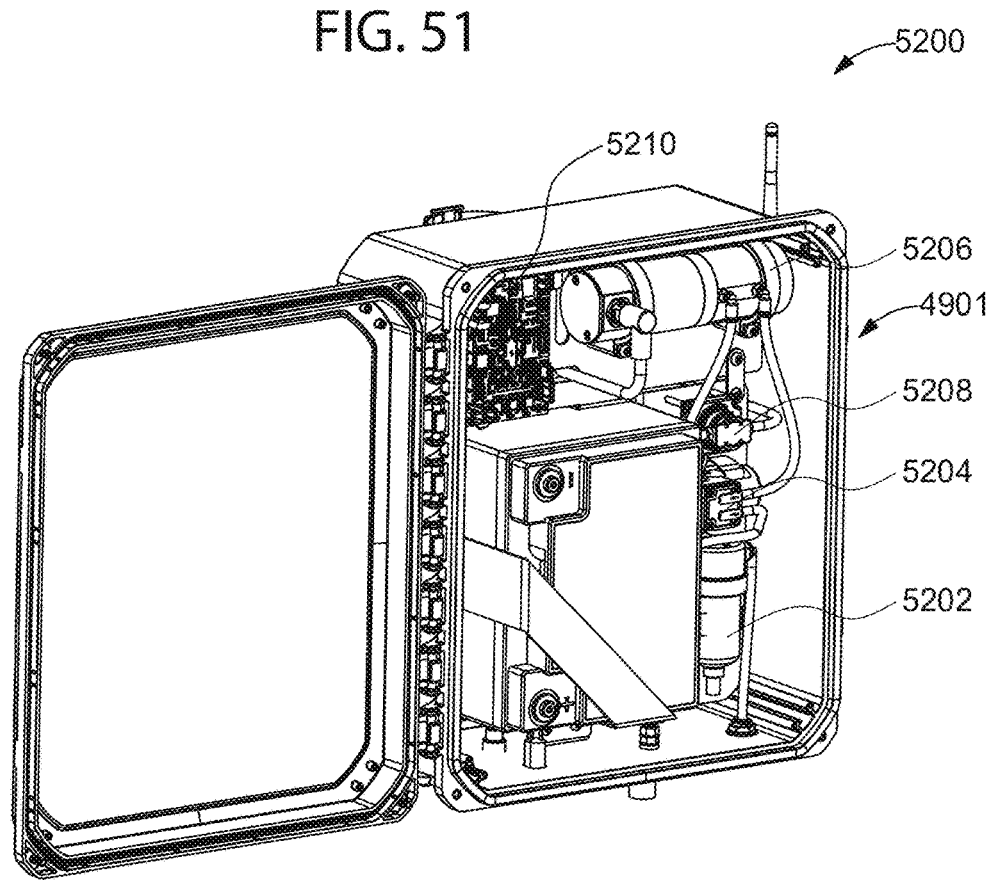
Figure 53:
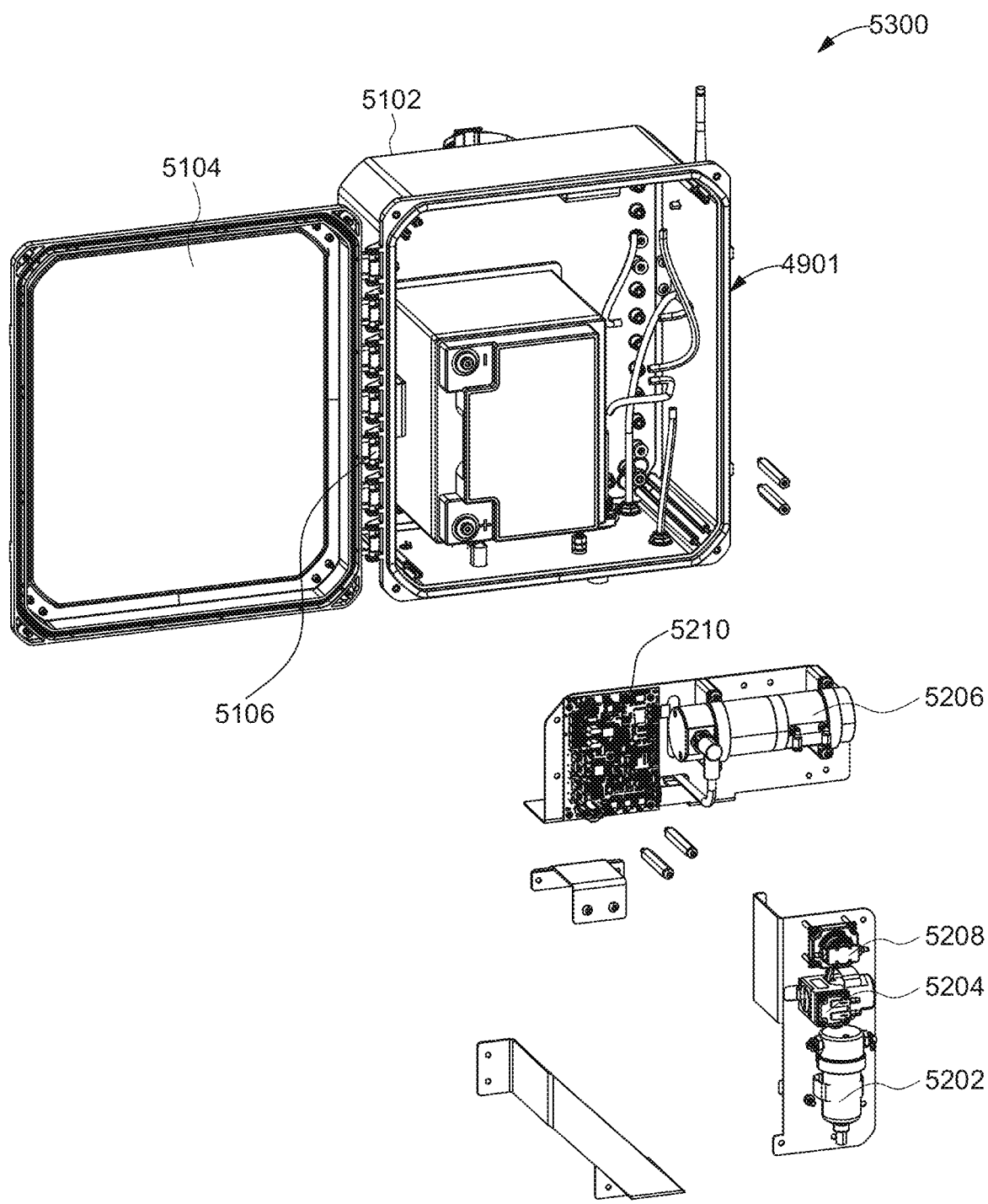

Referring now to FIGS. 51-53, various views 5100, 5200, 5300 of the air quality monitor 4901 are illustrated, in accordance with some configurations of the present disclosure. As shown, the air quality monitor 4901 includes a housing 5102 having a door 5104. For example, the door 5104 may be hinged to the housing 5102, to allow the door 5104 to be closed (as shown in FIG. 51) and opened (as shown in FIG. 52). As such, the door 5104 may be hinged to the housing 5102 via one or more hinges 5106. As shown in FIGS. 52-53, the housing 5102 may include at least one internal atmospheric sensor and a at least one external atmospheric sensor. The at least one internal atmospheric sensor may be configured to detect composition of the air sample that is received inside the housing 5102. The at least one external atmospheric sensor may be configured to detect composition of the atmospheric air surrounding the air quality monitor 4901.

Figure 54:
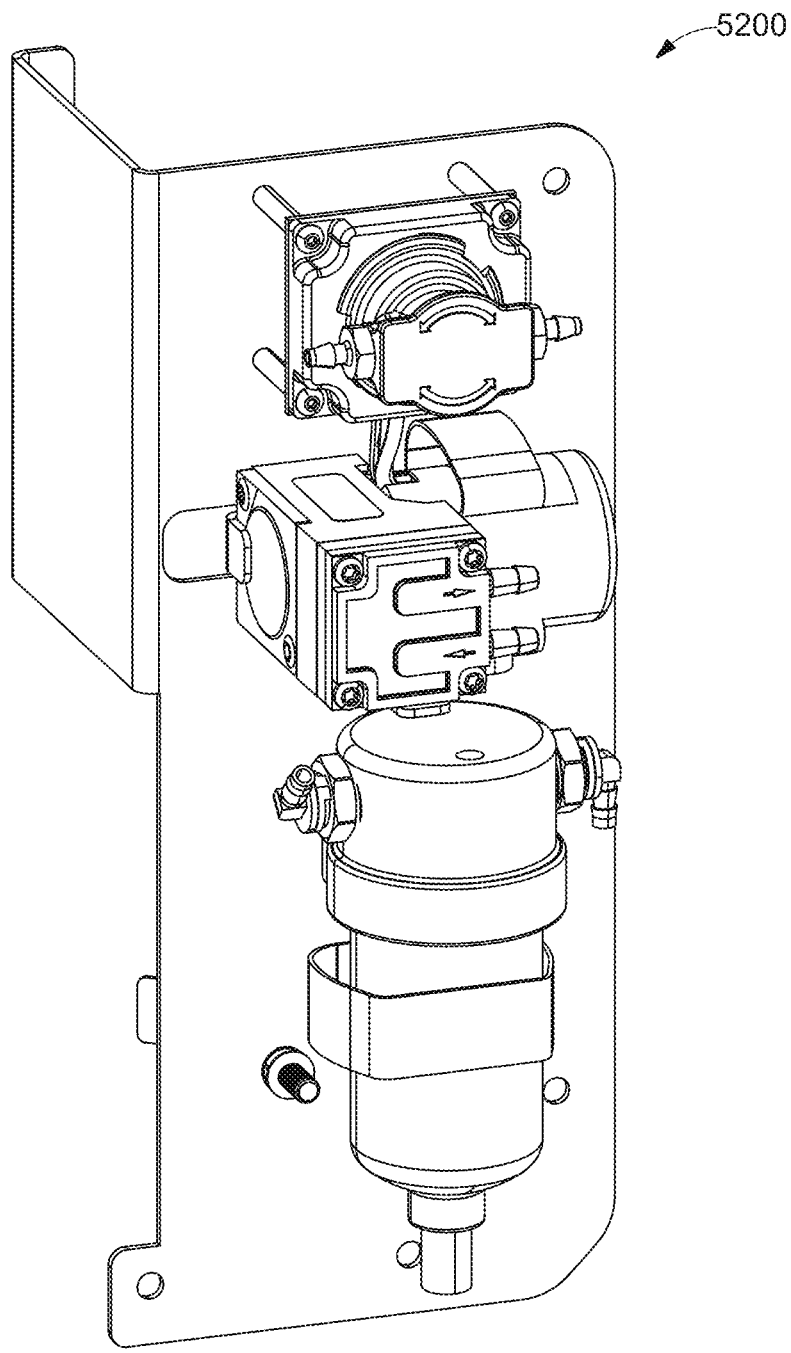
FIG. 54 illustrates a magnified view of a separator, in accordance with some configurations of the present disclosure.

In some configurations, the air quality monitor 4901 may further include a separator 5202 configured to separate liquid (e.g., water) from the air sample. To this end, the separator 5202 may include filter. A magnified view of the separator 5202 is further shown in FIG. 54. The air quality monitor 4901 may further include a diaphragm pump 5204. Further, the air quality monitor 4901 may include a methane (CH4) sensor 5206 configured to detect the presence and concentration of the methane gas in the air sample. The air quality monitor 4901 may further include a Barometer pressure sensor 5208. Further to these components, the air quality monitor 4901 may include a communication module 5210 including a printed circuit board. The communication module 5210 may be configured to perform processing of the data gathered by the sensors and further communicate the data to a remote location over a wireless or a wired communication network. The air quality monitor 4901 may further include a batter 5212 to supply electric power to the communication module 5210 and the other components within the housing 5102.

In one example, the present disclosure may include a sensor system configured to monitor compounds in air and collocate weather measurements with self-powering, sample conditioning, edge processing, and/or communication capability.

In another example, the present disclosure may include a method including: analyzing spectra for at least one of denoising, debiasing, peak alignment, speciation, or unknown compound and residual bias and noise compensation.

In another example, the present disclosure may include a method including detecting, localizing, and/or quantifying a site emission using a single static point sensor sensitive to at least one target compound and providing collocated measurement of weather.

Furthermore, the method may include the measurement of weather includes at least wind speed and wind direction determined based on atmospheric simulations and inverse methods.

In another example, the present disclosure may include a method including: qualifying of emission type using statistical inference, which at least distinguishes a normal emission from a leak.

In another example, the present disclosure may include a method including detecting at least one emission; and determining whether at least one emission is from one or more leaks.

In another example, the present disclosure may include a method for the calculation of total site emissions.

In another example, the present disclosure may include a method for the estimation of total flux emission of landfills using one or more of surface concentrations and/or local weather measurements together with a transport simulation.

In another example, the present disclosure may include a method for the estimation of the detection area of a sensor system using transport simulation.

In another example, the present disclosure may include a method for optimizing a formation of sensor system networks relying on detection threshold and detection speed requirements together with a large-scale transport simulation.

In another example, the present disclosure may include a method to triage and report emission flags for maintenance based on their location, quantification, and qualification.

In another example, the present disclosure may include an actionability engine for the tracking and suggestion of practices, equipment, and manpower for proper leak maintenance.

In another example, the present disclosure may include an actionability engine for the identification of repeat-offending components and component types.

In another example, the present disclosure may include a n actionability engine for tracking of emission reduction goals.

In another example, the present disclosure may include a system including a computing device including one or more processors and memory storing instructions that, when executed by the one or more processors, cause the system to perform one of the methods described.

In another example, the present disclosure may include one or more sensors in communication with the computing device and configured to detect one or more emissions, wherein the computing device is configured to identify a leak based on the detected one or more emissions.

The system may further include using one or more weather simulations and the detected one or more emissions to identify the leak.

In another example, the present disclosure may include a method including determining one or more characteristics of one or more site emissions using a single static point sensor sensitive to at least one target compound and providing collocated measurement of weather. In another example, the present disclosure may further include quantifying the one or more site emissions by measuring a plume cross section across varying wind. And, the method may further include quantifying the one or more site emissions by estimating of an emission flux from concentration and weather measurements using an inverse transport simulation of a digital twin.

In another example, the present disclosure may include a deriving localized site emissions concentration and weather measurements using an inverse transport simulation of a digital twin.

In another example, the present disclosure may include a method including localizing site emissions by distinguishing between emission sources at a zone, equipment group, and/or component level emissions.

In another example, the present disclosure may include a method including: qualifying of emission type using statistical inference, which at least distinguishes a normal emission from a leak by categorizing emission events based on their intensity, frequency and/or composition.

In another example, the present disclosure may include a method for the estimation of emission localization, quantification and localization using operational data streams, maintenance and inspection reports and raw inspection data.

In another example, the present disclosure may include a method for the commoditization of emission estimation and measurement through certification, carbon credit and carbon offsets.

In another example, the present disclosure may include a method for preventative maintenance scheduling based on emission estimation and measurements.

In another example, the present disclosure may include a method for calculating and optimizing emission reduction costs for different operational strategies based on sensor measurements, geography, production data, equipment, maintenance data, labor costs, and/or other available data. In another example, the present disclosure may further include a method including the sensor measurements include weather and chemical concentration measurements.

In another example, the present disclosure may include a method for generating an atmospheric digital twin using site metadata for simulating atmospheric transport.

In another example, the present disclosure may include a method for quantifying error in localization and quantification of emissions of a site, using uncertainty quantification and prior probability of weather measurement precision and accuracy, modeling uncertainty and compound sensing accuracy and precision.

In another example, the present disclosure may include a location method for locating an emission source of a target substance at a site, based on an analysis of representative circular normal distributions in relation with a mapping of a weighted mean of the plurality of first predicted substance concentrations grouped in a predetermined number of feature groups.

In another example, the present disclosure may include a total emissions quantification method for quantifying emissions of a target substance at a site, based on the analysis of representative circular normal distributions in relation with the mapping.

In another example, the present disclosure may include an operating emissions quantification method for quantifying emissions of a target substance from operating devices at a site.

In another example, the present disclosure may include an asset appraisal method for tagging equipment handling a target substance at a site, based on a plurality of two-dimensional images of the site.

In another example, the present disclosure may include an alert calibration method for training a prediction model, validating a plurality of first predicted substance concentrations of the target substance.

In another example, the present disclosure may include a communications method for improving transmission of onsite parameters measured at a site, for example, by transmitting the time-averaged set of individual atmospheric readings to a first server, over a wireless network and increasing a power of transmission.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

The controllers, computing devices, server devices, and other components of systems can include machine-readable media and one or more processors, Programmable Logic Controllers, Distributed Control Systems, secure processors, memory, and the like. Secure storage may also be implemented as a secure flash memory, secure serial EEPROM, secure field programmable gate array, or secure application-specific integrated circuit. Processors can be standard central processing units or secure processors. Secure processors can be special-purpose processors that can withstand sophisticated attacks that attempt to extract data or programming logic. A secure processor may not have debugging pins that enable an external debugger to monitor the secure processor's execution or registers. In other embodiments, the system may employ a secure field programmable gate array, a smartcard, or other secure devices. Other types of computing devices can also be used.

Memory can include standard memory, secure memory, or a combination of both memory types. By employing a secure processor and/or secure memory, the system can ensure that both data and instructions are highly secure. Memory can be incorporated into the other components of the controller system and can store computer-executable or processor-executable instructions, including routines executed by a programmable computing device. In some embodiments, the memory can store programs for preset configurations. Stored programs (e.g., simulation programs, calibration programs, graphic mapping programs, etc.) can be modified by a subject, operator, or remote manager to provide flexibility.

The present disclosure contemplates methods, systems, and program products on any machine-readable media for accomplishing various operations. The embodiments of the present disclosure may be implemented using existing computer processors, or by a special-purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general-purpose computer, special purpose computer, or special purpose processing machines to perform a certain function or group of functions. The machine-readable media can be part of sensors, computing devices, or other components disclosed herein.

Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments necessarily need to exhibit such advantages to fall within the scope of the technology. Accordingly, the disclosure and associated technology can encompass other embodiments not expressly shown or described herein. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Implementation of the techniques, blocks, steps, and means described above may be done in various ways. For example, these techniques, blocks, steps, and means may be implemented in hardware, software, or a combination thereof. For a digital hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof. For analog circuits, they can be implemented with discreet components or using monolithic microwave integrated circuit (MMIC), radio frequency integrated circuit (RFIC), and/or micro electro-mechanical systems (MEMS) technologies.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

The methods, systems, devices, graphs, and/or tables discussed herein are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of +20% or +10%, +5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of +20% or +10%, +5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

While illustrative and presently preferred embodiments of the disclosed systems, methods, and/or machine-readable media have been described in detail herein, it is to be understood that the inventive concepts may be otherwise variously embodied and employed, and that the appended claims are intended to be construed to include such variations, except as limited by the prior art. While the principles of the disclosure have been described above in connection with specific apparatuses and methods, it is to be clearly understood that this description is made only by way of example and not as limitation on the scope of the disclosure.

The invention claimed is:

1. A location method for locating an emission source of a target substance at a site, the location method comprising:
   providing a first air quality monitor comprising:
      a first sensor responsive to the target substance; and
      a first location at which the first air quality monitor is located on the site;
   measuring a first set of onsite parameters with the first air quality monitor over a period of time to obtain a plurality of individual measurements of each parameter of the first set of onsite parameters, wherein the plurality of individual measurements of the first set of onsite atmospheric parameters comprises:
      a first measured substance concentration of the target substance measured with the first air quality monitor; and
      a first set of individual atmospheric readings, wherein the first set of individual atmospheric readings comprises at least one of atmospheric reading selected from:
         a barometric pressure,
         an air temperature, and
         a humidity level;
   transmitting the first measured substance concentration to a first server;
   transmitting the first set of individual atmospheric readings to the first server;
   procuring a regional atmospheric parameter for the site from a second server;
   training a prediction model associated with the first air quality monitor:
   obtaining a plurality of first predicted substance concentrations of the target substance corresponding to the first air quality monitor from the prediction model, with at least:
      the first set of individual atmospheric readings; and
      the regional atmospheric parameter for the site;
   wherein the plurality of first predicted substance concentrations is obtained over a predefined period at a predefined frequency;
   generating a mapping of a weighted mean of the plurality of first predicted substance concentrations grouped in each feature group of a predetermined number of feature groups, wherein the predetermined number of feature groups together are representative of feature values over a predetermined range;
   obtaining a location map of a plurality of emission sources at the site, the location map comprising a location and an identity associated with each of the plurality of emission sources;
   for each emission source of the plurality of emission sources:
      generating a simulated plume model, based on a wind-direction; and
      calculating a plurality of representative circular normal distributions for each air quality monitor, using the simulated plume model, by setting a plurality of presumed flux values to the simulated plume model;
   performing an analysis of the plurality of representative circular normal distributions in relation with the mapping to identify a relevant representative circular normal distribution from the plurality of representative circular normal distributions, wherein the relevant representative circular normal distribution is indicative of a target emission source; and
   determining the target emission source, based on the analysis and the location map.

2. The location method of claim 1,
   wherein each feature group is associated with a wind-direction bucket; and
   wherein a predetermined number of wind-direction buckets together are representative of wind-directions over a full circle.

3. The location method of claim 2, wherein generating the mapping and further comprising:
   comparing a plurality of first measured substance concentrations with the plurality of first predicted substance concentrations of the target substance to create at least one adjustment factor;
   obtaining from the prediction model, a wind-direction contribution value representative of a contribution of the wind-direction in each of the plurality of first predicted substance concentrations as predicted by the prediction model;
   adjusting a plurality of wind-direction contribution values corresponding to the plurality of first predicted substance concentrations, using the at least one adjustment factor to obtain a plurality of adjusted wind-direction contribution values;
   grouping the plurality of adjusted wind-direction contribution values into the predetermined number of wind-direction buckets;
   for each of the predetermined number of wind-direction buckets, determining a weighted mean of the plurality of first predicted substance concentrations grouped in each wind-direction bucket of the predetermined number of wind-direction buckets; and
   generating the mapping of the weighted mean of the plurality of first predicted substance concentrations grouped in each wind-direction bucket of the predetermined number of wind-direction buckets, for wind directions in a full circle.

4. The location method of claim 3, wherein obtaining the wind-direction contribution values further comprises:

varying a value associated with a wind-direction, when values associated with remaining readings of the first set of individual atmospheric readings are fixed;

obtaining, from the prediction model, a first predicted substance concentrations of the target substance, for each variation of the value associated with the wind-direction;

comparing the first predicted substance concentrations with the first measured substance concentration of the target substance measured with the first air quality monitor; and determining the wind-direction contribution values, based on the comparison.

5. The location method of claim 3, wherein obtaining the wind-direction contribution value from the prediction model further comprises:

analyzing an opposite sub-tree for each decision node associated with the wind-direction within the prediction model.

6. The location method of claim 1, wherein the location map is obtained using drone imagery, and wherein the location map is created by:

obtaining a plurality of two-dimensional images using the drone imagery; and extracting three-dimensional measurements corresponding to the plurality of two-dimensional images, wherein each of the three-dimensional measurements comprises:

a distance between two points lying on a plane parallel to a photographic image plane, corresponding to measured associated distances on the plurality of two-dimensional images, using a scale.

7. The location method of claim 1, wherein the prediction model is based on a machine learning model, wherein the machine learning model is:

a tree-based model; and a gradient tree-boosting algorithm.

8. The location method of claim 1, wherein transmitting the first measured substance concentration to the first server further comprises:

increasing a power of transmission, when the first air quality monitor is intermittently transmitting the first measured substance concentration to the first server.

9. The location method of claim 8 and further comprising:

obtaining a battery level from a battery; and modifying a rate of transmission of the first measured substance concentration based on the battery level.

10. The location method of claim 1, wherein transmitting the first set of individual atmospheric readings to the first server further comprises:

averaging the first set of individual atmospheric readings over an averaging-time to create at least one time-averaged first set of individual atmospheric readings; and transmitting the least one time-averaged first set of individual atmospheric readings to the first server, over a cellular network.

11. The location method of claim 1, wherein the regional atmospheric parameter for the site is a height of planetary boundary layer (hPBL), wherein the hPBL is procured from the second server.

* * * * *